United States Patent
Satoh et al.

(10) Patent No.: US 7,531,554 B2
(45) Date of Patent: May 12, 2009

(54) 4-OXOQUINOLINE COMPOUND AND USE THEREOF AS HIV INTEGRASE INHIBITOR

(75) Inventors: Motohide Satoh, Osaka (JP); Takashi Matsuda, Osaka (JP); Satoshi Okuda, Osaka (JP); Hiroshi Kawakami, Osaka (JP); Hisateru Aramaki, Osaka (JP); Hisashi Shinkai, Osaka (JP); Yuji Matsuzaki, Osaka (JP); Wataru Watanabe, Osaka (JP); Kazunobu Yamataka, Osaka (JP); Shinichi Kiyonari, Osaka (JP); Shuichi Wamaki, Osaka (JP); Mitsuru Takahashi, Osaka (JP); Naohito Yamada, Osaka (JP); Akemi Nagao, Osaka (JP)

(73) Assignee: Japan Tobacco Inc. (JP)

( * ) Notice: Subject to any disclaimer, the term of this patent is extended or adjusted under 35 U.S.C. 154(b) by 644 days.

(21) Appl. No.: 11/133,470

(22) Filed: May 20, 2005

(65) Prior Publication Data

US 2006/0019906 A1    Jan. 26, 2006

(30) Foreign Application Priority Data

May 20, 2004  (JP) .............................. 2004-151034

(51) Int. Cl.
*C07D 215/04* (2006.01)
*A61K 31/44* (2006.01)

(52) U.S. Cl. ..................... 514/313; 514/314; 546/153; 546/159

(58) Field of Classification Search ................. 546/159, 546/153; 514/313, 314
See application file for complete search history.

(56) References Cited

U.S. PATENT DOCUMENTS

| | | | |
|---|---|---|---|
| 3,472,859 A | 10/1969 | Lesher et al. | |
| 5,217,972 A | 6/1993 | Grohe et al. | |
| 5,519,016 A | 5/1996 | Kimura et al. | |
| 5,688,791 A | 11/1997 | Kimura et al. | |
| 5,985,894 A | 11/1999 | Clemence et al. | |
| 6,034,086 A | 3/2000 | Kimura et al. | |
| 6,248,736 B1 | 6/2001 | Turner et al. | |
| 6,248,738 B1 | 6/2001 | Dickinson et al. | |
| 6,248,739 B1 | 6/2001 | Turner et al. | |
| 6,387,926 B1 | 5/2002 | Bhide et al. | |
| 6,559,145 B2 | 5/2003 | Ciske et al. | |
| 6,602,883 B1 | 8/2003 | Bhide et al. | |
| 6,730,682 B2 | 5/2004 | Schnute et al. | |
| 6,982,091 B2 * | 1/2006 | Pauletti et al. | 424/430 |
| 7,176,220 B2 * | 2/2007 | Satoh et al. | 514/312 |
| 2002/0019397 A1 | 2/2002 | Schnute et al. | |
| 2002/0103220 A1 | 8/2002 | Schnute | |
| 2004/0127708 A1 | 7/2004 | Fuji et al. | |
| 2004/0180910 A1 | 9/2004 | Schnute et al. | |
| 2004/0198716 A1 | 10/2004 | Arad et al. | |
| 2005/0239819 A1 | 10/2005 | Satoh et al. | |
| 2005/0288326 A1 * | 12/2005 | Matsuzaki et al. | 514/312 |
| 2006/0058286 A1 * | 3/2006 | Krystal et al. | 514/220 |

FOREIGN PATENT DOCUMENTS

| | | |
|---|---|---|
| CA | 2470365 | 6/2004 |
| EP | 498721 B1 | 8/1992 |
| EP | 1140851 | 10/2001 |
| EP | 1375486 A1 | 1/2004 |
| EP | 1 564 210 A1 | 8/2005 |
| JP | A-48-26772 | 9/1973 |
| JP | 4-360872 A2 | 12/1992 |
| JP | 6-116241 A | 4/1994 |
| JP | 6-199835 A | 7/1994 |
| JP | 6-271568 A | 9/1994 |
| JP | 8-183775 A | 7/1996 |
| JP | 10-316570 A | 12/1998 |
| JP | 2002-293745 | 10/2002 |

(Continued)

OTHER PUBLICATIONS

AIDSinfo, HIV and Its Treatment-Approved Anti-HIV Medications, pp. 1-2, revised Feb. 2008, Available at http://www.fda.gov/oashi/aids/virals.html.*

(Continued)

*Primary Examiner*—D. Margaret Seaman
(74) *Attorney, Agent, or Firm*—Finnegan, Henderson, Farabow, Garrett & Dunner, LLP

(57) ABSTRACT

Provision of a compound having an anti-HIV activity, particularly an integrase inhibitory activity.

A 4-oxoquinoline compound represented by the following formula [I] or a pharmaceutically acceptable salt thereof:

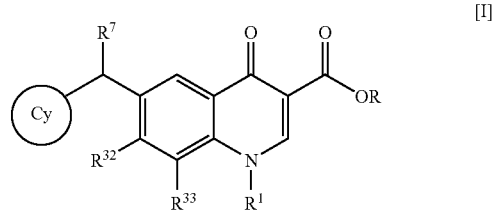

wherein each symbol is as defined in the specification.

The present invention also relates to a pharmaceutical composition containing the 4-oxoquinoline compound or a pharmaceutically acceptable salt thereof, and a pharmaceutically acceptable carrier; an integrase inhibitor, an antiviral agent, anti-HIV agent, and the like, which contains the 4-oxoquinoline compound or a pharmaceutically acceptable salt thereof as an active ingredient; an anti-HIV composition containing the 4-oxoquinoline compound or a pharmaceutically acceptable salt thereof, and one or more other kinds of anti-HIV activity substances as active ingredients; an anti-HIV agent containing the 4-oxoquinoline compound or a pharmaceutically acceptable salt thereof as an active ingredient, which is used for a multiple drug therapy with other anti-HIV agent(s), and the like.

14 Claims, No Drawings

FOREIGN PATENT DOCUMENTS

| | | |
|---|---|---|
| JP | A-2002-534416 | 10/2002 |
| JP | A-2002-534417 | 10/2002 |
| JP | 3567162 B1 | 9/2004 |
| WO | WO 97/38999 | 10/1997 |
| WO | WO 98/45269 | 10/1998 |
| WO | WO 99/01434 | 1/1999 |
| WO | WO 00/01714 | 1/2000 |
| WO | WO 00/40561 | 7/2000 |
| WO | WO 00/40563 | 7/2000 |
| WO | WO 01/02385 A1 | 1/2001 |
| WO | WO 01/98275 | 12/2001 |
| WO | WO 02/04422 A2 | 1/2002 |
| WO | WO 02/04444 | 1/2002 |
| WO | WO 02/36734 | 5/2002 |
| WO | WO 02/055079 | 7/2002 |
| WO | WO 02/070486 | 9/2002 |
| WO | WO 02/076939 A2 | 10/2002 |
| WO | WO 2004/046115 | 6/2004 |

OTHER PUBLICATIONS

Guidelines for the Use of Antiretroviral Agents in HIV-Infected Adults and Adolescents, Aug. 13, 2001.

Hirao, I. et al., *Antibacterial Activities of Oxodihydroquinoline Carboxylic Acid Derivatives*, Memoirs Department of Engineering, 14:21-32 (1990).

Hirao, I. et al., *Studies on the Synthesis of Quinoline Compounds, I.* Memoirs Kyushu Inst. Tech. (Eng.), 14:13-16 (1984).

Baker et al., *Irreversible enzyme inhibitors. 191. Hydrophobic bonding to some dehydrogenases by 6-, 7-, or 8-substituted-4-hydroxyquinoline-3-carboxylic acids.* J. Med. Chem., vol. 15, No. 3, Table 1, pp. 235-237, (1972).

Vincent et al., *Characterization of human immunodeficiency virus type 1 integrase expressed in Escherichia coli and analysis of variants with amino- terminal mutations*, J. Virol., vol. 67, pp. 425-437 (1993).

International Search Report for PCT/JP2005/009718 dated Aug. 25, 2005.

Abdul-Ahad, Europ. *J. Med. Chem.*, 17(4), pp. 301-306 (1982).

Baker, *J. Med. Chem.*, 15(3), pp. 235-237 (1972).

Stefenrich, Farmaro, Edizionie-Scientifica 42(1), pp. 3-16, 1987.

Walton, *Antimicrobial Agents & Chemotherapy* 32(7) pp. 1086-1089, 1988.

Yoshimoto, *J. Med. Chem.*, 19(1), pp. 71-98 (1976).

* cited by examiner

4-OXOQUINOLINE COMPOUND AND USE THEREOF AS HIV INTEGRASE INHIBITOR

CROSS-REFERENCE TO RELATED APPLICATIONS

This application claims the benefit of priority under 35 U.S.C. §119(a) to JP 2004-151034 filed May 20, 2004, which is incorporated herein by reference.

TECHNICAL FIELD

The present invention relates to a novel 4-oxoquinoline compound or a pharmaceutically acceptable salt thereof. In addition, the present invention relates to a pharmaceutical composition comprising the 4-oxoquinoline compound or a pharmaceutically acceptable salt thereof, and a pharmaceutically acceptable carrier; an integrase inhibitor, an antiviral agent, an anti-HIV agent, and the like, comprising the 4-oxoquinoline compound or a pharmaceutically acceptable salt thereof as an active ingredient; an anti-HIV composition comprising the 4-oxoquinoline compound or a pharmaceutically acceptable salt thereof, and one or more other kinds of anti-HIV active substances as an active ingredient; an anti-HIV agent comprising the 4-oxoquinoline compound or a pharmaceutically acceptable salt thereof as an active ingredient, which is used for a multiple drug therapy with other anti-HIV agents(s); and the like.

BACKGROUND ART

HIV (Human Immunodeficiency Virus (type 1)) belonging to retrovirus is a causative virus of AIDS (Acquired Immunodeficiency Syndrome).

HIV targets CD4 positive cell groups such as helper T cell, macrophage and dendritic cell and destroys these immunocompetent cells to cause immunodeficiency.

Accordingly, a pharmaceutical agent that eradicates HIV in a living organism or suppresses its growth is effective for the treatment or prophylaxis of AIDS.

HIV possesses a bimolecular RNA gene in a shell, which is covered with an envelope protein. The RNA codes for several enzymes (protease, reverse transcriptase, integrase) characteristic of the virus and the like. Translated reverse transcriptase and integrase are present in the shell, and protease is present inside and outside the shell.

HIV contacts and invades a host cell, causes uncoating, and releases a complex of RNA and integrase and the like into the cytoplasm. From the RNA, DNA is transcribed by reverse transcriptase, and a full length double stranded DNA is produced. The DNA moves into the nucleus of the host cell and is incorporated by integrase into the DNA of the host cell. The incorporated DNA is converted to an mRNA by polymerase of the host cell, from which mRNA various proteins necessary for forming a virus are synthesized by HIV protease and the like, and a virus particle is finally formed, which then undergoes budding and its release.

These virus specific enzymes are considered to be essential for the growth of HIV. These enzymes are drawing attention as the target of the development of antiviral agents, and several anti-HIV agents have been already developed.

For example, zidovudine, didanosine, lamivudine, and the like have been already on the market as reverse transcriptase inhibitors, and indinavir, nelfinavir, and the like as protease inhibitors.

In addition, a multiple drug combination therapy concurrently using these pharmaceutical agents has been employed. For example, a combined use of two reverse transcriptase inhibitors (zidovudine and didanosine), and a combined use of three agents of reverse transcriptase inhibitors (zidovudine and lamivudine) and a protease inhibitor (nelfinavir) have been clinically applied. Such multiple drug combination therapy is becoming a mainstream of AIDS therapy (see Guidelines for the Use of Antiretroviral Agents in HIV-Infected Adults and Adolescents, Aug. 13, 2001).

However, some of these pharmaceutical agents are known to cause side effects such as liver function failure, central nervous disorders (e.g., vertigo), and the like. In addition, acquisition of resistance to a pharmaceutical agent causes a problem. Even worse, emergence of an HIV that shows multiple drug resistance in a multiple drug combination therapy has been known.

Under the circumstances, a further development of a novel pharmaceutical agent, particularly a development of an anti-HIV agent based on a new mechanism, has been desired, wherein a development of an anti-HIV agent having an integrase inhibitory activity is expected, because an integrase characteristic of retrovirus is an essential enzyme for the growth of HIV.

Nevertheless, an effective integrase inhibitor has not been found as yet.

The compounds having an integrase inhibitory activity are described in the following.

WO02/070486 describes the following compounds [A], [B], and the like, as an anti-HIV agent having an integrase inhibitory activity (see WO02/070486 (p. 118, Example I-62, p. 203, Example I-152)).

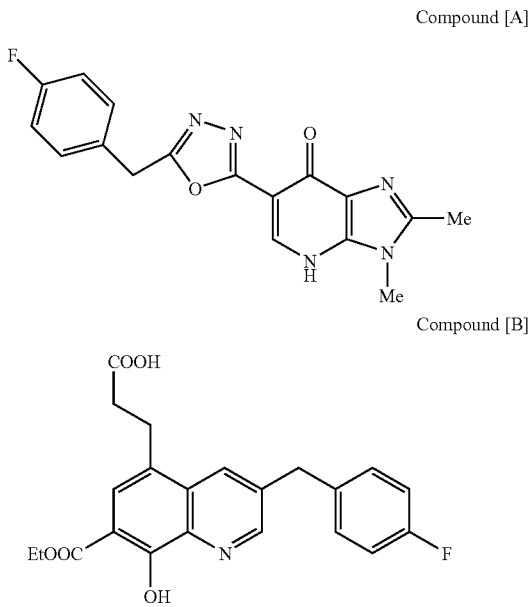

In addition, WO02/36734 describes the following compound [C] and the like, as an anti-HIV agent having an integrase inhibitory activity (see WO02/36734 (p. 106, Example 3)).

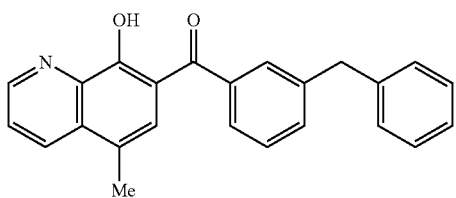
Compound [C]

WO02/055079 describes the following compound [D] and the like, as an anti-HIV agent having an integrase inhibitory activity (see WO02/055079 (p. 79, Example 1)).

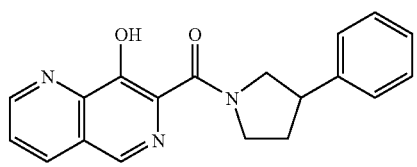
Compound [D]

However, these publications do not include 4-oxoquinoline compound disclosed in the present invention, or a description suggestive thereof.

Now, the compounds comparatively similar to the compound of the present invention are described.

U.S. Pat. No. 3,472,859 describes the following compound [E] and the like, as an anti-bacterial agent or an antimicrobial agent (see U.S. Pat. No. 3,472,859 (column 11, 1. 10)).

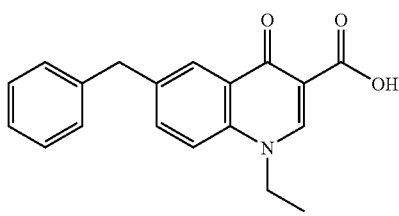
Compound [E]

In addition, JP-A-48-26772 describes the following compound [F] and the like, as a compound having an antimicrobial activity (see JP-A-48-26772 (p. 6, Example 9); Kyushu Kyoritsu University Research Report, Faculty of Engineering, No. 14, March 1990, pp. 21-32; Memoirs Kyushu Inst. Tech., (Eng.) No. 14, 1984, pp. 13-16).

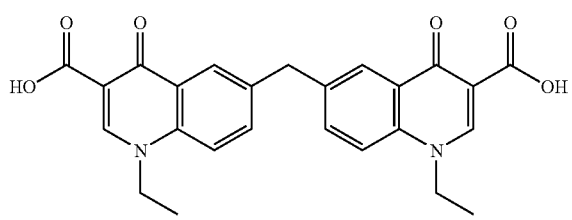
Compound [F]

Furthermore, the following compound [G] and the like are pharmacologically evaluated, as a dehydrogenase inhibitor (see Journal of Medicinal Chemistry, vol. 15, No. 3, pp. 235-237, 1972, Table 1).

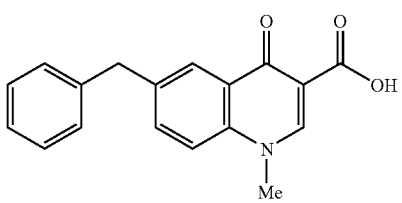
Compound [G]

In addition, JP-A-2002-534416 (patent family: WO00/40561, U.S. Pat. No. 6,248,739, EP1140850) describes the following compound [H] and the like, as a synthetic intermediate for a compound having an antivirus activity (see JP-A-2002-534416 (p. 141, Formula 60)).

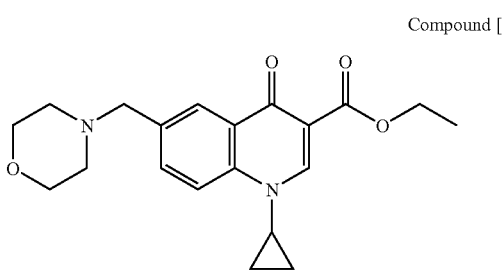
Compound [H]

JP-A-2002-534417 (patent family: WO00/40563, U.S. Pat. No. 6,248,736, EP1140851) also describes the following compound [J] and the like, as a synthetic intermediate for a compound having an antivirus activity (see JP-A-2002-534417 (p. 34, Formula 18)).

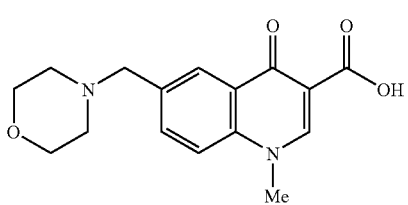
Compound [J]

Moreover, WO01/98275 (patent family: U.S. 2001/103220) also describes the following compound [K] and the like, as a synthetic intermediate for a compound having an antivirus activity (see WO01/98275 (p. 39, 1. 29)).

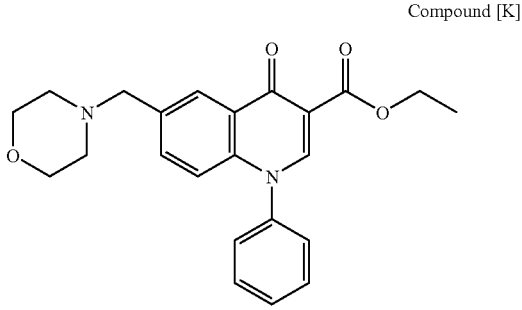
Compound [K]

JP-A-4-360872 (patent family: U.S. Pat. No. 5,985,894, EP498721B1) describes the following compound [L] and the like, as a compound having an antagonistic activity against anti-angiotensin II receptor (see JP-A-4-360872 (p. 64, Table 1)).

Compound [L]

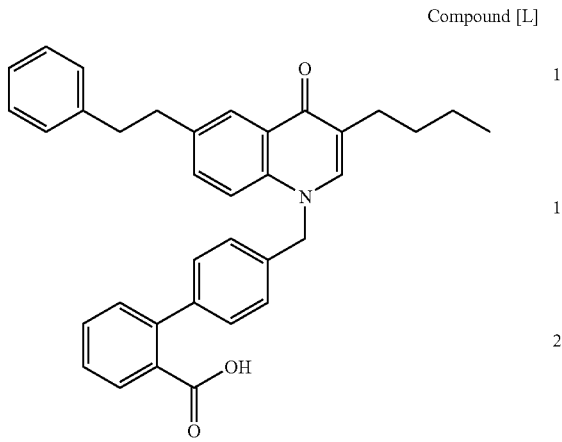

WO2004/046115 (patent family: JP-B-3567162) describes the following compounds [M] and the like, as an anti-HIV agent having an integrase inhibitory activity (see WO2004/046115).

Compound [M]

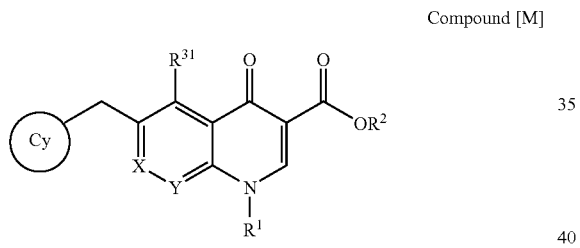

wherein ring Cy is an optionally substituted $C_{3-10}$ hydrocarbon group or an optionally substituted heterocyclic group, $R^1$ is an optionally substituted $C_{3-10}$ alkyl or the like, $R^2$ is a hydrogen atom or the like, $R^{31}$ is a hydrogen atom or the like, X is $C-R^{32}$ or a nitrogen atom, Y is $C-R^{33}$ or a nitrogen atom (wherein $R^{32}$ and $R^{33}$ are independently a hydrogen atom or the like).

DISCLOSURE OF THE INVENTION

From the findings obtained from pharmacological studies and clinical results heretofore, an anti-HIV agent is effective for the prophylaxis or treatment of AIDS, and particularly a compound having an integrase inhibitory activity can be an effective anti-HIV agent.

Therefore, an embodiment of present invention aims at providing a compound having an anti-HIV activity, particularly a compound having an integrase inhibitory activity.

The present inventors have conducted intensive studies in an attempt to find a compound having an anti-HIV activity, particularly a compound having an integrase inhibitory activity, and completed the present invention.

That is, the present invention relates to a 4-oxoquinoline compound represented by the following formula [I] having an integrase inhibitory activity (sometimes to be abbreviated as compound [I] in the present specification), a pharmaceutically acceptable salt thereof and use thereof.

[1] A 4-oxoquinoline Compound Represented by the Following Formula [I] or a pharmaceutically acceptable salt thereof:

[I]

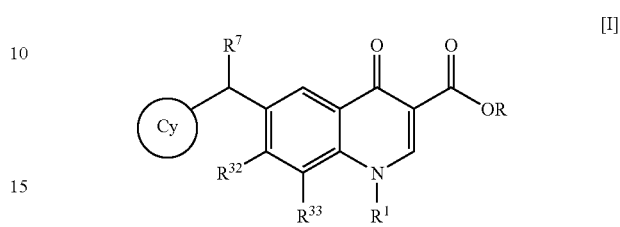

wherein
ring Cy is a group selected from the group consisting of

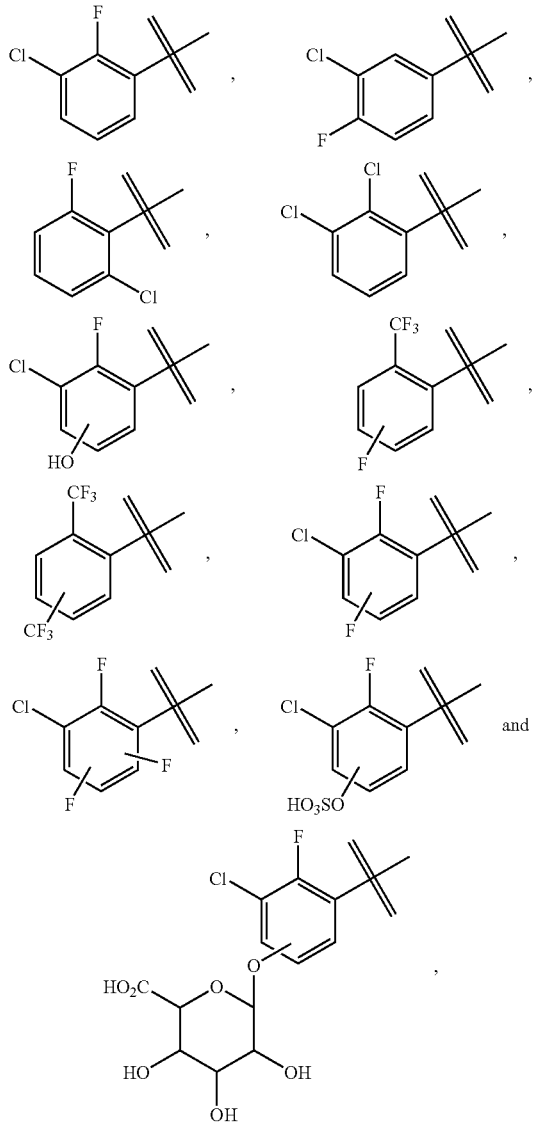

R is a hydrogen atom or $R^1$ is 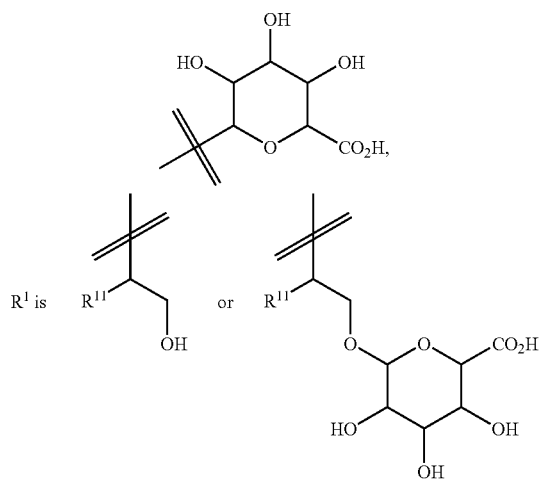

{wherein $R^{11}$ is —$(C_mH_{2m})$—$OR^{12}$, —$(C_mH_{2m})$—$SR^{12}$, —$(C_mH_{2m})$—$SO_2R^{12}$ (wherein $R^{12}$ is a $C_{1-4}$ alkyl group and m is an integer of 1 to 4), a saturated heterocyclic group, an isopropyl group or a tert-butyl group}, $R^{32}$ is a hydrogen atom, an ethyl group, a methoxy group, a hydroxyl group, a 2-hydroxyethoxy group, a 3-hydroxypropoxy group, a 4-hydroxybutyloxy group, a 2,2,2-trifluoroethyloxy group, —O—$(CH_2)_p$—$OR^{34}$, —O—$(CH_2)_p$—$NR^{35}R^{36}$, —O—$(CH_2)$—$CO_2R^{35}$, —O—$(CH_2)_p$—$CONR^{35}R^{37}$, —O—$(CH_2)_p$—$SO_2NR^{35}R^{37}$ (wherein $R^{34}$ is a $C_{1-4}$ alkyl group, $R^{35}$ and $R^{37}$ are the same or different and each is a hydrogen atom or a $C_{1-4}$ alkyl group, $R^{36}$ is a hydrogen atom, a $C_{1-4}$ alkyl group, an acetyl group or a mesyl group, and p is an integer of 1 to 4), a pyrrolidinyl group, a piperidinyl group, a piperazinyl group, a morpholinyl group, a thiomorpholinyl group (wherein each of the pyrrolidinyl group, piperidinyl group, piperazinyl group, morpholinyl group and thiomorpholinyl group is optionally substituted by 1 or 2 substituents selected from the group consisting of a hydroxyl group, a $C_{1-4}$ alkyl group, an oxo group, —$COR^{38}$, —$NR^{35}R^{37}$ and —$NR^{35}COR^{38}$, wherein $R^{35}$ and $R^{37}$ are as defined above and $R^{38}$ is a $C_{1-4}$ alkyl group), or

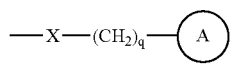

(wherein X is —O— or —NH—, ring A is a phenyl group or a heterocyclic group, wherein each of the phenyl group and the heterocyclic group is optionally substituted by 1 to 5 substituents, that is at least one group independently selected from a cyano group, a mesyl group, a $C_{1-4}$ alkyl group, —$CO_2R^{35}$, —$CONR^{35}R^{37}$, —$SO_2NR^{35}R^{37}$ and —$COR^{38}$, wherein $R^{35}$, $R^{37}$ and $R^{38}$ are as defined above, and q is 0 or an integer of 1 to 4), $R^{33}$ is a hydrogen atom, a hydroxyl group, —O—$(CH_2)_n$—$OR^{39}$, —O—$(CH_2)_n$—$NR^{39}R^{31}$ or —O—$(CH_2)_n$-Ph (wherein $R^{39}$ and $R^{31}$ are the same or different and each is a hydrogen atom or a $C_{1-4}$ alkyl group and n is an integer of 1 to 4)

$R^7$ is a hydrogen atom or a hydroxyl group, $R^{32}$ and $R^{33}$ may be linked to form an alkylenedioxy group, $R^1$ and $R^{33}$ may be linked to form

[structure with * showing $R^{33}$ side and $R^{13}$]

(wherein * shows the $R^{33}$ side and $R^{13}$ is a $C_{1-4}$ alkyl group optionally substituted by hydroxyl group(s)), provided that the compound represented by the formula [I] satisfies at least one condition of the following (1)-(7):

(1) the compound represented by the formula [I] is a compound represented by

[quinolone carboxylic acid structure with ring Cy]

wherein ring Cy is a group selected from the group consisting of

[eight substituted phenyl ring structures with various Cl, F, CF3, HO, HO3SO substituents] and -continued

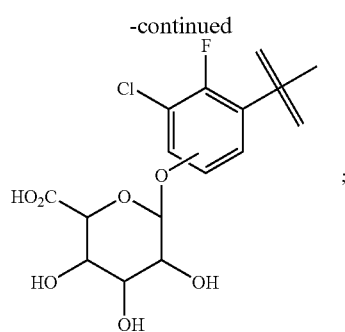
;

(2) the compound represented by the formula [I] is a compound represented by

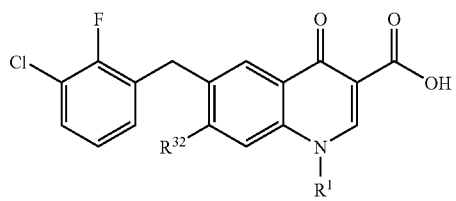

wherein $R^{32}$ is a hydrogen atom or a methoxy group, and $R^1$ is

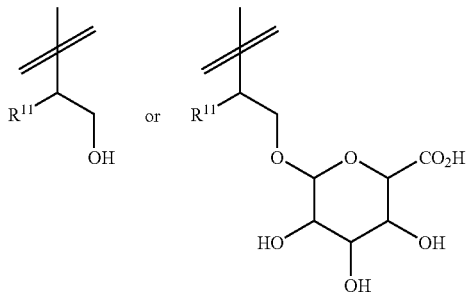

wherein $R^{11}$ is $—(C_mH_{2m})—OR^{12}$, $—(C_mH_{2m})—SR^{12}$, $—(C_mH_{2m})—SO_2R^{12}$ (wherein $R^{12}$ and m are as defined above), or a saturated heterocyclic group;

(3) the compound represented by the formula [I] is a compound represented by

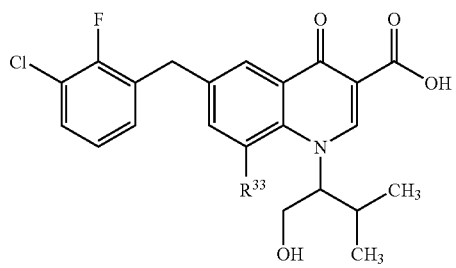

wherein R is a hydroxyl group, $—O—(CH_2)_n—OR^{39}$, $—O—(CH_2)_n—NR^{39}R^{31}$, or $—O—(CH_2)_n$-Ph (wherein $R^{31}$, $R^{39}$ and n are as defined above);

(4) the compound represented by the formula [I] is a compound represented by

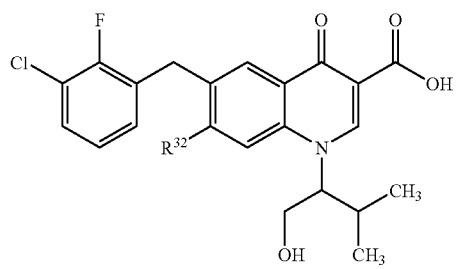

wherein $R^{32}$ is an ethyl group, a 4-hydroxybutyloxy group, a 2,2,2-trifluoroethyloxy group, $—O—(CH_2)_p—OR^{34}$, $—O—(CH_2)_p—NR^{35}R^{36}$, $—O—(CH_2)_p—CO_2R^{35}$, $—O—(CH_2)_p—CONR^{35}R^{37}$, $—O—(CH_2)_p—SO_2NR^{35}R^{36}$, (wherein $R^{34}$, $R^{35}$, $R^{36}$, $R^{37}$ and p are as defined above), a pyrrolidinyl group, a piperidinyl group, a piperazinyl group, a morpholinyl group, a thiomorpholinyl group (wherein each of the pyrrolidinyl group, piperidinyl group, piperazinyl group, morpholinyl group and thiomorpholinyl group is optionally substituted by 1 or 2 substituents selected from the group consisting of a hydroxyl group, a $C_{1-4}$ alkyl group, an oxo group, $—COR^{38}$, $—NR^{35}R^{37}$ and $—NR^{35}COR^{38}$, wherein $R^{35}$, $R^{37}$ and $R^{38}$ are as defined above), or

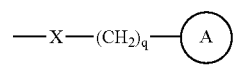

wherein X, ring A and q are as defined above;

(5) the compound represented by the formula [I] is a compound represented by

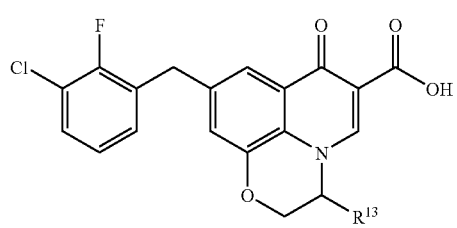

wherein $R^{13}$ is as defined above;

(6) the compound represented by the formula [I] is a compound represented by

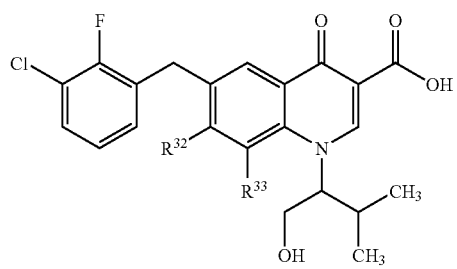

wherein R³² and R³³ are linked to form an alkylenedioxy group; and (7) the compound represented by the formula [I] is
6-(2-chloro-6-fluorobenzyl)-1-(1-(hydroxymethyl)-2-methylpropyl)-7-methoxy-4-oxo-1,4-dihydroquinoline-3-carboxylic acid (Example 7-1),
6-(2,3-dichlorobenzyl)-1-(1-(hydroxymethyl)-2-methylpropyl)-7-methoxy-4-oxo-1,4-dihydroquinoline-3-carboxylic acid (Example 7-2),
6-(3-chloro-2-fluorobenzyl)-7-(2-hydroxyethoxy)-1-(1-(hydroxymethyl)-2-methylpropyl)-4-oxo-1,4-dihydroquinoline-3-carboxylic acid (Example 7-3),
6-(3-chloro-2-fluorobenzyl)-1-(1-(hydroxymethyl)-2-methylpropyl)-7-(3-hydroxypropoxy)-4-oxo-1,4-dihydroquinoline-3-carboxylic acid (Example 7-4),
6-(3-chloro-2-fluorobenzyl)-7-hydroxy-1-(1-(hydroxymethyl)-2-methylpropyl)-4-oxo-1,4-dihydroquinoline-3-carboxylic acid (Example 7-5),
6-(3-chloro-2-fluorobenzyl)-1-(2,2-dimethyl-1-(hydroxymethyl)propyl)-7-(morpholin-4-yl)-4-oxo-1,4-dihydroquinoline-3-carboxylic acid (Example 7-6),
6-((3-chloro-2-fluorophenyl)-hydroxy-methyl)-1-(1-hydroxymethyl-2-methylpropyl)-7-methoxy-4-oxo-1,4-dihydroquinoline-3-carboxylic acid (Examples 7-7 and 7-8), or
6-[6-(3-chloro-2-fluorobenzyl)-1-(1-hydroxymethyl-2-methylpropyl)-7-methoxy-4-oxo-1,4-dihydroquinoline-3-carbonyloxy]-3,4,5-trihydroxytetrahydropyran-2-carboxylic acid (Examples 7-10)

[2] the 4-oxoquinoline Compound of the Above-mentioned [1], Wherein in the Formula [I], R is a hydrogen atom, ring Cy is a group selected from the group consisting of

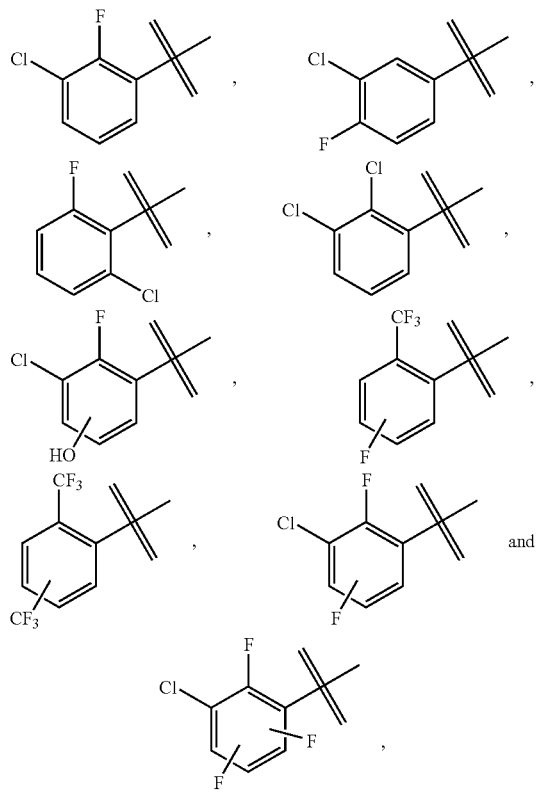

R¹ is

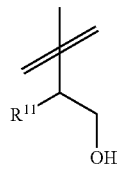

{wherein $R^{11}$ is —$(C_mH_{2m})$—$OR^{12}$, —$(C_mH_{2m})$—$SR^{12}$, —$(C_mH_{2m})$—$SO_2R^{12}$ (wherein $R^{12}$ is a $C_{1-4}$ alkyl group and m is an integer of 1 to 4), a saturated heterocyclic group, an isopropyl group or a tert-butyl group}, $R^{32}$ is a hydrogen atom, an ethyl group, a methoxy group, a hydroxyl group, a 2-hydroxyethoxy group, a 3-hydroxypropoxy group, a 4-hydroxybutyloxy group, a 2,2,2-trifluoroethyloxy group, —O—$(CH_2)_p$—$OR^{34}$, —O—$(CH_2)_p$—$NR^{35}R^{36}$, —O—$(CH_2)_p$—$CO_2R^{35}$, —O—$(CH_2)_p$—$CONR^{35}R^{37}$, —O—$(CH_2)_p$—$SO_2NR^{35}R^{37}$ (wherein $R^{34}$ is a $C_{1-4}$ alkyl group, $R^{35}$ and $R^{37}$ are the same or different and each is a hydrogen atom or a $C_{1-4}$ alkyl group, $R^{36}$ is a hydrogen atom, a $C_{1-4}$ alkyl group, an acetyl group or a mesyl group, and p is an integer of 1 to 4), a pyrrolidinyl group, a piperidinyl group, a piperazinyl group, a morpholinyl group, a thiomorpholinyl group (wherein each of the pyrrolidinyl group, piperidinyl group, piperazinyl group, morpholinyl group and thiomorpholinyl group is optionally substituted by 1 or 2 substituents selected from the group consisting of a hydroxyl group, a $C_{1-4}$ alkyl group, an oxo group, —COR, —$NR^{35}R^{37}$ and —$NR^{35}COR^{38}$, wherein $R^{35}$ and $R^{37}$ are as defined above and $R^{38}$ is a $C_{1-4}$ alkyl group), or

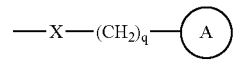

(wherein X is —O— or —NH—, ring A is a phenyl group or a heterocyclic group, wherein each of the phenyl group and the heterocyclic group is optionally substituted by 1 to 5 substituents, that is at least one group independently selected from a cyano group, a mesyl group, a $C_{1-4}$ alkyl group, —$CO_2R^{35}$, —$CONR^{35}R^{37}$, —$SO_2NR^{35}R^{37}$ and —$COR^{38}$, wherein $R^{35}$, $R^{37}$ and $R^{38}$ are as defined above, and q is 0 or an integer of 1 to 4), $R^{33}$ is a hydrogen atom, a hydroxyl group, —O—$(CH_2)_n$—$OR^{39}$, —O—$(CH_2)_n$—$NR^{39}R^{31}$ or —O—$(CH_2)_n$-Ph (wherein $R^{39}$ and $R^{31}$ are the same or different and each is a hydrogen atom or a $C_{1-4}$ alkyl group and n is an integer of 1 to 4), $R^7$ is a hydrogen atom or a hydroxyl group, $R^{32}$ and $R^{33}$ may be linked to form an alkylenedioxy group, $R^1$ and $R^{33}$ may be linked to form

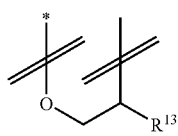

(wherein * shows the $R^{33}$ side and $R^{13}$ is a $C_{1-4}$ alkyl group optionally substituted by hydroxyl group(s)), provided that the compound represented by the formula [I] satisfies at least one condition of the following (1)-(7):

(1) the compound represented by the formula [I] is a compound represented by

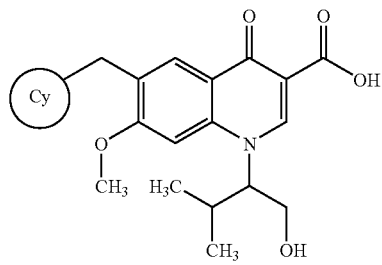

wherein ring Cy is a group selected from the group consisting of

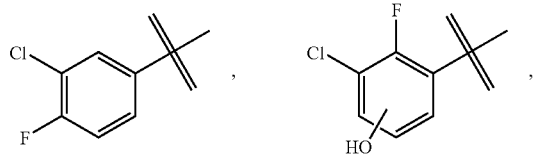

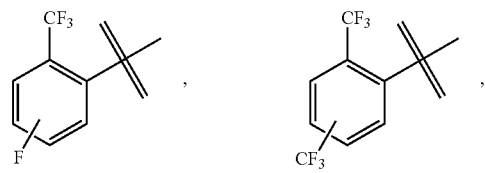

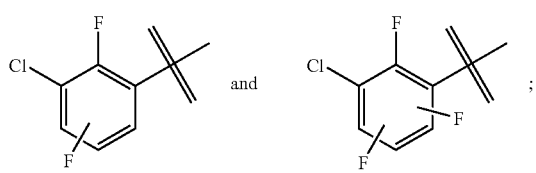

(2) the compound represented by the formula [I] is a compound represented by

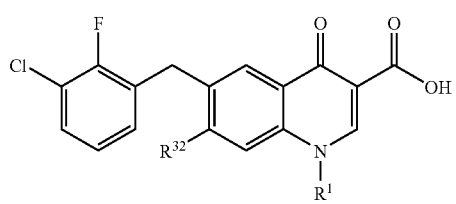

wherein $R^{32}$ is a hydrogen atom or a methoxy group, and $R^1$ is

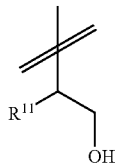

wherein $R^{11}$ is $-(C_mH_{2m})-OR_{12}$, $-(C_mH_{2m})-SR^{12}$, $-(C_mH_{2m})-SO_2R^{12}$ (wherein $R^{12}$ and m are as defined above), or a saturated heterocyclic group;

(3) the compound represented by the formula [I] is a compound represented by

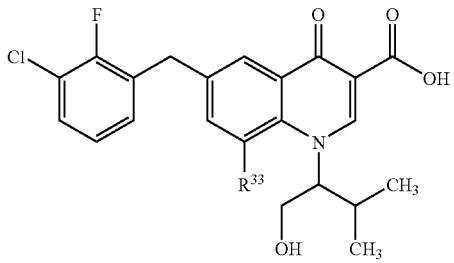

wherein $R^{33}$ is a hydroxyl group, $-O-(CH_2)_n-OR^{39}$, $-O-(CH_2)_n-NR^{39}R^{31}$ or $-O-(CH_2)_n$-Ph (wherein $R^{31}$, $R^{39}$ and n are as defined above);

(4) the compound represented by the formula [I] is a compound represented by

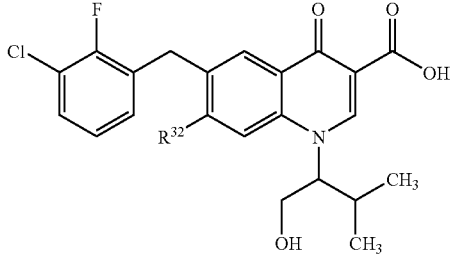

wherein $R^{32}$ is an ethyl group, a 4-hydroxybutyloxy group, a 2,2,2-trifluoroethyloxy group, $-O-(CH_2)_p-OR^{34}$, $-O-(CH_2)_p-NR^{35}R^{36}$, $-O-(CH_2)_p-CO_2R^{35}$, $-O-(CH_2)_p-CONR^{35}R^{37}$, $-O-(CH_2)_p-SO_2NR^{35}R^{37}$ (wherein $R^{34}$, $R^{35}$, $R^{36}$, $R^{37}$ and p are as defined above), a pyrrolidinyl group, a piperidinyl group, a piperazinyl group, a morpholinyl group, a thiomorpholinyl group (wherein each of the pyrrolidinyl group, piperidinyl group, piperazinyl group, morpholinyl group and thiomorpholinyl group is optionally substituted by 1 or 2 substituents selected from the group consisting of a hydroxyl group, a $C_{1-4}$ alkyl group, an oxo group, $-COR^{38}$, $-NR^{35}R^{37}$ and $-NR^{35}COR^{38}$, wherein $R^{35}$, $R^{37}$ and $R^{38}$ are as defined above), or

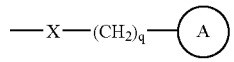

wherein X, ring A and q are as defined above;

(5) the compound represented by the formula [I] is a compound represented by

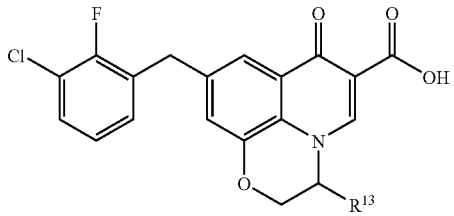

wherein $R^{13}$ is as defined above;

(6) the compound represented by the formula [I] is a compound represented by

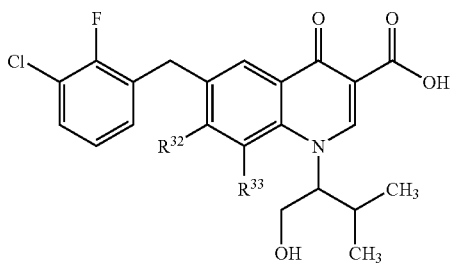

wherein $R^{32}$ and $R^{33}$ are linked to form an alkylenedioxy group; and (7) the Compound Represented by the Formula [I] is
6-(2-chloro-6-fluorobenzyl)-1-(1-(hydroxymethyl)-2-methylpropyl)-7-methoxy-4-oxo-1,4-dihydroquinoline-3-carboxylic acid (Example 7-1),
6-(2,3-dichlorobenzyl)-1-(1-(hydroxymethyl)-2-methylpropyl)-7-methoxy-4-oxo-1,4-dihydroquinoline-3-carboxylic acid (Example 7-2),
6-(3-chloro-2-fluorobenzyl)-7-(2-hydroxyethoxy)-1-(1-(hydroxymethyl)-2-methylpropyl)-4-oxo-1,4-dihydroquinoline-3-carboxylic acid (Example 7-3),
6-(3-chloro-2-fluorobenzyl)-1-(1-(hydroxymethyl)-2-methylpropyl)-7-(3-hydroxypropoxy)-4-oxo-1,4-dihydroquinoline-3-carboxylic acid (Example 7-4),
6-(3-chloro-2-fluorobenzyl)-7-hydroxy-1-(1-(hydroxymethyl)-2-methylpropyl)-4-oxo-1,4-dihydroquinoline-3-carboxylic acid (Example 7-5),
6-(3-chloro-2-fluorobenzyl)-1-(2,2-dimethyl-1-(hydroxymethyl)propyl)-7-(morpholin-4-yl)-4-oxo-1,4-dihydroquinoline-3-carboxylic acid (Example 7-6), or
6-((3-chloro-2-fluorophenyl)-hydroxy-methyl)-1-(1-hydroxymethyl-2-methylpropyl)-7-methoxy-4-oxo-1,4-dihydroquinoline-3-carboxylic acid (Examples 7-7 and 7-8), or a pharmaceutically acceptable salt thereof;

[3] the 4-oxoquinoline compound of the above-mentioned [1], which is selected from the group consisting of
6-(3-chloro-4-fluorobenzyl)-1-((1S)-1-(hydroxymethyl)-2-methylpropyl)-7-methoxy-4-oxo-1,4-dihydroquinoline-3-carboxylic acid (Example 1-1),
6-(3-chloro-2,6-difluorobenzyl)-1-((1S)-1-(hydroxymethyl)-2-methylpropyl)-7-methoxy-4-oxo-1,4-dihydroquinoline-3-carboxylic acid (Example 1-2),
6-(3-chloro-2-fluoro-6-hydroxybenzyl)-1-((1S)-1-(hydroxymethyl)-2-methylpropyl)-7-methoxy-4-oxo-1,4-dihydroquinoline-3-carboxylic acid (Example 1-3),
6-(3-chloro-2-fluoro-4-hydroxybenzyl)-1-((1S)-1-(hydroxymethyl)-2-methylpropyl)-7-methoxy-4-oxo-1,4-dihydroquinoline-3-carboxylic acid (Example 1-4),
6-(3-chloro-2,4-difluorobenzyl)-1-((1S)-1-(hydroxymethyl)-2-methylpropyl)-7-methoxy-4-oxo-1,4-dihydroquinoline-3-carboxylic acid (Example 1-5),
6-(3-chloro-2-fluoro-5-hydroxybenzyl)-1-((1S)-1-(hydroxymethyl)-2-methylpropyl)-7-methoxy-4-oxo-1,4-dihydroquinoline-3-carboxylic acid (Example 1-6),
6-(3-chloro-2,4,5-trifluorobenzyl)-1-((1S)-1-(hydroxymethyl)-2-methylpropyl)-7-methoxy-4-oxo-1,4-dihydroquinoline-3-carboxylic acid (Example 1-7),
6-(3-fluoro-2-(trifluoromethyl)benzyl)-1-((1S)-1-(hydroxymethyl)-2-methylpropyl)-7-methoxy-4-oxo-1,4-dihydroquinoline-3-carboxylic acid (Example 1-8),
6-(2,5-di(trifluoromethyl)benzyl)-1-((1S)-1-(hydroxymethyl)-2-methylpropyl)-7-methoxy-4-oxo-1,4-dihydroquinoline-3-carboxylic acid (Example 1-9),
6-(4-fluoro-2-(trifluoromethyl)benzyl)-1-((1S)-1-(hydroxymethyl)-2-methylpropyl)-7-methoxy-4-oxo-1,4-dihydroquinoline-3-carboxylic acid (Example 1-10),
6-(5-fluoro-2-(trifluoromethyl)benzyl)-1-((1S)-1-(hydroxymethyl)-2-methylpropyl)-7-methoxy-4-oxo-1,4-dihydroquinoline-3-carboxylic acid (Example 1-11),
6-(2-fluoro-6-(trifluoromethyl)benzyl)-1-((1S)-1-(hydroxymethyl)-2-methylpropyl)-7-methoxy-4-oxo-1,4-dihydroquinoline-3-carboxylic acid (Example 1-12),
6-(3-chloro-2-fluorobenzyl)-1-((1S)-2-hydroxy-1-(tetrahydropyran-4-yl)ethyl)-7-methoxy-4-oxo-1,4-dihydroquinoline-3-carboxylic acid (Example 2-1),
6-(3-chloro-2-fluorobenzyl)-1-(2-hydroxy-1-(piperidin-4-yl)ethyl)-7-methoxy-4-oxo-1,4-dihydroquinoline-3-carboxylic acid hydrochloride (Example 2-2),
6-(3-chloro-2-fluorobenzyl)-1-((1R)-1-(hydroxymethyl)-2-(methylthio)ethyl)-7-methoxy-4-oxo-1,4-dihydroquinoline-3-carboxylic acid (Example 2-3),
6-(3-chloro-2-fluorobenzyl)-1-((1R)-1-(hydroxymethyl)-2-mesylethyl)-7-methoxy-4-oxo-1,4-dihydroquinoline-3-carboxylic acid (Example 2-4),
6-(3-chloro-2-fluorobenzyl)-1-((1R)-1-(hydroxymethyl)-2-methyl-2-(methylthio)propyl)-7-methoxy-4-oxo-1,4-dihydroquinoline-3-carboxylic acid (Example 2-5),
6-(3-chloro-2-fluorobenzyl)-1-((1R)-1-(hydroxymethyl)-2-mesyl-2-methylpropyl)-7-methoxy-4-oxo-1,4-dihydroquinoline-3-carboxylic acid (Example 2-6),
6-(3-chloro-2-fluorobenzyl)-1-((1R)-1-(hydroxymethyl)-2-(methylthio)ethyl)-4-oxo-1,4-dihydroquinoline-3-carboxylic acid (Example 2-7),
6-(3-chloro-2-fluorobenzyl)-1-((1R)-1-(hydroxymethyl)-2-mesylethyl)-4-oxo-1,4-dihydroquinoline-3-carboxylic acid (Example 2-8),
6-(3-chloro-2-fluorobenzyl)-1-((1R)-1-(hydroxymethyl)-2-methyl-2-(methylthio)propyl)-4-oxo-1,4-dihydroquinoline-3-carboxylic acid (Example 2-9),
6-(3-chloro-2-fluorobenzyl)-1-((1R)-1-(hydroxymethyl)-2-mesyl-2-methylpropyl)-4-oxo-1,4-dihydroquinoline-3-carboxylic acid (Example 2-10),
6-(3-chloro-2-fluorobenzyl)-1-((1R,2R)-1-(hydroxymethyl)-2-methoxypropyl)-7-methoxy-4-oxo-1,4-dihydroquinoline-3-carboxylic acid (Example 2-11),
6-(3-chloro-2-fluorobenzyl)-1-((1S)-1-(hydroxymethyl)-3-(methylthio)propyl)-7-methoxy-4-oxo-1,4-dihydroquinoline-3-carboxylic acid (Example 2-12), 6-(3-chloro-2-fluorobenzyl)-1-((1S)-1-(hydroxymethyl)-3-mesylpropyl)-7-methoxy-4-oxo-1,4-dihydroquinoline-3-carboxylic acid (Example 2-13), 6-(3-chloro-2-fluorobenzyl)-1-((1R)-1-(hydroxymethyl)-2-methoxyethyl)-4-oxo-1,4-dihydroquinoline-3-carboxylic acid (Example 2-14), 6-(3-chloro-2-fluorobenzyl)-1-((1R,2R)-1-(hydroxymethyl)-2-methoxypropyl)-4-oxo-1,4-dihydroquinoline-3-carboxylic acid (Example 2-15), 6-(3-chloro-2-fluorobenzyl)-1-((1S)-1-(hydroxymethyl)-3-(methylthio)propyl)-4-oxo-1,4-dihydroquinoline-3-carboxylic acid (Example 2-16), 6-(3-chloro-2-fluorobenzyl)-1-((1S)-1-(hydroxymethyl)-3-mesylpropyl)-4-oxo-1,4-dihydroquinoline-3-carboxylic acid (Example 2-17), 6-(3-chloro-2-fluorobenzyl)-1-((1R)-1-(hydroxymethyl)-2-methoxyethyl)-7-methoxy-4-oxo-1,4-dihydroquinoline-3-carboxylic acid (Example 2-18), 6-(3-chloro-2-fluorobenzyl)-8-(2-hydroxyethoxy)-1-((1S)-1-(hydroxymethyl)-2-methylpropyl)-4-oxo-1,4-dihydroquinoline-3-carboxylic acid (Example 3-1), 6-(3-chloro-2-fluorobenzyl)-1-((1S)-1-(hydroxymethyl)-2-methylpropyl)-8-(3-hydroxypropoxy)-4-oxo-1,4-dihydroquinoline-3-carboxylic acid (Example 3-2), 6-(3-chloro-2-fluorobenzyl)-8-(4-hydroxybutoxy)-1-((1S)-1-(hydroxymethyl)-2-methylpropyl)-4-oxo-1,4-dihydroquinoline-3-carboxylic acid (Example 3-3), 6-(3-chloro-2-fluorobenzyl)-1-((1S)-1-(hydroxymethyl)-2-methylpropyl)-8-(2-methoxyethoxy)-4-oxo-1,4-dihydroquinoline-3-carboxylic acid (Example 3-4), 6-(3-chloro-2-fluorobenzyl)-8-hydroxy-1-((1S)-1-(hydroxymethyl)-2-methylpropyl)-4-oxo-1,4-dihydroquinoline-3-carboxylic acid (Example 3-5), 6-(3-chloro-2-fluorobenzyl)-8-(2-(dimethylamino)ethoxy)-1-((1S)-1-(hydroxymethyl)-2-methylpropyl)-4-oxo-1,4-dihydroquinoline-3-carboxylic acid (Example 3-6), 6-(3-chloro-2-fluorobenzyl)-1-((1S)-1-(hydroxymethyl)-2-methylpropyl)-8-(3-methoxypropoxy)-4-oxo-1,4-dihydroquinoline-3-carboxylic acid (Example 3-7), 6-(3-chloro-2-fluorobenzyl)-1-((1S)-1-(hydroxymethyl)-2-methylpropyl)-8-(4-methoxybutoxy)-4-oxo-1,4-dihydroquinoline-3-carboxylic acid (Example 3-8), 8-benzyloxy-6-(3-chloro-2-fluorobenzyl)-1-((1S)-1-(hydroxymethyl)-2-methylpropyl)-4-oxo-1,4-dihydroquinoline-3-carboxylic acid (Example 3-9), 6-(3-chloro-2-fluorobenzyl)-1-((1S)-1-(hydroxymethyl)-2-methylpropyl)-7-(2-methoxyethoxy)-4-oxo-1,4-dihydroquinoline-3-carboxylic acid (Example 4-1), 6-(3-chloro-2-fluorobenzyl)-7-(2-(dimethylamino)ethoxy)-1-((1S)-1-(hydroxymethyl)-2-methylpropyl)-4-oxo-1,4-dihydroquinoline-3-carboxylic acid (Example 4-2), 6-(3-chloro-2-fluorobenzyl)-1-((1S)-1-(hydroxymethyl)-2-methylpropyl)-7-((methylamino)sulfonylmethoxy)-4-oxo-1,4-dihydroquinoline-3-carboxylic acid (Example 4-3), 6-(3-chloro-2-fluorobenzyl)-7-ethyl-1-((1S)-1-(hydroxymethyl)-2-methylpropyl)-4-oxo-1,4-dihydroquinoline-3-carboxylic acid (Example 4-4), 6-(3-chloro-2-fluorobenzyl)-7-(4-hydroxybutoxy)-1-((1S)-1-(hydroxymethyl)-2-methylpropyl)-4-oxo-1,4-dihydroquinoline-3-carboxylic acid (Example 4-5), 6-(3-chloro-2-fluorobenzyl)-7-(3-(dimethylamino)propoxy)-1-((1S)-1-(hydroxymethyl)-2-methylpropyl)-4-oxo-1,4-dihydroquinoline-3-carboxylic acid (Example 4-6), 6-(3-chloro-2-fluorobenzyl)-7-(4-(dimethylamino)butoxy)-1-((1S)-1-(hydroxymethyl)-2-methylpropyl)-4-oxo-1,4-dihydroquinoline-3-carboxylic acid (Example 4-7), 6-(3-chloro-2-fluorobenzyl)-1-((1S)-1-(hydroxymethyl)-2-methylpropyl)-7-(3-methoxypropoxy)-4-oxo-1,4-dihydroquinoline-3-carboxylic acid (Example 4-8), 6-(3-chloro-2-fluorobenzyl)-1-((1S)-1-(hydroxymethyl)-2-methylpropyl)-7-(morpholin-4-yl)-4-oxo-1,4-dihydroquinoline-3-carboxylic acid (Example 4-9), 6-(3-chloro-2-fluorobenzyl)-1-((1S)-1-(hydroxymethyl)-2-methylpropyl)-7-(4-methylpiperazin-1-yl)-4-oxo-1,4-dihydroquinoline-3-carboxylic acid (Example 4-10), 7-(4-acetylpiperazin-1-yl)-6-(3-chloro-2-fluorobenzyl)-1-((1S)-1-(hydroxymethyl)-2-methylpropyl)-4-oxo-1,4-dihydroquinoline-3-carboxylic acid (Example 4-11), 6-(3-chloro-2-fluorobenzyl)-1-((1S)-1-(hydroxymethyl)-2-methylpropyl)-4-oxo-7-(piperazin-1-yl)-1,4-dihydroquinoline-3-carboxylic acid (Example 4-12), 6-(3-chloro-2-fluorobenzyl)-1-((1S)-1-(hydroxymethyl)-2-methylpropyl)-4-oxo-7-(2-(piperidin-1-yl)ethoxy)-1,4-dihydroquinoline-3-carboxylic acid (Example 4-13), 6-(3-chloro-2-fluorobenzyl)-1-((1S)-1-(hydroxymethyl)-2-methylpropyl)-7-(1-methylpiperidin-4-yloxy)-4-oxo-1,4-dihydroquinoline-3-carboxylic acid (Example 4-14), 6-(3-chloro-2-fluorobenzyl)-7-(4-ethylpiperazin-1-yl)-1-((1S)-1-(hydroxymethyl)-2-methylpropyl)-4-oxo-1,4-dihydroquinoline-3-carboxylic acid (Example 4-15), 6-(3-chloro-2-fluorobenzyl)-1-((1S)-1-(hydroxymethyl)-2-methylpropyl)-7-(2-(morpholin-4-yl)ethoxy)-4-oxo-1,4-dihydroquinoline-3-carboxylic acid (Example 4-16), 6-(3-chloro-2-fluorobenzyl)-1-((1S)-1-(hydroxymethyl)-2-methylpropyl)-4-oxo-7-(2-(pyrrolidin-1-yl)ethoxy)-1,4-dihydroquinoline-3-carboxylic acid (Example 4-17), 7-(2-aminoethoxy)-6-(3-chloro-2-fluorobenzyl)-1-((1S)-1-(hydroxymethyl)-2-methylpropyl)-4-oxo-1,4-dihydroquinoline-3-carboxylic acid hydrochloride (Example 4-18), 7-(3-aminopropoxy)-6-(3-chloro-2-fluorobenzyl)-1-((1S)-1-(hydroxymethyl)-2-methylpropyl)-4-oxo-1,4-dihydroquinoline-3-carboxylic acid hydrochloride (Example 4-19), 6-(3-chloro-2-fluorobenzyl)-1-((1S)-1-(hydroxymethyl)-2-methylpropyl)-4-oxo-7-(pyridin-3-yloxy)-1,4-dihydroquinoline-3-carboxylic acid hydrochloride (Example 4-20), 6-(3-chloro-2-fluorobenzyl)-1-((1S)-1-(hydroxymethyl)-2-methylpropyl)-7-(4-hydroxypiperidin-1-yl)-4-oxo-1,4-dihydroquinoline-3-carboxylic acid (Example 4-21), 6-(3-chloro-2-fluorobenzyl)-7-(3,5-dimethylpiperazin-1-yl)-1-((1S)-1-(hydroxymethyl)-2-methylpropyl)-4-oxo-1,4-dihydroquinoline-3-carboxylic acid (Example 4-22), 6-(3-chloro-2-fluorobenzyl)-1-((1S)-1-(hydroxymethyl)-2-methylpropyl)-7-((3R)-3-hydroxypyrrolidin-1-yl)-4-oxo-1,4-dihydroquinoline-3-carboxylic acid (Example 4-23), 6-(3-chloro-2-fluorobenzyl)-1-((1S)-1-(hydroxymethyl)-2-methylpropyl)-7-((3S)-3-hydroxypyrrolidin-1-yl)-4-oxo-1,4-dihydroquinoline-3-carboxylic acid (Example 4-24), 6-(3-chloro-2-fluorobenzyl)-1-((1S)-1-(hydroxymethyl)-2-methylpropyl)-4-oxo-7-(piperidin-4-yloxy)-1,4-dihydroquinoline-3-carboxylic acid (Example 4-25), 7-((3S)-3-(acetylamino)pyrrolidin-1-yl)-6-(3-chloro-2-fluorobenzyl)-1-((1S)-1-(hydroxymethyl)-2-methylpropyl)-4-oxo-1,4-dihydroquinoline-3-carboxylic acid (Example 4-26), 7-((3R)-3-(acetylamino)pyrrolidin-1-yl)-6-(3-chloro-2-fluorobenzyl)-1-((1S)-1-(hydroxymethyl)-2-methylpropyl)-4-oxo-1,4-dihydroquinoline-3-carboxylic acid (Example 4-27), 6-(3-chloro-2-fluorobenzyl)-7-((dimethylamino)sulfonylmethoxy)-1-((1S)-1-(hydroxymethyl)-2-methylpropyl)-4-oxo-1,4-dihydroquinoline-3-carboxylic acid (Example 4-28), 6-(3-chloro-2-fluorobenzyl)-1-((1S)-1-(hydroxymethyl)-2-methylpropyl)-7-((3R)-3-methylpiperazin-1-yl)-4-oxo-1,4-dihydroquinoline-3-carboxylic acid (Example 4-29), 6-(3-chloro-2-fluorobenzyl)-1-((1S)-1-(hydroxymethyl)-2-methylpropyl)-7-((3S)-3-methylpiperazin-1-yl)-4-oxo-1,4-dihydroquinoline-3-carboxylic acid (Example 4-30), 6-(3-chloro-2-fluorobenzyl)-7-(2,6-dimethylmorpholin-4-yl)-1-((1S)-1-(hydroxymethyl)-2-methylpropyl)-4-oxo-1,4-dihydroquinoline-3-carboxylic acid (Example 4-31), 6-(3-chloro-2-fluorobenzyl)-1-((1S)-1-(hydroxymethyl)-2-methylpropyl)-4-oxo-7-(thiomorpholin-4-yl)-1,4-dihydroquinoline-3-carboxylic acid (Example 4-32), 6-(3-chloro-2-fluorobenzyl)-1-((1S)-1-(hydroxymethyl)-2-methylpropyl)-4-oxo-7-(2-(piperazin-1-yl)ethoxy)-1,4-dihydroquinoline-3-carboxylic acid dihydrochloride (Example 4-33), 7-(4-aminobutoxy)-6-(3-chloro-2-fluorobenzyl)-1-((1S)-1-(hydroxymethyl)-2-methylpropyl)-4-oxo-1,4-dihydroquinoline-3-carboxylic acid hydrochloride (Example 4-34), 6-(3-chloro-2-fluorobenzyl)-1-((1S)-1-(hydroxymethyl)-2-methylpropyl)-4-oxo-7-(3-oxopiperazin-1-yl)-1,4-dihydroquinoline-3-carboxylic acid (Example 4-35), 6-(3-chloro-2-fluorobenzyl)-1-((1S)-1-(hydroxymethyl)-2-methylpropyl)-4-oxo-7-(tetrahydropyran-4-yloxy)-1,4-dihydroquinoline-3-carboxylic acid (Example 4-36), 6-(3-chloro-2-fluorobenzyl)-1-((1S)-1-(hydroxymethyl)-2-methylpropyl)-4-oxo-7-((3R)-pyrrolidin-3-yloxy)-1,4-dihydroquinoline-3-carboxylic acid hydrochloride (Example 4-37), 7-((3S)-3-aminopyrrolidin-1-yl)-6-(3-chloro-2-fluorobenzyl)-1-((1S)-1-(hydroxymethyl)-2-methylpropyl)-4-oxo-1,4-dihydroquinoline-3-carboxylic acid (Example 4-38), 7-((3R)-3-aminopyrrolidin-1-yl)-6-(3-chloro-2-fluorobenzyl)-1-((1S)-1-(hydroxymethyl)-2-methylpropyl)-4-oxo-1,4-dihydroquinoline-3-carboxylic acid (Example 4-39), 6-(3-chloro-2-fluorobenzyl)-7-(1-(ethoxycarbonyl)piperidin-4-ylamino)-1-((1S)-1-(hydroxymethyl)-2-methylpropyl)-4-oxo-1,4-dihydroquinoline-3-carboxylic acid (Example 4-40), 7-(2-(acetylamino)ethoxy)-6-(3-chloro-2-fluorobenzyl)-1-((1S)-1-(hydroxymethyl)-2-methylpropyl)-4-oxo-1,4-dihydroquinoline-3-carboxylic acid (Example 4-41), 6-(3-chloro-2-fluorobenzyl)-1-((1S)-1-(hydroxymethyl)-2-methylpropyl)-4-oxo-7-(piperidin-4-ylamino)-1,4-dihydroquinoline-3-carboxylic acid (Example 4-42), 7-benzyloxy-6-(3-chloro-2-fluorobenzyl)-1-((1S)-1-(hydroxymethyl)-2-methylpropyl)-4-oxo-1,4-dihydroquinoline-3-carboxylic acid (Example 4-43), 6-(3-chloro-2-fluorobenzyl)-1-((1S)-1-(hydroxymethyl)-2-methylpropyl)-4-oxo-7-phenoxy-1,4-dihydroquinoline-3-carboxylic acid (Example 4-44), 7-((1-acetylpiperidin-4-yl)oxy)-6-(3-chloro-2-fluorobenzyl)-1-((1S)-1-(hydroxymethyl)-2-methylpropyl)-4-oxo-1,4-dihydroquinoline-3-carboxylic acid (Example 4-45), 6-(3-chloro-2-fluorobenzyl)-1-((1S)-1-(hydroxymethyl)-2-methylpropyl)-4-oxo-7-((3S)-pyrrolidin-3-yloxy)-1,4-dihydroquinoline-3-carboxylic acid hydrochloride (Example 4-46), 6-(3-chloro-2-fluorobenzyl)-1-((1S)-1-(hydroxymethyl)-2-methylpropyl)-4-oxo-7-((3S)-tetrahydrofuran-3-yloxy)-1,4-dihydroquinoline-3-carboxylic acid (Example 4-47), 6-(3-chloro-2-fluorobenzyl)-1-((1S)-1-(hydroxymethyl)-2-methylpropyl)-4-oxo-7-((3R)-tetrahydrofuran-3-yloxy)-1,4-dihydroquinoline-3-carboxylic acid (Example 4-48), 6-(3-chloro-2-fluorobenzyl)-1-((1S)-1-(hydroxymethyl)-2-methylpropyl)-7-(2-(mesylamino)ethoxy)-4-oxo-1,4-dihydroquinoline-3-carboxylic acid (Example 4-49), 7-(carboxymethoxy)-6-(3-chloro-2-fluorobenzyl)-1-((1S)-1-(hydroxymethyl)-2-methylpropyl)-4-oxo-1,4-dihydroquinoline-3-carboxylic acid (Example 4-50), 6-(3-chloro-2-fluorobenzyl)-1-((1S)-1-(hydroxymethyl)-2-methylpropyl)-7-(2-(4-methylpiperazin-1-yl)ethoxy)-4-oxo-1,4-dihydroquinoline-3-carboxylic acid ditrifluoroacetate (Example 4-51), 7-((aminosulfonyl)methoxy)-6-(3-chloro-2-fluorobenzyl)-1-((1S)-1-(hydroxymethyl)-2-methylpropyl)-4-oxo-1,4-dihydroquinoline-3-carboxylic acid (Example 4-52), 6-(3-chloro-2-fluorobenzyl)-7-((dimethylaminocarbonyl)methoxy)-1-((1S)-1-(hydroxymethyl)-2-methylpropyl)-4-oxo-1,4-dihydroquinoline-3-carboxylic acid (Example 4-53), 6-(3-chloro-2-fluorobenzyl)-1-((1S)-1-(hydroxymethyl)-2-methylpropyl)-7-((3S)-1-methylpyrrolidin-3-yloxy)-4-oxo-1,4-dihydroquinoline-3-carboxylic acid trifluoroacetate (Example 4-54), 6-(3-chloro-2-fluorobenzyl)-1-((1S)-1-(hydroxymethyl)-2-methylpropyl)-7-((3R)-1-methylpyrrolidin-3-yloxy)-4-oxo-1,4-dihydroquinoline-3-carboxylic acid trifluoroacetate (Example 4-55), 6-(3-chloro-2-fluorobenzyl)-7-(4-cyanobenzyloxy)-1-((1S)-1-(hydroxymethyl)-2-methylpropyl)-4-oxo-1,4-dihydroquinoline-3-carboxylic acid (Example 4-56), 7-(4-carboxybenzyloxy)-6-(3-chloro-2-fluorobenzyl)-1-((1S)-1-(hydroxymethyl)-2-methylpropyl)-4-oxo-1,4-dihydroquinoline-3-carboxylic acid (Example 4-57), 7-(4-(aminocarbonyl)benzyloxy)-6-(3-chloro-2-fluorobenzyl)-1-((1S)-1-(hydroxymethyl)-2-methylpropyl)-4-oxo-1,4-dihydroquinoline-3-carboxylic acid (Example 4-58), 6-(3-chloro-2-fluorobenzyl)-1-((1S)-1-(hydroxymethyl)-2-methylpropyl)-4-oxo-7-(pyridin-2-ylmethoxy)-1,4-dihydroquinoline-3-carboxylic acid (Example 4-59), 6-(3-chloro-2-fluorobenzyl)-1-((1S)-1-(hydroxymethyl)-2-methylpropyl)-4-oxo-7-(pyridin-4-ylmethoxy)-1,4-dihydroquinoline-3-carboxylic acid (Example 4-60), 6-(3-chloro-2-fluorobenzyl)-1-((1S)-1-(hydroxymethyl)-2-methylpropyl)-4-oxo-7-(pyridin-3-ylmethoxy)-1,4-dihydroquinoline-3-carboxylic acid (Example 4-61), 6-(3-chloro-2-fluorobenzyl)-1-((1S)-1-(hydroxymethyl)-2-methylpropyl)-4-oxo-7-(2,2,2-trifluoroethyloxy)-1,4-dihydroquinoline-3-carboxylic acid (Example 4-62), 7-(4-(aminosulfonyl)benzyloxy)-6-(3-chloro-2-fluorobenzyl)-1-((1S)-1-(hydroxymethyl)-2-methylpropyl)-4-oxo-1,4-dihydroquinoline-3-carboxylic acid (Example 4-63), 6-(3-chloro-2-fluorobenzyl)-1-((1S)-1-(hydroxymethyl)-2-methylpropyl)-7-(1-mesylpiperidin-4-yloxy)-4-oxo-1,4-dihydroquinoline-3-carboxylic acid (Example 4-64), (3S)-8-(3-chloro-2-fluorobenzyl)-3-isopropyl-6-oxo-2,3-dihydro-6H-1-oxa-3a-aza-phenalene-5-carboxylic acid (Example 5-1), 8-(3-chloro-2-fluorobenzyl)-3-hydroxymethyl-6-oxo-2,3-dihydro-6H-1-oxa-3a-aza-phenalene-5-carboxylic acid (Example 5-2), 10-(3-chloro-2-fluorobenzyl)-5-((1S)-1-hydroxymethyl-2-methylpropyl)-8-oxo-2,3,5,8-tetrahydro-1,4-dioxa-5-azaphenanthrene-7-carboxylic acid (Example 6-1), 6-(2-chloro-6-fluorobenzyl)-1-((1S)-1-(hydroxymethyl)-2-methylpropyl)-7-methoxy-4-oxo-1,4-dihydroquinoline-3-carboxylic acid (Example 7-1), 6-(2,3-dichlorobenzyl)-1-((1S)-1-(hydroxymethyl)-2-methylpropyl)-7-methoxy-4-oxo-1,4-dihydroquinoline-3-carboxylic acid (Example 7-2), 6-(3-chloro-2-fluorobenzyl)-7-(2-hydroxyethoxy)-1-((1S)-1-(hydroxymethyl)-2-methylpropyl)-4-oxo-1,4-dihydroquinoline-3-carboxylic acid (Example 7-3), 6-(3-chloro-2-fluorobenzyl)-1-((1S)-1-(hydroxymethyl)-2-methylpropyl)-7-(3-hydroxypropoxy)-4-oxo-1,4-dihydroquinoline-3-carboxylic acid (Example 7-4), 6-(3-chloro-2-fluorobenzyl)-7-hydroxy-1-((1S)-1-(hydroxymethyl)-2-methylpropyl)-4-oxo-1,4-dihydroquinoline-3-carboxylic acid (Example 7-5), 6-(3-chloro-2-fluorobenzyl)-1-((1S)-2,2-dimethyl-1-(hydroxymethyl)propyl)-7-(morpholin-4-yl)-4-oxo-1,4-dihydroquinoline-3-carboxylic acid (Example 7-6), 6-((3-chloro-2-fluorophenyl)-hydroxy-methyl)-1-((1S)-1-hydroxymethyl-2-methylpropyl)-7-methoxy-4-oxo-1,4-dihydroquinoline-3-carboxylic acid (Examples 7-7 and 7-8), 1-[(1S)-1-((2R,3R,4S,5S,6S)-6-carboxy-3,4,5-trihydroxytetrahydropyran-2-yloxymethyl)-2-methylpropyl]-6-(3-chloro-2-fluorobenzyl)-7-methoxy-4-oxo-1,4-dihydroquinoline-3-carboxylic acid (Examples 7-9), (2S,3S,4S,5R,6S)-6-[6-(3-chloro-2-fluorobenzyl)-1-((1S)-1-hydroxymethyl-2-methylpropyl)-7-methoxy-4-oxo-1,4-dihydroquinoline-3-carbonyloxy]-3,4,5-trihydroxytetrahydropyran-2-carboxylic acid morphline salt (Examples 7-10), 6-[4-((2S,3R,4S,5S,6S)-6-carboxy-3,4,5-trihydroxytetrahydropyran-2-yloxy)-3-chloro-2-fluorobenzyl]-1-((1S)-1-hydroxymethyl-2-methylpropyl)-7-methoxy-4-oxo-1,4-dihydroquinoline-3-carboxylic acid (Examples 7-11), and 6-(3-chloro-2-fluoro-4-sodiumsulfonatobenzyl)-1-((1S)-1-hydroxymethyl-2-methylpropyl)-7-methoxy-4-oxo-1,4-dihydroquinoline-3-carboxylic acid (Examples 7-12), or a pharmaceutically acceptable salt thereof;

[4] a pharmaceutical composition comprising a 4-oxoquinoline compound of any of the above-mentioned [1] to [3] or a pharmaceutically acceptable salt thereof, and a pharmaceutically acceptable carrier;

[5] an integrase inhibitor comprising a 4-oxoquinoline compound of any of the above-mentioned [1] to [3] or a pharmaceutically acceptable salt thereof as an active ingredient;

[6] an antiviral agent comprising a 4-oxoquinoline compound of any of the above-mentioned [1] to [3] or a pharmaceutically acceptable salt thereof as an active ingredient;

[7] an anti-HIV agent comprising a 4-oxoquinoline compound of any of the above-mentioned [1] to [3] or a pharmaceutically acceptable salt thereof as an active ingredient;

[8] an anti-HIV composition comprising a 4-oxoquinoline compound of any of the above-mentioned [1] to [3] or a pharmaceutically acceptable salt thereof, and one or more other kinds of anti-HIV active substances, as an active ingredient;

[9] an anti-HIV agent comprising a 4-oxoquinoline compound of any of the above-mentioned [1] to [3] or a pharmaceutically acceptable salt thereof as an active ingredient, which is used for a multiple drug combination therapy with other anti-HIV agent(s);

[10] use of a 4-oxoquinoline compound of any of the above-mentioned [1] to [3] or a pharmaceutically acceptable salt thereof, for the production of an integrase inhibitor;

[11] use of a 4-oxoquinoline compound of any of the above-mentioned [1] to [3] or a pharmaceutically acceptable salt thereof, for the production of an antiviral agent;

[12] use of a 4-oxoquinoline compound of any of the above-mentioned [1] to [3] or a pharmaceutically acceptable salt thereof, for the production of an anti-HIV agent;

[13] a method for inhibiting integrase, comprising administering a pharmaceutically effective amount of a 4-oxoquinoline compound of any of the above-mentioned [1] to [3] or a pharmaceutically acceptable salt thereof to a mammal;

[14] a method for the prophylaxis or treatment of a viral infection, comprising administering a pharmaceutically effective amount of a 4-oxoquinoline compound of any of the above-mentioned [1] to [3] or a pharmaceutically acceptable salt thereof to a mammal;

[15] a method for the prophylaxis or treatment of an HIV infection, comprising administering a pharmaceutically effective amount of a 4-oxoquinoline compound of any of the above-mentioned [1] to [3] or a pharmaceutically acceptable salt thereof to a mammal;

[16] the method for the prophylaxis or treatment of an HIV infection according to the above-mentioned [15], which further comprises administering a pharmaceutically effective amount of one or more other kinds of anti-HIV active substances to mammal;

[17] a pharmaceutical composition for inhibiting integrase, comprising a 4-oxoquinoline compound of any of the above-mentioned [1] to [3] or a pharmaceutically acceptable salt thereof, and a pharmaceutically acceptable carrier;

[18] an antiviral composition comprising a 4-oxoquinoline compound of any of the above-mentioned [1] to [3] or a pharmaceutically acceptable salt thereof, and a pharmaceutically acceptable carrier;

[19] an anti-HIV composition comprising a 4-oxoquinoline compound of any of the above-mentioned [1] to [3] or a pharmaceutically acceptable salt thereof, and a pharmaceutically acceptable carrier;

[20] a commercial pakage comprising the composition of the above-mentioned [17] and a written matter associated therewith, the written matter stating that the composition can or should be used for inhibiting integrase;

[21] a commercial pakage comprising the composition of the above-mentioned [18] and a written matter associated therewith, the written matter stating that the composition can or should be used for the prophylaxis or treatment of a viral infection;

[22] a commercial pakage comprising the composition of the above-mentioned [19] and a written matter associated therewith, the written matter stating that the composition can or should be used for the prophylaxis or treatment of an HIV infection.

The compounds of the present invention show a high inhibitory activity against HIV integrase.

Therefore, these compounds can be pharmaceutical agents effective for, for example, the prophylaxis or treatment of AIDS, as integrase inhibitors, antiviral agents, anti-HIV agents, and the like, having an HIV integrase inhibitory activity. In addition, by a combined use with other anti-HIV agent(s) such as protease inhibitor, reverse transcription enzyme inhibitor, and the like, they can be more effective anti-HIV agents. Furthermore, having high inhibitory activity specific for integrase, they can be pharmaceutical agents safe for human body with a fewer side effects.

The definitions of respective substituents, respective symbols and respective moieties used in the present specification are as follows.

The "$C_{1-4}$ alkyl group" means a straight chain or branched chain alkyl group having 1 to 4 carbon atoms, which is specifically exemplified by a methyl group, an ethyl group, a propyl group, an isopropyl group, a butyl group, a isobutyl group, a sec-butyl group and a tert-butyl group.

The ring Cy is a group selected from the group consisting of

 , 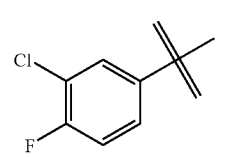 ,

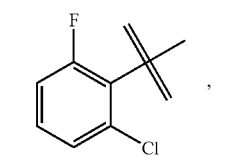 , 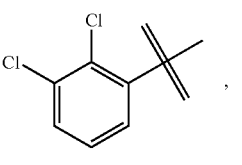 ,

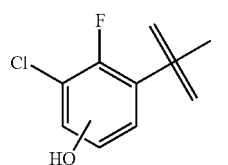 , 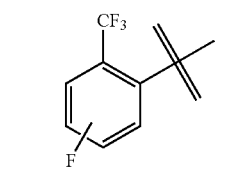 ,

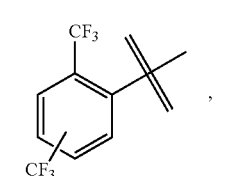 , 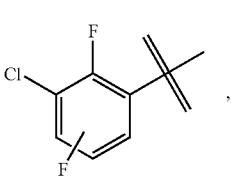 ,

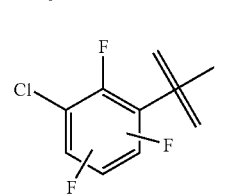 , 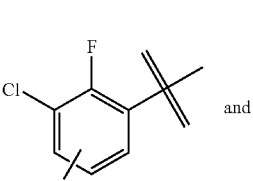 ,

 , 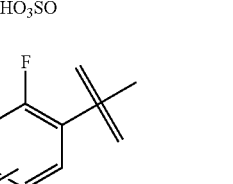 and

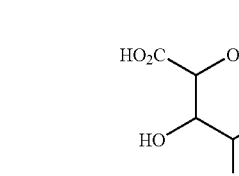

wherein the position of substitution of OH—, F—, $CF_3$—, $HO_3SO$— and

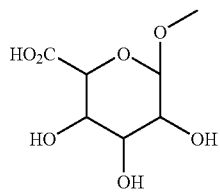

in the above-mentioned phenyl group is not particularly limited.

The ring Cy is preferably

 , 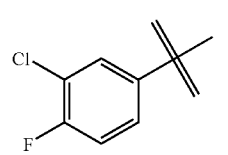 ,

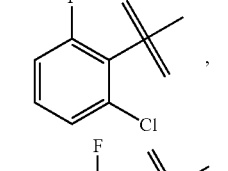 , 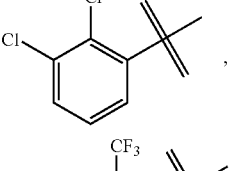 ,

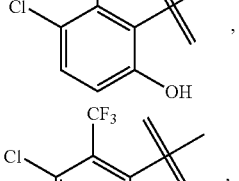 , 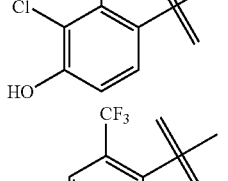 ,

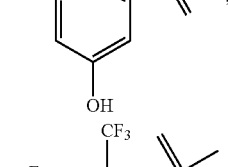 , 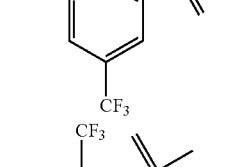 ,

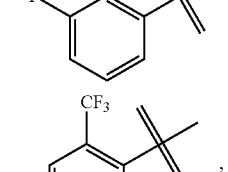 , 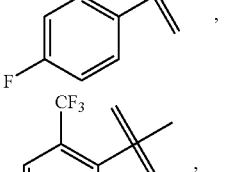 ,

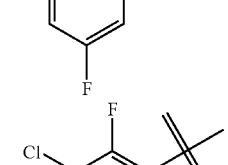 , 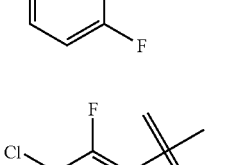 ,

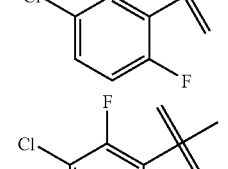 , 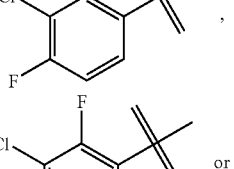 ,

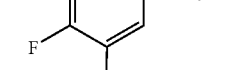 , 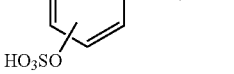 ,

 ,  or

-continued

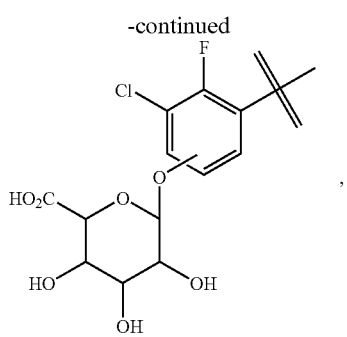

more preferably

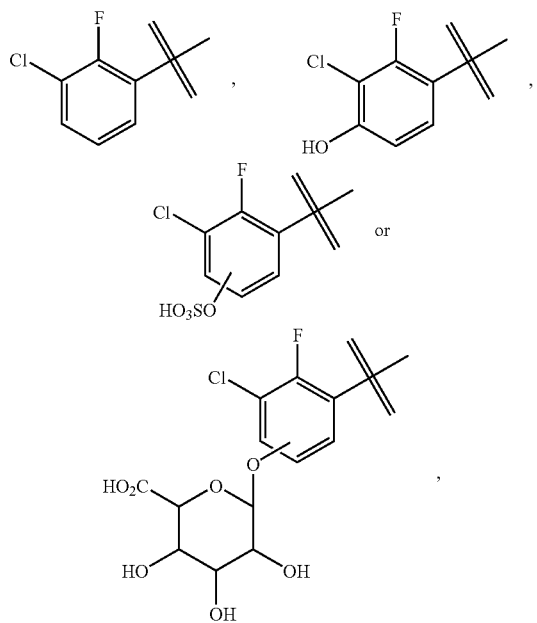

and paticularly preferably

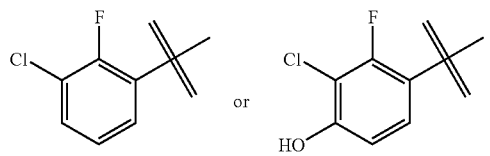

R is a hydrogen atom or

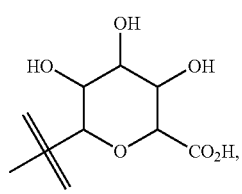

preferably a hydrogen atom.

$R^1$ is

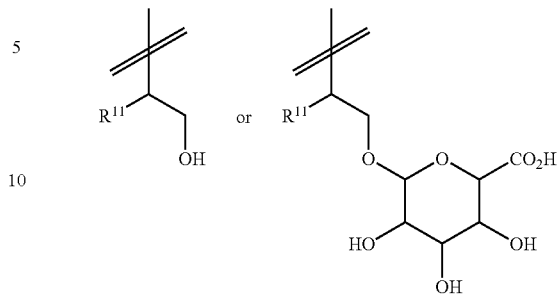

wherein $R^{11}$ is —$(C_mH_{2m})$—$OR^{12}$, —$(C_mH_{2m})$—$SR^{12}$, —$(C_mH_{2m})$—$SO_2R^{12}$ (wherein $R^{12}$ is a $C_{1-4}$ alkyl group and m is an integer of 1 to 4), a saturated heterocyclic group, an isopropyl group or a tert-butyl group.

As "—$(C_mH_{2m})$—", straight chain or branched chain alkylene can be mentioned, which is specifically exemplified by methylene, ethylene, trimethylene, tetramethylene,

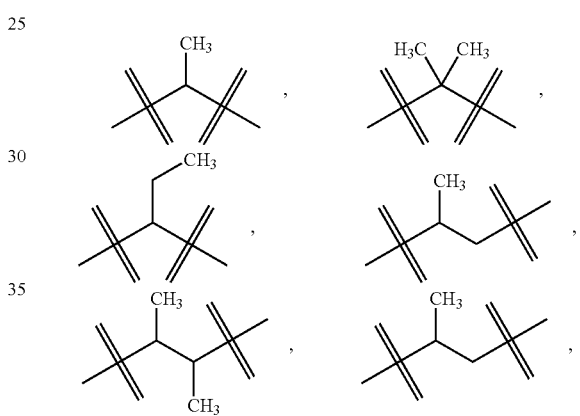

and the like.

m is preferably an integer of 1 to 3.

"—$(C_mH_{2m})$—" is preferably

methylene or ethylene.

$R^{12}$ is preferably a methyl group.

The "saturated heterocyclic group" for $R^{11}$ is a saturated heterocyclic group having, besides carbon atom, at least one hetero atom selected from an oxygen atom, a sulfur atom and a nitrogen atom. The hetero atom is preferably an oxygen atom or a nitrogen atom. The number of hetero atom is preferably 1 or 2, more preferably 1. The size of the ring is preferably a 5- or 6-membered ring, more preferably a 6-membered ring.

As the "saturated heterocyclic group", a pyrrolidinyl group, a tetrahydrofuranyl group, a tetrahydrothiofuranyl group, a piperidinyl group, a tetrahydropyranyl group, a tetrahydrothiopyranyl group, a piperazinyl group, a morpholinyl group, a thiomorpholinyl group, and the like can be specifically mentioned. As the saturated heterocyclic group for $R^{11}$, a piperidinyl group and a tetrahydropyranyl group are preferable.

The position of the bond in the "saturated heterocyclic group" is not particularly limited.

$R^1$ is preferably

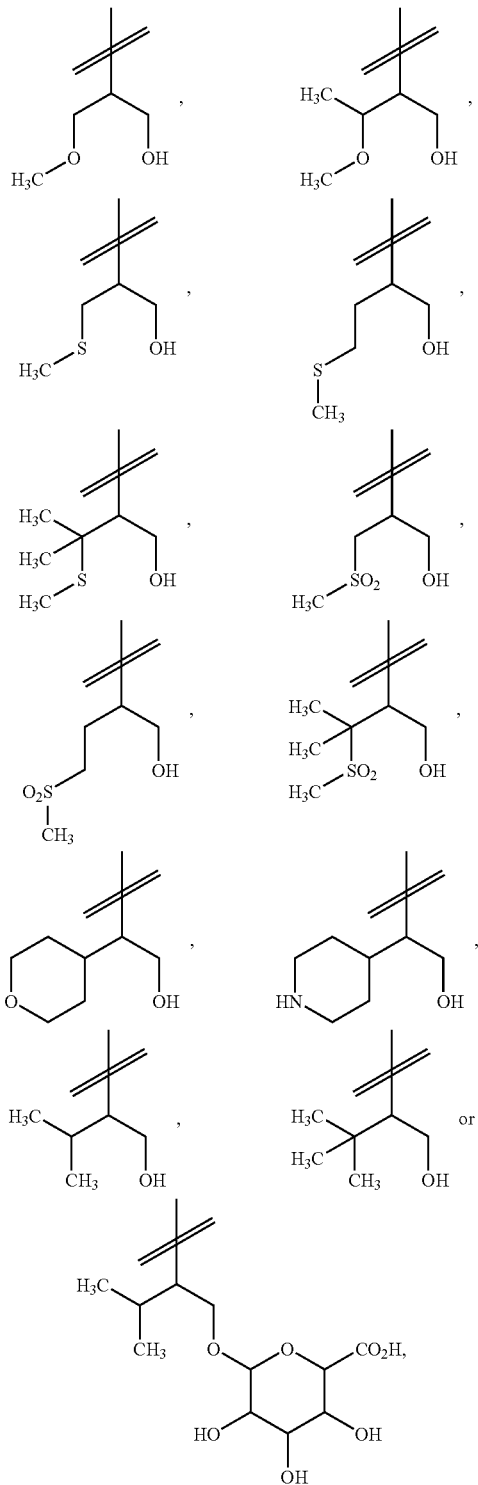

more preferably

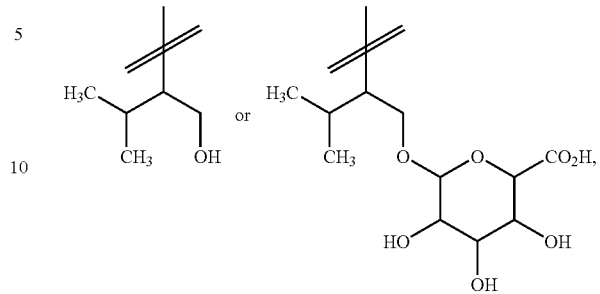

still more preferably

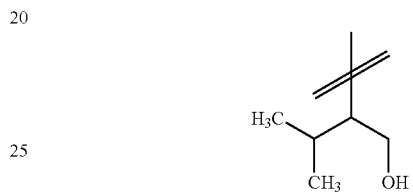

and particularly preferably

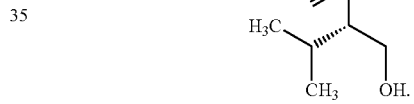

$R^{32}$ is a hydrogen atom, an ethyl group, a methoxy group, a hydroxyl group, a 2-hydroxyethoxy group, a 3-hydroxypropoxy group, a 4-hydroxybutyloxy group, a 2,2,2-trifluoroethyloxy group, —O—$(CH_2)_p$—$OR^{34}$, —O—$(CH_2)_p$—$NR^{35}R^{36}$, —O—$(CH_2)_p$—$CO_2R^{35}$, —O—$(CH_2)_p$—$CONR^{35}R^{37}$, —O—$(CH_2)_p$—$SO_2NR^{35}R^{37}$ (wherein $R^{34}$ is a $C_{1-4}$ alkyl group, $R^{35}$ and $R^{37}$ are the same or different and each is a hydrogen atom or a $C_{1-4}$ alkyl group, $R^{36}$ is a hydrogen atom, a $C_{1-4}$ alkyl group, an acetyl group or a mesyl group, and p is an integer of 1 to 4), a pyrrolidinyl group, a piperidinyl group, a piperazinyl group, a morpholinyl group, a thiomorpholinyl group (wherein each of the pyrrolidinyl group, piperidinyl group, piperazinyl group, morpholinyl group and thiomorpholinyl group is optionally substituted by 1 or 2 substituents selected from the group consisting of a hydroxyl group, a $C_{1-4}$ alkyl group, an oxo group, —$COR^{38}$, —$NR^{35}R^{37}$ and —$NR^{35}COR^{38}$, wherein $R^{35}$ and $R^{37}$ are as defined above, $R^{38}$ is a $C_{1-4}$ alkyl group, and the position of the bond of the pyrrolidinyl group, piperidinyl group, piperazinyl group, morpholinyl group and thiomorpholinyl group in compound [I] is not particularly limited, and when the pyrrolidinyl group, piperidinyl group, piperazinyl group, morpholinyl group and thiomorpholinyl group have a substituent, the substitutable position of these groups is also not particularly limited), or

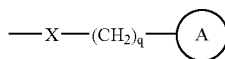

wherein X is —O— or —NH—, ring A is a phenyl group or a heterocyclic group, where each of the phenyl group and heterocyclic group is optionally substituted by 1 to 5, preferably 1 to 3, more preferably 1, substituent(s) selected from the group consisting of a cyano group, a mesyl group, a $C_{1-4}$ alkyl group, —$CO_2R^{35}$, —$CONR^{35}R^{37}$, —$SO_2NR^{35}R^{37}$ and —$COR^{38}$, wherein $R^{35}$, $R^{37}$ and $R^{38}$ are as defined above, q is 0 or an integer of 1 to 4, and the position of the bond of —X—$(CH_2)_q$— to the phenyl group and heterocyclic group is not particularly limited. When the phenyl group and heterocyclic group have a substituent, the substitutable position of the phenyl group and heterocyclic group is also not particularly limited.

The "heterocyclic group" for ring A is a "saturated heterocyclic group" as defined above or an "unsaturated heterocyclic group", and is a heterocyclic group having, besides carbon atom, at least one hetero atom selected from an oxygen atom, a sulfur atom and a nitrogen atom. The hetero atom is preferably an oxygen atom or a nitrogen atom. The number of hetero atom is preferably 1 or 2, more preferably 1. The size of the ring is preferably a 5- or 6-membered ring, more preferably a 6-membered ring.

As the "saturated heterocyclic group" for ring A, a pyrrolidinyl group, a tetrahydrofuranyl group, a tetrahydrothiofuranyl group, a piperidinyl group, a tetrahydropyranyl group, a tetrahydrothiopyranyl group, a piperazinyl group, a morpholinyl group, a thiomorpholinyl group, and the like can be specifically mentioned. As the saturated heterocyclic group for ring A, a pyrrolidinyl group, a tetrahydrofuranyl group, a piperidinyl group, a tetrahydropyranyl group, a piperazinyl group and a morpholinyl group are preferable.

As the "unsaturated heterocyclic group" for ring A, a pyridinyl group, a pyrazinyl group, a pyridazinyl group, a pyrrolyl group, a furyl group, a thienyl group, an imidazolyl group, an oxazolyl group, a thiazolyl group, and the like can be specifically mentioned. The unsaturated heterocyclic group for ring A is preferably a pyridinyl group.

$R^{34}$ is preferably a methyl group.

$R^{35}$ is preferably a hydrogen atom, a methyl group or an ethyl group.

$R^{36}$ is preferably a hydrogen atom, a methyl group, an acetyl group or a mesyl group.

$R^{37}$ is preferably a hydrogen atom or a methyl group.

$R^{38}$ is preferably a methyl group.

q is preferably 0, 1 or 2.

$R^{32}$ is preferably a hydrogen atom, an ethyl group, a methoxy group, a hydroxyl group, a 2-hydroxyethoxy group, a 3-hydroxypropoxy group, a 4-hydroxybutyloxy group, a 2,2,2-trifluoroethyloxy group,

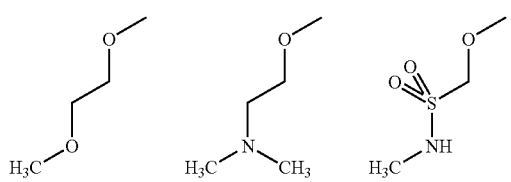

-continued

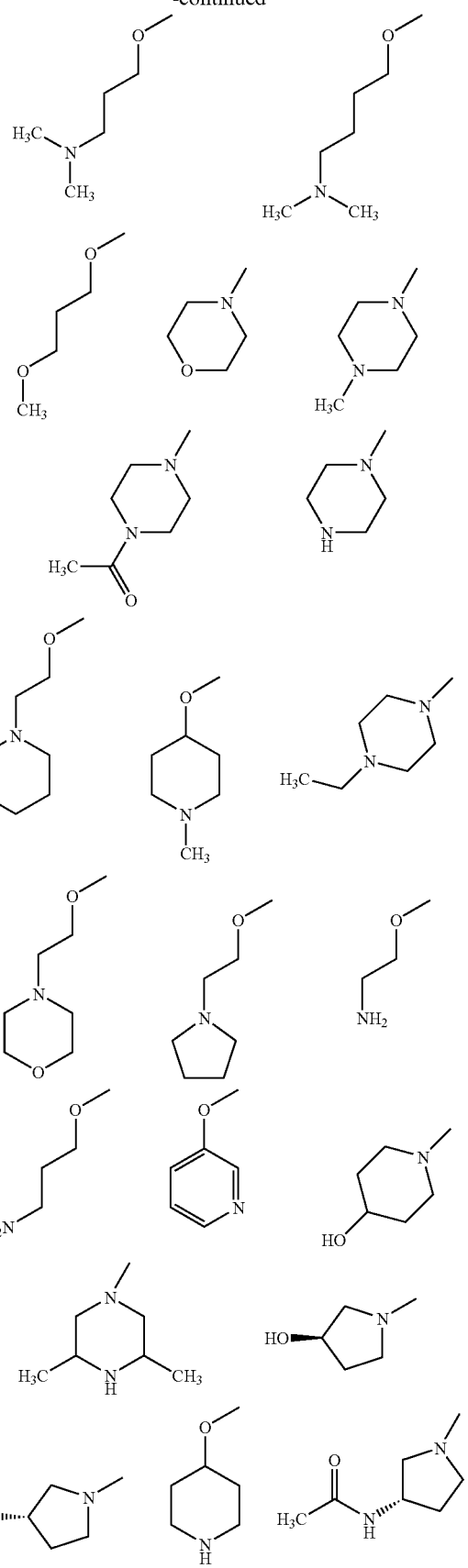

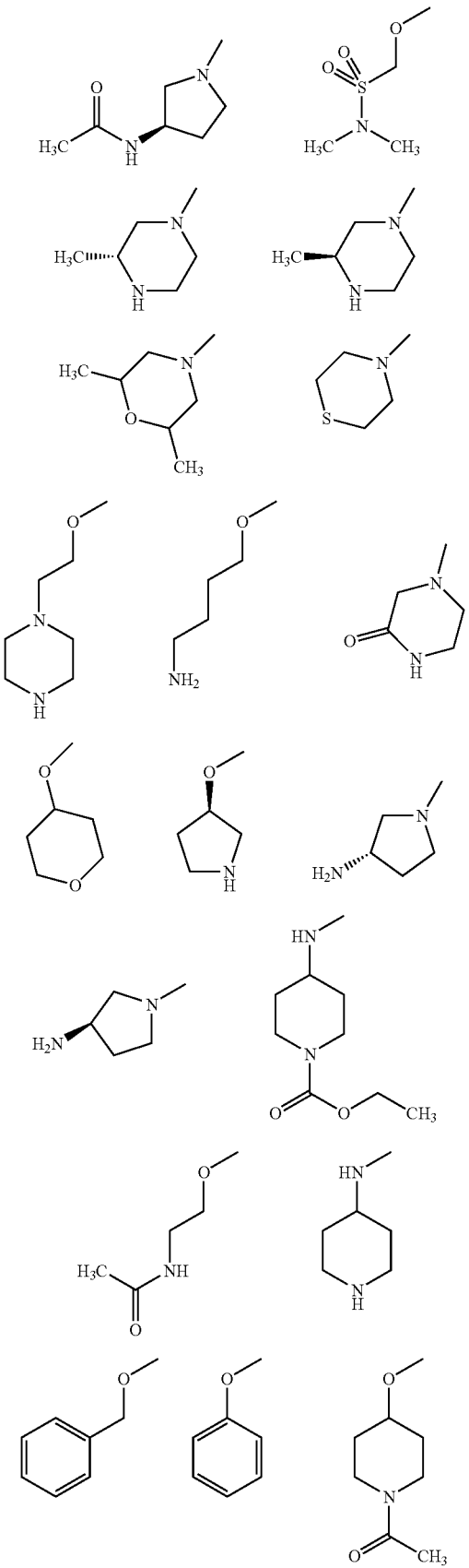
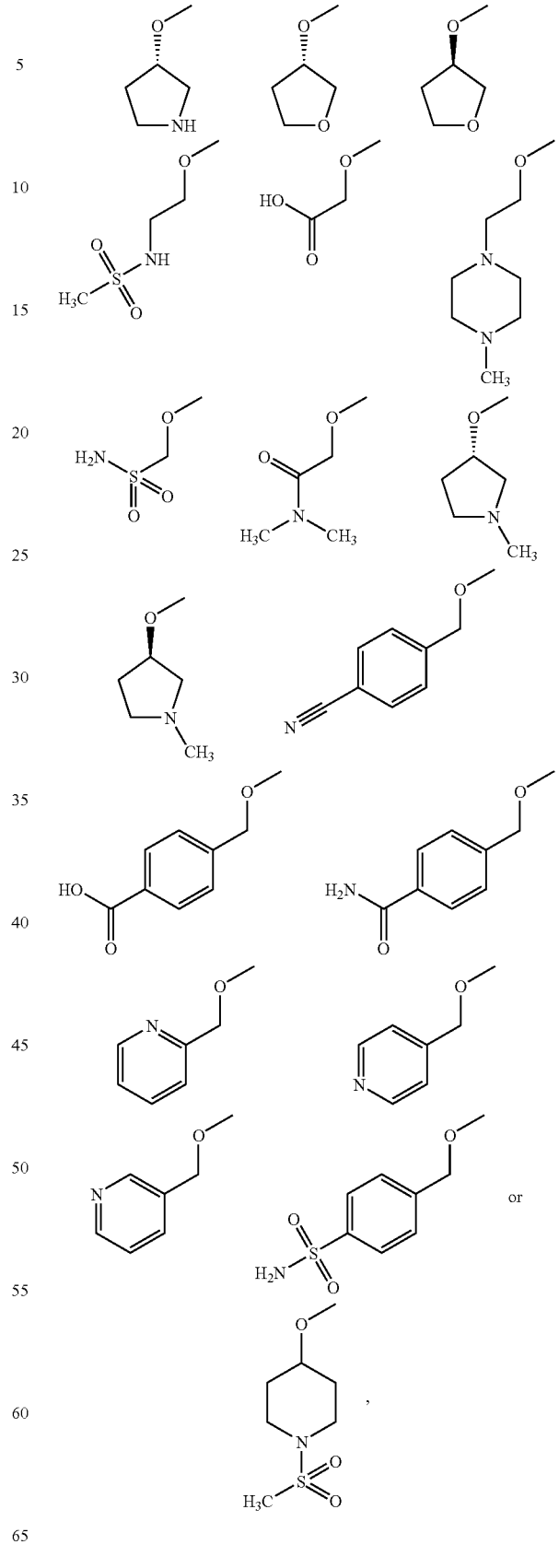
and particularly preferably a methoxy group.

$R^{33}$ is a hydrogen atom, a hydroxyl group, —O—$(CH_2)_n$—$OR^{39}$, —O—$(CH_2)_n$—$NR^{39}R^{31}$ or —O—$(CH_2)_n$-Ph (wherein $R^{39}$ and $R^{31}$ are the same or different and each is a hydrogen atom or a $C_{1-4}$ alkyl group and n is an integer of 1 to 4).

$R^{31}$ is preferably a hydrogen atom or a methyl group.

$R^{39}$ is preferably a hydrogen atom or a methyl group.

$R^{33}$ is preferably a hydrogen atom, a hydroxyl group, 2-hydroxyethoxy, 3-hydroxypropoxy, 4-hydroxybutoxy, 2-methoxyethoxy, 3-methoxypropoxy, 4-methoxybutoxy, 2-(dimethylamino)ethoxy or benzyloxy, particularly preferably a hydrogen atom.

$R^7$ is a hydrogen atom or a hydroxyl group.

In compound [I], $R^{32}$ and $R^{33}$ may be linked to form an alkylenedioxy group.

The "alkylenedioxy group" is —O—$(CH_2)$—O—, —O—$(CH_2)_2$—O— or —O—$(CH_2)_3$—O—, preferably —O—$(CH_2)_2$—O—.

In compound [I], $R^1$ and $R^{33}$ may be linked to form

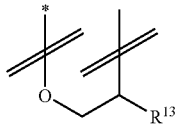

wherein * shows the $R^{33}$ side and $R^{13}$ is a $C_{1-4}$ alkyl group optionally substituted by hydroxyl group(s).

The "$C_{1-4}$ alkyl group optionally substituted by a hydroxyl group" for $R^{13}$ is the above-defined "$C_{1-4}$ alkyl group" optionally substituted by 1 to 3, preferably 1, hydroxyl group(s), and also includes unsubstituted alkyl group.

When the $C_{1-4}$ alkyl group of the "$C_{1-4}$ alkyl group optionally substituted by hydroxyl group(s)" for $R^{13}$ is substituted by hydroxyl group(s), the position of the substitution of the $C_{1-4}$ alkyl group with hydroxyl group(s) is not particularly limited.

As the "$C_{1-4}$ alkyl group optionally substituted by hydroxyl group(s)", a methyl group, an ethyl group, a propyl group, an isopropyl group, a butyl group, an isobutyl group, a sec-butyl group, a tert-butyl group, a hydroxymethyl group, a 2-hydroxyethyl group, a 1-hydroxy-1-methylethyl group, a 1-(hydroxymethyl)ethyl group, a 3-hydroxypropyl group, a 4-hydroxybutyl group, a 1-hydroxyethyl group, and the like can be specifically mentioned.

$R^{13}$ is preferably an isopropyl group or a hydroxymethyl group.

The compound represented by the formula [I] satisfies at least one condition from the above-mentioned (1)-(7).

As a preferable embodiment of the compound of the present invention, a compound having superior pharmacological activity (e.g., a compound having a high HIV integrase-inhibitory activity, a compound having a high anti-HIV activity), a compound showing fine bioavailability (e.g., a compound showing high oral absorbability, a compound showing high cell membrane permeability, a compound stable to metabolic enzyme, a compound maintained at high blood concentration for a long time, a compound showing low binding rate is to a protein), a highly safe compound (e.g., a compound showing low inhibitory activity against P450 (CYP)) and the like can be mentioned.

The "pharmaceutically acceptable salt thereof" may be any salt as long as it forms a non-toxic salt with the compounds of the above-mentioned formula [I], and can be obtained by a reaction with an inorganic acid such as hydrochloric acid, sulfuric acid, phosphoric acid, hydrobromic acid, and the like; an organic acid such as oxalic acid, malonic acid, citric acid, fumaric acid, lactic acid, malic acid, succinic acid, tartaric acid, acetic acid, trifluoroacetic acid, gluconic acid, ascorbic acid, methanesulfonic acid, benzenesulfonic acid, and the like; an inorganic base such as sodium hydroxide, potassium hydroxide, calcium hydroxide, magnesium hydroxide, ammonium hydroxide, and the like; an organic base such as methylamine, diethylamine, triethylamine, triethanolamine, ethylenediamine, tris(hydroxymethyl)methylamine, guanidine, choline, cinchonine, morpholine, and the like; or an amino acid such as lysine, arginine, alanine, and the like. The present invention also encompasses hydrate and solvate of each compound.

The compound represented by the above-mentioned formula [I] has various isomers. When, for example, an asymmetric carbon atom is present, an enantiomer and a diastereomer are present as stereoisomers based thereon. Therefore, the present invention encompasses all such isomers and a mixture thereof. The compound of the present invention is preferably one isolated or purified from various isomers, by-products, metabolites or prodrugs and having a purity of preferably not less than 90%, more preferably not less than 95%.

As the compound represented by the formula [I] or a pharmaceutically acceptable salt thereof, 6-(3-chloro-4-fluorobenzyl)-1-((1S)-1-(hydroxymethyl)-2-methylpropyl)-7-methoxy-4-oxo-1,4-dihydroquinoline-3-carboxylic acid (Example 1-1), 6-(3-chloro-2,6-difluorobenzyl)-1-((1S)-1-(hydroxymethyl)-2-methylpropyl)-7-methoxy-4-oxo-1,4-dihydroquinoline-3-carboxylic acid (Example 1-2), 6-(3-chloro-2-fluoro-6-hydroxybenzyl)-1-((1S)-1-(hydroxymethyl)-2-methylpropyl)-7-methoxy-4-oxo-1,4-dihydroquinoline-3-carboxylic acid (Example 1-3), 6-(3-chloro-2-fluoro-4-hydroxybenzyl)-1-((1S)-1-(hydroxymethyl)-2-methylpropyl)-7-methoxy-4-oxo-1,4-dihydroquinoline-3-carboxylic acid (Example 1-4), 6-(3-chloro-2,4-difluorobenzyl)-1-((1S)-1-(hydroxymethyl)-2-methylpropyl)-7-methoxy-4-oxo-1,4-dihydroquinoline-3-carboxylic acid (Example 1-5), 6-(3-chloro-2-fluoro-5-hydroxybenzyl)-1-((1S)-1-(hydroxymethyl)-2-methylpropyl)-7-methoxy-4-oxo-1,4-dihydroquinoline-3-carboxylic acid (Example 1-6), 6-(3-chloro-2,4,5-trifluorobenzyl)-1-((1S)-1-(hydroxymethyl)-2-methylpropyl)-7-methoxy-4-oxo-1,4-dihydroquinoline-3-carboxylic acid (Example 1-7), 6-(3-fluoro-2-(trifluoromethyl)benzyl)-1-((1S)-1-(hydroxymethyl)-2-methylpropyl)-7-methoxy-4-oxo-1,4-dihydroquinoline-3-carboxylic acid (Example 1-8), 6-(2,5-di(trifluoromethyl)benzyl)-1-((1S)-1-(hydroxymethyl)-2-methylpropyl)-7-methoxy-4-oxo-1,4-dihydroquinoline-3-carboxylic acid (Example 1-9), 6-(4-fluoro-2-(trifluoromethyl)benzyl)-1-((1S)-1-(hydroxymethyl)-2-methylpropyl)-7-methoxy-4-oxo-1,4-dihydroquinoline-3-carboxylic acid (Example 1-10), 6-(5-fluoro-2-(trifluoromethyl)benzyl)-1-((1S)-1-(hydroxymethyl)-2-methylpropyl)-7-methoxy-4-oxo-1,4-dihydroquinoline-3-carboxylic acid (Example 1-11), 6-(2-fluoro-6-(trifluoromethyl)benzyl)-1-((1S)-1-(hydroxymethyl)-2-methylpropyl)-7-methoxy-4-oxo-1,4-dihydroquinoline-3-carboxylic acid (Example 1-12), 6-(3-chloro-2-fluorobenzyl)-1-((1S)-2-hydroxy-1-(tetrahydropyran-4-yl)ethyl)-7-methoxy-4-oxo-1,4-dihydroquinoline-3-carboxylic acid (Example 2-1), 6-(3-chloro-2-fluorobenzyl)-1-(2-hydroxy-1-(piperidin-4-yl)ethyl)-7-methoxy-4-oxo-1,4-dihydroquinoline-3-carboxylic acid hydrochloride (Example 2-2), 6-(3-chloro-2-fluorobenzyl)-1-((1R)-1-(hydroxymethyl)-2-(methylthio)ethyl)-7-methoxy-4-oxo-1,4-dihydroquinoline-3-carboxylic acid (Example 2-3), 6-(3-chloro-2-fluorobenzyl)-1-((1R)-1-(hydroxymethyl)-2-mesylethyl)-7-methoxy-4-oxo-1,4-dihydroquinoline-3-carboxylic acid (Example 2-4), 6-(3-chloro-2-fluorobenzyl)-1-((1R)-1-(hydroxymethyl)-2-methyl-2-(methylthio)propyl)-7-methoxy-4-oxo-1,4-dihydroquinoline-3-carboxylic acid (Example 2-5), 6-(3-chloro-2-fluorobenzyl)-1-((1R)-1-(hydroxymethyl)-2-mesyl-2-methylpropyl)-7-methoxy-4-oxo-1,4-dihydroquinoline-3-carboxylic acid (Example 2-6), 6-(3-chloro-2-fluorobenzyl)-1-((1R)-1-(hydroxymethyl)-2-(methylthio)ethyl)-4-oxo-1,4-dihydroquinoline-3-carboxylic acid (Example 2-7), 6-(3-chloro-2-fluorobenzyl)-1-((1R)-1-(hydroxymethyl)-2-mesylethyl)-4-oxo-1,4-dihydroquinoline-3-carboxylic acid (Example 2-8), 6-(3-chloro-2-fluorobenzyl)-1-((1R)-1-(hydroxymethyl)-2-methyl-2-(methylthio)propyl)-4-oxo-1,4-dihydroquinoline-3-carboxylic acid (Example 2-9), 6-(3-chloro-2-fluorobenzyl)-1-((1R)-1-(hydroxymethyl)-2-mesyl-2-methylpropyl)-4-oxo-1,4-dihydroquinoline-3-carboxylic acid (Example 2-10), 6-(3-chloro-2-fluorobenzyl)-1-((1R,2R)-1-(hydroxymethyl)-2-methoxypropyl)-7-methoxy-4-oxo-1,4-dihydroquinoline-3-carboxylic acid (Example 2-11), 6-(3-chloro-2-fluorobenzyl)-1-((1S)-1-(hydroxymethyl)-3-(methylthio)propyl)-7-methoxy-4-oxo-1,4-dihydroquinoline-3-carboxylic acid (Example 2-12), 6-(3-chloro-2-fluorobenzyl)-1-((1S)-1-(hydroxymethyl)-3-mesylpropyl)-7-methoxy-4-oxo-1,4-dihydroquinoline-3-carboxylic acid (Example 2-13), 6-(3-chloro-2-fluorobenzyl)-1-((1R)-1-(hydroxymethyl)-2-methoxyethyl)-4-oxo-1,4-dihydroquinoline-3-carboxylic acid (Example 2-14), 6-(3-chloro-2-fluorobenzyl)-1-((1R,2R)-1-(hydroxymethyl)-2-methoxypropyl)-4-oxo-1,4-dihydroquinoline-3-carboxylic acid (Example 2-15), 6-(3-chloro-2-fluorobenzyl)-1-((1S)-1-(hydroxymethyl)-3-(methylthio)propyl)-4-oxo-1,4-dihydroquinoline-3-carboxylic acid (Example 2-16), 6-(3-chloro-2-fluorobenzyl)-1-((1S)-1-(hydroxymethyl)-3-mesylpropyl)-4-oxo-1,4-dihydroquinoline-3-carboxylic acid (Example 2-17), 6-(3-chloro-2-fluorobenzyl)-1-((1R)-1-(hydroxymethyl)-2-methoxyethyl)-7-methoxy-4-oxo-1,4-dihydroquinoline-3-carboxylic acid (Example 2-18), 6-(3-chloro-2-fluorobenzyl)-8-(2-hydroxyethoxy)-1-((1S)-1-(hydroxymethyl)-2-methylpropyl)-4-oxo-1,4-dihydroquinoline-3-carboxylic acid (Example 3-1), 6-(3-chloro-2-fluorobenzyl)-1-((1S)-1-(hydroxymethyl)-2-methylpropyl)-8-(3-hydroxypropoxy)-4-oxo-1,4-dihydroquinoline-3-carboxylic acid (Example 3-2), 6-(3-chloro-2-fluorobenzyl)-8-(4-hydroxybutoxy)-1-((1S)-1-(hydroxymethyl)-2-methylpropyl)-4-oxo-1,4-dihydroquinoline-3-carboxylic acid (Example 3-3), 6-(3-chloro-2-fluorobenzyl)-1-((1S)-1-(hydroxymethyl)-2-methylpropyl)-8-(2-methoxyethoxy)-4-oxo-1,4-dihydroquinoline-3-carboxylic acid (Example 3-4), 6-(3-chloro-2-fluorobenzyl)-8-hydroxy-1-((1S)-1-(hydroxymethyl)-2-methylpropyl)-4-oxo-1,4-dihydroquinoline-3-carboxylic acid (Example 3-5)

6-(3-chloro-2-fluorobenzyl)-8-(2-(dimethylamino)ethoxy)-1-((1S)-1-(hydroxymethyl)-2-methylpropyl)-4-oxo-1,4-dihydroquinoline-3-carboxylic acid (Example 3-6), 6-(3-chloro-2-fluorobenzyl)-1-((1S)-1-(hydroxymethyl)-2-methylpropyl)-8-(3-methoxypropoxy)-4-oxo-1,4-dihydroquinoline-3-carboxylic acid (Example 3-7), 6-(3-chloro-2-fluorobenzyl)-1-((1S)-1-(hydroxymethyl)-2-methylpropyl)-8-(4-methoxybutoxy)-4-oxo-1,4-dihydroquinoline-3-carboxylic acid (Example 3-8), 8-benzyloxy-6-(3-chloro-2-fluorobenzyl)-1-((1S)-1-(hydroxymethyl)-2-methylpropyl)-4-oxo-1,4-dihydroquinoline-3-carboxylic acid (Example 3-9), 6-(3-chloro-2-fluorobenzyl)-1-((1S)-1-(hydroxymethyl)-2-methylpropyl)-7-(2-methoxyethoxy)-4-oxo-1,4-dihydroquinoline-3-carboxylic acid (Example 4-1), 6-(3-chloro-2-fluorobenzyl)-7-(2-(dimethylamino)ethoxy)-1-((1S)-1-(hydroxymethyl)-2-methylpropyl)-4-oxo-1,4-dihydroquinoline-3-carboxylic acid (Example 4-2), 6-(3-chloro-2-fluorobenzyl)-1-((1S)-1-(hydroxymethyl)-2-methylpropyl)-7-((methylamino)sulfonylmethoxy)-4-oxo-1,4-dihydroquinoline-3-carboxylic acid (Example 4-3), 6-(3-chloro-2-fluorobenzyl)-7-ethyl-1-((1S)-1-(hydroxymethyl)-2-methylpropyl)-4-oxo-1,4-dihydroquinoline-3-carboxylic acid (Example 4-4), 6-(3-chloro-2-fluorobenzyl)-7-(4-hydroxybutoxy)-1-((1S)-1-(hydroxymethyl)-2-methylpropyl)-4-oxo-1,4-dihydroquinoline-3-carboxylic acid (Example 4-5), 6-(3-chloro-2-fluorobenzyl)-7-(3-(dimethylamino)propoxy)-1-((1S)-1-(hydroxymethyl)-2-methylpropyl)-4-oxo-1,4-dihydroquinoline-3-carboxylic acid (Example 4-6), 6-(3-chloro-2-fluorobenzyl)-7-(4-(dimethylamino)butoxy)-1-((1S)-1-(hydroxymethyl)-2-methylpropyl)-4-oxo-1,4-dihydroquinoline-3-carboxylic acid (Example 4-7), 6-(3-chloro-2-fluorobenzyl)-1-((1S)-1-(hydroxymethyl)-2-methylpropyl)-7-(3-methoxypropoxy)-4-oxo-1,4-dihydroquinoline-3-carboxylic acid (Example 4-8), 6-(3-chloro-2-fluorobenzyl)-1-((1S)-1-(hydroxymethyl)-2-methylpropyl)-7-(morpholin-4-yl)-4-oxo-1,4-dihydroquinoline-3-carboxylic acid (Example 4-9), 6-(3-chloro-2-fluorobenzyl)-1-((1S)-1-(hydroxymethyl)-2-methylpropyl)-7-(4-methylpiperazin-1-yl)-4-oxo-1,4-dihydroquinoline-3-carboxylic acid (Example 4-10), 7-(4-acetylpiperazin-1-yl)-6-(3-chloro-2-fluorobenzyl)-1-((1S)-1-(hydroxymethyl)-2-methylpropyl)-4-oxo-1,4-dihydroquinoline-3-carboxylic acid (Example 4-11), 6-(3-chloro-2-fluorobenzyl)-1-((1S)-1-(hydroxymethyl)-2-methylpropyl)-4-oxo-7-(piperazin-1-yl)-1,4-dihydroquinoline-3-carboxylic acid (Example 4-12), 6-(3-chloro-2-fluorobenzyl)-1-((1S)-1-(hydroxymethyl)-2-methylpropyl)-4-oxo-7-(2-(piperidin-1-yl)ethoxy)-1,4-dihydroquinoline-3-carboxylic acid (Example 4-13), 6-(3-chloro-2-fluorobenzyl)-1-((1S)-1-(hydroxymethyl)-2-methylpropyl)-7-(1-methylpiperidin-4-yloxy)-4-oxo-1,4-dihydroquinoline-3-carboxylic acid (Example 4-14), 6-(3-chloro-2-fluorobenzyl)-7-(4-ethylpiperazin-1-yl)-1-((1S)-1-(hydroxymethyl)-2-methylpropyl)-4-oxo-1,4-dihydroquinoline-3-carboxylic acid (Example 4-15), 6-(3-chloro-2-fluorobenzyl)-1-((1S)-1-(hydroxymethyl)-2-methylpropyl)-7-(2-(morpholin-4-yl)ethoxy)-4-oxo-1,4-dihydroquinoline-3-carboxylic acid (Example 4-16), 6-(3-chloro-2-fluorobenzyl)-1-((1S)-1-(hydroxymethyl)-2-methylpropyl)-4-oxo-7-(2-(pyrrolidin-1-yl)ethoxy)-1,4-dihydroquinoline-3-carboxylic acid (Example 4-17), 7-(2-aminoethoxy)-6-(3-chloro-2-fluorobenzyl)-1-((1S)-1-(hydroxymethyl)-2-methylpropyl)-4-oxo-1,4-dihydroquinoline-3-carboxylic acid hydrochloride (Example 4-18), 7-(3-aminopropoxy)-6-(3-chloro-2-fluorobenzyl)-1-((1S)-1-(hydroxymethyl)-2-methylpropyl)-4-oxo-1,4-dihydroquinoline-3-carboxylic acid hydrochloride (Example 4-19), 6-(3-chloro-2-fluorobenzyl)-1-((1S)-1-(hydroxymethyl)-2-methylpropyl)-4-oxo-7-(pyridin-3-yloxy)-1,4-dihydroquinoline-3-carboxylic acid hydrochloride (Example 4-20), 6-(3-chloro-2-fluorobenzyl)-1-((1S)-1-(hydroxymethyl)-2-methylpropyl)-7-(4-hydroxypiperidin-1-yl)-4-oxo-1,4-dihydroquinoline-3-carboxylic acid (Example 4-21), 6-(3-chloro-2-fluorobenzyl)-7-(3,5-dimethylpiperazin-1-yl)-1-((1S)-1-(hydroxymethyl)-2-methylpropyl)-4-oxo-1,4-dihydroquinoline-3-carboxylic acid (Example 4-22), 6-(3-chloro-2-fluorobenzyl)-1-((1S)-1-(hydroxymethyl)-2-methylpropyl)-7-((3R)-3-hydroxypyrrolidin-1-yl)-4-oxo-1,4-dihydroquinoline-3-carboxylic acid (Example 4-23), 6-(3-chloro-2-fluorobenzyl)-1-((1S)-1-(hydroxymethyl)-2-methylpropyl)-7-((3S)-3-hydroxypyrrolidin-1-yl)-4-oxo-1,4-dihydroquinoline-3-carboxylic acid (Example 4-24), 6-(3-chloro-2-fluorobenzyl)-1-((1S)-1-(hydroxymethyl)-2-methylpropyl)-4-oxo-7-(piperidin-4-yloxy)-1,4-dihydroquinoline-3-carboxylic acid (Example 4-25), 7-((3S)-3-(acetylamino)pyrrolidin-1-yl)-6-(3-chloro-2-fluorobenzyl)-1-((1S)-1-(hydroxymethyl)-2-methylpropyl)-4-oxo-1,4-dihydroquinoline-3-carboxylic acid (Example 4-26), 7-((3R)-3-(acetylamino)pyrrolidin-1-yl)-6-(3-chloro-2-fluorobenzyl)-1-((1S)-1-(hydroxymethyl)-2-methylpropyl)-4-oxo-1,4-dihydroquinoline-3-carboxylic acid (Example 4-27), 6-(3-chloro-2-fluorobenzyl)-7-((dimethylamino)sulfonylmethoxy)-1-((1S)-1-(hydroxymethyl)-2-methylpropyl)-4-oxo-1,4-dihydroquinoline-3-carboxylic acid (Example 4-28), 6-(3-chloro-2-fluorobenzyl)-1-((1S)-1-(hydroxymethyl)-2-methylpropyl)-7-((3R)-3-methylpiperazin-1-yl)-4-oxo-1,4-dihydroquinoline-3-carboxylic acid (Example 4-29), 6-(3-chloro-2-fluorobenzyl)-1-((1S)-1-(hydroxymethyl)-2-methylpropyl)-7-((3S)-3-methylpiperazin-1-yl)-4-oxo-1,4-dihydroquinoline-3-carboxylic acid (Example 4-30), 6-(3-chloro-2-fluorobenzyl)-7-(2,6-dimethylmorpholin-4-yl)-1-((1S)-1-(hydroxymethyl)-2-methylpropyl)-4-oxo-1,4-dihydroquinoline-3-carboxylic acid (Example 4-31), 6-(3-chloro-2-fluorobenzyl)-1-((1S)-1-(hydroxymethyl)-2-methylpropyl)-4-oxo-7-(thiomorpholin-4-yl)-1,4-dihydroquinoline-3-carboxylic acid (Example 4-32), 6-(3-chloro-2-fluorobenzyl)-1-((1S)-1-(hydroxymethyl)-2-methylpropyl)-4-oxo-7-(2-(piperazin-1-yl)ethoxy)-1,4-dihydroquinoline-3-carboxylic acid dihydrochloride (Example 4-33), 7-(4-aminobutoxy)-6-(3-chloro-2-fluorobenzyl)-1-((1S)-1-(hydroxymethyl)-2-methylpropyl)-4-oxo-1,4-dihydroquinoline-3-carboxylic acid hydrochloride (Example 4-34), 6-(3-chloro-2-fluorobenzyl)-1-((1S)-1-(hydroxymethyl)-2-methylpropyl)-7-(3-oxopiperazin-1-yl)-4-oxo-1,4-dihydroquinoline-3-carboxylic acid (Example 4-35), 6-(3-chloro-2-fluorobenzyl)-1-((1S)-1-(hydroxymethyl)-2-methylpropyl)-4-oxo-7-(tetrahydropyran-4-yloxy)-1,4-dihydroquinoline-3-carboxylic acid (Example 4-36), 6-(3-chloro-2-fluorobenzyl)-1-((1S)-1-(hydroxymethyl)-2-methylpropyl)-4-oxo-7-((3R)-pyrrolidin-3-yloxy)-1,4-dihydroquinoline-3-carboxylic acid hydrochloride (Example 4-37), 7-((3S)-3-aminopyrrolidin-1-yl)-6-(3-chloro-2-fluorobenzyl)-1-((1S)-1-(hydroxymethyl)-2-methylpropyl)-4-oxo-1,4-dihydroquinoline-3-carboxylic acid (Example 4-38), 7-((3R)-3-aminopyrrolidin-1-yl)-6-(3-chloro-2-fluorobenzyl)-1-((1S)-1-(hydroxymethyl)-2-methylpropyl)-4-oxo-1,4-dihydroquinoline-3-carboxylic acid (Example 4-39), 6-(3-chloro-2-fluorobenzyl)-7-(1-(ethoxycarbonyl)piperidin-4-ylamino)-1-((1S)-1-(hydroxymethyl)-2-methylpropyl)-4-oxo-1,4-dihydroquinoline-3-carboxylic acid (Example 4-40), 7-(2-(acetylamino)ethoxy)-6-(3-chloro-2-fluorobenzyl)-1-((1S)-1-(hydroxymethyl)-2-methylpropyl)-4-oxo-1,4-dihydroquinoline-3-carboxylic acid (Example 4-41), 6-(3-chloro-2-fluorobenzyl)-1-((1S)-1-(hydroxymethyl)-2-methylpropyl)-4-oxo-7-(piperidin-4-ylamino)-1,4-dihydroquinoline-3-carboxylic acid (Example 4-42), 7-benzyloxy-6-(3-chloro-2-fluorobenzyl)-1-((1S)-1-(hydroxymethyl)-2-methylpropyl)-4-oxo-1,4-dihydroquinoline-3-carboxylic acid (Example 4-43), 6-(3-chloro-2-fluorobenzyl)-1-((1S)-1-(hydroxymethyl)-2-methylpropyl)-4-oxo-7-phenoxy-1,4-dihydroquinoline-3-carboxylic acid (Example 4-44), 7-((1-acetylpiperidin-4-yl)oxy)-6-(3-chloro-2-fluorobenzyl)-1-((1S)-1-(hydroxymethyl)-2-methylpropyl)-4-oxo-1,4-dihydroquinoline-3-carboxylic acid (Example 4-45), 6-(3-chloro-2-fluorobenzyl)-1-((1S)-1-(hydroxymethyl)-2-methylpropyl)-4-oxo-7-((3S)-pyrrolidin-3-yloxy)-1,4-dihydroquinoline-3-carboxylic acid hydrochloride (Example 4-46), 6-(3-chloro-2-fluorobenzyl)-1-((1S)-1-(hydroxymethyl)-2-methylpropyl)-4-oxo-7-((3S)-tetrahydrofuran-3-yloxy)-1,4-dihydroquinoline-3-carboxylic acid (Example 4-47), 6-(3-chloro-2-fluorobenzyl)-1-((1S)-1-(hydroxymethyl)-2-methylpropyl)-4-oxo-7-((3R)-tetrahydrofuran-3-yloxy)-1,4-dihydroquinoline-3-carboxylic acid (Example 4-48), 6-(3-chloro-2-fluorobenzyl)-1-((1S)-1-(hydroxymethyl)-2-methylpropyl)-7-(2-(mesylamino)ethoxy)-4-oxo-1,4-dihydroquinoline-3-carboxylic acid (Example 4-49), 7-(carboxymethoxy)-6-(3-chloro-2-fluorobenzyl)-1-((1S)-1-(hydroxymethyl)-2-methylpropyl)-4-oxo-1,4-dihydroquinoline-3-carboxylic acid (Example 4-50), 6-(3-chloro-2-fluorobenzyl)-1-((1S)-1-(hydroxymethyl)-2-methylpropyl)-7-(2-(4-methylpiperazin-1-yl)ethoxy)-4-oxo-1,4-dihydroquinoline-3-carboxylic acid ditrifluoroacetate (Example 4-51), 7-((aminosulfonyl)methoxy)-6-(3-chloro-2-fluorobenzyl)-1-((1S)-1-(hydroxymethyl)-2-methylpropyl)-4-oxo-1,4-dihydroquinoline-3-carboxylic acid (Example 4-52), 6-(3-chloro-2-fluorobenzyl)-7-((dimethylaminocarbonyl)methoxy)-1-((1S)-1-(hydroxymethyl)-2-methylpropyl)-4-oxo-1,4-dihydroquinoline-3-carboxylic acid (Example 4-53), 6-(3-chloro-2-fluorobenzyl)-1-((1S)-1-(hydroxymethyl)-2-methylpropyl)-7-((3S)-1-methylpyrrolidin-3-yloxy)-4-oxo-1,4-dihydroquinoline-3-carboxylic acid trifluoroacetate (Example 4-54), 6-(3-chloro-2-fluorobenzyl)-1-((1S)-1-(hydroxymethyl)-2-methylpropyl)-7-((3R)-1-methylpyrrolidin-3-yloxy)-4-oxo-1,4-dihydroquinoline-3-carboxylic acid trifluoroacetate (Example 4-55), 6-(3-chloro-2-fluorobenzyl)-7-(4-cyanobenzyloxy)-1-((1S)-1-(hydroxymethyl)-2-methylpropyl)-4-oxo-1,4-dihydroquinoline-3-carboxylic acid (Example 4-56), 7-(4-carboxybenzyloxy)-6-(3-chloro-2-fluorobenzyl)-1-((1S)-1-(hydroxymethyl)-2-methylpropyl)-4-oxo-1,4-dihydroquinoline-3-carboxylic acid (Example 4-57), 7-(4-(aminocarbonyl)benzyloxy)-6-(3-chloro-2-fluorobenzyl)-1-((1S)-1-(hydroxymethyl)-2-methylpropyl)-4-oxo-1,4-dihydroquinoline-3-carboxylic acid (Example 4-58), 6-(3-chloro-2-fluorobenzyl)-1-((1S)-1-(hydroxymethyl)-2-methylpropyl)-4-oxo-7-(pyridin-2-ylmethoxy)-1,4-dihydroquinoline-3-carboxylic acid (Example 4-59), 6-(3-chloro-2-fluorobenzyl)-1-((1S)-1-(hydroxymethyl)-2-methylpropyl)-4-oxo-7-(pyridin-4-ylmethoxy)-1,4-dihydroquinoline-3-carboxylic acid (Example 4-60), 6-(3-chloro-2-fluorobenzyl)-1-((1S)-1-(hydroxymethyl)-2-methylpropyl)-4-oxo-7-(pyridin-3-ylmethoxy)-1,4-dihydroquinoline-3-carboxylic acid (Example 4-61), 6-(3-chloro-2-fluorobenzyl)-1-((1S)-1-(hydroxymethyl)-2-methylpropyl)-4-oxo-7-(2,2,2-trifluoroethyloxy)-1,4-dihydroquinoline-3-carboxylic acid (Example 4-62), 7-(4-(aminosulfonyl)benzyloxy)-6-(3-chloro-2-fluorobenzyl)-1-((1S)-1-(hydroxymethyl)-2-methylpropyl)-4-oxo-1,4-dihydroquinoline-3-carboxylic acid (Example 4-63), 6-(3-chloro-2-fluorobenzyl)-1-((1S)-1-(hydroxymethyl)-2-methylpropyl)-7-(1-mesylpiperidin-4-yloxy)-4-oxo-1,4-dihydroquinoline-3-carboxylic acid (Example 4-64), (3S)-8-(3-chloro-2-fluorobenzyl)-3-isopropyl-6-oxo-2,3-dihydro-6H-1-oxa-3a-aza-phenalene-5-carboxylic acid (Example 5-1), 8-(3-chloro-2-fluorobenzyl)-3-hydroxymethyl-6-oxo-2,3-dihydro-6H-1-oxa-3a-aza-phenalene-5-carboxylic acid (Example 5-2), 10-(3-chloro-2-fluorobenzyl)-5-((1S)-1-hydroxymethyl-2-methylpropyl)-8-oxo-2,3,5,8-tetrahydro-1,4-dioxa-5-azaphenanthrene-7-carboxylic acid (Example 6-1), 6-(2-chloro-6-fluorobenzyl)-1-((1S)-1-(hydroxymethyl)-2-methylpropyl)-7-methoxy-4-oxo-1,4-dihydroquinoline-3-carboxylic acid (Example 7-1), 6-(2,3-dichlorobenzyl)-1-((1S)-1-(hydroxymethyl)-2-methylpropyl)-7-methoxy-4-oxo-1,4-dihydroquinoline-3-carboxylic acid (Example 7-2), 6-(3-chloro-2-fluorobenzyl)-7-(2-hydroxyethoxy)-1-((1S)-1-(hydroxymethyl)-2-methylpropyl)-4-oxo-1,4-dihydroquinoline-3-carboxylic acid (Example 7-3), 6-(3-chloro-2-fluorobenzyl)-1-((1S)-1-(hydroxymethyl)-2-methylpropyl)-7-(3-hydroxypropoxy)-4-oxo-1,4-dihydroquinoline-3-carboxylic acid (Example 7-4), 6-(3-chloro-2-fluorobenzyl)-7-hydroxy-1-((1S)-1-(hydroxymethyl)-2-methylpropyl)-4-oxo-1,4-dihydroquinoline-3-carboxylic acid (Example 7-5), 6-(3-chloro-2-fluorobenzyl)-1-((1S)-2,2-dimethyl-1-(hydroxymethyl)propyl)-7-(morpholin-4-yl)-4-oxo-1,4-dihydroquinoline-3-carboxylic acid (Example 7-6), 6-((3-chloro-2-fluorophenyl)-hydroxy-methyl)-1-((1S)-1-hydroxymethyl-2-methylpropyl)-7-methoxy-4-oxo-1,4-dihydroquinoline-3-carboxylic acid (Examples 7-7 and 7-8), 1-[(1S)-1-((2R,3R,4S,5S,6S)-6-carboxy-3,4,5-trihydroxytetrahydropyran-2-yloxymethyl)-2-methylpropyl]-6-(3-chloro-2-fluorobenzyl)-7-methoxy-4-oxo-1,4-dihydroquinoline-3-carboxylic acid (Examples 7-9), (2S,3S,4S,5R,6S)-6-[6-(3-chloro-2-fluorobenzyl)-1-((1S)-1-hydroxymethyl-2-methylpropyl)-7-methoxy-4-oxo-1,4-dihydroquinoline-3-carbonyloxy]-3,4,5-trihydroxytetrahydropyran-2-carboxylic acid morphline salt (Examples 7-10), 6-[4-((2S,3R,4S,5S,6S)-6-carboxy-3,4,5-trihydroxytetrahydropyran-2-yloxy)-3-chloro-2-fluorobenzyl]-1-((1S)-1-hydroxymethyl-2-methylpropyl)-7-methoxy-4-oxo-1,4-dihydroquinoline-3-carboxylic acid (Examples 7-11), and 6-(3-chloro-2-fluoro-4-sodiumsulfonatobenzyl)-1-((1S)-1-hydroxymethyl-2-methylpropyl)-7-methoxy-4-oxo-1,4-dihydroquinoline-3-carboxylic acid (Examples 7-12)

are preferable, 6-(3-chloro-2-fluoro-4-hydroxybenzyl)-1-((1S)-1-(hydroxymethyl)-2-methylpropyl)-7-methoxy-4-oxo-1,4-dihydroquinoline-3-carboxylic acid (Example 1-4), 6-((3-chloro-2-fluorophenyl)-hydroxy-methyl)-1-((1S)-1-hydroxymethyl-2-methylpropyl)-7-methoxy-4-oxo-1,4-dihydroquinoline-3-carboxylic acid (Examples 7-7 and 7-8), 1-[(1S)-1-((2R,3R,4S,5S,6S)-6-carboxy-3,4,5-trihydroxytetrahydropyran-2-yloxymethyl)-2-methylpropyl]-6-(3-chloro-2-fluorobenzyl)-7-methoxy-4-oxo-1,4-dihydroquinoline-3-carboxylic acid (Examples 7-9), (2S,3S,4S,5R,6S)-6-[6-(3-chloro-2-fluorobenzyl)-1-((1S)-1-hydroxymethyl-2-methylpropyl)-7-methoxy-4-oxo-1,4-dihydroquinoline-3-carbonyloxy]-3,4,5-trihydroxytetrahydropyran-2-carboxylic acid morphline salt (Examples 7-10), 6-[4-((2S,3R,4S,5S,6S)-6-carboxy-3,4,5-trihydroxytetrahydropyran-2-yloxy)-3-chloro-2-fluorobenzyl]-1-((1S)-1-hydroxymethyl-2-methylpropyl)-7-methoxy-4-oxo-1,4-dihydroquinoline-3-carboxylic acid (Examples 7-11), and 6-(3-chloro-2-fluoro-4-sodiumsulfonatobenzyl)-1-((1S)-1-hydroxymethyl-2-methylpropyl)-7-methoxy-4-oxo-1,4-dihydroquinoline-3-carboxylic acid (Examples 7-12)

are more preferable, and 6-(3-chloro-2-fluoro-4-hydroxybenzyl)-1-((1S)-1-(hydroxymethyl)-2-methylpropyl)-7-methoxy-4-oxo-1,4-dihydroquinoline-3-carboxylic acid (Example 1-4),and 6-((3-chloro-2-fluorophenyl)-hydroxy-methyl)-1-((1S)-1-hydroxymethyl-2-methylpropyl)-7-methoxy-4-oxo-1,4-dihydroquinoline-3-carboxylic acid (Examples 7-8, high polar) are particularly preferable.

The present invention also encompasses prodrugs and metabolites of each compound.

By the "prodrug" is meant a derivative of the compound of the present invention, which has a chemically or metabolically decomposable group and which, after administration to a body, restores to the original compound to show its inherent efficacy, including a complex and a salt, not involving a covalent bond.

The prodrug is utilized for, for example, improving absorption by oral administration or targeting of a target site.

As the site to be modified, highly reactive functional groups in the compound of the present invention, such as hydroxyl group, carboxyl group, amino group, thiol group, and the like, are mentioned.

Examples of the hydroxyl-modifying group include acetyl group, propionyl group, isobutyryl group, pivaloyl group, benzoyl group, 4-methylbenzoyl group, dimethylcarbamoyl group, sulfo group, and the like. Examples of the carboxyl-modifying group include ethyl group, pivaloyloxymethyl group, 1-(acetyloxy)ethyl group, 1-(ethoxycarbonyloxy)ethyl group, 1-(cyclohexyloxycarbonyloxy)ethyl group, carboxymethyl group, (5-methyl-2-oxo-1,3-dioxol-4-yl)methyl group, phenyl group, o-tolyl group, and the like. Examples of the amino-modifying group include hexylcarbamoyl group, 3-methylthio-1-(acetylamino)propylcarbonyl group, 1-sulfo-1-(3-ethoxy-4-hydroxyphenyl)methyl group, (5-methyl-2-oxo-1,3-dioxol-4-yl)methyl group, and the like.

The compound of the present invention can be administered to a mammal (human, mouse, rat, hamster, rabbit, cat, dog, bovine, sheep, monkey, and the like.) and the like as an anti-HIV agent or composition, an integrase inhibitor, an antiviral agent, and the like.

When the compound of the present invention is used as a pharmaceutical composition or preparation, it is generally admixed with pharmaceutically acceptable carriers, excipients, diluents, extending agents, disintegrants, stabilizers, preservatives, buffers, emulsifiers, flavoring agents, coloring agents, sweetening agents, thickeners, correctives, dissolution aids, and other additives, that are known per se, such as water, vegetable oil, alcohol (e.g., ethanol, benzyl alcohol, and the like.), polyethylene glycol, glycerol triacetate, gelatin, carbohydrate (e.g., lactose, starch, and the like.), magnesium stearate, talc, lanolin, petrolatum, and the like, formed into tablet, pill, powder, granule, suppository, injection, eye drop, liquid, capsule, troche, aerosol, elixir, suspension, emulsion, syrup, and the like by a conventional method, and administered systemically or topically, and orally or parenterally.

While the dose varies depending on age, body weight, symptom, treatment effect, administration method, and the like, it is generally 0.01 mg to 1 g once for an adult, which is given once to several times a day orally or in a dosage form of an injection such as intravenous injection and the like.

An anti-HIV agent is generally required to sustain its effect for a long time, so that can be effective not only for temporal suppression of viral growth but also prohibition of viral re-growth. This means that a prolonged administration is necessary and that a high single dose may be frequently inevitable to sustain effect for a longer period through the night. Such prolonged and high dose administration increases the risk of causing side effects.

In view of this, one of the preferable embodiments of the 4-oxoquinoline compound of the present invention is such compound permitting high absorption by oral administration, and such compound capable of maintaining blood concentration of the administered compound for an extended period of time. A compound showing metabolic resistance is also one of the preferable embodiments.

By the "prophylaxis of AIDS" is meant, for example, administration of a pharmaceutical agent to an individual who tested HIV positive but has not yet developed the disease state of AIDS; administration of a pharmaceutical agent to an individual who shows an improved disease state of AIDS after treatment but who carries HIV still to be eradicated and whose relapse of AIDS is worried; administration of a pharmaceutical agent before infection with HIV out of a fear of possible infection; and the like.

Examples of the "other anti-HIV agents" and "other anti-HIV active substances" to be used for a multiple drug combination therapy include an anti-HIV antibody, an HIV vaccine, immunostimulants such as interferon and the like, an HIV ribozyme, an HIV antisense drug, an HIV reverse transcriptase inhibitor, an HIV protease inhibitor, an HIV integrase inhibitor, an inhibitor of bond between a bond receptor (CD4, CXCR4, CCR5, and the like) of a host cell recognized by virus and the virus, and the like.

Specific examples of the HIV reverse transcriptase inhibitor include Retrovir® (zidovudine), Epivir® (lamivudine), Zerit® (sanilvudine), Videx® (didanosine), Hivid® (zalcitabine), Ziagen® (abacavir sulfate), Viramune® (nevirapine), Stocrin® (efavirenz), Rescriptor® (delavirdine mesylate), Combivir® (zidovudine+lamivudine), Trizivir® (abacavir sulfate+lamivudine+zidovudine), Coactinon® (emivirine), Phosphonovir®, Coviracil®, alovudine (3'-fluoro-3'-deoxythymidine), Thiovir (thiophosphonoformic acid), Capravirin (5-[(3,5-dichlorophenyl)thio]-4-isopropyl-1-(4-pyridylmethyl)imidazole-2-methanol carbamic acid), Tenofovir disoproxil fumarate ((R)-[[2-(6-amino-9H-purin-9-yl)-1-methylethoxy]methyl]phosphonic acid bis(isopropoxycarbonyloxymethyl)ester fumarate), DPC-083 ((4S)-6-chloro-4-[(1E)-cyclopropylethenyl]-3,4-dihydro-4-trifluoromethyl-2(1H)-quinazolinone), DPC-961 ((4S)-6-chloro-4-(cyclopropylethynyl)-3,4-dihydro-4-(trifluoromethyl)-2 (1H)-quinazolinone), DAPD ((−)-β-D-2,6-diaminopurine dioxolane), Immunocal, MSK-055, MSA-254, MSH-143, NV-01, TMC-120, DPC-817, GS-7340, TMC-125, SPD-754, D-A4FC, capravirine, UC-781, emtricitabine, alovudine, Phosphazid, BCH-10618, DPC-083, Etravirine, BCH-13520, MIV-210, Abacavir sulfate/lamivudine, GS-7340, GW-5634, GW-695634, and the like, wherein (R) means a registered trademark (hereinafter the same) and the names of other pharmaceutical agents are general names.

Specific examples of the HIV protease inhibitor include Crixivan® (indinavir sulfate ethanolate), saquinavir, Invirase® (saquinavir mesylate), Norvir® (ritonavir), Viracept® (nelfinavir mesylate), lopinavir, Prozei® (amprenavir), Kaletra® (ritonavir+lopinavir), mozenavir dimesylate ([4R-(4',5', 6β)]-1,3-bis[(3-aminophenyl)methyl]hexahydro-5,6-dihydroxy-4,7-bis(phenylmethyl)-2H-1,3-diazepin-2-one dimethanesulfonate), tipranavir (3'-[(1R)-1-[(6R)-5,6-dihydro-4-hydroxy-2-oxo-6-phenylethyl-6-propyl-2H-pyran-3-yl]propyl]-5-(trifluoromethyl)-2-pyridinesulfonamide), lasinavir (N-[5(S)-(tert-butoxycarbonylamino)-4(S)-hydroxy-6-phenyl-2(R)-(2,3,4-trimethoxybenzyl)hexanoyl]-L-valine 2-methoxyethylenamide), KNI-272 ((R)-N-tert-butyl-3-[(2S,3S)-2-hydroxy-3-N-[(R)-2-N-(isoquinolin-5-yloxyacetyl)amino-3-methylthiopropanoyl]amino-4-phenylbutanoyl]-5,5-dimethyl-1,3-thiazolidine-4-carboxamide), GW-433908, TMC-126, DPC-681, buckminsterfullerene, MK-944A (MK944 (N-(2(R)-hydroxy-1(S)-indanyl)-2(R)-phenylmethyl-4(S)-hydroxy-5-[4-(2-benzo[b]furanylmethyl)-2(S)-(tert-butylcarbamoyl)piperazin-1-yl]pentanamide)+indinavir sulfate), JE-2147 ([2(S)-oxo-4-phenylmethyl-3(S)-[(2-methyl-3-oxy) phenylcarbonylamino]-1-oxabutyl]-4-[(2-methylphenyl) methylamino]carbonyl-4(R)-5,5-dimethyl-1,3-thiazole), BMS-232632 (dimethyl (3S,8S,9S,12S)-3,12-bis(1,1-dimethylethyl)-8-hydroxy-4,11-dioxo-9-(phenylmethyl)-6-[[4-(2-pyridinyl)phenyl]methyl]-2,5,6,10,13-pentaazatetradecanedicarboxylate), DMP-850 ((4R,5S,6S,7R)-1-(3-amino-1H-indazol-5-ylmethyl)-4,7-dibenzyl-3-butyl-5,6-dihydroxyperhydro-1,3-diazepin-2-one), DMP-851, RO-0334649, Nar-DG-35, R-944, VX-385, TMC-114, Tipranavir, Fosamprenavir sodium, Fosamprenavir calcium, Darunavir, GW-0385, R-944, RO-033-4649 and AG-1859, and the like.

The HIV integrase inhibitor is exemplified by S-1360, L-870810, and the like, the DNA polymerase inhibitor or DNA synthesis inhibitor is exemplified by Foscavir®, ACH-126443 (L-2',3'-didehydro-dideoxy-5-fluorocytidine), entecavir ((1S,3S,4S)-9-[4-hydroxy-3-(hydroxymethyl)-2-methylenecyclopentyl]guanine), calanolide A ([10R-(10α,11β,12α)]-11,12-dihydro-12-hydroxy-6,6,10,11-tetramethyl-4-propyl-2H,6H,10H-benzo[1,2-b:3,4-b':5,6-b"]tripyran-2-one), calanolide B, NSC-674447 (1,1'-azobisformamide), Iscador (viscum alubm extract), Rubitecan, and the like, the HIV antisense drug is exemplified by HGTV-43, GEM-92, and the like, the anti-HIV antibody or other antibody is exemplified by NM-01, PRO-367, KD-247, Cytolin®, TNX-355 (CD4 antibody), AGT-1, PRO-140 (CCR5 antibody), Anti-CTLA-4Mab, and the like, the HIV vaccine or other vaccine is exemplified by ALVAC®, AIDSVAX®, Remune®, HIV gp41 vaccine, HIV gp120 vaccine, HIV gp140 vaccine, HIV gp160 vaccine, HIV p17 vaccine, HIV p24 vaccine, HIV p55 vaccine, AlphaVax Vector System, canarypox gp160 vaccine, AntiTat, MVA-F6 Nef vaccine, HIV rev vaccine, C4-V3 peptide, p2249f, VIR-201, HGP-30W, TBC-3B, PARTICLE-3B, Antiferon (interferon-α vaccine), and the like, the interferon or interferon agonist is exemplified by Sumiferon®, MultiFeron®, interferon-τ, Reticulose, human leukocyte interferon α, and the like, the CCR5 antagonist is exemplified by SCH-351125 and the like, the pharmaceutical agent acting on HIV p24 is exemplified by GPG-NH2 (glycyl-prolyl-glycinamide) and the like, the HIV fusion inhibitor is exemplified by FP-21399 (1,4-bis[3-[(2,4-dichlorophenyl)carbonylamino]-2-oxo-5,8-disodium sulfonyl]naphthyl-2,5-dimethoxyphenyl-1,4-dihydrazone), T-1249, Synthetic Polymeric Construction No3, pentafuside, FP-21399, PRO-542, Enfuvirtide, and the like, the IL-2 agonist or antagonist is exemplified by interleukin-2, Imunace®, Proleukin®, Multikine®, Ontak®, and the like, the TNF-α antagonist is exemplified by Thalomid® (thalidomide), Remicade® (infliximab), curdlan sulfate, the α-glucosidase inhibitor is exemplified by Bucast® and the like, the purine nucleoside phosphorylase inhibitor is exemplified by peldesine (2-amino-4-oxo-3H,5H-7-[(3-pyridyl)methyl]pyrrolo[3,2-d]pyrimidine) and the like, the apoptosis agonist or inhibitor is exemplified by Arkin Z®, Panavir®, Coenzyme Q10 (2-deca(3-methyl-2-butenylene)-5,6-dimethoxy-3-methyl-p-benzoquinone), and the like, the cholinesterase inhibitor is exemplified by Cognex® and the like, and the immunomodulator is exemplified by Imunox®, Prokine®, Met-enkephalin (6-de-L-arginine-7-de-L-arginine-8-de-L-valinamide-adrenorphin), WF-10 (10-fold dilute tetrachlorodecaoxide solution), Perthon, PRO-542, SCH-D, UK-427857, AMD-070, AK-602, and the like.

In addition, Neurotropin®, Lidakol®, Ancer 20®, Ampligen®, Anticort®, Inactivin®, and the like, PRO-2000, Rev M10 gene, HIV specific cytotoxic T cell (CTL immunotherapy, ACTG protocol 080 therapy, CD4-ζ gene therapy), SCA binding protein, RBC-CD4 complex, Motexafin gadolinium, GEM-92, CNI-1493, (+)-FTC, Ushercell, D2S, BufferGel®, VivaGel®, Glyminox vaginal gel, sodium lauryl sulfate, 2F5, 2F5/2G12, VRX-496, Ad5gag2, BG-777, IGIV-C, BILR-255, and the like are exemplified.

As the "other anti-HIV agents" and "other anti-HIV activity substances" to be used for a multiple drug combination therapy with the compound of the present invention, preferred are an HIV reverse transcriptase inhibitor and an HIV protease inhibitor. Two or three, or even a greater number of pharmaceutical agents can be used in combination, wherein a combination of pharmaceutical agents having different action mechanisms is one of the preferable embodiments. In addition, selection of pharmaceutical agents free of side effect duplication is preferable.

Specific examples of the combination of pharmaceutical agents include a combination of a group consisting of efavirenz, tenofovir, emtricitabine, indinavir, nelfinavir, atazanavir, ritonavir+indinavir, ritonavir+lopinavir, ritonavir+saquinavir, didanosine+lamivudine, zidovudine+didanosine, stavudine+didanosine, zidovudine+lamivudine, stavudine+lamivudine and emtriva, and 4-oxoquinoline compound [I] of the present invention (Guidelines for the Use of Antiretroviral Agents in HIV-Infected Adults and Adolescents. Aug. 13, 2001). Particularly preferred is a combined use of two agents with efavirenz, indinavir, nelfinavir, tenofovir, emtricitabine, zidovudine or lamivudine, and a combined use of three agents with zidovudine+lamivudine, tenofovir+lamivudine, tenofovir+zidovudine, tenofovir+efavirenz, tenofovir+nelfjinavir, tenofovir+indinavir, tenofovir+emtricitabine, emtricitabine+lamivudine, emtricitabine+zidovudine, emtricitabine+efavirenz, emtricitabine+nelfinavir, emtricitabine+indinavir, nelfinavir+lamivudine, nelfinavir+zidovudine, nelfinavir+efavirenz, nelfinavir+indinavir, efavirenz+lamivudine, efavirenz+zidovudine or efavirenz+indinavir.

Some examples of the production method of the compound used for embodiment of the present invention are shown in the following. However, the production method of the compound of the present invention is not limited to these examples.

Even in the absence of description in the production method, efficient production can be afforded by designs such as introducing, where necessary, a protecting group into a functional group followed by deprotection in a subsequent step; subjecting a functional group to each step as a precursor and converting the group to a desired functional group in a suitable step; exchanging the order of respective production methods and steps; and the like.

The work-up treatment in each step can be applied by a typical method, wherein isolation and purification is performed by selecting or combining conventional methods, as necessary, such as crystallization, recrystallization, distillation, partitioning, silica gel chromatography, preparative HPLC, and the like.

Production Method 1-1

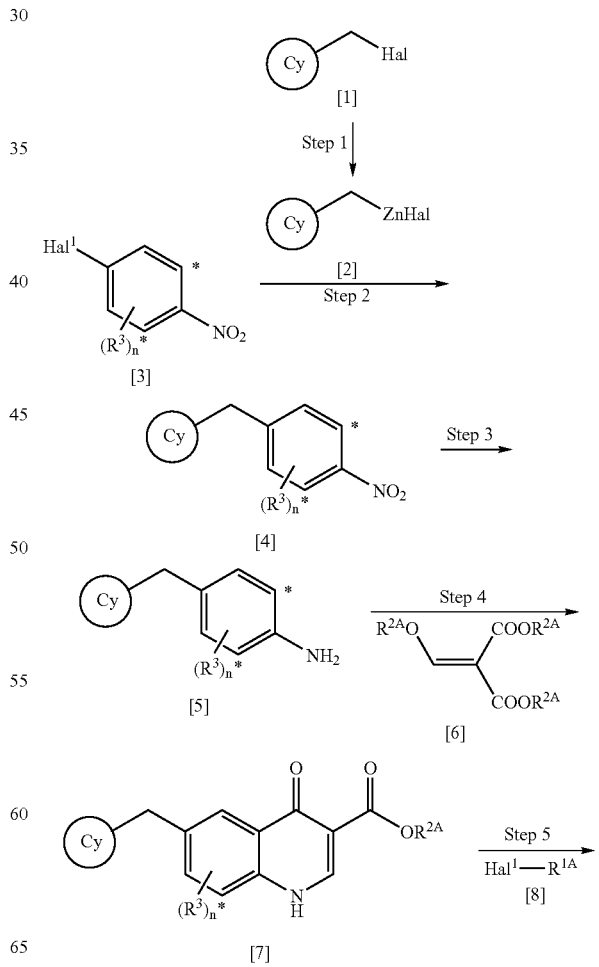

-continued

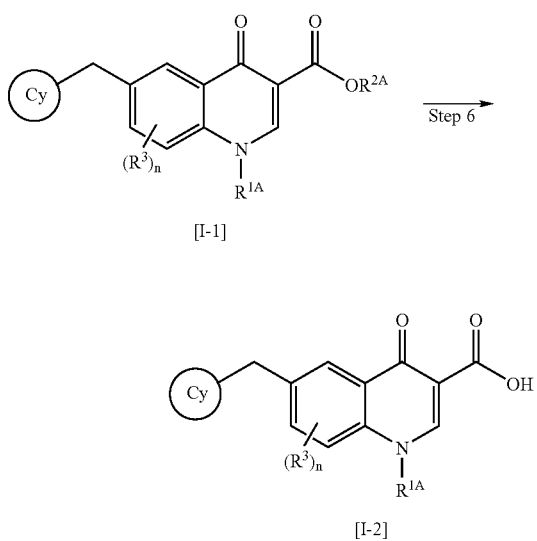

[I-1]

[I-2]

wherein Hal is a halogen atom such as chlorine atom, bromine atom, and the like, $Hal^1$ is a halogen atom such as bromine atom, iodine atom, and the like, $R^{1A}$ is as defined for $R^1$ above, $R^{2A}$ is a carboxyl-protecting group such as methyl, ethyl, benzyl, and the like, in compound [6], each $R^{2A}$ may be different but preferably the same, $(R^3)_n$ are the same or different and each is a substituent of $R^{32}$ or $R^{33}$, n is 0, 1 or 2, wherein substituent $R^3$ does not substitute at both the positions * at the same time, and other symbols are as defined above.

Step 1

Under an argon or nitrogen stream, zinc powder is reacted with 1,2-dibromoethane under heating in a solvent, and trimethylsilyl chloride is added to allow reaction. Then, a solution of compound [1] is added to the reaction mixture to allow reaction, whereby compound [2] can be obtained.

As preferable solvents, ether solvents such as 1,4-dioxane, diethyl ether, 1,2-dimethoxyethane, tetrahydrofuran (THF), and the like; hydrocarbon solvents such as benzene, toluene, hexane, xylene, and the like; and the like can be mentioned.

Step 2

Compound [2] is reacted with compound [3] in a solvent in the presence of a catalyst, in the presence of a ligand such as triphenylphosphine, tri(2-furyl)phosphine, and the like where necessary, under an argon or nitrogen stream, under cooling to heating, whereby compound [4] can be obtained.

As the catalyst, palladium catalysts such as bis(dibenzylideneacetone)palladium, tris(dibenzylideneacetone)dipalladium, dichlorobis(triphenylphosphine)palladium, dichlorobis(benzonitrile)palladium, dichloroethylenediaminepalladium, palladium acetate, tetrakis(triphenylphosphine)palladium, and the like; nickel catalyst and the like can be mentioned.

As preferable solvents, ether solvents such as 1,4-dioxane, diethyl ether, 1,2-dimethoxyethane, tetrahydrofuran (THF), and the like; hydrocarbon solvents such as benzene, toluene, hexane, xylene, and the like; and the like can be mentioned.

Step 3

Compound [4] is reduced by a conventional method such as reduction with zinc or iron under neutral or alkaline conditions; iron and acid; tin or tin(II) chloride and concentrated hydrochloric acid; alkali sulfide; alkaline hydrosulfite; and the like, catalytic reduction under hydrogen atmosphere; and the like, whereby compound [5] can be obtained.

For example, acetic acid and zinc powder are added to compound [4] under cooling, and reacted at room temperature, whereby compound [5] can be obtained. Alternatively, palladium-carbon is added to a solution of compound [4] in a mixed solvent of THF and methanol under a hydrogen atmosphere, and reacted at room temperature, whereby compound [5] can be obtained.

Step 4

Compound [5] is reacted with compound [6] in a solvent under heating.

As the solvent, alcohol solvents such as methanol, ethanol, n-propanol, isopropanol, and the like; hydrocarbon solvents such as benzene, toluene, hexane, xylene, and the like; halogen solvents such as dichloromethane, chloroform, carbon tetrachloride, 1,2-dichloroethane, and the like; ether solvents such as 1,4-dioxane, diethyl ether, 1,2-dimethoxyethane, tetrahydrofuran, and the like, a mixed solvent thereof, and the like can be mentioned.

Then, the solvent is evaporated, the residue is reacted under heating in a solvent such as diphenyl ether, a mixture of diphenyl ether and biphenyl (e.g., Dowtherm A, product name Fluka), and the like, whereby compound [7] can be obtained.

Step 5

Compound [7] is reacted with compound [8] in a solvent, in the presence of a base, whereby compound [I-1] can be obtained.

As the base, potassium carbonate, sodium carbonate, lithium hydride, sodium hydride, potassium hydride, and the like can be mentioned, with preference given to potassium carbonate.

As the solvent, hydrocarbon solvents such as benzene, toluene, hexane, xylene, and the like; ether solvents such as 1,4-dioxane, diethyl ether, 1,2-dimethoxyethane, tetrahydrofuran, and the like; polar solvents such as dimethylformamide, dimethyl sulfoxide, acetonitrile, and the like, a mixed solvent thereof and the like can be mentioned.

Step 6

Compound [I-1] is hydrolyzed in a solvent at room temperature to under heating, under the basic conditions with sodium hydroxide, potassium hydroxide, lithium hydroxide, and the like or acidic conditions with hydrochloric acid, sulfuric acid, and the like, whereby compound [I-2] can be obtained.

As the solvent, alcohol solvents such as methanol, ethanol, n-propanol, isopropanol, and the like; hydrocarbon solvents such as benzene, toluene, hexane, xylene, and the like; halogen solvents such as dichloromethane, carbon tetrachloride, 1,2-dichloroethane, and the like; ether solvents such as 1,4-dioxane, diethyl ether, 1,2-dimethoxyethane, tetrahydrofuran, and the like; polar solvents such as dimethylformamide, dimethyl sulfoxide, acetonitrile, and the like; water, a mixed solvent thereof and the like can be mentioned.

Production Method 1-2: Example of production method using compound [9] wherein hydroxyl-protecting group has been introduced Production Method 2-1

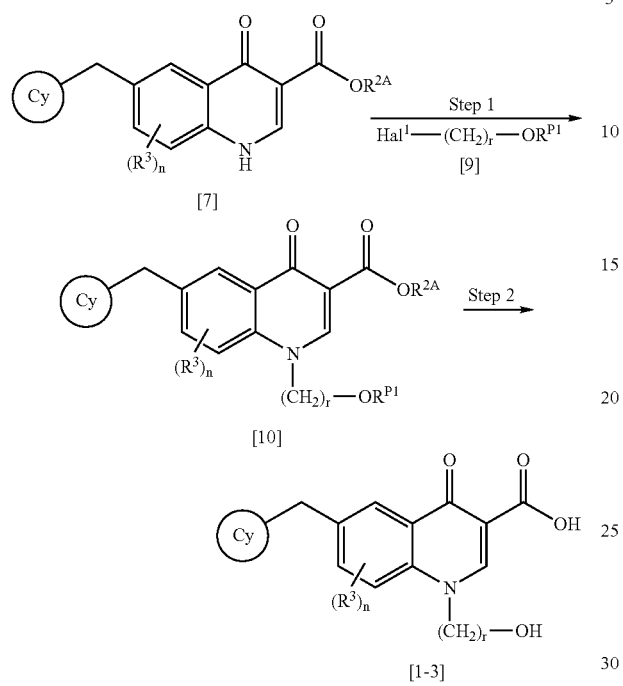

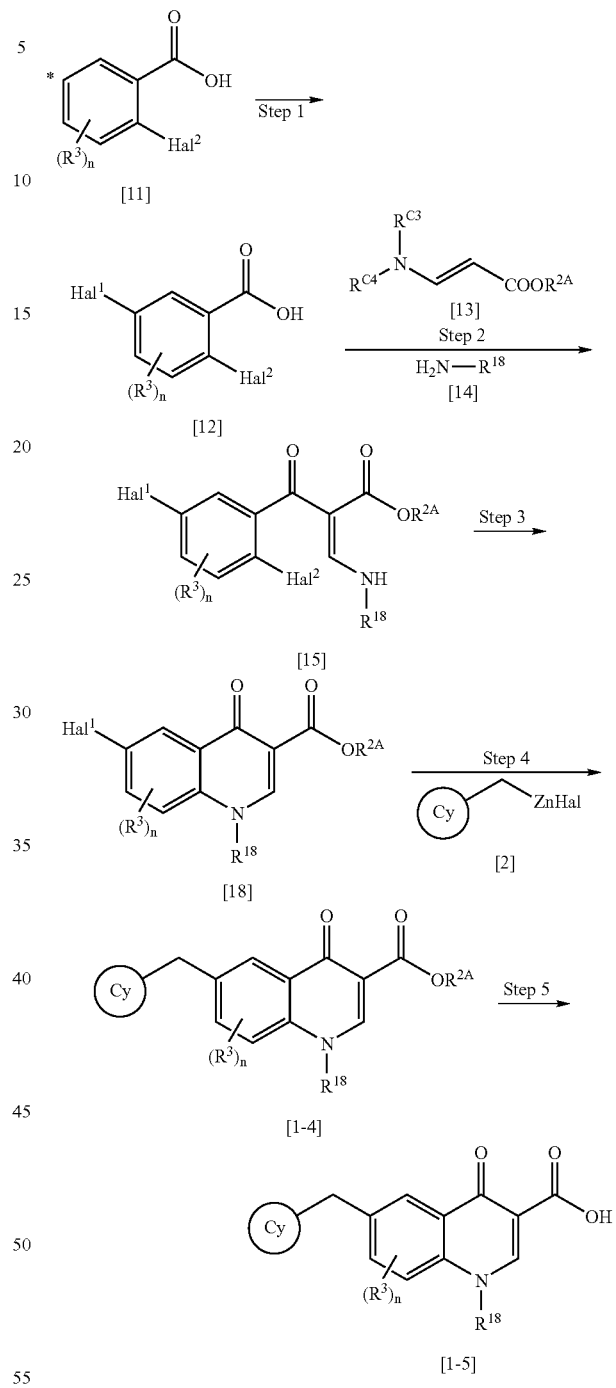

wherein r is an integer of 1 to 6, $R^{P1}$ is a hydroxyl-protecting group, and other symbols are as defined above.

Step 1

Compound [7] obtained in the same manner as in Production Method 1-1 and compound [9] are reacted in the same manner as in Step 5 of Production Method 1-1, whereby compound [10] can be obtained.

Step 2

Hydroxyl group and carboxyl group of compound [10] are deprotected by a conventional method, whereby compound [I-3] can be obtained.

As the hydroxyl-protecting group, an acetyl group, a methoxycarbonyl group, a methoxymethyl group, a methoxyethoxymethyl group, a trimethylsilyl group, a tert-butyldimethylsilyl group, a tert-butyldiphenylsilyl group, and the like can be mentioned.

For example, when $R^{P1}$ is an acetyl group or a methoxycarbonyl group, deprotection can be performed by reaction under heating in the presence of a base such as sodium hydroxide, potassium hydroxide, and the like. Alternatively, a treatment such as adding concentrated hydrochloric acid and heating; heating in concentrated ammonia; and the like may be also applied.

For example, when $R^{P1}$ is a tert-butyldimethylsilyl group, deprotection can be performed by a method such as a treatment with tetrabutylammonium fluoride at room temperature in THF; a heat treatment in the presence of sodium hydroxide in THF; a treatment with acetic acid-water-THF at room temperature to under heating; and the like. In this step, the deprotection of hydroxyl group and carboxyl group may be performed in two steps.

Compound [9] may be $Hal^1$-$R^1$ wherein $Hal^1$ and $R^1$ are as defined above.

wherein $Hal^2$ is a halogen atom, preferably fluorine atom or chlorine atom, $R^{C3}$ and $R^{C4}$ are the same or different and each is a lower alkyl group such as a methyl group, an ethyl group, and the like, $R^{1B}$ is as defined for the above-mentioned $R^1$, other symbols are as defined above, and substituent $R^3$ is not substituted at position *.

Step 1

$Hal^1$ is preferably bromine or iodine, and halogenating by a conventional method affords compound [12] from compound [11].

For example, compound [11] is reacted with a halogenating agent such as N-bromosuccinimide, N-iodosuccinimide, and the like at room temperature to under heating, in a solvent such as trifluoromethanesulfonic acid, acetic acid, concentrated sulfuric acid, DMF, and the like, whereby compound [12] can be obtained.

Step 2

Compound [12] is subjected to a conventional method, for example, by adding a halogenating agent such as oxalyl chloride, thionyl chloride, and the like, in a solvent such as hydrocarbon solvents (e.g., toluene, xylene, and the like); halogen solvents (e.g., dichloromethane, chloroform, carbon tetrachloride, 1,2-dichloroethane, and the like); ester solvents (e.g., ethyl acetate, and the like) and the like, under heating and the like, to give acid halide. Compound [13] may be in the form of E or Z.

Here, for example, when thionyl chloride is used as a halogenating agent, a catalytic amount of DMF may be added.

Then, compound [13] is added to react with the acid halide in a solvent at room temperature to under heating, in the presence of a base such as triethylamine, diisopropylethylamine, potassium carbonate, pyridine, and the like, and then reacted with compound [14] at room temperature to under heating, whereby compound [15] can be obtained.

As the solvent, hydrocarbon solvents such as benzene, toluene, hexane, xylene, and the like; halogen solvents such as dichloromethane, chloroform, carbon tetrachloride, 1,2-dichloroethane, and the like; ether solvents such as 1,4-dioxane, diethyl ether, 1,2-dimethoxyethane, tetrahydrofuran, and the like; polar solvents such as acetonitrile and the like; ester solvents such as ethyl acetate and the like, a mixed solvent thereof and the like can be mentioned.

Step 3

Compound [15] is reacted in a solvent in the presence of a base such as sodium carbonate, potassium carbonate, sodium hydroxide, potassium hydroxide, lithium hydroxide, potassium tert-butoxide, sodium hydride, potassium hydride, and the like, whereby compound [16] can be obtained.

As one of the preferable production methods, compound [15] is reacted in a solvent in the presence of 1,8-diazabicyclo[5.4.0]-7-undecene at room temperature to under heating, whereby compound [16] can be also obtained.

As the solvent, hydrocarbon solvents such as benzene, toluene, hexane, xylene, and the like; halogen solvents such as dichloromethane, carbon tetrachloride, 1,2-dichloroethane, and the like; ether solvents such as 1,4-dioxane, diethyl ether, 1,2-dimethoxyethane, tetrahydrofuran, and the like; polar solvents such as dimethylformamide, dimethyl sulfoxide, acetonitrile, and the like, a mixed solvent thereof and the like can be mentioned.

Step 4

Compound [16] is reacted with compound [2] in the same manner as in Step 2 of Production Method 1-1, whereby compound [I-4] can be obtained.

Step 5

Compound [I-4] is hydrolyzed in the same manner as in Step 6 of Production Method 1-1, whereby compound [I-5] can be obtained. Production Method 2-2: Example of production method including introduction-elimination step of hydroxyl-protecting group

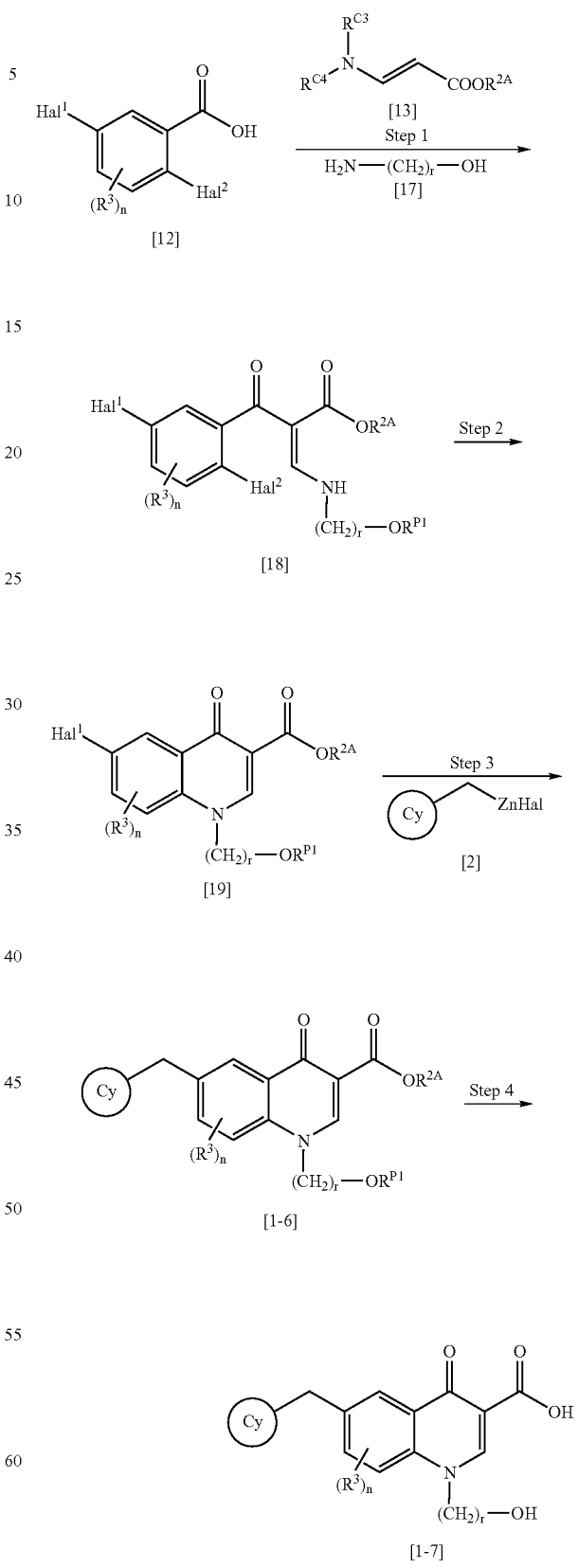

wherein each symbol is as defined above.

Step 1

Compound [12] obtained in the same manner as in Step 1 of Production Method 2-1 is reacted with compound [13] and then compound [17] in the same manner as in Step 2 of Production Method 2-1, whereby compound [18] can be obtained. Compound [13] may be in the form of E or Z.

Compound [17] may be $H_2N$—$R^1$.

Step 2

A protecting group is introduced into the hydroxyl group of compound [18] by a conventional method, and then the obtained compound is cyclized in the same manner as in Step 3 of Production Method 2-1, whereby compound [19] can be obtained.

Compound [18] is cyclized in the same manner as in Step 3 of Production Method 2-1, and then a protecting group is introduced into the hydroxyl group of the obtained compound by a conventional method, whereby compound [19] can be also obtained.

For example, when $R^{P1}$ is a tert-butyldimethylsilyl group, compound [18] needs only reacted with tert-butyldimethylsilyl chloride in the presence of imidazole, in DMF or a toluene solvent at room temperature.

When $R^{P1}$ is a methoxycarbonyl group, compound [18] needs only reacted with methyl chlorocarbonate in the presence of pyridine, in a chloroform solvent under cooling to room temperature.

In the case of $NH_2$—$R^{1A'}$ where $R^{1A'}$ is a $C_{1-10}$ alkyl group optionally substituted by at least one hydroxyl group, instead of compound [17], a similar production method can be used.

Step 3

Compound [19] is reacted with compound [2] in the same manner as in Step 2 of Production Method 1-1, whereby compound [I-6] can be obtained.

Step 4

Hydroxyl group and carboxyl group of compound [I-6] are deprotected in the same manner as in Step 2 of Production Method 1-2, whereby compound [I-7] can be obtained. In this Step, deprotection of hydroxyl group and carboxyl group can be performed in two steps.

Production Method 3 wherein $R^{a7'}$ is methyl, 2-hydroxyethyl, 3-hydroxypropyl, 4-hydroxybutyl, 2,2,2-trifluoroethyl, —$(CH_2)_p$—$OR^{34}$, —$(CH_2)_p$—$NR^{35}R^{36}$, —$(CH_2)_p$—$CO_2R^{35}$, —$(CH_2)_p$—$CONR^{35}R^{37}$, —$(CH_2)_p$—$SO_2NR^{35}R^{37}$, —$(CH_2)_q$-(ring A), —$(CH_2)_n$—$OR^{39}$, —$(CH_2)_n$—$NR^{39}R^{31}$ or —$(CH_2)_n$-Ph (wherein each symbol is as defined above), $R^2$ is a carboxyl-protecting group such as methyl, ethyl, benzyl, and the like, and other symbols are as defined above.

The fluorine atom on 4-oxoquinoline can be converted to —$OR^{a7'}$ by the reaction with a nucleating agent by a conventional method.

This production method is suitable for introducing a substituent into the 7- or 8-position of 4-oxoquinoline.

Production Method 3-1

An alkoxy group (—$OR^{a7'}$ group) is introduced into compound [21] by a conventional method, whereby compound [I-8] can be obtained.

For example, compound [21] is reacted with metal alkoxide in an alcohol solvent such as methanol, ethanol, propanol, butanol, and the like under heating, and then hydrolyzed, whereby compound [I-8] can be obtained.

It is only necessary to select a solvent and metal alkoxide corresponding to the desired alkoxy group, and in the case of a methoxy group, compound [21] is reacted with sodium methoxide or potassium methoxide in a methanol solvent, and in the case of an ethoxy group, reacted with sodium ethoxide or potassium ethoxide in an ethanol solvent.

Production Method 3-2

Compound [21] is aminated by a conventional method, whereby compound [I-9] can be obtained.

For example, compound [21] is reacted with amine in an inert organic solvent such as THF, dioxane, chloroform, dichloromethane, methanol, ethanol, pyridine, and the like under heating, to give compound [I-9].

Compound [I-9] can be also obtained by reacting with amine in DMF by irradiation of microwave.

Production Method 4

Examples of the production method of intermediate compound [12'] are given in the following.

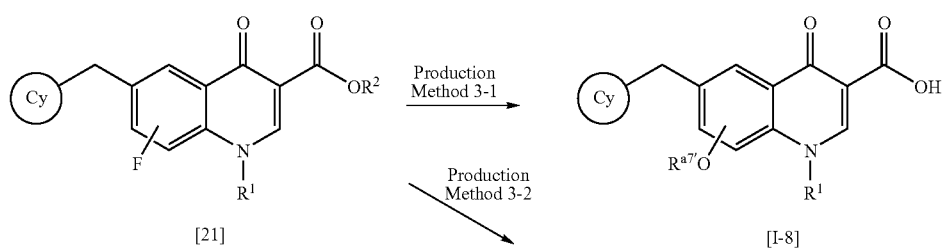

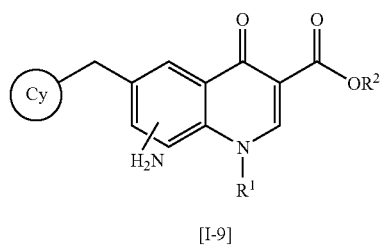

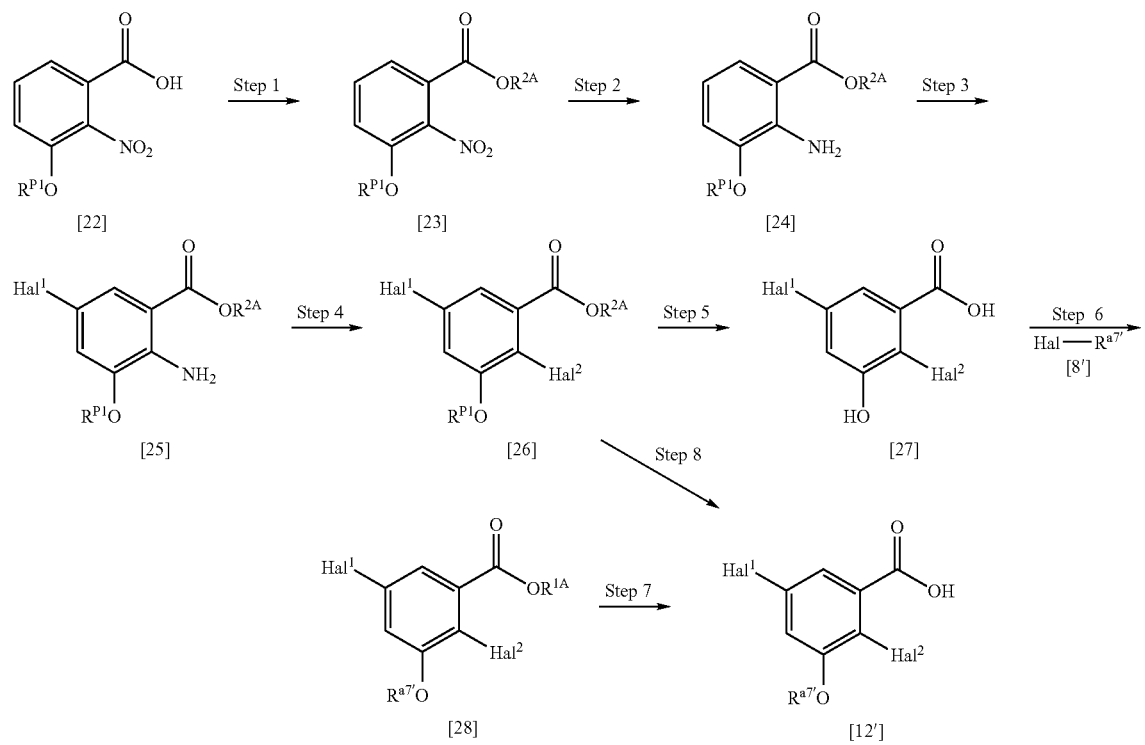

wherein each symbol is as defined above.

Step 1

A protecting group is introduced into the carboxyl group of compound [22] by a conventional method, whereby compound [23] can be obtained.

In the case of esterification, for example, compound [22] is reacted with an alkylating agent such as methyl iodide and the like, in a solvent such as DMF, THF, toluene, and the like in the presence of a base such as sodium carbonate, potassium carbonate, sodium hydride, potassium hydride, and the like, to give compound [23].

Step 2

Compound [23] is reduced by a conventional method in the same manner as in Step 3 of Production Method 1-1, whereby compound [24] can be obtained.

Step 3

Compound [24] is halogenated by a conventional method in the same manner as in Step 1 of Production Method 2-1, whereby compound [25] can be obtained.

Step 4

Compound [25] is diazotized with sodium nitrite and hydrochloric acid or sulfuric acid in water or an inert organic solvent such as THF, dioxane, ethyl acetate, chloroform, dichloromethane, methanol, ethanol, pyridine, and the like under cooling to room temperature, and then halogenated with copper (I) halide such as copper chloride and the like and concentrated hydrochloric acid under cooling to heating, whereby compound [26] can be obtained. Here, $Hal^2$ is preferably chlorine atom.

Step 5

The hydroxyl group and carboxyl group of compound [26] are deprotected by a conventional method, whereby compound [27] can be obtained.

For example, when $R^{P1}$ is a methyl group, compound [26] is reacted with boron tribromide in dichloromethane under cooling, and then hydrolyzed, whereby compound [27] can be obtained.

Step 6

Compound [27] is reacted with compound [8'] in a solvent in the presence of a base, whereby compound [28] can be obtained.

As compound [8'], for example, alkylating agent such as methoxymethyl chloride, and the like can be mentioned.

As the base, potassium carbonate, sodium carbonate, lithium hydride, sodium hydride, potassium hydride, and the like can be mentioned, with preference given to potassium carbonate.

As the solvent, alcohol solvents such as methanol, ethanol, n-propanol, isopropanol, and the like; hydrocarbon solvents such as benzene, toluene, hexane, xylene, and the like; halogen solvents such as dichloromethane, chloroform, carbon tetrachloride, 1,2-dichloroethane, and the like; ether solvents such as 1,4-dioxane, diethyl ether, 1,2-dimethoxyethane, tetrahydrofuran, and the like; polar solvents such as dimethylformamide, dimethyl sulfoxide, acetonitrile, and the like; water, a mixed solvent thereof and the like can be mentioned.

Step 7

Compound [28] is hydrolyzed by a conventional method in the same manner as in Step 6 of Production Method 1-1, whereby compound [12'] can be obtained.

Step 8

When, in compound [26], $R^{P1}$ is a desired substituent (=—$R^{a7'}$ group), compound [12'] can be obtained in the same manner as in Step 7.

Production Method 5

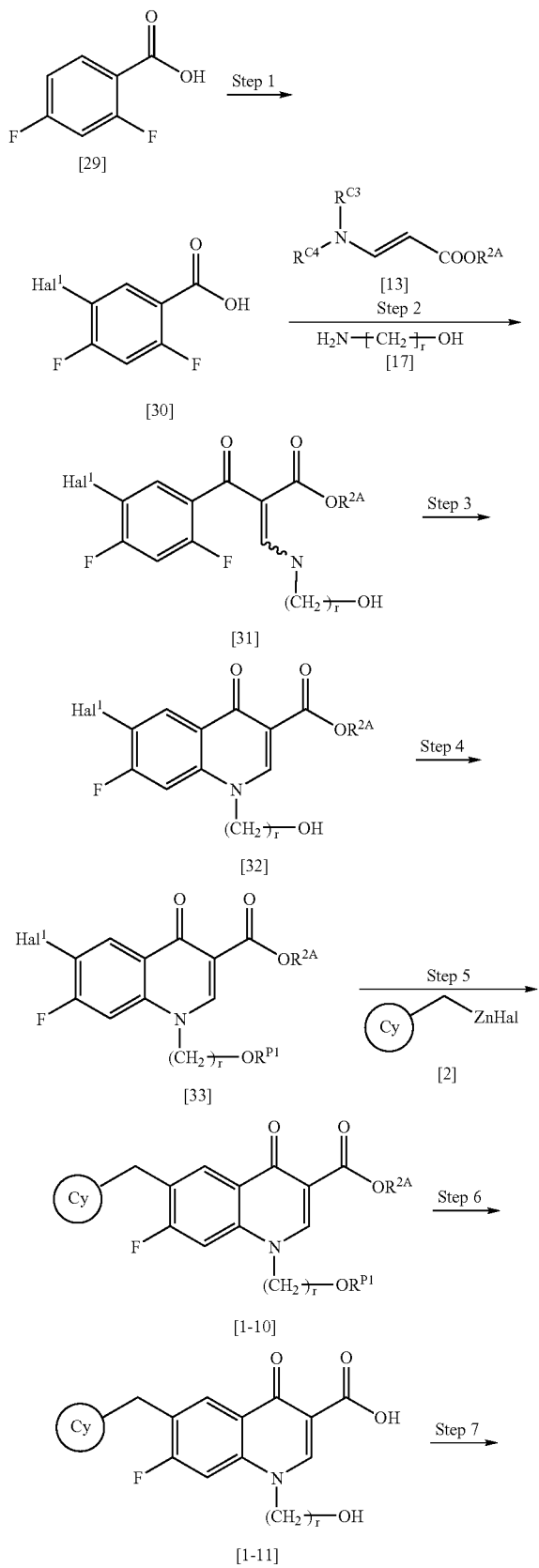

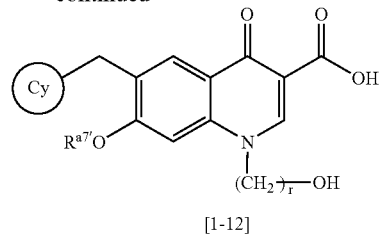

[1-12]

wherein each symbol is as defined above.

Step 1

Compound [29] is halogenated by a conventional method in the same manner as in Step 1 of Production Method 2-1, whereby compound [30] can be obtained.

Step 2

Compound [30] is reacted with compound [13] and then compound [17] in the same manner as in Step 2 of Production Method 2-1, whereby compound [31] can be obtained. Compound [13] may be in the the form of E or Z.

Compound [17] may be $H_2N—R^1$.

Step 3

Compound [31] is reacted in the same manner as in Step 3 of Production Method 2-1, whereby compound [32] can be obtained.

Step 4

Compound [32] is reacted in the same manner as in Step 2 of Production Method 2-2, whereby compound [33] can be obtained.

Step 5

Compound [33] is reacted with compound [2] in the same manner as in Step 2 of Production Method 1-1, whereby compound [I-10] can be obtained.

Step 6

Hydroxyl group and carboxyl group of compound [I-10] are deprotected in the same manner as in Step 2 of Production Method 1-2, whereby compound [I-11] can be obtained.

Step 7

An alkoxy group ($—OR^{a7'}$ group) is introduced into compound [I-11] by a conventional method in the same manner as in Production Method 3-1, whereby compound [I-12] can be obtained.

Compound [17] may be $H_2N—R^1$.

When $R^7$ in compound [I] is a hydroxyl group, compound [I] can be produced according to the above-mentioned methods 1-5 or in a similar manner.

EXAMPLES

Now, the 4-oxoquinoline compound represented by the formula [I] of the present invention or a pharmaceutically acceptable salt thereof, and a production method thereof are explained by way of Reference Examples, Preparation Examples and Examples, which are not to be construed as limitative.

Reference Example 1

Preparation of Solution of 2,3-dichlorobenzylzinc chloride in THF

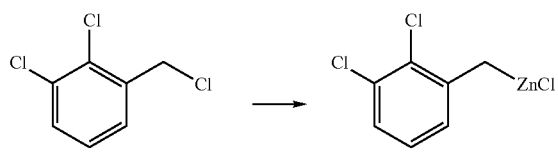

Under an argon stream, to a suspension of zinc powder (55.1 g, 843 mmol) in tetrahydrofuran (THF; 56 ml) was added 1,2-dibromoethane (2.9 ml, 33.8 mmol), and the mixture was heated under reflux for 5 min. Subsequently, trimethylsilyl chloride (8.6 ml, 67.5 mmol) was added at 0° C., and the mixture was stirred at 0° C. for 5 min. A solution of 2,3-dichlorobenzyl chloride (82.4 g, 421.7 mmol) in THF (330 ml) was added dropwise under ice-cooling, and after the completion of the dropwise addition, the mixture was allowed to warm to room temperature. The mixture was stirred for 1 hr to give a solution of 2,3-dichlorobenzylzinc chloride in THF.

Reference Example 2

Synthesis of 6-(2,3-dichlorobenzyl)-1,4-dihydro-1-(2-hydroxyethyl)-4-oxo-3-quinolinecarboxylic acid Step 1 Synthesis of 1,2-dichloro-3-(4-nitrobenzyl)benzene

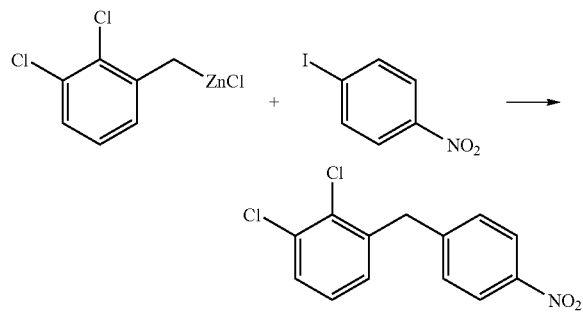

Under an argon stream, bis(dibenzylidenacetone)palladium(0) (3.2 g, 5.6 mmol) and tri(2-furyl)phosphine (2.6 g, 11.2 mmol) were dissolved in THF (310 ml), the reaction mixture of 2,3-dichlorobenzylzinc chloride (421.7 mmol) in THF obtained in Reference Example 1 was added dropwise under ice-cooling through a cannula, and then a solution of 4-iodonitrobenzene (70.0 g, 281 mmol) in THF (700 ml) was added dropwise, after which the mixture was stirred at room temperature for 2 hr, saturated aqueous ammonium chloride solution was added to the reaction mixture, and the mixture was filtered through celite. The filtrate was concentrated under reduced pressure, water was added to the residue, and the mixture was extracted with ethyl acetate. The organic layer was washed with water and saturated brine, and dried over sodium sulfate. After filtration, the filtrate was concentrated under reduced pressure, and the precipitated solid was collected by filtration on the way. The filtrate was again concentrated under reduced pressure, and the precipitated solid was collected by filtration on the way. The collected solids were combined washed with n-hexane and vacuum dried to give the object product (60.2 g, yield 76%) as a pale-brown solid.

$^1$H NMR (CDCl$_3$ 400 MHz) (δ) ppm: 4.24 (2H, s), 7.09 (1H, d, J=7.7 Hz), 7.18 (1H, dd, J=7.8 Hz, 7.9 Hz), 7.32 (2H, d, J=8.9 Hz), 7.40 (1H, d, J=8.0 Hz), 8.15 (2H, d, J=8.7 Hz)

MS (ESI) : M− 280

Step 2 Synthesis of 4-(2,3-dichlorobenzyl)phenylamine

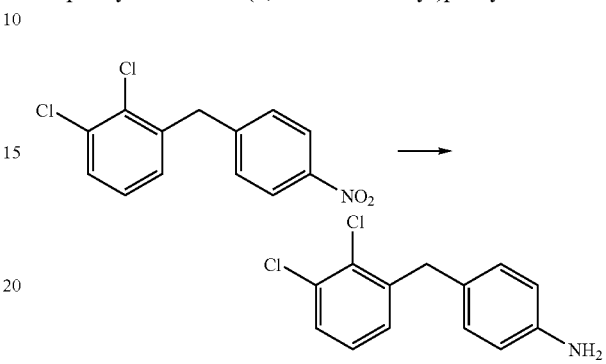

1,2-Dichloro-3-(4-nitrobenzyl)benzene (25.0 g, 88.6 mmol) obtained in Step 1 was dissolved in acetic acid (400 ml), zinc powder (70 g, 1.1 mol) was added by portions at 0° C., and the mixture was stirred at room temperature for 1 hr. The reaction mixture was filtered through celite and washed with ethanol. The filtrate was concentrated under reduced pressure, and the precipitated solid was collected by filtration on the way. The filtrated solid was washed with diethyl ether, and dissolved in ethyl acetate (500 ml) and water (500 ml), 4N aqueous sodium hydroxide solution was added to neutralize the aqueous layer. The organic layer was separated and the aqueous layer was further extracted with ethyl acetate. The organic layers were combined washed with water and saturated brine, and dried over sodium sulfate. After filtration, the filtrate was concentrated under reduced pressure, and the precipitated solid was collected by filtration on the way. The filtrated solid was washed with n-hexane and vacuum dried to give the object product (18.1 g, yield 81%) as a pale-brown solid.

$^1$H NMR (CDCl$_3$ 400 MHz) (δ) ppm: 3.52 (2H, brs), 4.01 (2H, s), 6.63 (2H, d, J=8.2 Hz), 6.97 (2H, d, J=8.1 Hz), 7.02 (1H, d, J=7.6 Hz), 7.09 (1H, dd, J=7.8 Hz, 7.8 Hz), 7.31 (1H, d, J=7.8 Hz)

MS (ESI): M+ 252

Step 3 Synthesis of ethyl 6-(2,3-dichlorobenzyl)-1,4-dihydro-4-oxo-3-quinolinecarboxylate

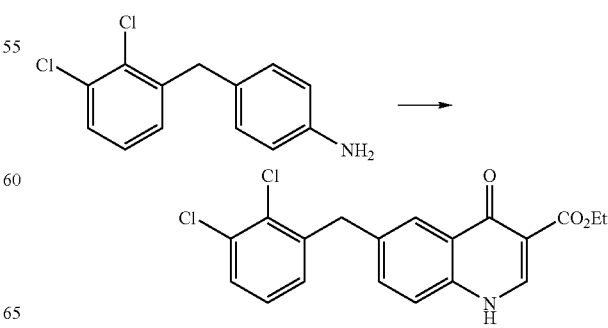

4-(2,3-Dichlorobenzyl)phenylamine (10.0 g, 39.7 mmol) obtained in Step 2 was dissolved in toluene (100 ml), diethyl ethoxymethylenemalonate (8.8 ml, 43.7 mmol) was added, and the mixture was heated under reflux for 3 hr. The reaction mixture was concentrated under reduced pressure, diphenyl ether (100 ml) was added to the residue to allow dissolution, and the mixture was stirred with heating at 250° C. for 3 hr. After allowing to cool, n-hexane was added to the reaction mixture, The precipitated solid was collected by filtration, washed with chloroform, and vacuum dried to give the object product (10.1 g, yield 68%) as a pale-yellow solid.

$^1$H NMR (DMSO-d$_6$ 400 MHz) (δ) ppm: 1.27 (3H, t, J=7.1 Hz), 4.20 (2H, q, J=7.1 Hz), 4.27 (2H, s), 7.34-7.41 (2H,m), 7.55-7.57 (3H, m), 7.90 (1H, s), 8.49 (1H, d, J=6.6 Hz), 12.26 (1H, brs)

MS (ESI): M+ 376

Step 4 Synthesis of ethyl 1-(2-acetoxyethyl)-6-(2,3-dichlorobenzyl)-1,4-dihydro-4-oxo-3-quinolinecarboxylate

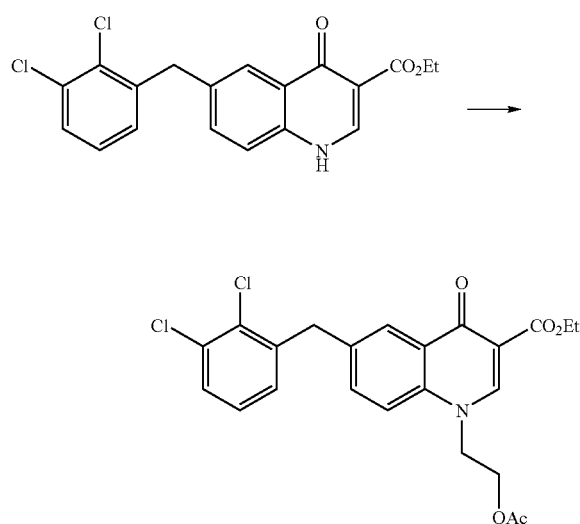

Ethyl 6-(2,3-dichlorobenzyl)-1,4-dihydro-4-oxo-3-quinolinecarboxylate (400 mg, 1.1 mmol) obtained in Step 3 was suspended in dimethylformamide (DMF; 8 ml), 2-bromoethyl acetate (152 μl, 1.4 mmol) and potassium carbonate (440 mg, 3.2 mmol) were added, and the mixture was stirred with heating at 80° C. 2-Bromoethyl acetate (152 μl, 1.4 mmol) was added twice on the way, and the mixture was stirred with heating at 80° C. for 1.5 hr in total. After allowing to cool, saturated aqueous ammonium chloride was added to the reaction mixture, and the precipitated solid was collected by filtration, washed with water, and vacuum dried to give the object product (468 mg, yield 95%) as a white solid.

$^1$H NMR (DMSO-d$_6$ 400 MHz) (δ) ppm: 1.25 (3H, t, J=9.3 Hz), 1.88 (3H, s), 4.20 (2H, q, J=9.3 Hz), 4.27 (2H, s), 4.33-4.41 (2H, m), 4.59-4.62 (2H, m), 7.32-7.41 (3H, m), 7.54 (1H, dd, J=2.9 Hz, 10.2 Hz), 7.64 (1H, dd, J=2.4 Hz, 11.2 Hz), 7.81 (1H, d, J=11.7 Hz), 7.88 (1H, d, J=2.4 Hz), 8.57 (1H, s)

Step 5 Synthesis of 6-(2,3-dichlorobenzyl)-1,4-dihydro-1-(2-hydroxyethyl)-4-oxo-3-quinolinecarboxylic acid

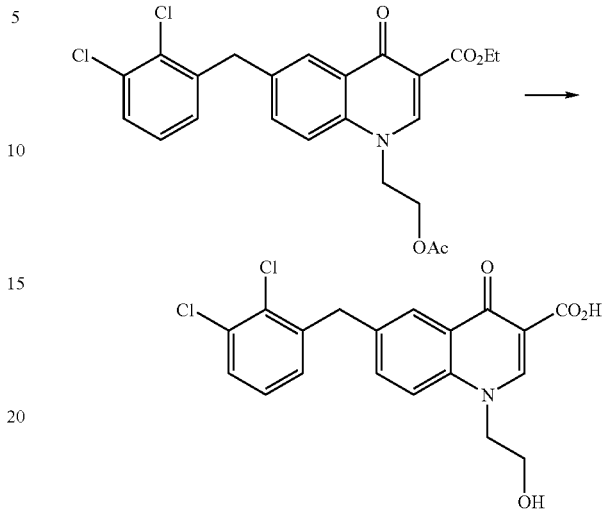

Ethyl 1-(2-acetoxyethyl)-6-(2,3-dichlorobenzyl)-1,4-dihydro-4-oxo-3-quinolinecarboxylate (6.0 g, 13.0 mmol) obtained in Step 4 was suspended in ethanol (480 ml), 4N aqueous sodium hydroxide solution (84 ml, 21 mmol) was added, and the mixture was heated under reflux for 30 min. After allowing to cool, the reaction mixture was partially concentrated under reduced pressure and hydrochloric acid was added. The precipitated solid was collected by filtration, washed with water and ethanol, and vacuum dried to give the object product (4.5 g, yield 85%) as a white solid.

$^1$H NMR (DMSO-d$_6$ 400 MHz) (δ) ppm: 3.75 (2H, t, J=4.7 Hz), 4.36 (2H, s), 4.60 (2H, t, J=4.8 Hz), 4.98 (1H, brs), 7.37-7.39 (1H, m), 7.45 (1H, dd, J=1.4, 7.6 Hz), 7.57 (1H, dd, J=1.5, 8.0 Hz), 7.81 (1H, dd, J=2.1, 8.9 Hz), 8.02 (1H, d, J=8.8 Hz), 8.15 (1H, d, J=1.8 Hz), 8.86 (1H, s), 15.18 (1H, brs)

MS (ESI) : M+ 392 m.p.: 247-249° C.

Reference Example 3

Synthesis of 6-(2,3-dichlorobenzyl)-1,4-dihydro-8-fluoro-1-(2-hydroxyethyl)-4-oxo-3-quinolinecarboxylic acid Step 1 Synthesis of 2,3-difluoro-5-iodobenzoic acid

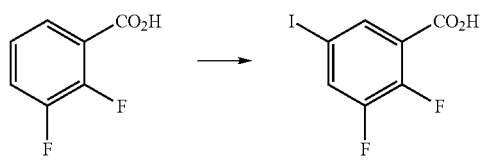

2,3-Difluorobenzoic acid (5.0 g, 31.6 mmol) was dissolved in trifluoromethanesulfonic acid (25 ml) and N-iodosuccinimide (8.55 g, 38.0 mmol) was cast by portions under an argon stream at 0° C. After stirring at room temperature for 3 hr, the reaction mixture was poured into sodium sulfite in ice water and stirred. The precipitated solid was collected by filtration, washed with water, and vacuum dried to give the object product (7.5 g, yield 84%) as a pale-pink solid.

$^1$H NMR (CDCl$_3$ 300 MHz) (δ) ppm: 7.74 (1H, m), 8.11 (1H, m)

MS (ESI): M− 283

Step 2 Synthesis of ethyl 2-(2,3-difluoro-5-iodobenzoyl)-3-(2-hydroxyethylamino)acrylate

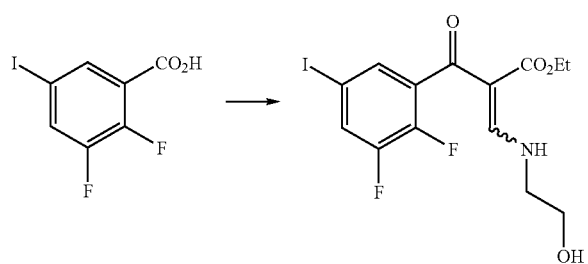

2,3-Difluoro-5-iodobenzoic acid (3.0 g, 10.6 mmol) obtained in Step 1 was dissolved in toluene, thionyl chloride (3.0 ml, 41.1 mmol) and DMF (catalytic amount) were added, and the mixture was heated under reflux for 3 hr. The reaction mixture was concentrated under reduced pressure and THF (15 ml) was added to the residue to allow dissolution. The mixture was added dropwise to a solution of ethyl 3-dimethylaminoacrylate (1.66 g, 11.6 mmol) and triethylamine (1.77 ml, 12.7 mmol) in THF (10 ml) and the mixture was stirred with heating at 50OC for 2.5 hr. After allowing to cool, the reaction mixture was filtered and washed with THF (10 ml). Aminoethanol (0.77 ml, 12.7 mmol) was added to the filtrate, and the mixture was stirred with heating at 40° C. for 1 hr. After allowing to cool, water was added to the reaction mixture and the mixture was extracted with ethyl acetate. The organic layer was washed with water and saturated brine, and dried over sodium sulfate. After filtration, the filtrate was concentrated under reduced pressure, and the obtained residue was purified by silica gel chromatography (ethyl acetate:hexane=2:1) to give the object product (3.8 g, yield 85%) as an E and Z mixed yellow solid.

$^1$H NMR (CDCl$_3$ 400 MHz) (δ) ppm: 0.91-1.09 (3H, m), 1.80-1.89 (1H, m), 3.52-3.63 (2H, m), 3.83-3.91 (2H, m), 3.98-4.09 (2H, m), 7.36-7.52 (2H, m), 8.15 (1H, d, J=14.4 Hz), 9.6 (0.22H, brs), 11.0 (0.78H, brs)

MS (ESI): M+ 426

Step 3 Synthesis of ethyl 2-(2,3-difluoro-5-iodobenzoyl)-3-[2-(tert-butyldimethylsilyloxy)ethylamino]acrylate

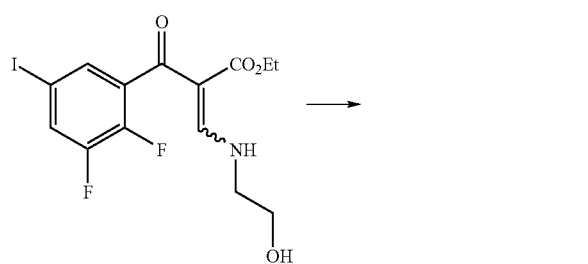

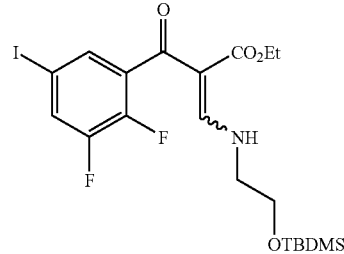

Ethyl 2-(2,3-difluoro-5-iodobenzoyl)-3-(2-hydroxyethylamino)acrylate (2.0 g, 4.7 mmol) obtained in Step 2 was dissolved in DMF (10 ml), imidazole (705 mg, 10.4 mmol) and tert-butyldimethylsilyl chloride (1.49 g, 9.9 mmol) were added, and the mixture was stirred at room temperature for 4 hr. Water was added to the reaction mixture and the mixture was extracted with ethyl acetate. The organic layer was washed with water and saturated brine, and dried over sodium sulfate. After filtration, the filtrate was concentrated under reduced pressure, and the obtained residue was purified by silica gel chromatography (ethyl acetate:hexane=1:4) to give the object product (2.3 g, yield 91%) as a white solid.

$^1$H NMR (CDCl$_3$ 300 MHz) (δ) ppm:0.07 (6H, s), 0.90 (9H, s), 1.07 (3H, t, J=7.1 Hz), 3.45-3.55 (2H, m), 3.70-3.80 (2H, m), 4.04 (2H, q, J=7.1 Hz), 7.30-7.50 (2H, m), 8.14 (1H, d, J=14.1 Hz), 10.80-11.10 (1H, m)

MS (ESI): M+ 540

Step 4 Synthesis of ethyl 1,4-dihydro-8-fluoro-6-iodo-1-[2-(tert-butyldimethylsilyloxy)ethyl]-4-oxo-3-quinolinecarboxylate

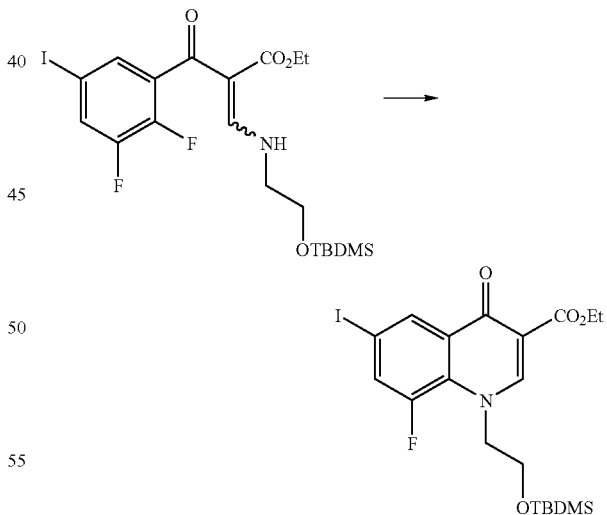

Ethyl 2-(2,3-difluoro-5-iodobenzoyl)-3-[2-(tert-butyldimethylsilyloxy)ethylamino]acrylate (2.3 g, 4.3 mmol) obtained in Step 3 was dissolved in THF (25 ml), sodium hydride (256 mg, 6.4 mmol) was added under ice-cooling and the mixture was stirred at 0° C. for 1 hr. 1N Hydrochloric acid (6.4 ml, 6.4 mmol) was added to neutralize the reaction mixture. Water was further added and the mixture was extracted with ethyl acetate. The organic layer was washed with water and saturated brine, and dried over sodium sulfate. After filtration, the filtrate was concentrated under reduced pressure. The obtained residue was purified by silica gel chromatography (ethyl acetate:hexane=1:2 to ethyl acetate:hexane=2:1) to give the object product (2.0 g, yield 92%) as a white solid.

1H NMR (CDCl$_3$ 300 MHz) (δ) ppm: −0.12 (6H, s), 0.79 (9H, s), 1.38 (3H, t, J=7.1 Hz), 3.90-4.00 (2H, m), 4.37 (2H, q, J=7.1 Hz), 4.40-4.50 (2H, m), 7.69 (1H, dd, J=2.0 Hz, 13.7 Hz), 8.40 (1H, s), 8.69 (1H, d, J=2.0 Hz)

MS (ESI): M+ 520

Step 5 Synthesis of ethyl 6-(2,3-dichlorobenzyl)-1,4-dihydro-8-fluoro-1-[2-(tert-butyldimethylsilyloxy)ethyl]-4-oxo-3-quinolinecarboxylate

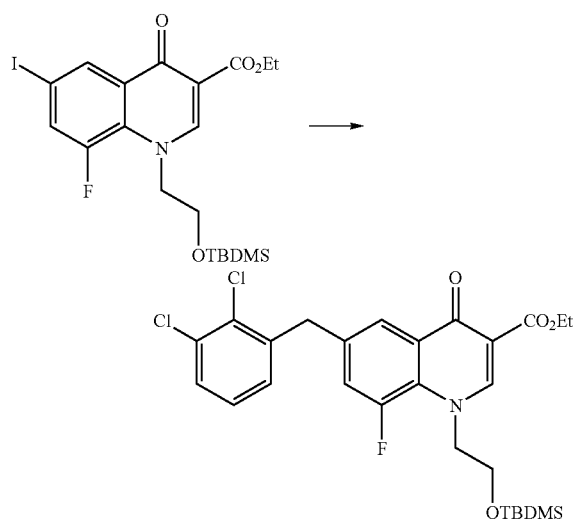

Under an argon stream, the 1M THF solution (2.9 ml, 2.9 mmol) of 2,3-dichlorobenzylzinc chloride obtained in the same manner as in Reference Example 1 was added to THF (20 ml), then bis(dibenzylideneacetone)palladium(0) (22 mg, 0.039 mmol), tri(2-furyl)phosphine (18 mg, 0.077 mmol) and ethyl 1,4-dihydro-8-fluoro-6-iodo-1-[2-(tert-butyldimethylsilyloxy)ethyl]-4-oxo-3-quinolinecarboxylate (1.0 g, 1.9 mmol) obtained in Step 4 were added. The mixture was stirred at room temperature for 17 hr, a solution (1.0 ml, 1.0 mmol) of 2,3-dichlorobenzylzinc chloride in THF was further added, and the mixture was heated under reflux for 1 hr. After allowing to cool, saturated aqueous ammonium chloride solution was added to the reaction mixture, and the insoluble material was filtered through celite. The filtrate was extracted with ethyl acetate. The organic layer was washed with water and saturated brine, and dried over sodium sulfate. After filtration, the filtrate was concentrated under reduced pressure, and the obtained residue was crudely purified by silica gel chromatography (ethyl acetate:hexane=1:1) and successively purified by PTLC (ethyl acetate:chloroform=1:2) to give the object product (562 mg, yield 53%) as a pale-yellow oil.

$^1$H NMR (CDCl$_3$ 300 MHz) (δ) ppm: −0.13 (6H, s), 0.79 (9H, s), 1.38 (3H, t, J=7.1 Hz), 3.90-4.00 (2H, m), 4.23 (2H,s), 4.37 (2H, q, J=7.1 Hz), 4.40-4.50 (2H, m), 7.10-7.50 (4H, m), 8.20-8.30 (1H, m), 8.39 (1H, s)

MS (ESI): M+ 552

Step 6 Synthesis of ethyl 6-(2,3-dichlorobenzyl)-1,4-dihydro-8-fluoro-1-(2-hydroxyethyl)-4-oxo-3-quinolinecarboxylate

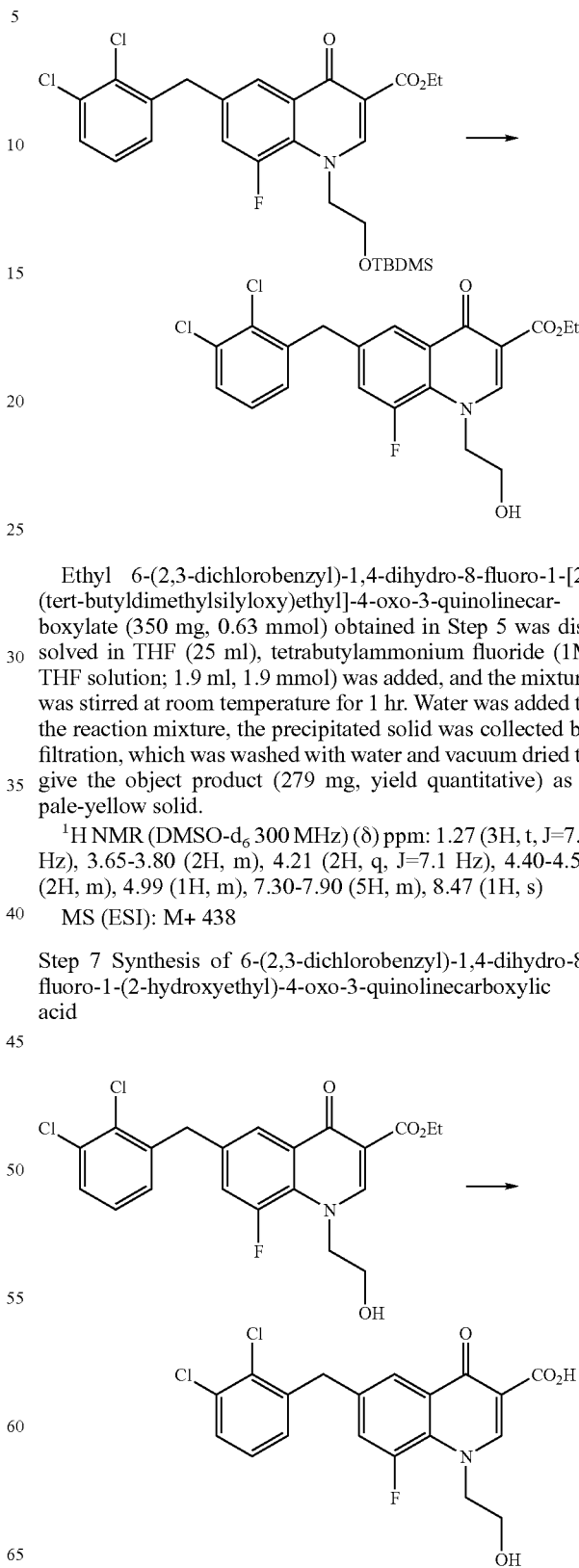

Ethyl 6-(2,3-dichlorobenzyl)-1,4-dihydro-8-fluoro-1-[2-(tert-butyldimethylsilyloxy)ethyl]-4-oxo-3-quinolinecarboxylate (350 mg, 0.63 mmol) obtained in Step 5 was dissolved in THF (25 ml), tetrabutylammonium fluoride (1M THF solution; 1.9 ml, 1.9 mmol) was added, and the mixture was stirred at room temperature for 1 hr. Water was added to the reaction mixture, the precipitated solid was collected by filtration, which was washed with water and vacuum dried to give the object product (279 mg, yield quantitative) as a pale-yellow solid.

$^1$H NMR (DMSO-d$_6$ 300 MHz) (δ) ppm: 1.27 (3H, t, J=7.1 Hz), 3.65-3.80 (2H, m), 4.21 (2H, q, J=7.1 Hz), 4.40-4.50 (2H, m), 4.99 (1H, m), 7.30-7.90 (5H, m), 8.47 (1H, s)

MS (ESI): M+ 438

Step 7 Synthesis of 6-(2,3-dichlorobenzyl)-1,4-dihydro-8-fluoro-1-(2-hydroxyethyl)-4-oxo-3-quinolinecarboxylic acid Ethyl 6-(2,3-dichlorobenzyl)-1,4-dihydro-8-fluoro-1-(2-hydroxyethyl)-4-oxo-3-quinolinecarboxylate (80 mg, 0.18 mmol) obtained in Step 6 was dissolved in a mixed solvent of ethanol (2 ml) and THF (1 ml), 1N aqueous sodium hydroxide solution (1 ml, 1.0 mmol) was added, and the mixture was stirred with heating at 60° C. for 1 hr. After allowing to cool, 10% aqueous citric acid solution was added to the reaction mixture. The precipitated solid was collected by filtration, washed with 30% aqueous ethanol and vacuum dried to give the object product (70 mg, yield 93%) as a white solid.

$^1$H NMR (DMSO-$d_6$ 300 MHz) (δ) ppm: 3.78 (2H, m), 4.35 (2H, s), 4.64 (2H, m), 5.00 (1H, m), 7.39 (2H, m), 7.47 (1H, m), 7.58 (1H, m), 8.00 (1H, m), 8.81 (1H, s), 14.80 (1H, s)

MS (ESI) : M+409

Reference Example 4

Step 1

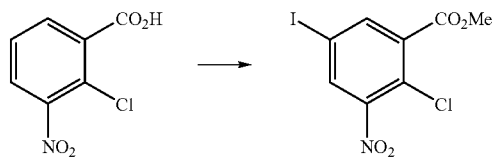

2-Chloro-3-nitrobenzoic acid (6.00 g, 29.77 mmol) was dissolved in trifluoromethanesulfonic acid (40 ml) and N-iodosuccinimide (7.37 g, 32.76 mmol) was added by portions at 0° C. After stirring at 40° C. for 4 hr, the reaction mixture was added to ice water. After stirring, the precipitated solid was collected by filtration, washed with water and vacuum dried. The obtained solid was dissolved in methanol (50 ml), concentrated sulfuric acid (catalytic amount) was added, and the mixture was heated under reflux for 5.5 hr. The reaction mixture was concentrated under reduced pressure, and the obtained residue was purified by silica gel chromatography (ethyl acetate:hexane=1:4) to give the object product (5.35 g, yield 53%) as a pale-yellow solid.

$^1$H NMR (CDCl$_3$ 300 MHz) (δ) ppm: 3.98 (3H, s), 8.11 (1H, d, J=2.1 Hz), 8.24 (1H, d, J=2.1 Hz)

Step 2

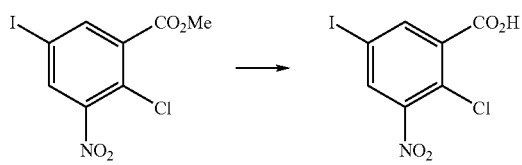

The compound (5.35 g, 15.67 mmol) obtained in Step 1 was dissolved in methanol (25 ml), 4N aqueous potassium hydroxide solution (10.00 ml, 4.00 mmol) was added, and the mixture was heated under reflux for 30 min. After allowing to cool, 1N hydrochloric acid was added to the reaction mixture. The precipitated solid was collected by filtration and vacuum dried to give the object product (4.99 g, yield 97%) as a white solid.

$^1$H NMR (CDCl$_3$ 300 MHz) (δ) ppm: 8.14 (1H, d, J=2.0 Hz), 8.39 (1H, d, J=2.1 Hz)

Step 3

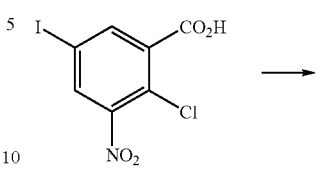

The compound (4.99 g, 15.24 mmol) obtained in Step 2 was dissolved in toluene (50 ml), thionyl chloride (5.00 ml, 68.54 mmol) and dimethylformamide (catalytic amount) were added, and the mixture was heated under reflux for 1 hr. The reaction mixture was concentrated under reduced pressure, and tetrahydrofuran (80 ml) was added to the residue to allow dissolution. The obtained solution was added dropwise to a solution of ethyl 3-dimethylaminoacrylate (2.29 g, 16.00 mmol) and triethylamine (2.55 ml, 18.30 mmol) in tetrahydrofuran (50 ml), and the mixture was stirred with heating at 50° C. for 10 hr. After allowing to cool, aminoethanol (1.10 ml, 18.23 mmol) was added to the reaction mixture, and the mixture was stirred with heating at 40° C. for 1.5 hr. After allowing to cool, water was added to the reaction mixture and the mixture was extracted with ethyl acetate. The organic layer was washed with water and saturated brine in this order and dried over sodium sulfate. After filtration, the filtrate was concentrated under reduced pressure, and the obtained residue was purified by silica gel chromatography (ethyl acetate:hexane=2:1) to give the object product (5.35 g, yield 75%) comprising an E form and a Z form in a mixture as a yellow solid.

$^1$H NMR (CDCl$_3$ 300 MHz) (δ) ppm: 0.82-1.01 (3H, m), 3.63 (2H, br), 3.85-4.06 (4H, m), 7.65-7.68 (1H, m), 8.02-8.06 (1H, m), 8.21-8.36 (1H, m), 9.78 (0.16H, br), 11.15 (0.84H, br)

Step 4

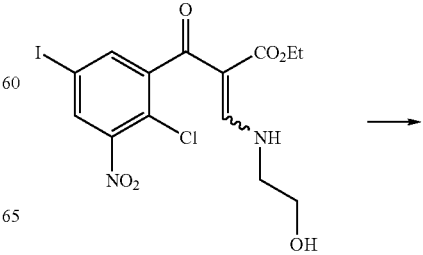

-continued

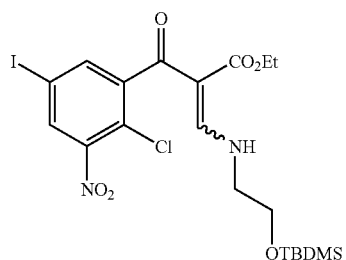

The compound (5.35 g, 11.42 mmol) obtained in Step 3 was dissolved in dimethylformamide (50 ml), imidazole (1.71 g, 25.12 mmol) and tert-butyldimethylsilyl chloride (3.62 g, 24.02 mmol) were added, and the mixture was stirred at room temperature for 30 min. Water was added to the reaction mixture and the mixture was extracted with ethyl acetate. The organic layer was washed with water and saturated brine in this order and dried over sodium sulfate. After filtration, the filtrate was concentrated under reduced pressure to give a crude product (7.10 g) as a pale-yellow solid.

Step 5

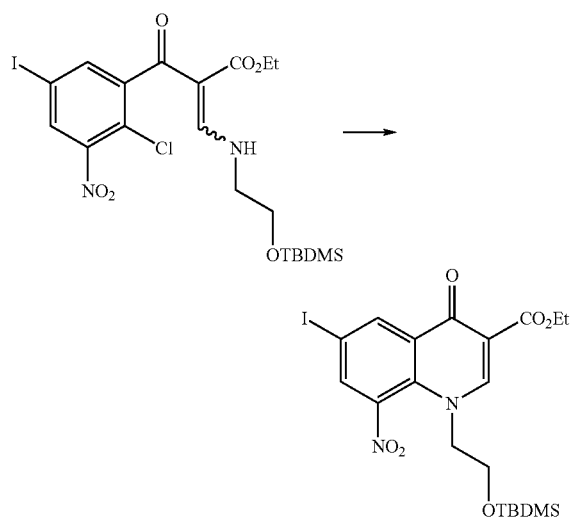

The crude product (7.10 g) obtained in Step 4 was dissolved in tetrahydrofuran (70 ml), sodium hydride (731 mg, 18.27 mmol) was added under ice-cooling, and the mixture was stirred at 0° C. for 45 min. 1N Hydrochloric acid (18.3 ml) and water were added to the reaction mixture and the mixture was stirred and extracted with ethyl acetate. The organic layer was washed with water and saturated brine in this order, and dried over sodium sulfate. After filtration, the filtrate was concentrated under reduced pressure and purified by silica gel chromatography (ethyl acetate:hexane=1:4 to 1:2) to give the object product (5.58 g, yield 84%) as a yellow solid.

$^1$H NMR (CDCl$_3$ 300 MHz) (δ) ppm: −0.14 (6H, s), 0.73 (9H, s), 1.39 (3H, t, J=7.1 Hz), 3.74 (2H, t, J=4.6 Hz), 4.02 (2H, t, J=4.6 Hz), 4.39 (2H, q, J=7.1 Hz), 8.13 (1H, d, J=2.2 Hz), 8.50 (1H, s), 9.02 (1H, d, J=2.2 Hz)

Step 6

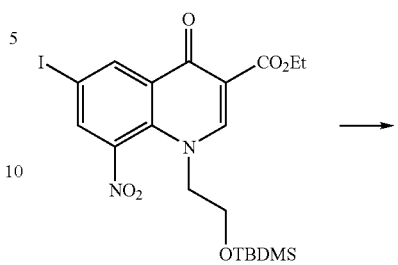

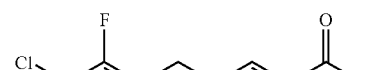

The compound (5.00 g, 9.15 mmol) obtained in Step 5 was dissolved in tetrahydrofuran (100 ml) and bis(dibenzylidenacetone)palladium(0) (105 mg, 0.18 mmol) and tri(2-furyl)phosphine (85 mg, 0.37 mmol) were added under an argon stream. A solution of 3-chloro-2-fluorobenzylzinc bromide (11.90 mmol) in tetrahydrofuran prepared as in Reference Example 9, Step 4 to be mentioned later was added dropwise at 60° C. After the completion of the dropwise addition, the mixture was heated under reflux for 4 hr. After allowing to cool, saturated aqueous ammonium chloride solution was added to the reaction mixture and an insoluble material was filtered through celite. The filtrate was extracted with ethyl acetate. The organic layer was washed with water and saturated brine in this order and dried over sodium sulfate. After filtration, the filtrate was concentrated under reduced pressure, and the obtained residue was purified by silica gel chromatography (ethyl acetate:hexane=1:2 to 1:1) to give the object product (2.67 g, yield 52%) as a brown oil.

$^1$H NMR (CDCl$_3$ 300 MHz) (δ) ppm: −0.19 (6H, s), 0.70 (9H, s), 1.39 (3H, t, J=7.1 Hz), 3.73 (2H, t, J=4.6 Hz), 4.03 (2H, t, J=4.6 Hz), 4.14 (2H, s), 4.38 (2H, q, J=7.1 Hz), 7.02-7.14 (2H, m), 7.29-7.35 (1H, m), 7.73 (1H, d, J=2.2 Hz), 8.50(1H, s), 8.59 (1H, s)

Step 7

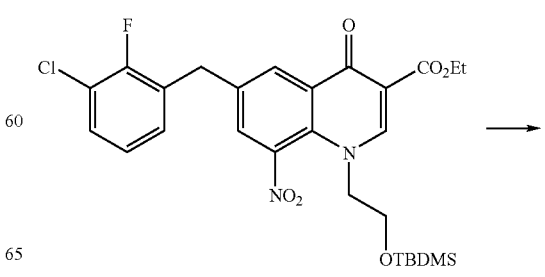

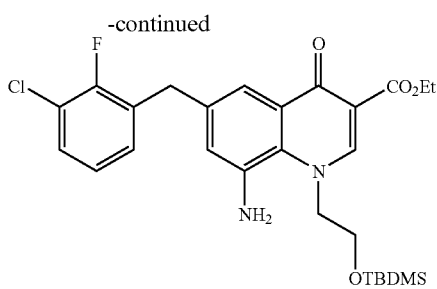

The compound (1.00 g, 1.79 mmol) obtained in Step 6 was dissolved in acetic acid (20 ml), zinc powder (1.16 g, 17.76 mmol) was added, and the mixture was stirred at room temperature for 4 hr. The reaction mixture was filtered through celite and saturated aqueous sodium hydrogen carbonate was added to the filtrate. The mixture was extracted with ethyl acetate. The organic layer was washed with saturated aqueous sodium hydrogen carbonate, water and saturated brine in this order, and dried over sodium sulfate. After filtration, the filtrate was concentrated under reduced pressure, and the obtained residue was purified by silica gel chromatography (ethyl acetate). Diethyl ether was added and the mixture was sonicated, filtered and vacuum dried to give the object product (730 mg, yield 77%) as a pale-orange solid.

$^1$H NMR (CDCl$_3$ 300 MHz) (δ) ppm: −0.06 (6H, s), 0.77 (9H, s), 1.41(3H, t, J=7.1 Hz), 4.01 (2H, s), 4.08 (2H, t, J=4.7 Hz), 4.39 (2H, q, J=7.1 Hz), 4.50 (2H, brs), 4.75 (2H, t, J=4.7 Hz), 6.81 (1H, s), 6.94-7.08 (2H, m), 7.20-7.26 (1H, m), 7.91 (1H, s), 8.34 (1H, s)

Step 8

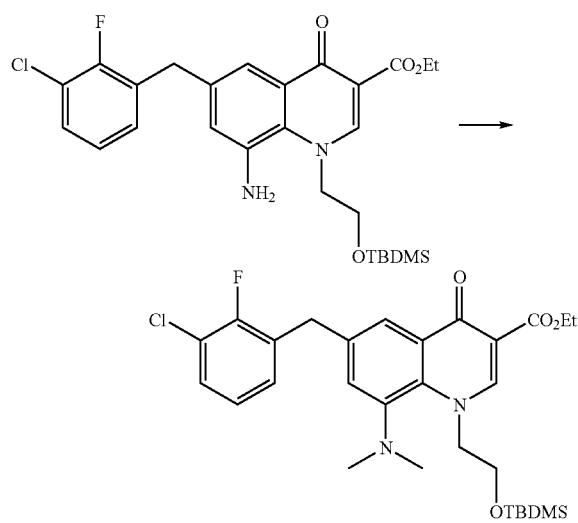

The compound (100 mg, 0.19 mmol) obtained in Step 7 was dissolved in dimethylformamide (2 ml), methyl iodide (0.029 ml, 0.47 mmol) and sodium hydride (23 mg, 0.56 mmol) were added, and the mixture was stirred at room temperature for 2 hr. 10% Aqueous citric acid solution was added to the reaction mixture, and the mixture was stirred and extracted with ethyl acetate. The organic layer was washed with water and saturated brine in this order, and dried over sodium sulfate. After filtration, the filtrate was concentrated under reduced pressure and subjected to silica gel chromatography (ethyl acetate:hexane=2:1) to give a crudely purified product (45 mg) as a pale-red solid.

$^1$H NMR (CDCl$_3$ 300 MHz) (δ) ppm: −0.33-0.29 (6H, m), 0.64-0.69 (9H, m), 1.23-1.41 (3H, m), 2.66-2.70 (6H, m), 3.55-3.59 (2H, m), 4.36-4.42 (4H, m), 4.82-4.96 (2H, m), 6.96-7.11 (2H, m), 7.23-7.30 (2H, m), 8.16-8.15 (1H, m), 8.40-8.66 (1H, m)

Step 9

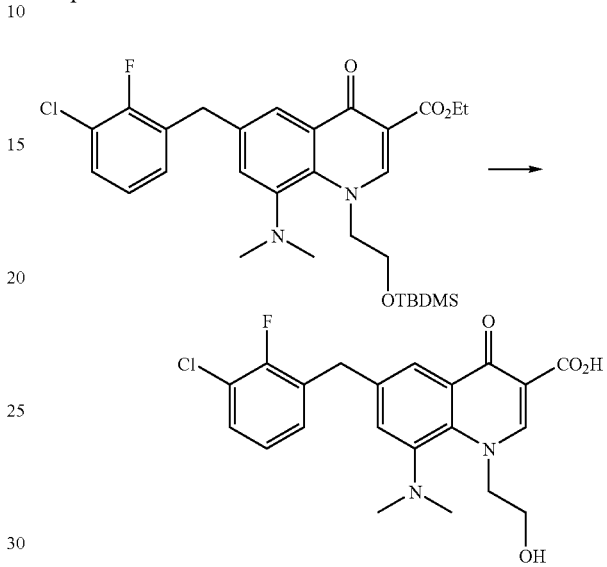

The crudely purified product (45 mg) obtained in Step 8 was dissolved in tetrahydrofuran (1 ml), 1M THF solution (1.00 ml, 1.00 mmol) of tetrabutylammonium fluoride was added, and the mixture was stirred at room temperature for 5 min. Ethanol (1 ml) and 1N aqueous sodium hydroxide solution (1 ml, 1.00 mmol) were added to the reaction mixture, and the mixture was heated under reflux for 2 hr. After allowing to cool, 10% aqueous citric acid solution was added to the reaction mixture and the mixture was stirred and extracted twice with chloroform. The organic layer was washed with saturated brine and dried over sodium sulfate. After filtration, the filtrate was concentrated under reduced pressure and applied to silica gel chromatography (chloroform:methanol: acetic acid=10:1:0.1) to give a crudely purified product. Aqueous ethanol was added to the crudely purified product and the mixture was sonicated, filtered and vacuum dried to give the object product (22 mg, yield 27%) as a beige solid.

$^1$H NMR (DMSO-d$_6$ 300 MHz) (δ) ppm: 2.67 (6H, s), 3.39 (2H, m), 4.21 (2H, s), 4.72 (1H, t), 4.97 (2H, t), 7.20-7.22 (1H, m), 7.40-7.50 (2H, m), 7.65 (1H, s), 7.84 (1H, s), 15.10 (1H, s)

MS (ESI): M+ 419

Reference Example 5

Step 1

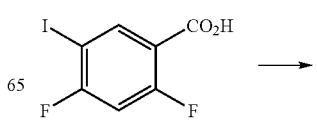

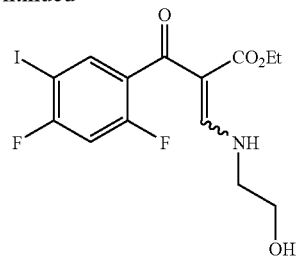

2,4-Difluoro-5-iodobenzoic acid (3.00 g, 10.60 mmol) obtained in Reference Example 10, Step 1 to be mentioned later was dissolved in toluene (10 ml), thionyl chloride (3.00 ml, 41.10 mmol) and dimethylformamide (catalytic amount) were added, and the mixture was heated under reflux for 1.5 hr. The reaction mixture was concentrated under reduced pressure, and tetrahydrofuran (15 ml) was added to the residue to allow dissolution. The obtained solution was added dropwise to a solution of ethyl 3-dimethylaminoacrylate (1.66 g, 11.60 mmol) and triethylamine (1.77 ml, 12.70 mmol) in tetrahydrofuran (10 ml), and the mixture was stirred with heating at 50° C. for 2.5 hr. After allowing to cool, the reaction mixture was filtered, and washed with tetrahydrofuran (10 ml). Aminoethanol (0.77 ml, 12.76 mmol) was added to the filtrate, and the mixture was stirred with heating at 40° C. for 1 hr. After allowing to cool, water was added to the reaction mixture and the mixture was extracted with ethyl acetate. The organic layer was washed with water and saturated brine in this order and dried over sodium sulfate. After filtration, the filtrate was concentrated under reduced pressure, and the obtained residue was purified by silica gel chromatography (ethyl acetate:hexane=2:1) to give a crudely purified product (3.00 g, yield 67%) comprising an E form and a Z form in a mixture as a yellow solid.

Step 2

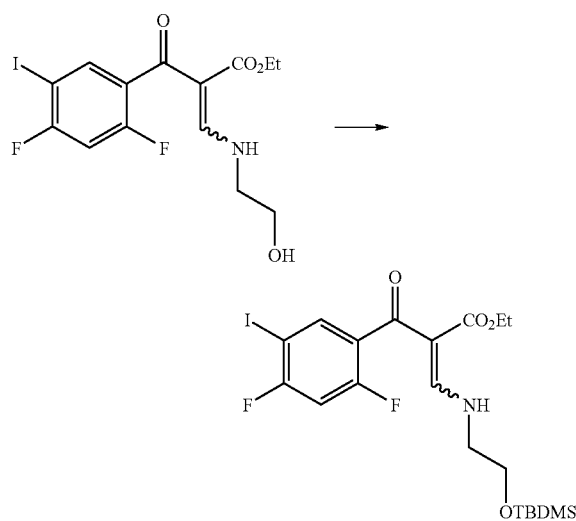

The compound (3.00 g, 7.06 mmol) obtained in Step 1 was dissolved in dimethylformamide (15 ml), imidazole (1.06 g, 15.52 mmol) and tert-butyldimethylsilyl chloride (2.23 g, 14.82 mmol) were added, and the mixture was stirred for at room temperature for 14 hr. Water was added to the reaction mixture and the mixture was extracted with ethyl acetate. The organic layer was washed with water and saturated brine in this order and dried over sodium sulfate. After filtration, the filtrate was concentrated under reduced pressure, and the obtained residue was purified by silica gel chromatography (ethyl acetate:hexane=1:4) to give the object product (3.22 g, yield 85%) as a white solid.

$^1$H NMR (CDCl$_3$ 300MHz) (δ) ppm: 0.06 (6H, s), 0.90 (9H, s), 1.08 (3H, t, J=7.1 Hz), 3.51 (2H, br), 3.79 (2H, t, J=4.9 Hz), 4.05 (2H, q, J=7.1 Hz), 6.78 (1H, dd, J=7.9, 9.4 Hz), 7.71 (1H, dd, J=7.3, 7.3 Hz), 8.11 (1H, d, J=14.0 Hz), 10.91 (1H, br)

Step 3

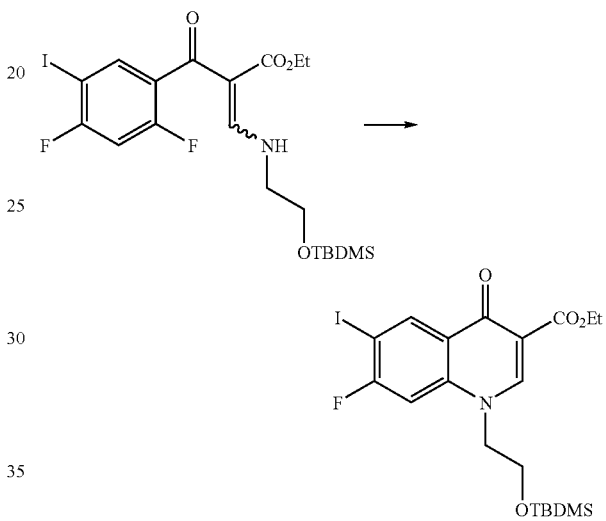

The compound (3.22 g, 5.97 mmol) obtained in Step 2 was dissolved in tetrahydrofuran (35 ml), sodium hydride (358 mg, 8.95 mmol) was added under ice-cooling, and the mixture was stirred at 0° C. for 2.5 hr. 1N Hydrochloric acid (8.90 ml, 8.90 mmol) and water (35 ml) were added to the reaction mixture and the mixture was stirred. The precipitated solid was collected by filtration and purified by silica gel chromatography (ethyl acetate:hexane=1:2 to 2:1) to give the object product (2.52 g, yield 81%) as a pale-yellow solid.

$^1$H NMR (CDCl$_3$ 300 MHz) (δ) ppm: −0.11 (6H, s), 0.79 (9H, s), 1.39 (3H, t, J=7.1 Hz), 3.96 (2H, t, J=4.8 Hz), 4.23 (2H, t, J=4.8 Hz), 4.38 (2H, q, J=7.1 Hz), 7.14 (1H, d, J=9.3 Hz), 8.47 (1H, s), 8.93 (1H, d, J=7.2 Hz)

Step 4

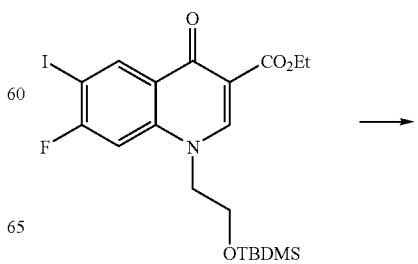

-continued

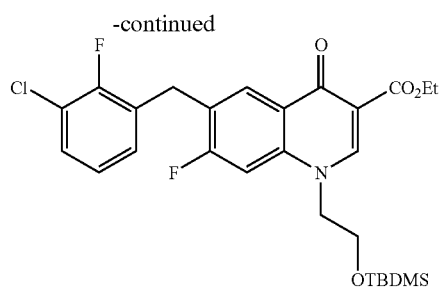

The compound (1.00 g, 1.93 mmol) obtained in Step 3 was dissolved in tetrahydrofuran (20 ml), bis(dibenzylidenacetone)palladium(0) (22 mg, 0.039 mmol) and tri(2-furyl)phosphine (18 mg, 0.077 mmol) were added under an argon stream. A solution of 3-chloro-2-fluorobenzylzinc bromide (2.89 mmol) in tetrahydrofuran prepared as mentioned above was added dropwise at 60° C. After the completion of the dropwise addition, the mixture was heated under reflux for 1 hr. After allowing to cool, saturated aqueous ammonium chloride solution was added to the reaction mixture and the insoluble material was filtered through celite. The filtrate was extracted with ethyl acetate. The organic layer was washed with water and saturated brine in this order and dried over sodium sulfate. After filtration, the filtrate was concentrated under reduced pressure, and the obtained residue was purified by silica gel chromatography (ethyl acetate:hexane=2:1) to give the object product (573 mg, yield 55%) as a pale-yellow solid.

$^1$H NMR (CDCl$_3$ 300 MHz) (δ) ppm: −0.12(6H, s), 0.78 (9H, s), 1.38 (3H, t, J=7.1 Hz), 3.99 (2H, t), 4.13 (2H, s), 4.23 (2H, t), 4.37 (2H, q, J=7.1 Hz), 6.96-7.13 (3H,m), 7.25-7.31 (1H, m), 8.39 (1H, d), 8.46 (1H, s)

Step 5

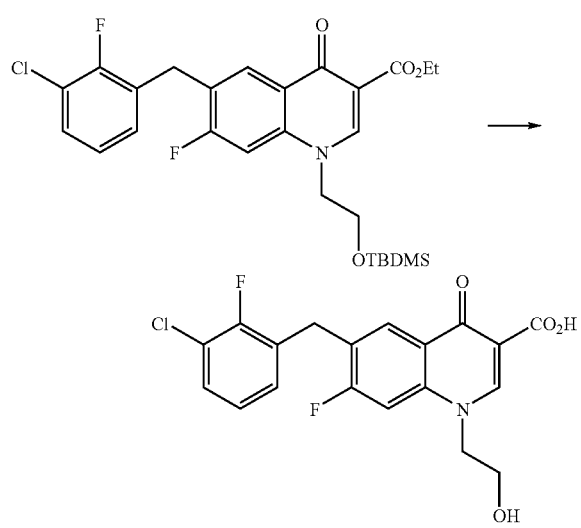

The compound (170 mg, 0.32 mmol) obtained in Step 4 was dissolved in tetrahydrofuran (1 ml), 2N aqueous sodium hydroxide solution (4.00 ml, 2.00 mmol) was added, and the mixture was heated under reflux for 3.5 hr. After allowing to cool, 10% aqueous citric acid solution was added to the reaction mixture. The precipitated solid was collected by filtration, washed with 50% aqueous ethanol and vacuum dried to give the object product (117 mg, yield 94%) as a white solid.

$^1$H NMR (DMSO-d$_6$ 300 MHz) (δ) ppm: 3.73 (2H, br), 4.25 (2H, s), 4.58 (2H, br), 4.96 (1H, br), 7.19-7.22 (1H, m), 7.30-7.36 (1H, m), 7.49-7.54 (1H, m), 8.03 (1H, d), 8.30 (1H, d), 8.88 (1H, s), 15.42 (1H, brs)

Step 6

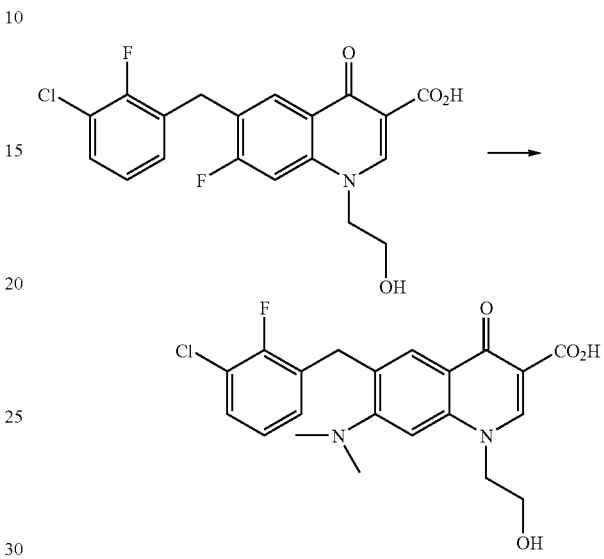

The compound (65 mg, 0.17 mmol) obtained in Step 5 was dissolved in dimethylformamide (2.5 ml) and exposed to microwave at SOW for 20 min at not more than 120° C. After allowing to cool, 10% aqueous citric acid solution was added to the reaction mixture. The precipitated solid was collected by filtration, washed with water and vacuum dried to give the object product (66 mg, yield 96%) as a yellow white solid.

$^1$H NMR (DMSO-d$_6$ 300 MHz) (δ) ppm: 2.88 (6H, s), 3.70-3.80 (2H, m), 4.22 (2H, s), 4.60-4.70 (2H, m), 5.05 (1H, t), 7.20-7.31 (3H, m), 7.50-7.60 (1H, m), 7.80 (1H, s), 8.78 (1H, s), 15.30-15.40 (1H, brs)

MS (ESI): M+ 419

Reference Example 6

Step 1

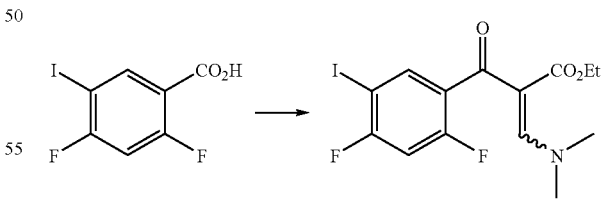

2,4-Difluoro-5-iodobenzoic acid (5.00 g, 17.60 mol) was dissolved in toluene (25 ml), oxalyl chloride (2.00 ml, 22.93 mmol) and dimethylformamide (catalytic amount) were added, and the mixture was stirred at room temperature for 12 hr. After filtration of the reaction mixture, the filtrate was concentrated under reduced pressure. Toluene (20 ml) was added and the insoluble material was filtered through celite. The filtrate was concentrated under reduced pressure and tetrahydrofuran (20 ml) was added to the obtained residue to allow dissolution. The obtained solution was added dropwise to a solution of ethyl 3-dimethylaminoacrylate (3.28 g, 22.91 mmol) and triethylamine (3.70 ml, 26.55 mmol) in tetrahydrofuran (20 ml), and the mixture was heated under reflux for 1 hr. After allowing to cool, water and ethyl acetate (50 ml) were added to the reaction mixture. The mixture was stirred and partitioned. The organic layer was washed with 1N hydrochloric acid (20 ml), water (200 ml) and saturated brine in this order, and dried over sodium sulfate. After filtration, the filtrate was concentrated under reduced pressure to give a crude product (7.24 g) as a brown oil.

Step 2

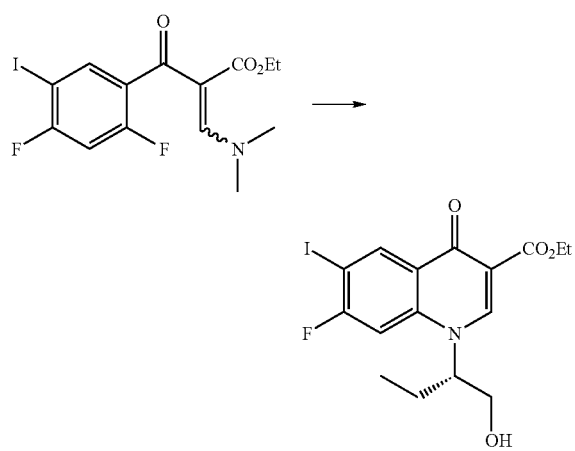

The crude product (7.24 g) obtained in Step 1 was dissolved in tetrahydrofuran (20 ml), (S)-2-amino-1-butanol (1.89 g, 21.24 mmol) was added, and the mixture was stirred with heating at 60° C. for 1.5 hr. After allowing to cool, the reaction mixture was concentrated under reduced pressure, and the obtained residue was dissolved in dimethylformamide (20 ml). Potassium carbonate (7.33 g, 53.02 mmol) was added, and the mixture was stirred with heating at 70° C. for 1 hr. After allowing to cool, the reaction mixture was concentrated under reduced pressure, water (150 ml) was added to the residue, and the mixture was stirred at room temperature for 30 min. The precipitated solid was collected by filtration. The obtained solid was washed with water (50 ml) and then with a mixed solvent (50 ml) of hexane:diethyl ether=7:3, and vacuum dried to give the object product (4.69 g, yield 61%) as a white solid.

$^1$H NMR (CDCl$_3$ 300 MHz) (δ) ppm: 0.97 (3H, t, J=7.4 Hz), 1.40 (3H, t, J=7.1 Hz), 1.95-2.05 (1H, m), 2.11-2.21 (1H, m), 4.05 (1H, br), 4.34-4.39 (5H, m), 5.59 (1H, br), 7.30 (1H, d, J=10.0 Hz), 8.04 (1H, d, J=7.1 Hz), 8.58 (1H, s)

Step 3

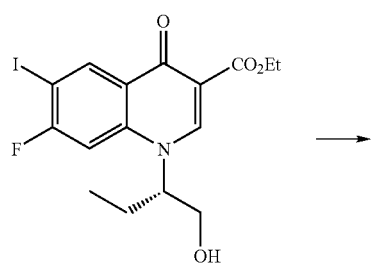

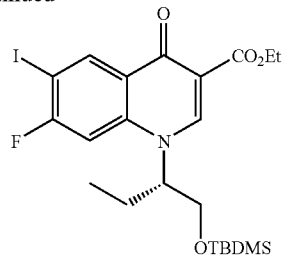

The compound (4.69 g, 10.82 mmol) obtained in Step 2 was dissolved in dimethylformamide (20 ml), imidazole (950 mg, 13.95 mmol) and tert-butyldimethylsilyl chloride (1.95 g, 12.96 mmol) were added, and the mixture was stirred at room temperature for 14.5 hr. Water was added to the reaction mixture and the mixture was extracted with ethyl acetate (50 ml). The organic layer was washed 3 times with water and with saturated brine in this order, and dried over sodium sulfate. After filtration, the filtrate was concentrated under reduced pressure, and the obtained residue was purified by silica gel chromatography (ethyl acetate:hexane=3:7) to give the object product (5.06 g, yield 86%) as a yellow oil.

$^1$H NMR (CDCl$_3$ 300 MHz) (δ) ppm: −0.08 (3H, s), −0.05 (3H, s), 0.77 (9H, s), 0.98 (3H, t, J=7.5 Hz), 1.40 (3H, t, J=7.2 Hz), 1.94-2.10 (2H, m), 3.90 (2H, br), 4.35-4.43 (3H, m), 7.26 (1H, d, J=9.9 Hz), 8.59 (1H, s), 8.95 (1H, d, J=7.2 Hz)

Step 4

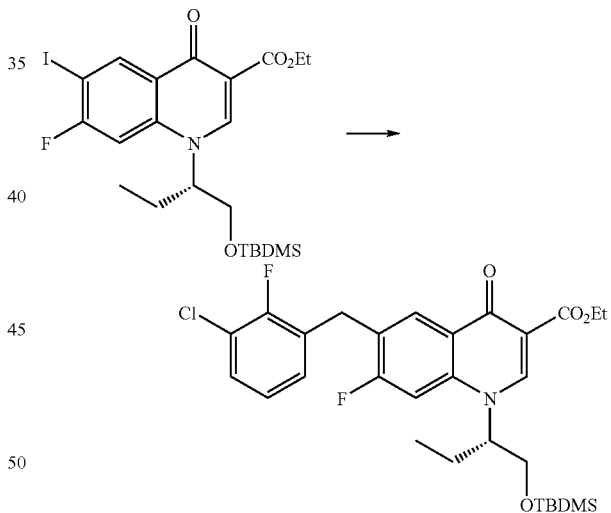

The compound (5.06 g, 9.24 mmol) obtained in Step 3 was dissolved in tetrahydrofuran (20 ml), and bis(dibenzylidenacetone)palladium(0) (266 mg, 0.46 mmol) and tri(2-furyl)phosphine (215 mg, 0.92 mmol) were added under an argon stream. A solution of 3-chloro-2-fluorobenzylzinc bromide (18.50 mmol) in tetrahydrofuran prepared as mentioned above was added dropwise and, after the completion of the dropwise addition, the mixture was stirred with heating at 60° C. for 1 hr. After allowing to cool, water and ethyl acetate were added to the reaction mixture and the mixture was stirred and partitioned. The organic layer was washed with 1N hydrochloric acid, water, saturated aqueous sodium hydrogen carbonate and saturated brine in this order, and dried over sodium sulfate. After filtration, the filtrate was concentrated under reduced pressure and the obtained residue was purified by silica gel chromatography (ethyl acetate:hexane=1:1 to 2:1) to give the object product (3.86 g, yield 74%) as a brown oil.

$^1$H NMR (CDCl$_3$ 300 MHz) (δ) ppm: −0.10 (3H, s), −0.06 (3H, s), 0.752 (9H, s), 0.98 (3H, t, J=7.4 Hz), 1.403H, t, J=7.1 Hz), 1.90-2.12 (2H, m), 3.89 (2H, br), 4.12 (2H, s), 4.35-4.49 (3H, m), 6.97-7.08 (2H, m), 7.22-7.29 (2H, m), 8.40 (1H, d, J=8.7 Hz), 8.58 (1H, s)

Step 5

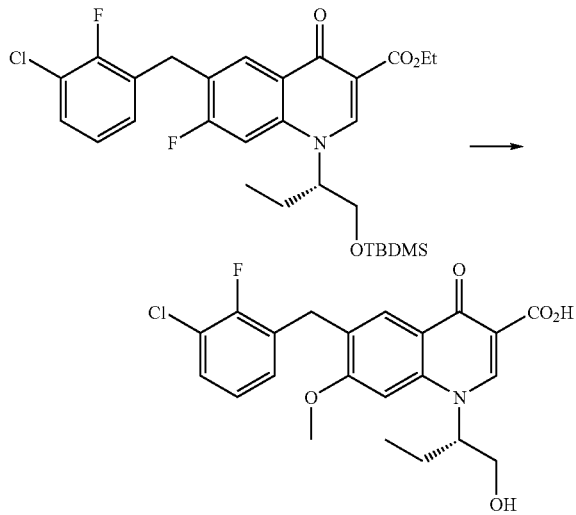

A solution (40.00 ml, 0.20 mol) of 28% sodium methoxide methanol and water (2.00 ml, 0.11 mol) were added to the compound (3.86 g, 6.85 mmol) obtained in Step 4, and the mixture was heated under reflux for 5.5 hr. After allowing to cool, the reaction mixture was concentrated under reduced pressure, and 6N hydrochloric acid was added to the obtained residue. The mixture was stirred and extracted twice with ethyl acetate. The organic layer was washed with water and saturated brine in this order, dried over magnesium sulfate, filtered and concentrated under reduced pressure. The obtained residue was recrystallized from ethanol (200 ml) to give the object product (2.03 g, yield 68%) as a white solid.

$^1$H NMR(DMSO-d$_6$ 300 MHz) (δ) ppm: 0.87 (3H, t, J=7.3 Hz), 1.80-2.10 (2H, m), 3.70-3.90 (2H, m), 4.02 (3H, s), 4.11 (2H, s), 5.00-5.19 (2H, m), 7.16-7.24 (2H, m), 7.44-7.48 (2H, m), 8.04 (1H, s), 8.78 (1H, s), 15.44 (1H, s)

MS (ESI): M+ 434

Reference Example 7

Step 1

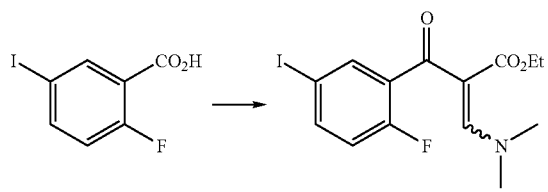

2-Fluoro-5-iodobenzoic acid (6.60 g, 24.81 mmol) was dissolved in chloroform (70 ml), oxalyl chloride (4.30 ml, 49.29 mmol) and dimethylformamide (catalytic amount) were added, and the mixture was stirred at room temperature for 3 hr. The reaction mixture was concentrated under reduced pressure, and chloroform (35 ml) was added to the residue to allow dissolution. The obtained solution was added dropwise to a solution of ethyl 3-dimethylaminoacrylate (4.26 g, 29.75 mmol) and triethylamine (5.19 ml, 37.24 mmol) in chloroform (35 ml). The mixture was stirred at room temperature for 15 hr. Water was added to the reaction mixture to allow partitioning. The organic layer was washed with saturated brine and dried over sodium sulfate. After filtration, the filtrate was concentrated under reduced pressure. The obtained residue was purified by silica gel chromatography (ethyl acetate:hexane=1:2 to 1:1) to give the object product (6.40 g, yield 66%), comprising an E form and a Z form in a mixture, as an orange solid.

$^1$H NMR (CDCl$_3$ 400 MHz) (δ) ppm: 0.94 (3H, t, J=7.2 Hz), 2.88 (3H, brs), 3.31 (3H, brs), 3.97 (2H, q), 6.78 (1H, dd, J=8.4, 10.0 Hz), 7.65-7.67 (1H, m), 7.78 (1H, s), 7.85 (1H, brs)

MS (ESI): M+ 392

Step 2

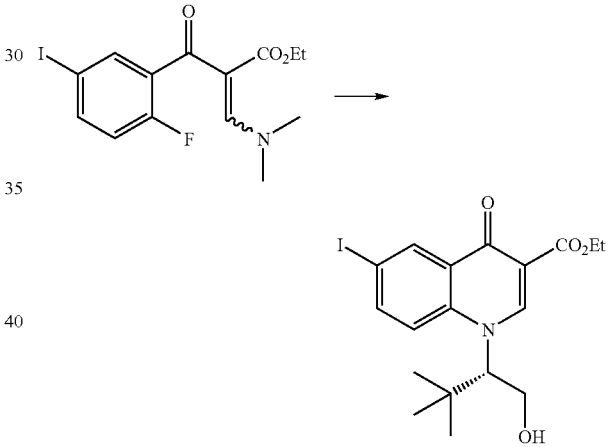

The compound (300 mg, 0.77 mmol) obtained in Step 1 was dissolved in tetrahydrofuran (1.5 ml), (S)-(+)-tert-Leucinol (0.12 ml, 0.92 mmol) was added, and the mixture was stirred with heating at 60° C. for 1 hr. The reaction mixture was concentrated under reduced pressure, and the obtained residue was dissolved in dimethylformamide (1.2 ml). Potassium carbonate (318 mg, 2.30 mmol) was added, and the mixture was stirred with heating at 70° C. for 5.5 hr. After cooling, 1N hydrochloric acid (5 ml) was added to the reaction mixture and the mixture was stirred under ice-cooling for 30 min. The precipitated solid was collected by filtration and the obtained solid was washed with 30% aqueous ethanol (6 ml) and then with a mixed solvent (5 ml) of hexane:diethyl ether=2:1 and vacuum dried to give the object product (276 mg, yield 81%) as a pale-yellow solid.

$^1$H NMR (CDCl$_3$ 300 MHz) (δ) ppm: 0.98 (9H, s), 1.41 (3H, t, J=7.0 Hz), 4.25-4.41 (4H, m), 4.64-4.70 (1H, m), 5.14 (1H, br), 7.46 (1H, d, J=9.0 Hz), 7.89 (1H, dd, J=2.2, 9.1 Hz), 8.06 (1H, d, J=2.1 Hz), 8.69 (1H, s)

Step 3

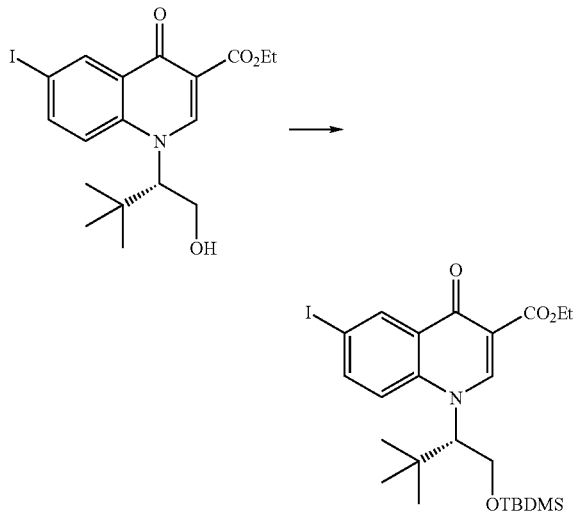

The compound (276 mg, 0.62 mmol) obtained in Step 2 was dissolved in dimethylformamide (1 ml), imidazole (51 mg, 0.75 mmol) and tert-butyldimethylsilyl chloride (122 mg, 0.81 mmol) were added, and the mixture was stirred at room temperature for 30 min. Water was added to the reaction mixture and the mixture was extracted twice with ethyl acetate. The organic layer was washed twice with water and with saturated brine in this order, and dried over sodium sulfate. After filtration, the filtrate was concentrated under reduced pressure, and the obtained residue was purified by silica gel chromatography (ethyl acetate:hexane=3:5) to give the object product (314 mg, yield 91%) as a white amorphous.

$^1$H NMR (CDCl$_3$ 300 MHz) (δ) ppm: −0.09 (3H, s), −0.01 (3H, s), 0.66 (9H, s), 1.04 (9H, s), 1.41 (3H, t, J=7.2 Hz), 4.10-4.14 (2H, m), 4.40 (2H, q, J=7.0 Hz), 4.58-4.63 (1H, m), 7.39 (1H, d, J=9.3 Hz), 7.89 (1H, dd, J=2.2, 8.8 Hz), 8.67 (1H, s), 8.87 (1H, d, J=2.1 Hz)

Step 4

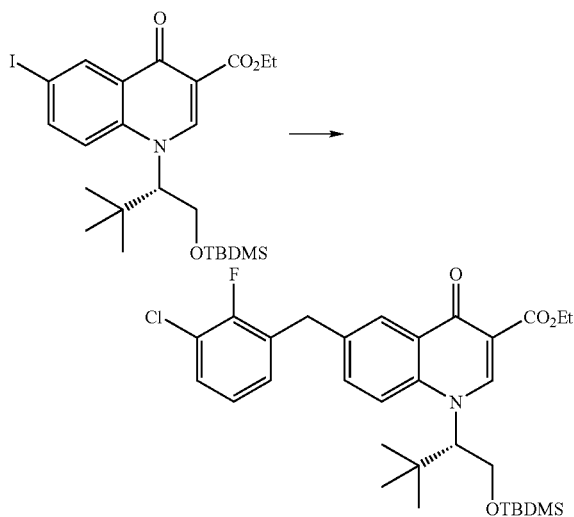

The compound (314 mg, 0.56 mmol) obtained in Step 3 was dissolved in tetrahydrofuran (1.2 ml), and bis(dibenzylidenacetone)palladium(0) (16 mg, 0.028 mmol) and tri(2-furyl)phosphine (13 mg, 0.056 mmol) were added under an argon stream. A solution of 3-chloro-2-fluorobenzylzinc bromide (1.13 mmol) in tetrahydrofuran prepared as mentioned above was added dropwise and, after the completion of the dropwise addition, the mixture was stirred with heating at 50° C. for 1.5 hr. After allowing to cool, water and ethyl acetate were added to the reaction mixture and stirred, and the insoluble material was filtered through celite. The filtrate was partitioned, and the organic layer was washed with water and saturated brine in this order and dried over sodium sulfate. After filtration, the filtrate was concentrated under reduced pressure and the obtained residue was purified by silica gel chromatography (ethyl acetate:hexane=1:1) to give the object product (283 mg, yield 87%) as a brown amorphous form.

$^1$H NMR (CDCl$_3$ 400 MHz) (δ) ppm: −0.11 (3H, s), −0.01 (3H, s), 0.63 (9H, s), 1.06 (9H, s), 1.41 (3H, t, J=7.0 Hz), 4.08-4.16 (4H, m), 4.38 (2H, q, J=7.0 Hz), 4.61-4.67 (1H, m), 6.95-7.08 (2H, m), 7.23-7.27 (1H, m), 7.47-7.49 (1H, m), 7.53-7.55 (1H, m), 8.41 (1H, d, J=2.0 Hz), 8.68 (1H, s)

Step 5

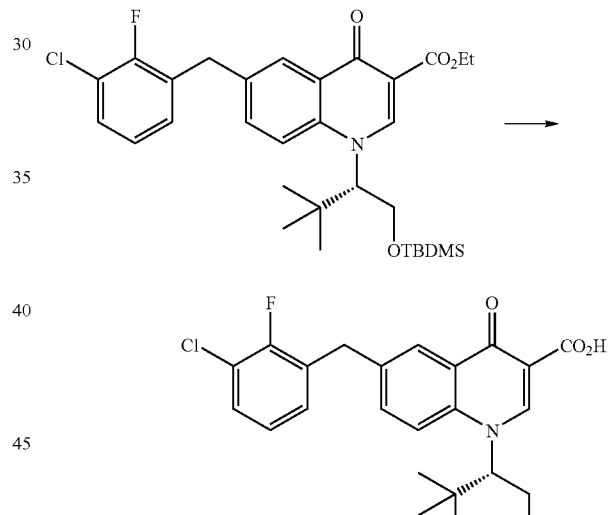

The compound (283 mg, 0.49 mmol) obtained in Step 4 was dissolved in ethanol (2 ml), 1N aqueous sodium hydroxide solution (1.00 ml, 1.00 mmol) was added, and the mixture was heated under reflux for 1 hr. After allowing to cool, acetic acid (0.35 ml) was added to the reaction mixture and the mixture was stirred. The precipitated solid was collected by filtration. The obtained solid was suspended in diethyl ether (10 ml), filtered and vacuum dried to give the object product (157 mg, yield 74%) as a white solid.

$^1$H NMR (DMSO-d$_6$ 400 MHz) (δ) ppm: 1.00 (9H, s), 4.07-4.12 (2H, m), 4.30 (2H, s), 5.12-5.14 (2H, m), 7.20-7.25 (1H, m), 7.40-7.45 (1H, m), 7.51-7.53 (1H, m), 7.87 (1H, d), 8.25 (1H, s), 8.41 (1H, d, J=9.2 Hz), 8.85 (1H, s), 15.20-15.21 (1H, br)

MS (ESI): M+ 432

Reference Example 8

Step 1

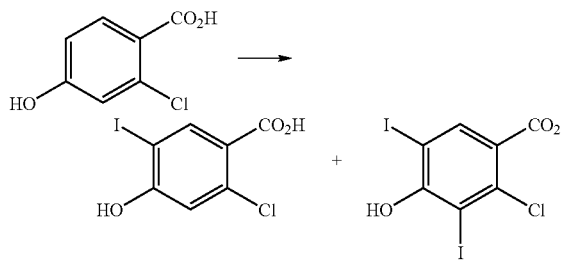

2-Chloro-4-hydroxybenzoic acid (5.18 g, 30.02 mmol) was dissolved in trifluoromethanesulfonic acid (25 g) and N-iodosuccinimide (6.75 g, 30.00 mmol) was added by portions at 0° C. After stirring at room temperature for 15 hr, trifluoromethanesulfonic acid (25 g) was further added, and N-iodosuccinimide (2.02 g, 8.98 mmol) was added by portions at 0° C. After stirring at room temperature for 13.5 hr, the reaction mixture was added to ice water (300 ml), and the mixture was stirred for 2 hr. The precipitated solid was collected by filtration, washed with water, and vacuum dried to give a mixture (8:2) (5.76 g) of 2-chloro-4-hydroxy-5-iodobenzoic acid and 2-chloro-3,5-diiodo-4-hydroxybenzoic acid.

Step 2

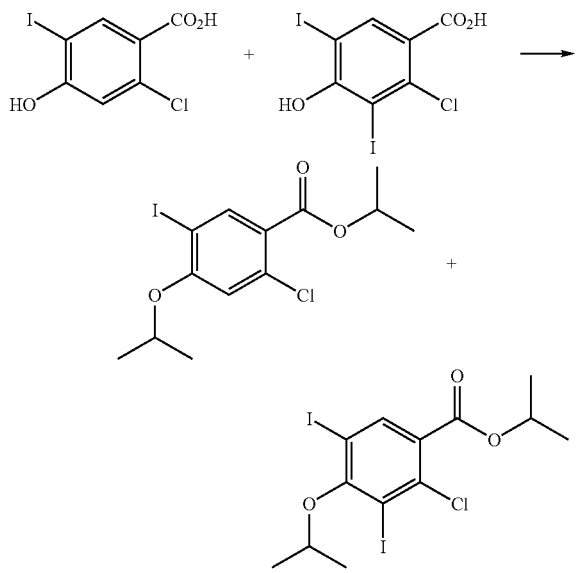

A mixture (3.89 g) obtained in Step 1 was dissolved in dimethylformamide (20 ml), potassium carbonate (8.97 g, 64.90 mmol) and isopropyl iodide (6.50 ml, 65.15 mmol) were added, and the mixture was stirred with heating at 80° C. for 2.5 hr. The reaction mixture was added to 1N hydrochloric acid (100 ml), toluene (100 ml) was further added, and the mixture was stirred. The insoluble material was filtered through celite. The filtrate was partitioned. The organic layer was washed three times with water, and dried over sodium sulfate. After filtration, the filtrate was concentrated under reduced pressure, and the obtained residue was purified by silica gel chromatography (ethyl acetate:hexane=1:9) to give the object product as a mixture (4.08 g).

Step 3

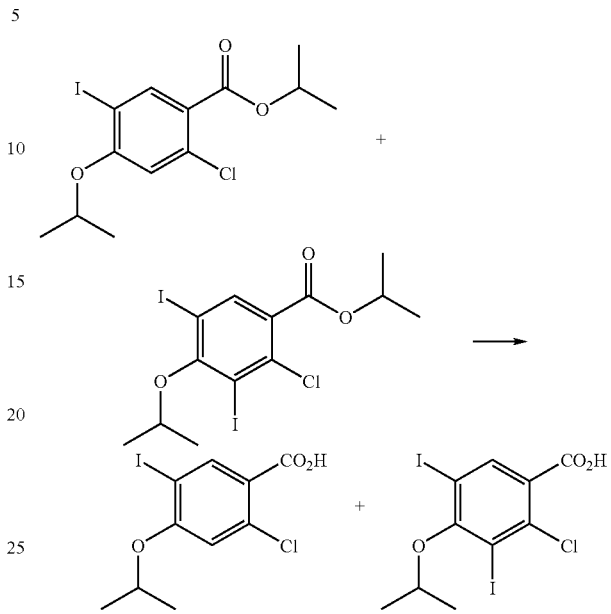

The mixture (4.08 g) obtained in Step 2 was dissolved in ethanol (20 ml), 1N aqueous sodium hydroxide solution (20.00 ml, 20.00 mmol) was added, and the mixture was heated under reflux for 24 hr. After allowing to cool, 1N hydrochloric acid (30 ml) was added to the reaction mixture and the mixture was stirred and extracted three times with ethyl acetate. The organic layer was washed with water and saturated brine in this order, and dried over sodium sulfate. After filtration, the filtrate was concentrated under reduced pressure to give the object product as a mixture (3.40 g).

Step 4

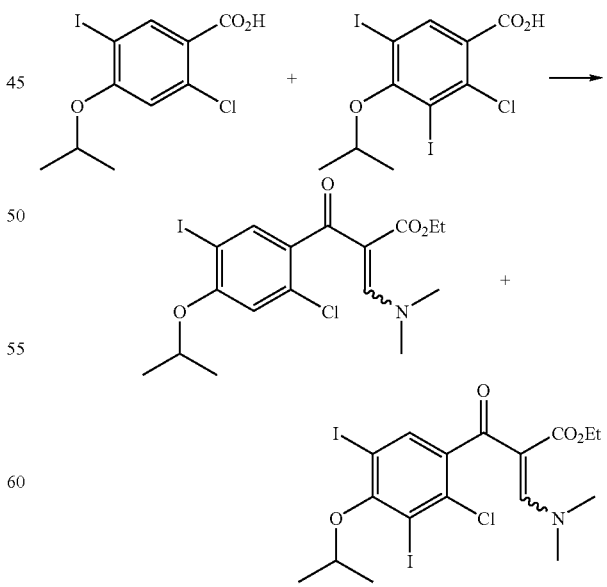

The mixture (3.40 g) obtained in Step 3 was dissolved in toluene (35 ml), thionyl chloride (3.40 ml, 46.61 mmol) and dimethylformamide (catalytic amount) were added, and the mixture was heated under reflux for 1.5 hr. The reaction mixture was concentrated under reduced pressure, and tetrahydrofuran (25 ml) was added to the residue to allow dissolution. The obtained solution was added dropwise to a solution of ethyl 3-dimethylaminoacrylate (4.29 g, 30.00 mmol) and triethylamine (4.17 ml, 30.00 mmol) in tetrahydrofuran (10 ml), and the mixture was heated under reflux for 14 hr. After allowing to cool, water and ethyl acetate were added to the reaction mixture, and the mixture was stirred and partitioned. The organic layer was washed with water and saturated brine in this order, and dried over sodium sulfate. After filtration, the filtrate was concentrated under reduced pressure, and the obtained residue was purified by silica gel chromatography (ethyl acetate:hexane=1:1.5 to 1.5:1) to give the object product as a mixture (2.71 g).

Step 5

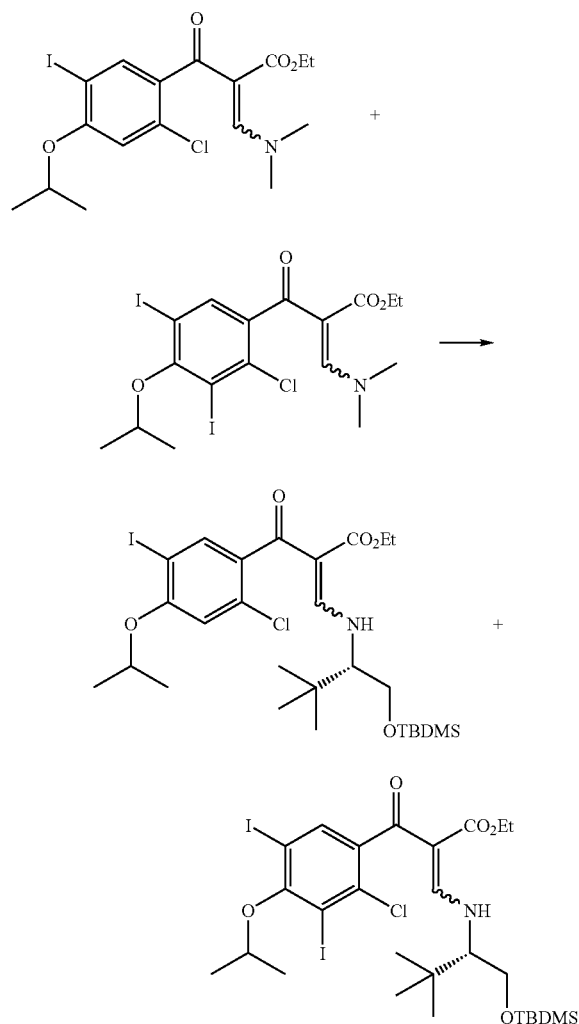

The mixture (300 mg) obtained in Step 4 was dissolved in tetrahydrofuran (2 ml), (S)-(+)-tert-Leucinol (0.10 ml, 0.77 mmol) was added, and the mixture was heated under reflux for 20 min. After allowing to cool, the reaction mixture was concentrated under reduced pressure, and the obtained residue was dissolved in dimethylformamide (4 ml). Imidazole (110 mg, 1.61 mmol) and tert-butyldimethylsilyl chloride (214 mg, 1.42 mmol) were added, and the mixture was stirred at room temperature for 20 min. Water was added to the reaction mixture and the mixture was extracted with ethyl acetate. The organic layer was washed with water and saturated brine in this order and dried over sodium sulfate. After filtration, the filtrate was concentrated under reduced pressure, and the obtained residue was purified by silica gel chromatography (ethyl acetate:hexane=1:4) to give the object product as a mixture (391 mg).

Step 6

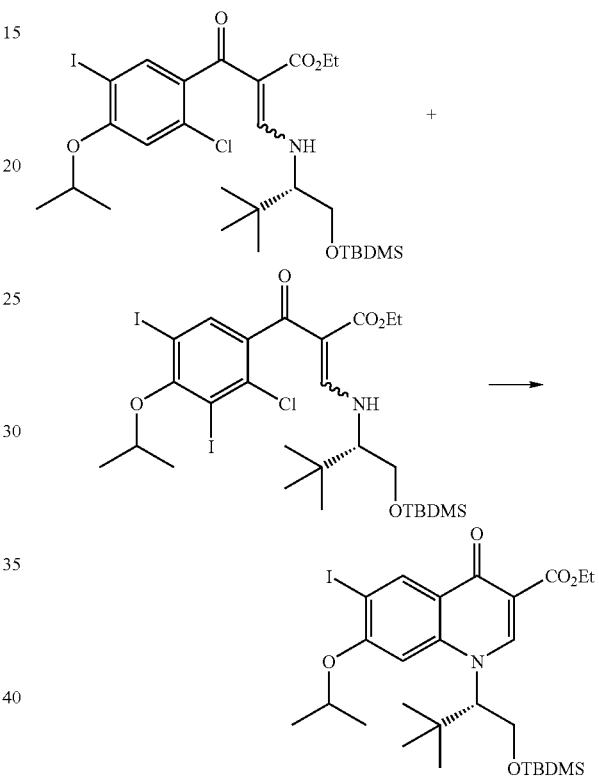

The mixture (391 mg) obtained in Step 5 was dissolved in toluene (5 ml), sodium hydride (29 mg, 0.73 mmol) was added under ice-cooling, and the mixture was stirred at room temperature for 30 min. Dimethylformamide (3 ml), potassium carbonate (100 mg, 0.72 mmol) and ethyl iodide (0.058 ml, 0.73 mmol) were added to the reaction mixture, and the mixture was stirred with heating at 60° C. for 30 min. After allowing to cool, the reaction mixture was added to ice water and 1N hydrochloric acid was added for neutralization. The mixture was extracted with ethyl acetate. The organic layer was washed with water and saturated brine in this order, and dried over sodium sulfate. After filtration, the filtrate was concentrated under reduced pressure, and the obtained residue was purified by silica gel chromatography (ethyl acetate:hexane=4:5 to 2:1) to give object product (258 mg, yield 19%) as a pale-yellow white solid.

$^1$H NMR (CDCl$_3$, 300 MHz) (δ) ppm: −0.09 (3H, s), 0.00 (3H, s), 0.67 (9H, s), 1.05 (9H, s), 1.40 (3H, t, J=7.1 Hz), 1.46 (6H, d, J=6.0 Hz), 4.09-4.20 (2H, m), 4.39 (2H, q, J=7.1 Hz), 4.43-4.49 (1H, m), 4.61-4.69 (1H, m), 6.87 (1H, s), 8.60 (1H, s), 8.94 (1H, s)

Step 7

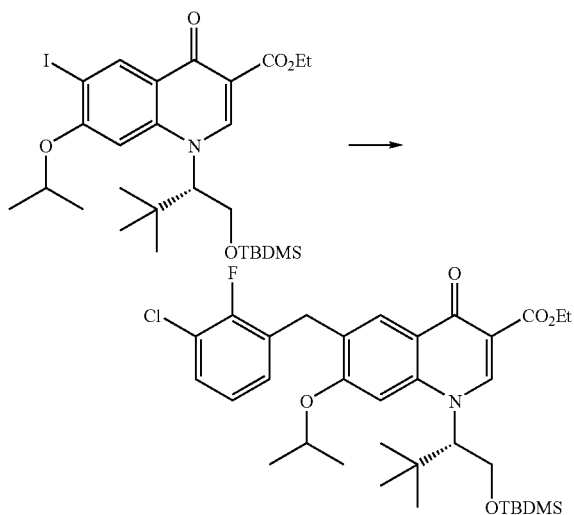

The compound (258 mg, 0.42 mmol) obtained in Step 6 was dissolved in tetrahydrofuran (5 ml), and bis(dibenzylidenacetone)palladium(0) (9.7 mg, 0.017 mmol) and tri(2-furyl)phosphine (7.8 mg, 0.034 mmol) were added under an argon stream. A solution of 3-chloro-2-fluorobenzylzinc bromide (0.63 mmol) in tetrahydrofuran prepared as mentioned above was added dropwise at 60° C. and, after the completion of the dropwise addition, the mixture was heated under reflux for 1 hr. After allowing to cool, saturated aqueous ammonium chloride solution was added to the reaction mixture, and the mixture was stirred and filtered through celite. Water was added to the filtrate and the mixture was extracted with ethyl acetate. The organic layer was washed with water and saturated brine in this order and dried over sodium sulfate. After filtration, the filtrate was concentrated under reduced pressure, and the obtained residue was crudely purified by silica gel chromatography (ethyl acetate:hexane=1:1 to 2:1) to give a crudely purified product (216 mg) as a pale-yellow oil.

Step 8

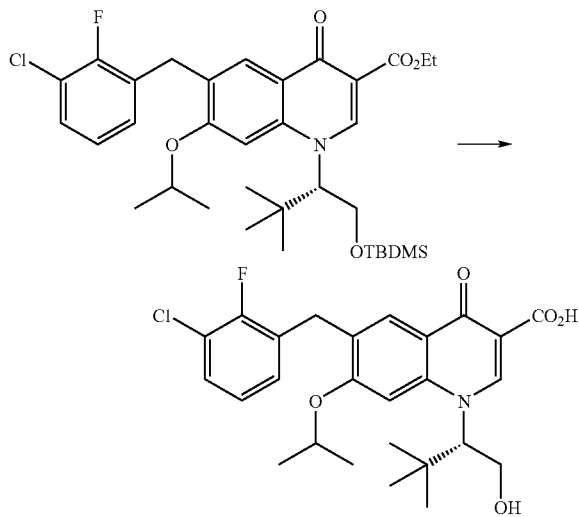

The crudely purified product (216 mg) obtained in Step 7 was dissolved in a mixed solvent of ethanol (2 ml) and tetrahydrofuran (1 ml), 1N aqueous sodium hydroxide solution (2.00 ml, 2.00 mmol) was added, and the mixture was heated under reflux for 1 hr. After allowing to cool, 10% aqueous citric acid solution was added to the reaction mixture and, after stirring, the mixture was extracted with ethyl acetate. The organic layer was washed with water and saturated brine in this order, and dried over sodium sulfate. After filtration, the filtrate was concentrated under reduced pressure. The residue was treated with a mixed solvent of diethyl ether and hexane. After filtration, the obtained solid was vacuum dried to give the object product (140 mg, yield 68%) as a white solid.

$^1$H NMR (DMSO-$d_6$ 300 MHz) (δ) ppm: 0.97 (9H, s), 1.18 (3H, d, J=5.9 Hz), 1.26 (3H, d, J=6.0 Hz), 4.04-4.09 (4H, m), 5.09-5.13 (3H, m), 7.12-7.21 (2H, m), 7.43-7.51 (2H, m), 8.19 (1H, s), 8.78 (1H, s), 15.46 (1H, s)

MS (ESI): M+ 490

Reference Example 9

Step 1

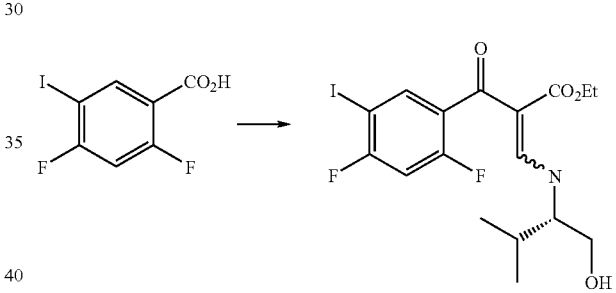

2,4-Difluoro-5-iodobenzoic acid (650.57 g, 2.29 mol) was dissolved in toluene (1300 ml), thionyl chloride (184 ml, 2.52 mol) and dimethylformamide (catalytic amount) were added, and the mixture was stirred at 90° C. for 2 hr. After allowing to cool, the reaction mixture was concentrated under reduced pressure. The residue was dissolved in toluene (330 ml), and the toluene solution was concentrated under reduced pressure, and this step was repeated. The residue was dissolved in toluene (690 ml) solution, the obtained solution was added dropwise to a solution of ethyl 3-dimethylaminoacrylate (361.52 g, 2.525 mol) and diisopropylethylamine (480 ml, 2.75 mol) in toluene (690 ml), and the mixture was stirred with heating at 90° C for 3 hr. After allowing to cool, (S)-(+)-valinol (260.00 g, 2.52 mol) was added to the reaction mixture, and the mixture was stirred at room temperature for 1 hr. Water (2600 ml) was added to partition the reaction mixture, and the aqueous layer was extracted with toluene (680 ml). The organic layers were combined and washed twice with water (2000 ml), and dried over sodium sulfate. After filtration, the filtrate was concentrated under reduced pressure to give a crude product (1180 g) as a brown oil.

Step 2

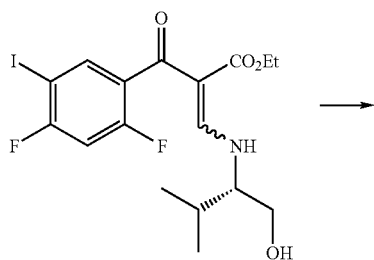

The crude product (1180 g) obtained in Step 1 was dissolved in dimethylformamide (2500 ml) and pulverized potassium carbonate (292.00 g, 1.06 mol) was added. The mixture was stirred at room temperature for 22 hr. The reaction mixture was added to ice water (ca. 10 L) and the mixture was stirred for 30 min. After stirring, the precipitated solid was collected by filtration, and washed with water (2000 ml). The obtained solid was vacuum dried and suspended in ethyl acetate (5000 ml). The suspension was filtered and vacuum dried to give the object product (774.63 g, yield 82%) as a yellow white solid.

$^1$H NMR (DMSO-$d_6$ 300 MHz) (δ) ppm: 0.72 (3H, d, J=6.6 Hz), 1.10 (3H, d, J=6.6 Hz), 1.28 (3H, t, J=7.0 Hz), 2.27 (1H, br), 3.77 (1H, br), 3.86 (1H, br), 4.23 (2H, q, J=7.0 Hz), 4.56 (1H, br), 5.12 (1H, t, J=4.9 Hz), 8.09 (1H, d, J=11.1 Hz), 8.62 (1H, d, J=7.5 Hz), 8.68 (1H, s)

MS (ESI): M+ 448

Step 3

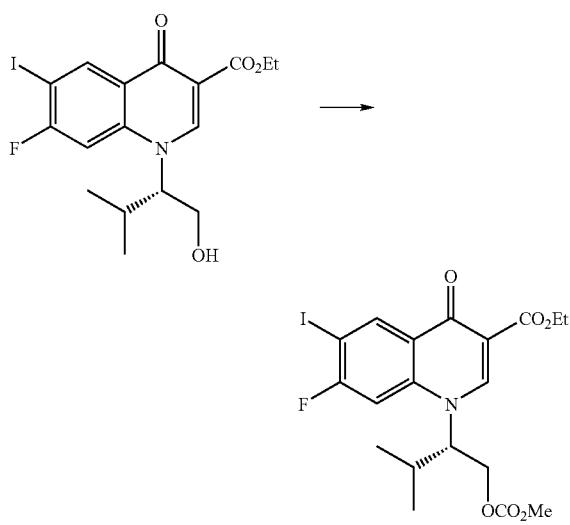

The compound (626.15 g, 1.40 mol) obtained in Step 2 was dissolved in chloroform (1250 ml), and pyridine (433 ml, 5.60 mol) and 4-(dimethylamino)pyridine (17.10 g, 0.14 mol) were added. A solution of methyl chloroformate (529.30 g, 5.60 mol) in chloroform (1250 ml) was added dropwise at not more than 10° C. and, after completion of the dropwise addition, the mixture was stirred at the same temperature for 30 min. The reaction mixture was washed with water (1250 ml), 2N hydrochloric acid (1250 ml), water (630 ml) and saturated aqueous sodium hydrogen carbonate (630 ml) in this order and dried over magnesium sulfate. After filtration, the filtrate was concentrated under reduced pressure to give a crude product (834.02 g) as a brown oil.

Step 4

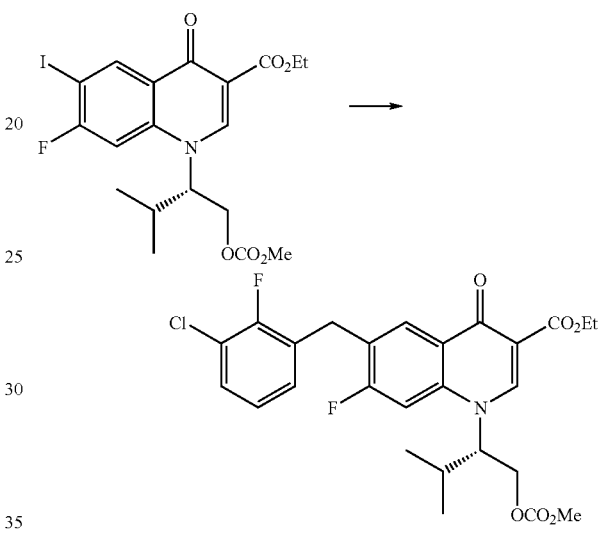

(preparation of a solution of 3-chloro-2-fluorobenzylzinc bromide in tetrahydrofuran)

Under an argon stream, zinc powder (113.02 g, 1.73 mol) was suspended in tetrahydrofuran (350 ml), 1,2-dibromoethane (1.207 ml, 14.00 mmol) and trimethylsilyl chloride (8.88 ml, 70.00 mmol) were added at 60° C., and the mixture was stirred with heating for 30 min. A solution of 3-chloro-2-fluorobenzyl bromide (406.73 g, 1.82 mol) in tetrahydrofuran (700 ml) was added dropwise at 60° C. The mixture was stirred under heating for 1 hr to give a 3-chloro-2-fluorobenzylzinc bromide solution (Main Step)

The crude product (834.02 g) obtained in Step 3 was dissolved in tetrahydrofuran (1060 ml) and, under an argon stream, dichlorobis(triphenylphosphine)palladium(II) (19.65 g, 28.00 mmol) was added, a solution of 3-chloro-2-fluorobenzylzinc bromide (1.82 mol) was added dropwise at 60° C and, after the completion of the dropwise addition, the mixture was heated under reflux for 1.5 hr. After allowing to cool, toluene (2120 ml) and 20% aqueous ammonium chloride solution (1410 ml) was added to the reaction mixture, and the mixture was stirred and partitioned. The organic layer was washed twice with 20% aqueous ammonium chloride solution (710 ml) and twice with saturated aqueous sodium hydrogen carbonate (710 ml) in this order and dried over magnesium sulfate. After filtration, the filtrate was concentrated under reduced pressure to give a crude product (849.34 g) as a brown oil.

Step 5

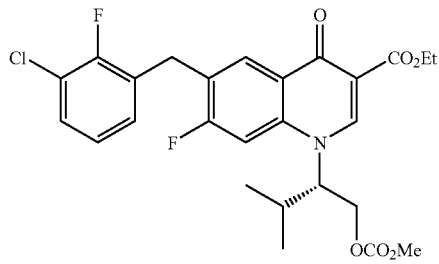

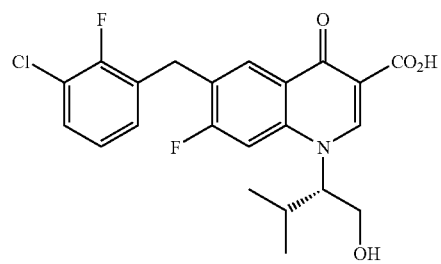

The crude product (849.34 g) obtained in Step 4 was dissolved in isopropanol (1100 ml), 4N aqueous sodium hydroxide solution (1050 ml, 4.20mmol) was added, and the mixture was stirred with heating at 50° C. for 1.5 hr. Activated carbon (37 g) was added to the reaction mixture, and the mixture was stirred at room temperature for 30 min and filtered through celite. 6N Hydrochloric acid (740 ml) and ethyl acetate (3650 ml) were added to the filtrate and the mixture was stirred and partitioned. The organic layer was concentrated under reduced pressure and the residue was suspended in isopropanol (1070 ml) and stirred at 60° C. for 1 hr. After allowing to cool, the solid was collected by filtration. The obtained solid was washed with isopropanol (740 ml) and vacuum dried to give the object product (446.51 g, yield 73%) as a pale-yellow solid.

$^1$H NMR (DMSO-$d_6$ 400 MHz) ($\delta$) ppm: 0.71 (3H, d, J=6.5 Hz), 1.13 (3H, d, J=6.5 Hz), 2.36 (1H, br), 3.77 (1H, br), 3.94 (1H, br), 4.25 (2H, s), 4.77 (1H, br), 5.16 (1H, t, J=2.4 Hz), 7.19-7.23 (1H, m), 7.32-7.35 (1H, m), 7.48-7.52 (1H, m), 8.24-8.28 (2H, m), 9.00 (1H, s), 15.00 (1H, s)

MS (ESI): M+ 436

Step 6

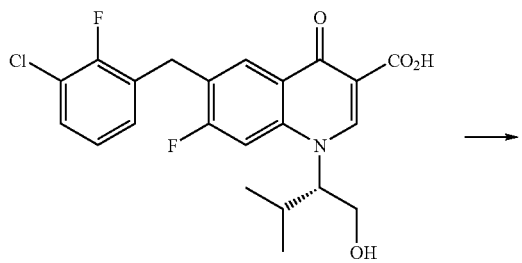

-continued

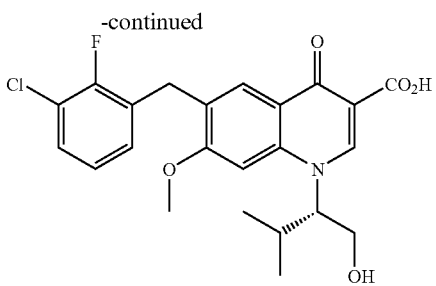

The compound (443.59 g, 1.02 mol) obtained in Step 5 was dissolved in methanol (2400 ml), 28% sodium methoxide methanol solution (2077 ml, 10.17 mol) and water (44.30 ml, 2.46 mol) were added, and the mixture was heated under reflux for 17.5 hr. Activated carbon (22 g) was added to the reaction mixture and the mixture was stirred at room temperature for 1 hr and filtered through celite. The filtrate was concentrated under reduced pressure and water (1770 ml) was added to the residue. Under ice-cooling, the mixture was stirred for 1 hr and 6N hydrochloric acid (1790 ml) was further added. The mixture was stirred at room temperature for 2 hr and ethyl acetate (1770 ml) was added. After stirring, the mixture was partitioned. The organic layer was washed twice with 10% brine (890 ml), and dried over sodium sulfate. After filtration, the filtrate was concentrated under reduced pressure, and a part of the residue was recrystallized several times (final recrystallization solvent was methanol-water) to give the object product (28.60 g, yield 67%) as a white solid.

$^1$H NMR (DMSO-$d_6$ 400 MHz) ($\delta$) ppm: 0.72 (3H, d, J=6.5 Hz), 1.16 (3H, d, J=6.5 Hz), 2.30-2.50 (1H, m), 3.70-3.90 (1H, m), 3.90-4.00 (1H, m), 4.03 (3H, s), 4.12 (2H, s), 4.80-4.90 (1H, m), 5.19 (1H, t, J=5.2 Hz), 7.19-7.25 (2H, m), 7.46-7.51 (2H, m), 8.04 (1H, s), 8.88 (1H, s), 15.44 (1H, s)

MS (ESI) : M+ 448

Reference Example 10

Step 1

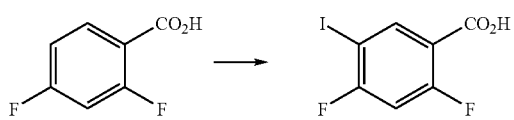

2,4-Difluorobenzoic acid (600.00 g, 3.80 mol) was dissolved in concentrated sulfuric acid (2400 ml), and N-iodosuccinimide (854.40 g, 3.60 mol) was added by portions at not more than 5° C. After the completion of the addition, the mixture was stirred at the same temperature for 3 hrs. The reaction mixture was poured into ice water (ca. 10 L), then 10% aqueous sodium sulfite solution (40 ml) was added, and the mixture was stirred for 30 min. The precipitate was collected by filtration, suspended in water (ca. 3 L), and repeatedly filtered until the pH becomes not less than 3. The obtained wet crystals (1677 g) were recrystallized from 50% aqueous ethanol (3000 ml) to give the object product (824.70 g, yield 76%) as a white solid.

$^1$H NMR (CDCl$_3$ 300 MHz) ($\delta$) ppm: 6.94 (1H, dd, J=10.3, 10.3 Hz), 8.46 (1H, d, J=7.5 Hz)

Step 2

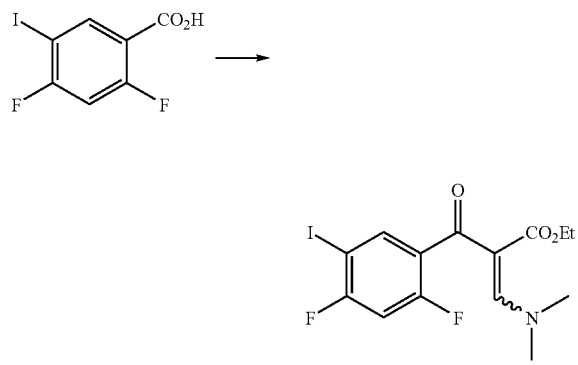

The compound (150.00 g, 0.53 mol) obtained in Step 1 was dissolved in ethyl acetate (750 ml), oxalyl chloride (51.0 ml, 0.581 mol) and dimethylformamide (catalytic amount) were added, and the mixture was stirred at room temperature for 3.5 hr. After filtration of the reaction mixture, the filtrate was concentrated under reduced pressure. The residue was dissolved in toluene (150 ml), concentrated under reduced pressure, and repeated the operation. A solution prepared by adding tetrahydrofuran (300 ml) to the residue to allow dissolution was added dropwise to a solution of ethyl 3-dimethylaminoacrylate (83.2 g, 0.581 mol) and triethylamine (96 ml, 0.686 mol) in tetrahydrofuran (450 ml), and the mixture was heated under reflux for 15 hr. After allowing to cool, the reaction mixture was filtered, and the filtrate was concentrated under reduced pressure. Ethyl acetate (750 ml) was added to the residue to allow dissolution, and the mixture was washed with aqueous ammonium chloride (400 ml), saturated aqueous sodium hydrogen carbonate (200 ml) and saturated brine in this order, and dried over sodium sulfate. After filtration, the filtrate was concentrated under reduced pressure to give a crude product (206.50 g) as a brown oil.

Step 3

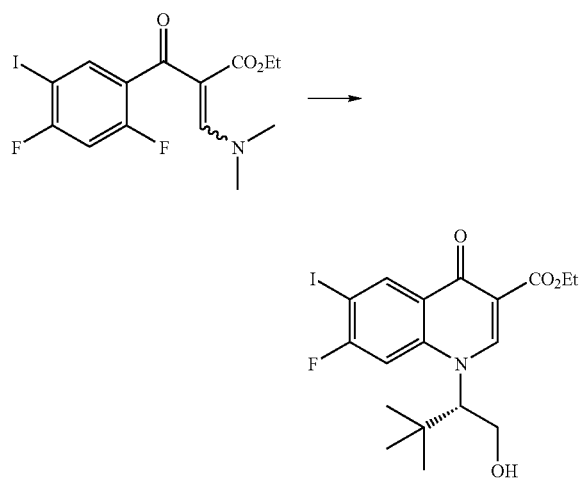

The crude product (206.50 g) obtained in Step 2 was dissolved in tetrahydrofuran (800 ml), (S)-(+)-tert-leucinol hydrochloride (81.10 g, 0.53 mol) and triethylamine (74 ml, 0.53 mol) were added, and the mixture was stirred at room temperature for 50 min. After filtration of the reaction mixture, the filtrate was concentrated under reduced pressure, and the obtained residue was dissolved in dimethylformamide (1000 ml). Potassium carbonate (146.0 g, 1.06 mol) was added, and the mixture was stirred with heating at 90° C. for 3 hr. Under ice-cooling, the reaction mixture was added to water (700 ml), and the precipitated solid was collected by filtration and washed with water. The solid was collected by filtration, suspended in 30% aqueous ethanol (1000 ml), and collected by filtration. This operation was repeated with a mixed solution of hexane:ether=1:1. After filtration, the solid was vacuum dried to give the object product (184.74 g, yield 76%) as a white solid.

$^1$H NMR (DMSO-$d_6$ 400 MHz) (δ) ppm: 0.968 (9H, s), 1.27 (3H, t), 3.96-3.98 (2H, m), 4.18-4.27 (2H, m), 4.80 (1H, t, J=7.0 Hz), 5.05 (1H, br), 8.22 (1H, d, J=11.2 Hz), 8.60 (1H, s), 8.61 (1H, d, J=7.2 Hz)

Step 4

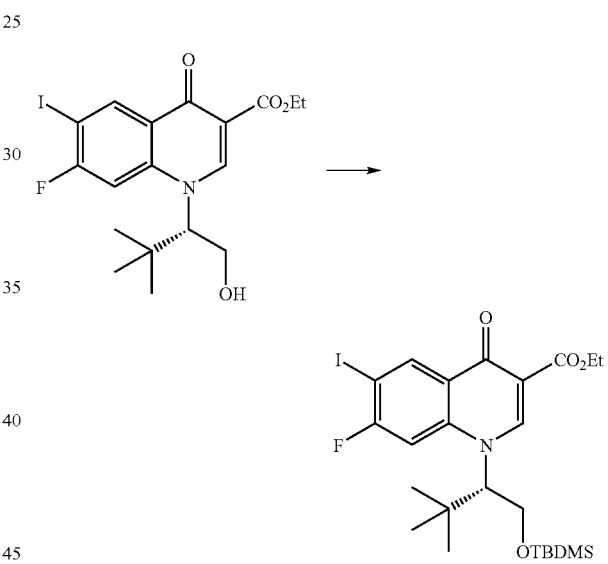

The compound (150.00 g, 0.33 mol) obtained in Step 3 was dissolved in dimethylformamide (600 ml), imidazole (28.80 g, 0.42 mol) and tert-butyldimethylsilyl chloride (28.80 g, 0.42 mol) were added, and the mixture was stirred at room temperature for 6 hr. Water (1200 ml) was added to the reaction mixture and extracted with ethyl acetate (800 ml). The organic layer was washed 3 times with water and with saturated brine in this order, and dried over sodium sulfate. After filtration, the filtrate was concentrated under reduced pressure, and the obtained residue was purified by silica gel chromatography (ethyl acetate:hexane=1:3 to 1:2) to give the object product (164.30 g, yield 88%) as a white amorphous form.

$^1$H NMR (CDCl$_3$ 300 MHz) (δ) ppm: −0.08 (3H, s), 0.00 (3H, s), 0.67 (9H, s), 1.06 (9H, s), 1.41 (3H, t, J=7.1 Hz), 4.05-4.18 (2H, m), 4.36-4.43 (3H, m), 7.32 (1H, d, J=10.3 Hz), 8.65 (1H, s), 8.95 (1H, d, J=7.4 Hz)

Step 5

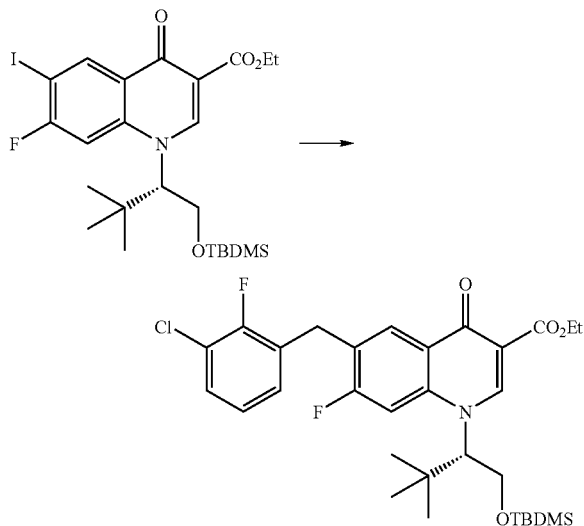

The compound (75.0 g, 0.13 mol) obtained in Step 4 was dissolved in tetrahydrofuran (580 ml), and under an argon stream, bis(dibenzylidenacetone)palladium(0) (2.99 g, 5.20 mmol) and tri(2-furyl)phosphine (2.41 g, 10.38 mmol) were added, a solution of 3-chloro-2-fluorobenzylzinc bromide (0.17 mol) in tetrahydrofuran was added dropwise at 60° C. and, after the completion of the dropwise addition, the mixture was heated under reflux for 2 hr. After allowing to cool, ethyl acetate (75 ml) and saturated aqueous ammonium chloride solution (38 ml) were added to the reaction mixture, and the mixture was stirred at room temperature for 30 min and partitioned. The organic layer was washed twice with water (75 ml) and with saturated brine (200 ml) in this order, and dried over sodium sulfate. After filtration, the filtrate was concentrated under reduced pressure, and the obtained residue was purified by silica gel chromatography (ethyl acetate: hexane=1:2 to 1:1) to give the object product (66.80 g, yield 73%) as a brown amorphous form.

$^1$H NMR (CDCl$_3$ 300 MHz) (δ) ppm: −0.10 (3H, s), −0.01 (3H, s), 0.64 (9H, s), 1.06 (9H, s), 1.40 (3H, t, J=7.1 Hz), 4.04-4.15 (4H, m), 4.35-4.46 (3H, m), 6.95-7.03 (2H, m), 7.24-7.31 (2H, m), 8.38 (1H, d, J=8.8 Hz), 8.66 (1H, s)

Step 6

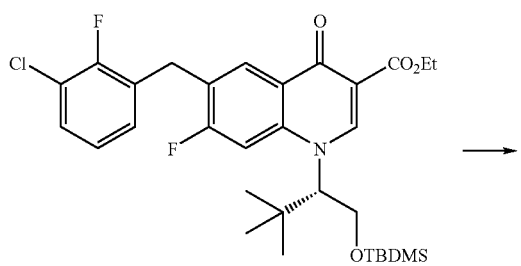

-continued

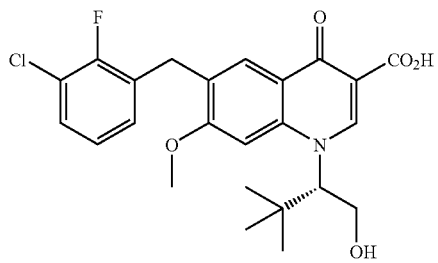

The compound (2.41 g, 4.07 mmol) obtained in Step 5 was dissolved in methanol (20 ml), 28% sodium methoxide methanol solution (8.4 ml, 40.70 mmol) and water (0.15 ml, 8.14 mmol) were added, and the mixture was heated under reflux for 18 hr. Water (1.4 ml) was added to the reaction mixture, and the mixture was stirred at room temperature for 1.5 hr and filtered through celite. The filtrate was concentrated under reduced pressure. Water (25 ml) and 2N hydrochloric acid (20 ml) were added to the residue and, after stirring for 5 min, the mixture was extracted with ethyl acetate. The organic layer was washed with water and saturated brine, and dried over sodium sulfate. After filtration, the filtrate concentrated under reduced pressure. The residue was sonicated with hexane (20 ml), stood still and decanted to remove hexane. This operation was repeated 3 times. Diethyl ether (30 ml) was added to the residue, and after sonication, the solid was collected by filtration. The obtained solid was dissolved in ethyl acetate (15 ml) by heating, hexane (15 ml) was added and the mixture was recrystallized to give the object product (1.21 g, yield 64%) as a white solid.

$^1$H NMR (DMSO-d$_6$ 300 MHz) (δ) ppm: 0.99 (9H, s), 3.99-4.11 (7H, m), 5.11-5.20 (2H, m), 7.19-7.25 (2H, m), 7.49-7.52 (2H, m), 8.03 (1H, s), 8.78 (1H, s), 15.39 (1H, s)

MS (ESI): M+ 462

Reference Example 11

Step 1

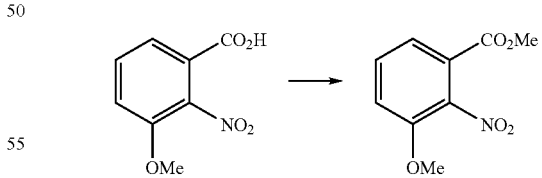

3-Methoxy-2-nitrobenzoic acid (20.00 g, 0.10 mol) was dissolved in dimethylformamide (100 ml), potassium carbonate (28.10 g, 0.20 mol) and methyl iodide (7.60 ml, 0.12 mol) were added, and the mixture was stirred at room temperature for 1 hr. The reaction mixture was added to water (300 ml) and the mixture was stirred. The precipitated solid was collected by filtration, washed with water (200 ml) and vacuum dried to give a crude product (23.90 g) as a white solid.

Step 2

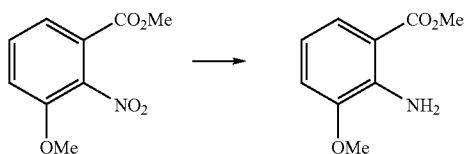

The crude product (23.90 g) obtained in Step 1 was suspended in a mixed solvent of tetrahydrofuran (150 ml) and methanol (50 ml), and 5% palladium-carbon (containing water) (2.30 g) was added. The mixture was stirred under a hydrogen atmosphere at room temperature for 19.5 hr. Ethyl acetate (200 ml) was added to the reaction mixture and filtered through celite. The filtrate was concentrated under reduced pressure and water was removed azeotropically with toluene to give a crude product (18.80 g) as a brown oil.

Step 3

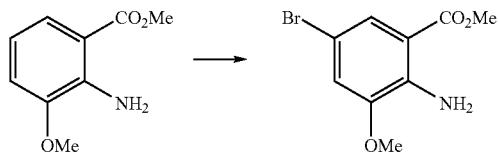

The crude product (18.80 g) obtained in Step 2 was dissolved in dimethylformamide (200 ml) and N-bromosuccinimide (17.98 g, 0.10 mol) was added by portions at 5° C. After the completion of the addition, the mixture was stirred at the same temperature for 30 min. The reaction mixture was poured into water (500 ml) and extracted twice with ethyl acetate (300 ml). The organic layer was washed with water (300 ml), saturated aqueous sodium hydrogen carbonate and saturated brine in this order, and dried over sodium sulfate. After filtration, the filtrate was concentrated under reduced pressure, and the obtained residue was purified by silica gel chromatography (chloroform) to give the object product (25.11 g, yield 95%) as a yellow oil.

$^1$H NMR (CDCl$_3$ 300 MHz) (δ) ppm: 3.86 (6H, s), 6.02 (2H, brs), 6.90 (1H, s), 7.60 (1H, s)

Step 4

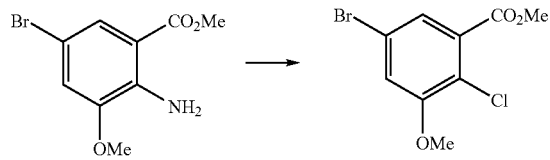

The compound (25.11 g, 96.54 mmol) obtained in Step 3 was suspended in water (50 ml), concentrated hydrochloric acid (25 ml) is was added, and an aqueous solution (100 ml) of sodium nitrite (7.33 g, 106.22 mmol) was added dropwise at 5° C. After the completion of the dropwise addition, the mixture was stirred at the same temperature for 5 min. This reaction mixture was added dropwise to a solution of copper (I) chloride (9.55 g, 96.47 mmol) in concentrated hydrochloric acid (75 ml) at room temperature. After the completion of the dropwise addition, the mixture was stirred at room temperature for 13 hr. Water (200 ml) was added to the reaction mixture, and extracted with ethyl acetate (400 ml). The organic layer was washed with water (400 ml) and saturated brine in this order and dried over sodium sulfate. After filtration, the filtrate was concentrated under reduced pressure to give the object product (15.18 g, yield 56%) as an orange solid.

$^1$H NMR (CDCl$_3$ 300 MHz) (δ) ppm: 3.92 (3H, s), 3.93 (3H, s), 7.16 (1H, d, J=2.1 Hz), 7.49 (1H, d, J=2.2 Hz)

Step 5

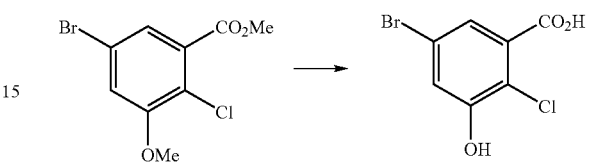

The compound (74.80 g, 0.27 mol) obtained in Step 4 was dissolved in dichloromethane (300 ml), and 1M boron tribromide/dichloromethane solution (700 ml, 0.70 mol) was added dropwise at not more than 10° C. After the completion of the dropwise addition, the mixture was stirred at room temperature for 1.5 hr. The reaction mixture was added to ice water (1500 ml) and the precipitated solid was collected by filtration. The filtrate was partitioned, and the aqueous layer was extracted with ethyl acetate (200 ml). The organic layers were combined and concentrated under reduced pressure. The solid was collected by filtration and the residue was dissolved in diethyl ether (1000 ml). 1N Aqueous sodium hydroxide solution (1000 ml) was added and the mixture was extracted. 2N Hydrochloric acid (500 ml) was added to the aqueous layer and the mixture was stirred and extracted with ethyl acetate (800 ml). The mixture was partitioned. The organic layer was washed with water and saturated brine in this order, dried over sodium sulfate, filtered, and concentrated under reduced pressure to give the object product (63.83 g, yield 95%) as a beige solid.

$^1$H NMR (DMSO-d$_6$ 300 MHz) (δ) ppm: 7.23 (1H, d, J=2.4 Hz), 7.28 (1H, d, J=2.4 Hz), 10.99 (1H, s), 13.55 (1H, brs)

Step 6

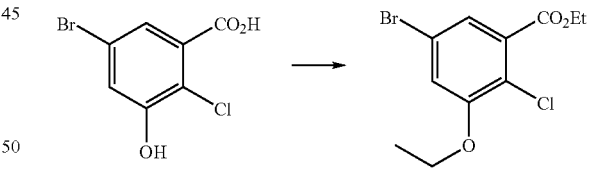

The compound (63.83 g, 0.25 mol) obtained in Step 5 was dissolved in dimethylformamide (400 ml), potassium carbonate (87.70 g, 0.64 mol) and ethyl iodide (81.20 ml, 1.02 mol) were added, and the mixture was stirred with heating at 50° C. for 3 hr. Saturated aqueous ammonium chloride (600 ml) and ethyl acetate (400 ml) were added to the reaction mixture and partitioned. The aqueous layer was extracted with ethyl acetate (400 ml). The organic layers were combined, washed with brine (3 times) and saturated brine in this order, dried over sodium sulfate, filtered and concentrated under reduced pressure to give the object product (76.38 g, yield 98%) as a brown solid.

$^1$H NMR(CDl$_3$ 400 MHz) (δ) ppm: 1.39 (3H, t, J=7.2 Hz), 1.48 (3H, t), 4.11 (2H, q), 4.38 (2H, q, J=7.2 Hz), 7.12 (1H, d, J=2.0 Hz), 7.42 (1H, d, J=2.0 Hz)

Step 7

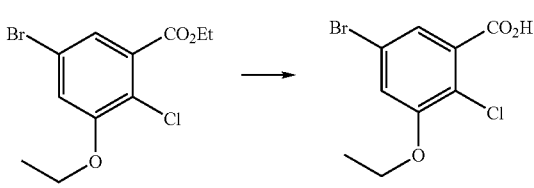

The compound (76.38 g, 0.25 mol) obtained in Step 6 was dissolved in ethanol (250 ml), 8N aqueous sodium hydroxide solution (62.00 ml, 0.50 mol) was added, and the mixture was stirred with heating at 50° C. for 30 min. 2N hydrochloric acid (250 ml) was added to the reaction mixture under ice-cooling. The mixture was stirred and extracted twice with ethyl acetate (350 ml). The organic layer was washed with water and saturated brine in this order and dried over sodium sulfate. After filtration, the filtrate was concentrated under reduced pressure to give the object product (68.79 g, yield 99%) as a pale-brown solid.

$^1$H NMR(CDCl$_3$ 400 MHz) ($\delta$) ppm: 1.50 (3H, t, J=6.8 Hz), 4.12 (2H, q, J=6.8 Hz), 7.19 (1H, d, J=2.4 Hz), 7.65 (1H, d, J=2.4 Hz)

Step 8

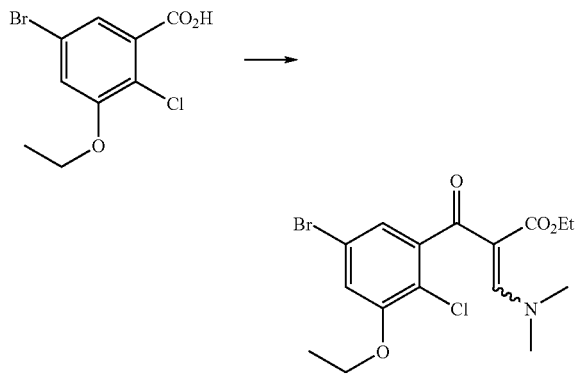

The compound (85.17 g, 0.31 mol) obtained in Step 7 was dissolved in toluene (450 ml), thionyl chloride (44.40 ml, 0.61 mol) and dimethylformamide (catalytic amount) were added, and the mixture was stirred at 90° C. for 1 hr. After allowing to cool, the reaction mixture was concentrated under reduced pressure, and the residue was dissolved in toluene. The mixture was concentrated under reduced pressure, and this operation was repeated several times. The residue was dissolved in tetrahydrofuran (250 ml) and the obtained solution was added dropwise to a solution of ethyl 3-dimethylaminoacrylate (43.60 g, 0.31 mol) and triethylamine (50.90 ml, 0.37 mol) in tetrahydrofuran (200 ml) and the mixture was heated under reflux for 15 hr. After allowing to cool, water (300 ml) and ethyl acetate (500 ml) were added to the reaction mixture and the mixture was stirred and partitioned. The organic layer was washed with water (300 ml) and saturated brine in this order, and dried over sodium sulfate. After filtration, the filtrate was concentrated under reduced pressure to give a crude product (124.80 g) as a brown oil.

Step 9

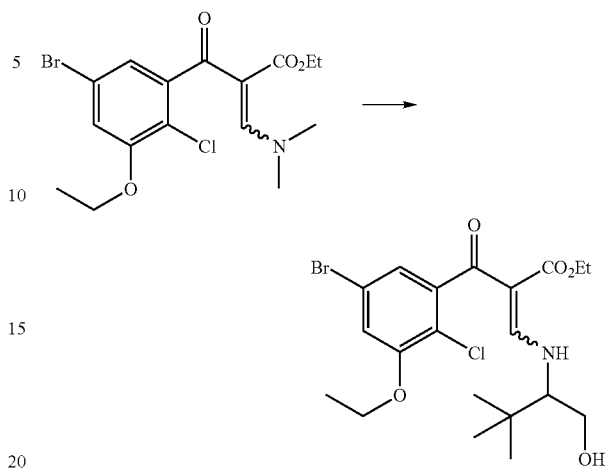

The crude product (124.80 g) obtained in Step 8 was dissolved in tetrahydrofuran (500 ml), (S)-(+)-tert-leucinol hydrochloride (46.80 g, 0.31 mol) and triethylamine (42.50 ml, 0.31 mol) were added, and the mixture was stirred at room temperature for 40 min. After filtration of the reaction mixture, the filtrate was concentrated under reduced pressure, and the obtained residue was dissolved in ethyl acetate (800 ml), washed twice with water and with saturated brine in this order, and dried over sodium sulfate. After filtration, the filtrate was concentrated under reduced pressure to give a crude product (131.30 g) as a brown oil.

Step 10

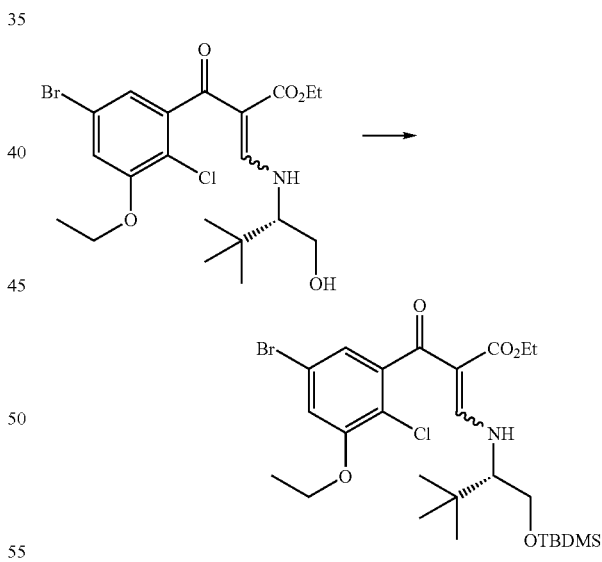

The crude product (131.30 g) obtained in Step 9 was dissolved in dimethylformamide (400 ml), imidazole (27.00 g, 0.40 mol) and tert-butyldimethylsilyl chloride (41.30 g, 0.27 mol) were added, and the mixture was stirred at room temperature for 14 hr. Water was added to the reaction mixture and the mixture was extracted twice with ethyl acetate (500 ml). The organic layer was washed 3 times with water and with saturated brine in this order, and dried over sodium sulfate. After filtration, the filtrate was concentrated under reduced pressure to give a crude product (159.80 g) as a brown oil.

Step 11

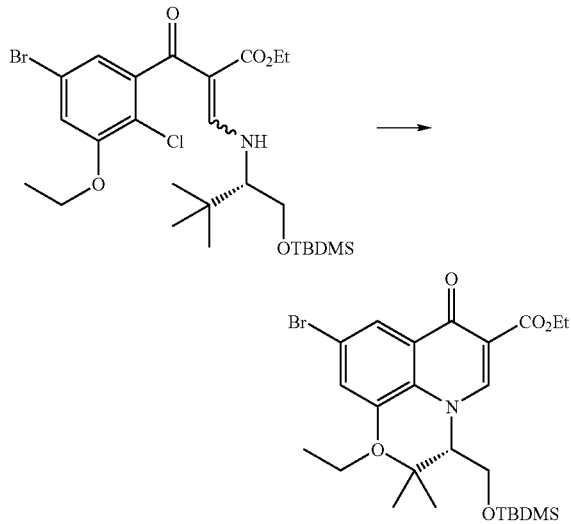

The crude product (159.80 g) obtained in Step 10 was dissolved in toluene (1100 ml), sodium hydride (15.80 g, 0.40 mol) was added, and the mixture was stirred with heating at 100° C. for 14 hr. 1N Hydrochloric acid (400 ml) was added to the reaction mixture under ice-cooling and the mixture was stirred and partitioned. The organic layer was washed with water and saturated brine in this order and dried over sodium sulfate. After filtration, the filtrate was concentrated under reduced pressure and the obtained residue was dissolved in dimethylformamide (500 ml). Potassium carbonate (42.10 g, 0.31 mol) and ethyl iodide (24.40 ml, 0.31 mol) were added, and the mixture was stirred with heating at 50° C. for 1.5 hr. Saturated aqueous ammonium chloride solution (400 ml) was added to the reaction mixture under ice-cooling. The mixture was stirred and extracted twice with ethyl acetate. The organic layer was washed with water, twice with brine and with saturated brine in this order, and dried over sodium sulfate. After filtration, the filtrate was concentrated under reduced pressure, and the obtained residue was purified by silica gel chromatography (ethyl acetate:hexane=1:3 to 2:3) to give the object product (76.50 g, yield 45%) as a brown oil.

$^1$H NMR(CDCl$_3$ 400 MHz) (δ) ppm: −0.05 (3H, s), 0.01 (3H, s), 0.73 (9H, s), 0.98 (9H, s), 1.40 (3H, t), 1.53-1.59 (3H, m), 4.10-4.24 (4H, m), 4.34-4.44 (2H, m), 6.10-6.14 (1H, m), 7.22 (1H, s), 8.32 (1H, t, J=2.4 Hz), 8.70 (1H, s)

Step 12

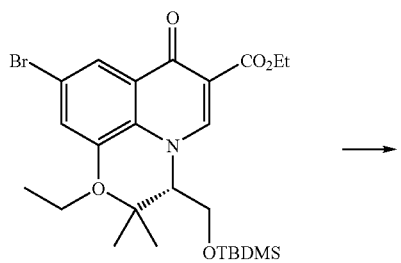

-continued

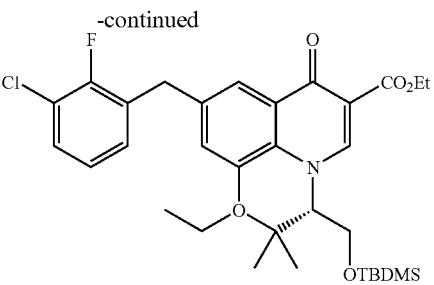

The compound (76.50 g, 0.14 mol) obtained in Step 11 was dissolved in tetrahydrofuran (500 ml), and, under an argon stream, bis(dibenzylidenacetone)palladium(0) (3.17 g, 5.51 mmol) and tri(2-furyl)phosphine (2.56 g, 11.03 mmol) were added, a solution of 3-chloro-2-fluorobenzylzinc bromide (0.28 mol) in tetrahydrofuran prepared as mentioned above was added dropwise at 60° C. and, after the completion of the dropwise addition, the mixture was heated under reflux for 2.5 hr. After allowing to cool, saturated aqueous ammonium chloride solution (600 ml) was added to the reaction mixture and, after stirring at room temperature for 1 hr, the mixture was filtered through celite. After partitioning, the aqueous layer was extracted twice with ethyl acetate. The organic layer was concentrated under reduced pressure, re-dissolved in ethyl acetate and combined with the extract mentioned above. This organic layer was washed with 1N hydrochloric acid and saturated brine in this order, dried over sodium sulfate, and after filtration, the filtrate was concentrated under reduced pressure. The obtained residue was dissolved in dimethylformamide (400 ml), potassium carbonate (19.00 g, 0.14 mol) and ethyl iodide (11.00 ml, 0.14 mol) were added, and the mixture was stirred with heating at 50° C. for 1.5 hr. Under ice-cooling, saturated aqueous ammonium chloride solution (400 ml) was added to the reaction mixture and the mixture was stirred and extracted with ethyl acetate (500 ml). The organic layer was washed with water, brine (twice) and saturated brine, and dried over sodium sulfate. After filtration, the filtrate was concentrated under reduced pressure, and the obtained residue was purified by silica gel chromatography (ethyl acetate:hexane=1:2 to 1:1) to give the object product (72.10 g, yield 85%) as a brown oil.

$^1$H NMR(CDCl$_3$ 400 MHz) (δ) ppm: −0.07 (3H, s), 0.00 (3H, s), 0.70 (9H, s), 1.24 (9H, s), 1.39 (3H, t, J=7.2 Hz), 1.51-1.54 (3H, m), 4.05 (2H, s), 4.07-4.19 (4H, m), 4.33-4.45 (2H, m), 6.12-6.15 (1H, m), 6.99-7.02 (2H, m), 7.04-7.09 (1H, m), 7.19-7.25 (1H, m), 8.06 (1H, d, J=2.4 Hz), 8.69 (1H, s)

Step 13

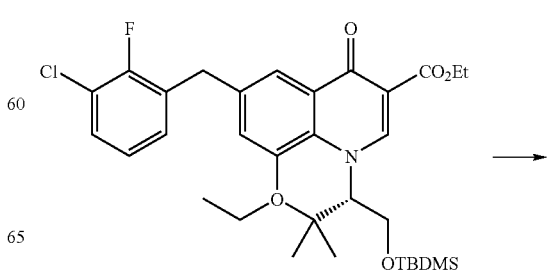

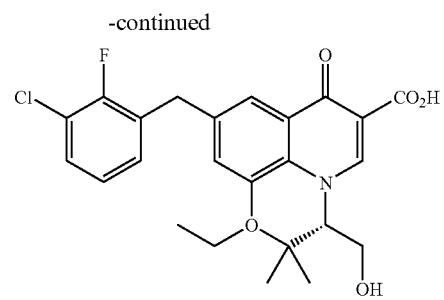

The compound (65.80 g, 0.11 mol) obtained in Step 12 was dissolved in ethanol (200 ml), 1N aqueous sodium hydroxide solution (640 ml, 0.64 mol) was added, and the mixture was heated under reflux for 2 hr. Under ice-cooling, 2N hydrochloric acid (350 ml) was added to the reaction mixture. The mixture was stirred and extracted twice with ethyl acetate. The organic layer was washed with water and saturated brine in this order, and dried over sodium sulfate. After filtration, the filtrate was concentrated under reduced pressure. Diethyl ether (500 ml) was added to the residue, and the mixture was sonicated. The obtained solid was collected by filtration and dissolved in ethyl acetate (250 ml) by heating. Hexane (50 ml) was added, and the precipitated solid was collected by filtration and vacuum dried to give the object product (41.10 g, yield 81%) as a white solid.

$^1$H NMR (DMSO-$d_6$ 400 MHz) (δ) ppm: 0.93 (9H, s), 1.49 (3H, t, J=6.9 Hz), 4.00 (2H, t, J=6.4 Hz), 4.20 (2H, s), 4.22-4.33 (2H, m), 5.12 (1H, t), 6.36 (1H, t, J=6.8 Hz), 7.21 (1H, m), 7.39-7.48(2H, m), 7.54 (1H, s), 7.79 (1H, s), 8.79 (1H, s), 15.04 (1H, s)

MS (ESI): M+ 476

Preparation Example 1

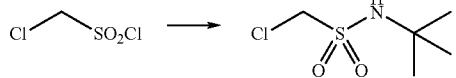

tert-Butylamine (0.77 g, 10.5 mmol) and N-methylmorpholine (1.21 ml, 11.0 mmol) were dissolved in diethyl ether (10 ml), a solution of chloromethanesulfonyl chloride (1.49 g, 10.0 mmol) in diethyl ether (20 ml) was added dropwise under ice-cooling, and the mixture was stirred for 3.5 hr. Ethyl acetate (10 ml) was added to the reaction mixture, and the mixture was washed with hydrochloric acid, water and saturated brine in this order, and dried over sodium sulfate. After filtration, the filtrate was concentrated under reduced pressure to give the object product (1.37 g, yield 74%) as a colorless oil.

$^1$H NMR(CDCl$_3$ 300 MHz) (δ) ppm: 1.41 (9H, s), 4.47 (2H, s), 4.60 (1H, s)

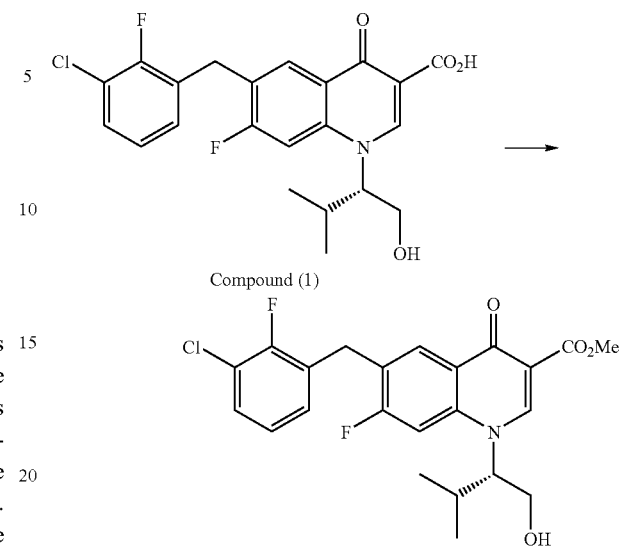

Compound (1)

Compound (1) (10.0 g, 22.9 mmol) was dissolved in dimethylformamide (50 ml), potassium carbonate (6.34 g, 45.9 mmol) and methyl iodide (2.14 ml, 34.4 mmol) were added, and the mixture was stirred overnight at room temperature. Hydrochloric acid was added to the reaction mixture, and the mixture was concentrated under reduced pressure. A mixed solvent of ethyl acetate (20 ml) and hexane (20 ml) was added to the obtained residue and the slurry was stirred, filtrated and vacuum dried to give the object product (6.49 g, yield 63%) as a white solid.

$^1$H NMR(DMSO-$d_6$ 300 MHz) (δ) ppm: 0.72 (3H, d, J=6.4 Hz), 1.10 (3H, d, J=6.4 Hz), 2.15-2.40 (1H, m), 3.70-3.80 (1H, m), 3.74 (3H, s), 3.80-3.95 (1H, m), 4.18 (2H, s), 4.50-4.60 (1H, m), 5.11 (1H, t, J=4.7 Hz), 7.18-7.26 (1H, m), 7.27-7.34 (1H, m), 7.46-7.55 (1H, m), 8.00 (1H, d, J=12.8 Hz), 8.11 (1H, d, J=9.1 Hz), 8.66 (1H, s)

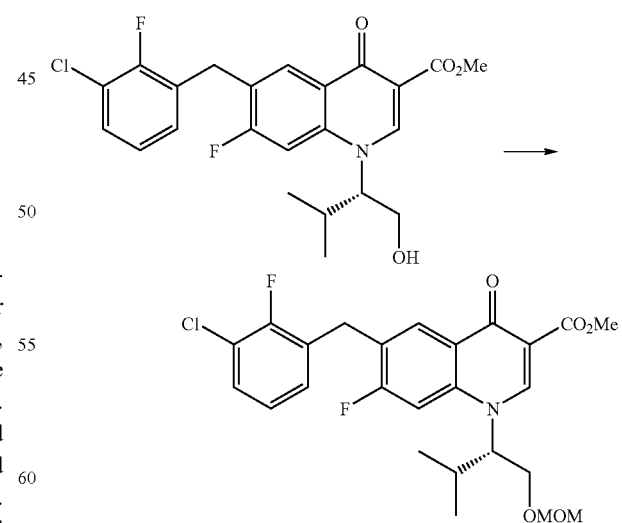

The compound (6.49 g, 14.4 mmol) obtained in the previous step was dissolved in chloroform (35 ml), chloromethyl methyl ether (1.31 ml, 17.3 mmol) and diisopropylethylamine (3.26 ml, 18.7 mmol) were added, and the mixture was stirred at room temperature for 4 days. Chloromethyl methyl ether (0.547 ml, 7.2 mmol) and diisopropylethylamine (1.25 ml, 7.2 mmol) were further added, and the mixture was further stirred at room temperature for 2 hr. Chloroform was added to the reaction mixture, washed with saturated aqueous sodium hydrogen carbonate and saturated brine in this order, and dried over sodium sulfate. After filtration, the filtrate was concentrated under reduced pressure to give the crude product (7.94 g).

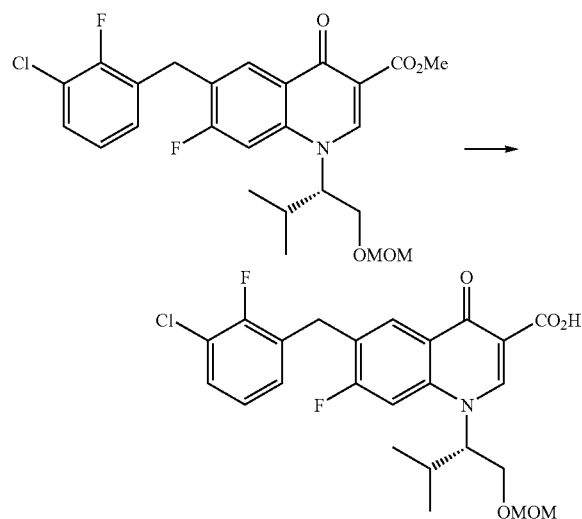

The crude product (7.94 g) obtained in the previous step was dissolved in isopropanol (40 ml), 4N aqueous sodium hydroxide solution (4.70 ml, 1.18 mmol) was added, and the mixture was stirred with heating at 70° C. for 2.5 hr. After allowing to cool, activated carbon (350 mg) was added to the reaction mixture and, after stirring, the mixture was filtered through celite. 1N Hydrochloric acid (20 ml) was added to the filtrate, and isopropanol was evaporated under reduced pressure. The residue was extracted twice with ethyl acetate and the organic layer was washed with saturated brine and dried over sodium sulfate. After filtration, the filtrate was concentrated under reduced pressure, and the obtained residue was purified by silica gel chromatography (chloroform:methanol=20:1) to give the object product (5.36 g, yield 77% two steps) as a yellow amorphous form.

$^1$H NMR(DMSO-$d_6$ 300 MHz) (δ) ppm: 0.73 (3H, d, J=6.5 Hz), 1.14 (3H, d, J=6.5 Hz), 2.30-2.50 (1H, m), 3.09 (3H, s), 3.80-3.90 (1H, m), 4.00-4.15 (1H, m), 4.26 (2H, s), 4.50 (1H, d, J=6.7 Hz), 4.55 (1H, d, J=6.7 Hz), 4.95-5.05 (1H, m), 7.18-7.28 (1H, m), 7.30-7.40 (1H, m), 7.48-7.58 (1H, m), 8.25-8.40 (2H, m), 8.96 (1H, s), 14.95 (1H, s)

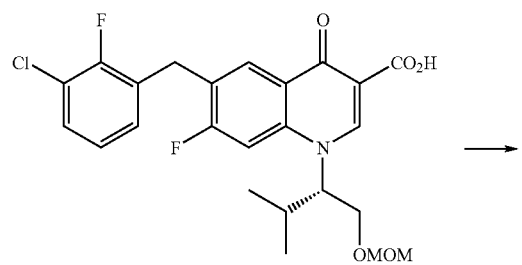

-continued

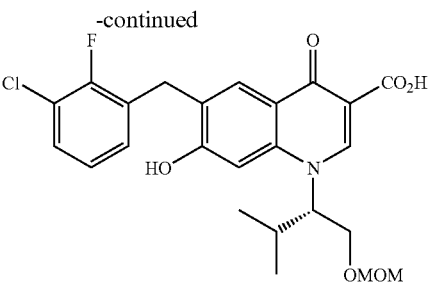

The compound (10.0 g, 20.8 mmol) obtained in the previous step was dissolved in dimethyl sulfoxide (50 ml), 4N aqueous sodium hydroxide solution (50.0 ml, 12.5 mmol) was added, and the mixture was stirred with heating at 100° C. for 2 days. After allowing to cool, 1N hydrochloric acid (200 ml) was added to the reaction mixture and the mixture was extracted 3 times with ethyl acetate (200 ml). The organic layer was washed twice with water (50 ml) and twice with saturated brine (50 ml) in this order, and dried over sodium sulfate. After filtration, the filtrate was concentrated under reduced pressure, chloroform (30 ml) was added to the obtained residue, and the slurry was stirred, filtered and vacuum dried to give the object product (7.12 g, yield 72%) as a white solid.

$^1$H NMR(DMSO-$d_6$ 400 MHz) (δ) ppm: 0.74 (3H, d, J=6.7 Hz), 1.07 (3H, d, J=6.7 Hz), 2.30-2.40 (1H, m), 3.05 (3H, s), 3.83-3.90 (1H, m), 4.03-4.11 (3H, m), 4.45-4.65 (3H, m), 7.12-7.17 (1H, m), 7.18-7.25 (1H, m), 7.32 (1H, s), 7.40-7.48 (1H, m), 7.98 (1H, s), 8.81 (1H, s), 11.17 (1H, s), 15.41 (1H, s)

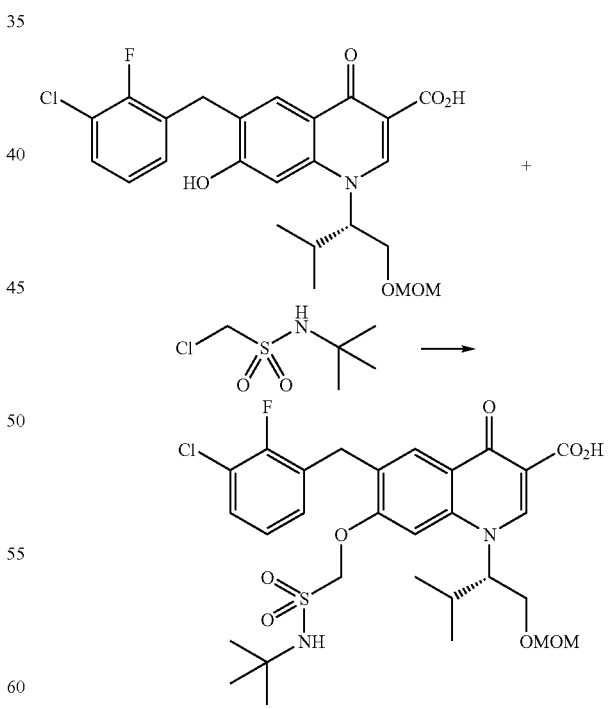

The compound (200 mg, 0.42 mmol) obtained in the previous step was dissolved in dimethylformamide (2 ml), potassium carbonate (116 mg, 0.84 mmol) and N-tert-butyl-C-chloromethanesulfonamide (155 mg, 0.84 mmol) were added, and the mixture was stirred with heating overnight at 60° C. After allowing to cool, the reaction mixture was neutralized by adding hydrochloric acid and extracted with ethyl acetate. The organic layer was washed with water and saturated brine in this order, and dried over sodium sulfate. After filtration, the filtrate was concentrated under reduced pressure, and the obtained residue was purified by PTLC (developing solvent chloroform:methanol=9:1) to give the object product (119 mg, yield 45%) as a yellow oil.

$^1$H NMR(DMSO-$d_6$ 300 MHz) (δ) ppm: 0.73 (3H, d, J=6.5 Hz), 1.15 (3H, d, J=6.5 Hz), 1.26 (9H, s), 2.30-2.50 (1H, m), 3.10 (3H, s), 3.70-3.90 (1H, m), 3.90-4.10 (1H, m), 4.26 (2H, s), 4.45-4.60 (2H, m), 5.00-5.15 (1H, m), 5.45 (1H, d, J=12.1 Hz), 5.56 (1H, d, J=12.1 Hz), 7.15-7.24 (1H, m), 7.25-7.40 (1H, m), 7.45-7.57 (2H, m), 7.78 (1H, s), 8.04 (1H, s), 8.88 (1H, s), 15.15 (1H, s)

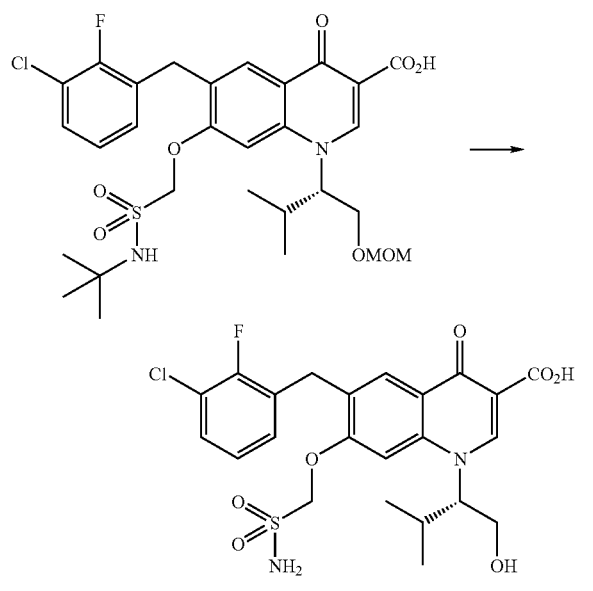

The compound (119 mg, 0.19 mmol) obtained in the previous step was dissolved in 1,4-dioxane (1 ml), 6N hydrochloric acid (1 ml) was added, and the mixture was stirred with heating at 90° C. for 4.5 hr. After allowing to cool, water was added to the reaction mixture, and the mixture was extracted with ethyl acetate. The organic layer was washed with water and saturated brine in this order and dried over sodium sulfate. After filtration, the filtrate was concentrated under reduced pressure, obtained residue was purified by PTLC (developing solvent chloroform:methanol=9:1) to give the object product (14 mg, yield 14%) as a white solid. $^1$H NMR(DMSO-$d_6$ 300 MHz) (δ) ppm: 0.73 (3H, d, J=6.4 Hz), 1.15 (3H, d, J=6.4 Hz), 2.30-2.50 (1H, m), 3.70-3.85 (1H, m), 3.90-4.05 (1H, m), 4.25 (2H, s), 4.75-4.90 (1H, m), 5.10-5.30 (1H, m), 5.40 (1H, d, J=12.0 Hz), 5.49 (1H, d, J=12.0 Hz), 7.10-7.60 (5H,m), 7.70 (1H, s), 8.01 (1H, s), 8.87 (1H, s), 15.30 (1H, s)

MS(ESI): M+ 527

Examples 1-7

In the same manner as in the above-mentioned Reference Examples and Preparation Example, the compounds of Examples 1-1 to 1-12, Examples 2-1 to 2-18, Examples 3-1 to 3-9, Examples 4-1 to 4-64, Example 5-1-5-2, Example 6-1 and Examples 7-1 to 7-12 were obtained. The chemical structural formulas thereof are respectively shown in Tables 1-7.

TABLE 1

| Ex. | Structural formula |
|-----|-------------------|
| 1-1 | |
| 1-2 | |
| 1-3 | |
| 1-4 | |
| 1-5 | |

TABLE 1-continued

| Ex. | Structural formula |
|---|---|
| 1-6 | (structure) |
| 1-7 | (structure) |
| 1-8 | (structure) |
| 1-9 | (structure) |
| 1-10 | (structure) |
| 1-11 | (structure) |
| 1-12 | (structure) |

TABLE 2

| Ex. | Structural formula |
|---|---|
| 2-1 | (structure) |
| 2-2 | (structure) |
| 2-3 | (structure) |

TABLE 2-continued

| Ex. | Structural formula |
|---|---|
| 2-4 | (structure) |
| 2-5 | (structure) |
| 2-6 | (structure) |
| 2-7 | (structure) |
| 2-8 | (structure) |

TABLE 2-continued

| Ex. | Structural formula |
|---|---|
| 2-9 | (structure) |
| 2-10 | (structure) |
| 2-11 | (structure) |
| 2-12 | (structure) |
| 2-13 | (structure) |

TABLE 2-continued
| Ex. | Structural formula |
|---|---|
| 2-14 | 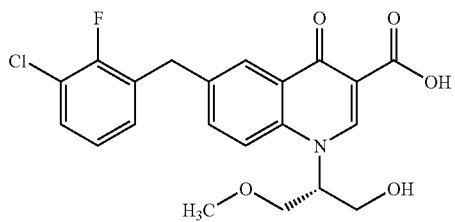 |
| 2-15 | 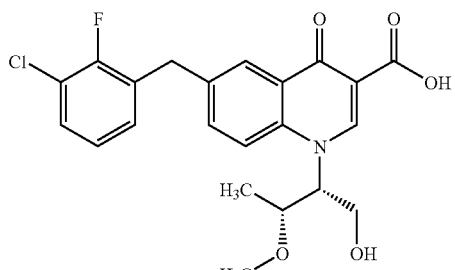 |
| 2-16 | 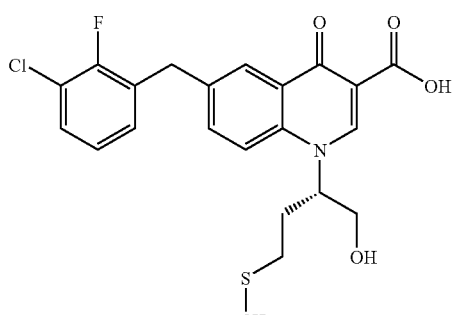 |
| 2-17 | 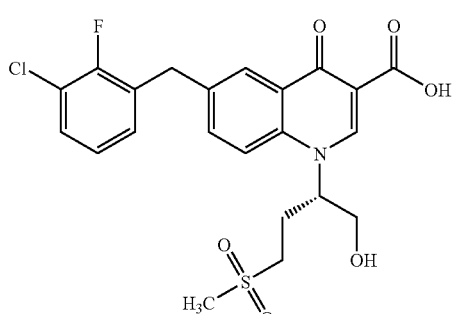 |
| 2-18 | 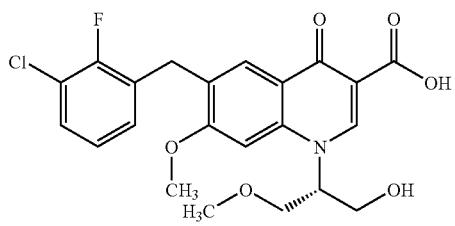 |
TABLE 3
| Ex. | Structural formula |
|---|---|
| 3-1 | 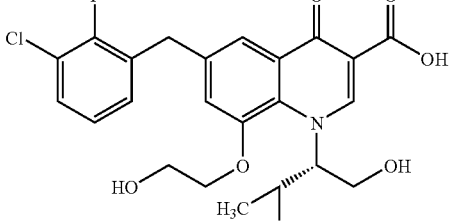 |
| 3-2 | 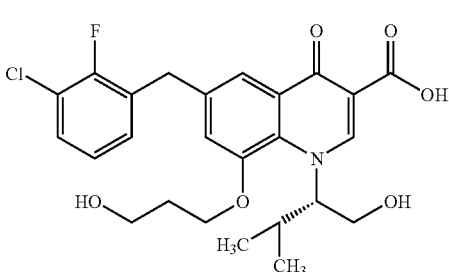 |
| 3-3 | 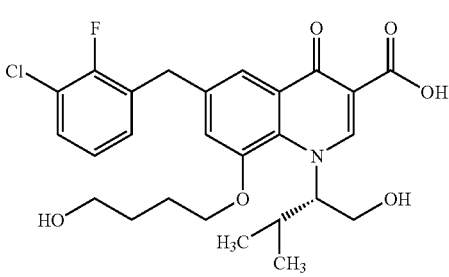 |
| 3-4 | 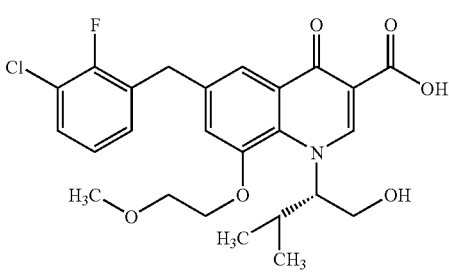 |
| 3-5 | 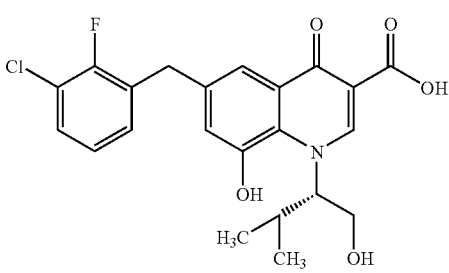 |

TABLE 3-continued

| Ex. | Structural formula |
|---|---|
| 3-6 | (structure) |
| 3-7 | (structure) |
| 3-8 | (structure) |
| 3-9 | (structure) |

TABLE 4

| Ex. | Structural formula |
|---|---|
| 4-1 | (structure) |
| 4-2 | (structure) |
| 4-3 | (structure) |
| 4-4 | (structure) |
| 4-5 | (structure) |
| 4-6 | (structure) |

TABLE 4-continued

| Ex. | Structural formula |
|---|---|
| 4-7 | (structure) |
| 4-8 | (structure) |
| 4-9 | (structure) |
| 4-10 | (structure) |
| 4-11 | (structure) |
| 4-12 | (structure) |
| 4-13 | (structure) |
| 4-14 | (structure) |
| 4-15 | (structure) |
| 4-16 | (structure) |

TABLE 4-continued

| Ex. | Structural formula |
|---|---|
| 4-17 | |
| 4-18 | |
| 4-19 | |
| 4-20 | |
| 4-21 | |
| 4-22 | |
| 4-23 | |
| 4-24 | |
| 4-25 | |
| 4-26 | |

TABLE 4-continued

| Ex. | Structural formula |
|---|---|
| 4-27 | |
| 4-28 | |
| 4-29 | |
| 4-30 | |
| 4-31 | |
| 4-32 | |
| 4-33 | |
| 4-34 | |
| 4-35 | |
| 4-36 | |

TABLE 4-continued

| Ex. | Structural formula |
|---|---|
| 4-37 | (structure) |
| 4-38 | (structure) |
| 4-39 | (structure) |
| 4-40 | (structure) |
| 4-41 | (structure) |
| 4-42 | (structure) |
| 4-43 | (structure) |
| 4-44 | (structure) |
| 4-45 | (structure) |
| 4-46 | (structure) |

TABLE 4-continued

| Ex. | Structural formula |
|---|---|
| 4-47 | |
| 4-48 | |
| 4-49 | |
| 4-50 | |
| 4-51 | |
| 4-52 | |
| 4-53 | |
| 4-54 | |
| 4-55 | |
| 4-56 | |

TABLE 4-continued

| Ex. | Structural formula |
|---|---|
| 4-57 | |
| 4-58 | |
| 4-59 | |
| 4-60 | |
| 4-61 | |

TABLE 4-continued

| Ex. | Structural formula |
|---|---|
| 4-62 | |
| 4-63 | |
| 4-64 | |

TABLE 5

| Ex. | Structural formula |
|---|---|
| 5-1 | |

TABLE 5-continued
| Ex. | Structural formula |
|---|---|
| 5-2 | 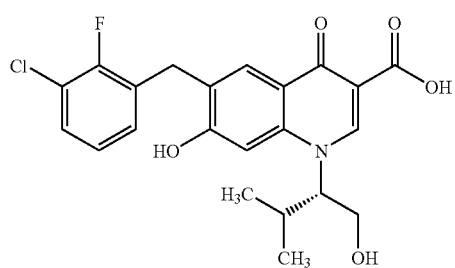 |
TABLE 6
| Ex. | Structural formula |
|---|---|
| 6-1 | |
TABLE 7
| Ex. | Structural formula |
|---|---|
| 7-1 | |
| 7-2 | |
| 7-3 | |
TABLE 7-continued
| Ex. | Structural formula |
|---|---|
| 7-4 | |
| 7-5 | |
| 7-6 | |
| 7-7 | low polar compound |
| 7-8 | high polar compound |

TABLE 7-continued

| Ex. | Structural formula |
|---|---|
| 7-9 | (structure: 6-(3-chloro-2-fluorobenzyl)-7-methoxy-1-[(S)-1-(glucuronyloxymethyl)-2-methylpropyl]-4-oxo-1,4-dihydroquinoline-3-carboxylic acid) |
| 7-10 | (structure: acyl glucuronide ester with morpholinium counterion) |
| 7-11 | (structure: phenyl glucuronide ether derivative) |
| 7-12 | (structure: phenyl sulfate sodium salt derivative) |

The mass spectrum data of the compounds of the present invention are shown in the following Table 8-Table 14.

TABLE 8

| Example | MS (ESI) |
|---|---|
| 1-1 | M + 448 |
| 1-2 | M + 466 |
| 1-3 | M + 464 |
| 1-4 | M + 464 |
| 1-5 | M + 466 |
| 1-6 | M + 464 |
| 1-7 | M + 484 |
| 1-8 | M + 482 |
| 1-9 | M + 532 |
| 1-10 | M + 482 |
| 1-11 | M + 482 |
| 1-12 | M + 482 |

TABLE 9

| Example | MS (ESI) |
|---|---|
| 2-1 | M + 490 |
| 2-2 | M + 489 |
| 2-3 | M + 466 |
| 2-4 | M + 498 |
| 2-5 | M + 494 |
| 2-6 | M + 526 |
| 2-7 | M + 436 |
| 2-8 | M + 468 |
| 2-9 | M + 464 |
| 2-10 | M + 496 |
| 2-11 | M + 464 |
| 2-12 | M + 480 |
| 2-13 | M + 512 |
| 2-14 | M + 420 |
| 2-15 | M + 434 |
| 2-16 | M + 450 |
| 2-17 | M + 482 |
| 2-18 | M + 450 |

TABLE 10

| Example | MS (ESI) |
|---|---|
| 3-1 | M + 478 |
| 3-2 | M + 492 |
| 3-3 | M + 506 |
| 3-4 | M + 492 |
| 3-5 | M + 434 |
| 3-6 | M + 505 |
| 3-7 | M + 506 |
| 3-8 | M + 520 |
| 3-9 | M + 524 |

TABLE 11

| Example | MS (ESI) |
|---|---|
| 4-1 | M + 492 |
| 4-2 | M + 505 |
| 4-3 | M + 541 |
| 4-4 | M + 446 |
| 4-5 | M + 506 |
| 4-6 | M + 519 |
| 4-7 | M + 533 |
| 4-8 | M + 506 |
| 4-9 | M + 503 |
| 4-10 | M + 516 |
| 4-11 | M + 544 |
| 4-12 | M + 502 |
| 4-13 | M + 545 |
| 4-14 | M + 531 |
| 4-15 | M + 530 |
| 4-16 | M + 547 |
| 4-17 | M + 531 |
| 4-18 | M + 477 |
| 4-19 | M + 491 |
| 4-20 | M + 545 |
| 4-21 | M + 517 |
| 4-22 | M + 530 |
| 4-23 | M + 503 |
| 4-24 | M + 503 |
| 4-25 | M + 517 |
| 4-26 | M + 544 |
| 4-27 | M + 544 |
| 4-28 | M + 555 |
| 4-29 | M + 516 |
| 4-30 | M + 516 |
| 4-31 | M + 531 |
| 4-32 | M + 519 |
| 4-33 | M + 546 |
| 4-34 | M + 505 |
| 4-35 | M + 516 |
| 4-36 | M + 518 |

TABLE 11-continued

| Example | MS (ESI) |
| --- | --- |
| 4-37 | M + 503 |
| 4-38 | M + 502 |
| 4-39 | M + 502 |
| 4-40 | M + 588 |
| 4-41 | M + 519 |
| 4-42 | M + 516 |
| 4-43 | M + 524 |
| 4-44 | M + 510 |
| 4-45 | M + 559 |
| 4-46 | M + 503 |
| 4-47 | M + 504 |
| 4-48 | M + 504 |
| 4-49 | M + 555 |
| 4-50 | M + 492 |
| 4-51 | M + 560 |
| 4-52 | M + 527 |
| 4-53 | M + 519 |
| 4-54 | M + 517 |
| 4-55 | M + 517 |
| 4-56 | M + 549 |
| 4-57 | M + 568 |
| 4-58 | M + 567 |
| 4-59 | M + 525 |
| 4-60 | M + 525 |
| 4-61 | M + 525 |
| 4-62 | M + 516 |
| 4-63 | M + 603 |
| 4-64 | M + 595 |

TABLE 12

| Example | MS (ESI) |
| --- | --- |
| 5-1 | M + 416 |
| 5-2 | M + 404 |

TABLE 13

| Example | MS (ESI) |
| --- | --- |
| 6-1 | M + 476 |

TABLE 14

| Example | MS (ESI) |
| --- | --- |
| 7-1 | M + 448 |
| 7-2 | M + 464 |
| 7-3 | M + 478 |
| 7-4 | M + 492 |
| 7-5 | M + 434 |
| 7-6 | M + 517 |
| 7-7 | M + 464 |
| 7-8 | M + 464 |
| 7-9 | M + 624 |
| 7-10 | M + 624 |
| 7-11 | M + 640 |
| 7-12 | M + 544 |

Experimental Example

The following explains evaluation methods of the HIV integrase inhibitory activity of the compound of the present invention.

(i) Construction of Recombinant Integrase Gene Expression System

HIV integrase full length gene (J. Virol., 67, 425-437 (1993)) in which phenylalanine at codon 185 was substituted by histidine, was inserted between the restriction enzyme NdeI and XhoI sites of plasmid pET21a(+) (Novagen), whereby an integrase expression vector pET21a-IN-F185H was constructed.

(ii) Production and Purification of Integrase Protein

Escherichia coli recombinant BL21(DE3) transformed with plasmid pET21a-IN-F185H obtained in (i) was shake cultured at 30° C. in a liquid medium containing ampicillin. When the culture reached the logarithmic growth phase, isopropyl-β-D-thiogalactopyranoside was added to promote expression of integrase gene. The culture was continued for 3 hr to promote accumulation of the integrase protein. The recombinant E. coli was collected in pellets by centrifugal separation and preserved at −80° C.

The E. coli was suspended in Lysis buffer (20 mM HEPES (pH 7.5), 5 mM DTT, 10 mM CHAPS, 10% glycerol) containing 1M sodium chloride and subjected to repeat pressurization and depressurization for rupture, and centrifugal separation at 4° C., 40,000×g, 60 min to recover a water-soluble fraction (supernatant). This was diluted 10-fold with Lysis buffer free of sodium chloride, mixed with SP-Sepharose (Pharmacia Corporation) and stirred at 4° C. for 60 min to allow adsorption of integrase protein to the resin. The resin was washed with Lysis buffer containing 100 mM sodium chloride and the integrase protein was eluted with Lysis buffer containing 1M sodium chloride.

The eluted integrase protein solution was subjected to a Superdex 75 (Pharmacia Corporation) column for gel filtration. The protein was eluted with Lysis buffer containing 1M sodium chloride.

The obtained fractions of the integrase protein were collected and preserved at −80° C.

(iii) Preparation of DNA Solution

The following DNA synthesized by Greiner was dissolved in TE buffer (10 mM Tris-hydrochloric acid (pH 8.0), 1 mM EDTA) and mixed with donor DNA, target DNA, and each complementary strand (+ and − strands) to 1 μM. The mixture was heated at 95° C. for 5 min, 80° C. for 10 min, 70° C. for 10 min, 60° C. for 10 min, 50° C. for 10 min and 40° C. for 10 min and kept at 25° C. to give a double stranded DNA, which was used for the test. Donor DNA (− strand having biotin attached to the 5' terminal) Donor + strand: 5'-Biotin-ACC CTT TTA GTC AGT GTG GAA AAT CTC TAG CA-3' (SEQ ID NO:1) Donor − strand: 5'-ACT GCT AGA GAT TTT CCA CAC TGA CTA AAA G-3' (SEQ ID NO:2) Target DNA (+, − strands both having digoxigenin added at 3' terminal) Target + strand: 5'-TGA CCA AGG GCT AAT TCA CT-Dig-3' (SEQ ID NO:3) Target − strand: 5'-AGT GAA TTA GCC CTT GGT CA-Dig-3' (SEQ ID NO:4)

(iv) Determination of Enzyme (HIV Integrase) Inhibitory Activity

The donor DNA was diluted with TE buffer to 10 nM, of which 50 μl was added to each well of streptavidin-coated microtiter plate (Roche) and allowed to adsorb at 37° C. for 60 min. The plate was washed with phosphate buffer (Dulbecco's PBS, Sanko Junyaku Co., Ltd.) containing 0.1% Tween 20 and phosphate buffer. Then, an enzyme reaction mixture (70 μl), a test substance (10 μl) diluted with the reaction mixture and 100 μg/ml integrase protein (10 μl) were added to each well and reacted at 37° C. for 60 min.

Then, 50 nM target DNA (10 μl) was added, reacted at 37° C. for 10 min and washed with phosphate buffer containing 0.1% Tween 20 to stop the reaction.

Then, 100 mU/ml peroxidase labeled anti-digoxigenin antibody solution (Roche, 100 μl) was added, and the mixture was reacted at 37° C. for 60 min, followed by washing with phosphate buffer containing 0.1% Tween 20.

A peroxidase color solution (Bio Rad, 100 μl) was added and allowed to react at room temperature for 4 min. The color reaction was stopped by adding 1N sulfuric acid (100 μl). The absorbance at 450 nm was measured.

The HIV integrase inhibitory activity ($IC_{50}$) of the compound of the present invention was calculated from the inhibition rate according to the following formula. The results are shown in Table 15.

inhibition rate (%)=[1−(Object−Blank)/(Control−Blank)]×100

Object; absorbance of well in the presence of test compound
Control; absorbance of well in the absence of test compound
Blank; absorbance of well in the absence of test compound, in the absence of integrase protein Evaluation of Antivirus Activity The effect of combined use of the compound of the present invention and existent anti-HIV agents can be determined in the following manner.

For example, the effect of combined use of two agents from existent nucleoside reverse transcriptase inhibitors (zidovudine, lamivudine, tenofovir), non-nucleoside reverse transcriptase inhibitors (efavirenz) or protease inhibitors (indinavir, nelfinavir) and test substance A, and the like are evaluated using CEM-SS cells infected with HIV-1 IIIB by XTT method.

In addition, the effect of combined use of three agents of test substance A, zidovudine and lamivudine, or test substance A, tenofovir and lamivudine, and the like is evaluated.

Prior to the combined use test, $IC_{50}$ and $CC_{50}$ of each pharmaceutical agent alone are measured. 5 concentrations of pharmaceutical agent A and 9 concentrations of pharmaceutical agent B, determined based on these results, are combined to evaluate the effect of combined use of two agents. For combined use of three agents, a high concentration pharmaceutical agent B and a pharmaceutical agent C are mixed and pharmaceutical agent A and the concentration are combined for evaluation.

The test results of the test substance and combination drug alone or in combination thereof are analyzed based on the programs of Prichard and Shipman MacSynergy II version 2.01 and Deltagraph version 1.5d. A three-dimensional plot is drawn from % inhibition at the concentrations of each combined pharmaceutical agent, obtained from 3 times of tests, with 95% (or 68%, 99%) confidence limits, and the effect of the combined use is evaluated based on the numerical values of $\mu M^2$% calculated therefrom. The criteria of evaluation are shown in the following.

Definition of interaction $\mu gm^2$%
Strong synergistic action >100
Slight synergistic action +51−+100
Additive action +50−−50
Slight antagonistic action −51−−100
Strong antagonistic action <−100

TABLE 15-1

| Example No. | Enzyme activity $IC_{50}$ (μM) |
|---|---|
| 1-1 | 0.019 |
| 1-2 | 0.0038 |
| 1-3 | 0.0078 |
| 1-4 | 0.025 |
| 1-5 | 0.0033 |
| 1-6 | 0.0046 |

TABLE 15-1-continued

| Example No. | Enzyme activity $IC_{50}$ (μM) |
|---|---|
| 1-7 | 0.0055 |
| 1-8 | — |
| 1-9 | — |
| 1-10 | 0.28 |
| 1-11 | — |
| 1-12 | 0.26 |

TABLE 15-2

| Example No. | Enzyme activity $IC_{50}$ (μM) |
|---|---|
| 2-1 | 0.0046 |
| 2-2 | 0.012 |
| 2-3 | 0.0068 |
| 2-4 | 0.010 |
| 2-5 | — |
| 2-6 | 0.0038 |
| 2-7 | 0.0081 |
| 2-8 | 0.020 |
| 2-9 | — |
| 2-10 | 0.0042 |
| 2-11 | 0.0050 |
| 2-12 | 0.0057 |
| 2-13 | 0.0069 |
| 2-14 | 0.013 |
| 2-15 | 0.0052 |
| 2-16 | 0.0058 |
| 2-17 | 0.014 |
| 2-18 | 0.0060 |

TABLE 15-3

| Example No. | Enzyme activity $IC_{50}$ (μM) |
|---|---|
| 3-1 | 0.0051 |
| 3-2 | 0.0047 |
| 3-3 | 0.0063 |
| 3-4 | 0.0045 |
| 3-5 | 0.0040 |
| 3-6 | 0.011 |
| 3-7 | 0.0047 |
| 3-8 | 0.0040 |
| 3-9 | 0.0050 |

TABLE 15-4a

| Example No. | Enzyme activity $IC_{50}$ (μM) |
|---|---|
| 4-1 | 0.0044 |
| 4-2 | 0.0060 |
| 4-3 | 0.0047 |
| 4-4 | 0.0047 |
| 4-5 | 0.0034 |
| 4-6 | 0.0063 |
| 4-7 | 0.0050 |
| 4-8 | 0.0047 |
| 4-9 | 0.0060 |
| 4-10 | 0.0062 |
| 4-11 | 0.0068 |
| 4-12 | 0.0073 |
| 4-13 | 0.0063 |
| 4-14 | 0.0054 |
| 4-15 | 0.011 |
| 4-16 | 0.0079 |
| 4-17 | 0.011 |
| 4-18 | 0.0048 |
| 4-19 | 0.0046 |
| 4-20 | 0.0093 |

TABLE 15-4a-continued

| Example No. | Enzyme activity IC$_{50}$ (µM) |
|---|---|
| 4-21 | 0.0066 |
| 4-22 | 0.0071 |
| 4-23 | 0.027 |
| 4-24 | 0.012 |
| 4-25 | 0.0041 |
| 4-26 | 0.0092 |
| 4-27 | 0.016 |
| 4-28 | 0.0045 |
| 4-29 | 0.0051 |
| 4-30 | 0.0061 |

TABLE 15-4b

| Example No. | Enzyme activity IC$_{50}$ (µM) |
|---|---|
| 4-31 | 0.013 |
| 4-32 | 0.0071 |
| 4-33 | 0.0057 |
| 4-34 | 0.0039 |
| 4-35 | 0.0060 |
| 4-36 | 0.0054 |
| 4-37 | 0.0044 |
| 4-38 | 0.012 |
| 4-39 | 0.0094 |
| 4-40 | 0.0068 |
| 4-41 | 0.0045 |
| 4-42 | 0.0079 |
| 4-43 | 0.0064 |
| 4-44 | 0.0049 |
| 4-45 | 0.013 |
| 4-46 | 0.0068 |
| 4-47 | 0.0066 |
| 4-48 | 0.0056 |
| 4-49 | 0.0051 |
| 4-50 | 0.0053 |
| 4-51 | 0.0060 |
| 4-52 | 0.0066 |
| 4-53 | 0.0050 |
| 4-54 | 0.0071 |
| 4-55 | 0.0076 |
| 4-56 | 0.0050 |
| 4-57 | 0.0038 |
| 4-58 | 0.0047 |
| 4-59 | 0.0036 |
| 4-60 | 0.0043 |

TABLE 15-4c

| Example No. | Enzyme activity IC$_{50}$ (µM) |
|---|---|
| 4-61 | 0.0049 |
| 4-62 | 0.0055 |
| 4-63 | 0.0036 |
| 4-64 | 0.0066 |

TABLE 15-5

| Example No. | Enzyme activity IC$_{50}$ (µM) |
|---|---|
| 5-1 | 0.16 |
| 5-2 | 0.047 |

TABLE 15-6

| Example No. | Enzyme activity IC$_{50}$ (µM) |
|---|---|
| 6-1 | 0.0059 |

TABLE 15-7

| Example No. | Enzyme activity IC$_{50}$ (µM) |
|---|---|
| 7-1 | 0.017 |
| 7-2 | 0.0045 |
| 7-3 | 0.0035 |
| 7-4 | 0.0036 |
| 7-5 | 0.0032 |
| 7-6 | 0.0043 |
| 7-7 | 0.017 |
| 7-8 | 0.039 |

INDUSTRIAL APPLICABILITY

The compounds of the present invention show a high inhibitory activity against HIV integrase.

Therefore, these compounds can be pharmaceutical agents effective for, for example, the prophylaxis or treatment of AIDS, as integrase inhibitors, antiviral agents, anti-HIV agents, and the like, having an HIV integrase inhibitory activity. In addition, by a combined use with other anti-HIV agent(s) such as protease inhibitor, reverse transcription enzyme inhibitor, and the like, they can be more effective anti-HIV agents. Furthermore, having high inhibitory activity specific for integrase, they can be pharmaceutical agents safe for human body with a fewer side effects.

This application is based on patent application No. 2004-151034 filed in Japan, the contents of which are hereby incorporated by reference.

Sequence Listing Free Text

SEQ ID; No 1: Donor + strand for determining HIV integrase activity

SEQ ID; No 2: Donor − strand for determining HIV integrase activity

SEQ ID; No 3: Target + strand for determining HIV integrase activity

SEQ ID; No 4: Target − strand for determining HIV integrase activity

The instant application includes a Statement Accompanying Sequence Listing, and a Sequence Listing in both paper and computer-readable formats.

What is claimed is:

1. A 4-oxoquinoline compound represented by the following formula [I] or a pharmaceutically acceptable salt thereof:

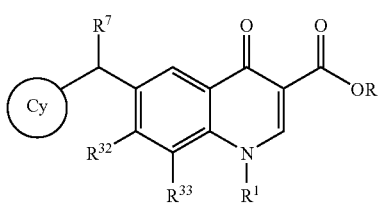

wherein ring Cy is a group selected from the group consisting of

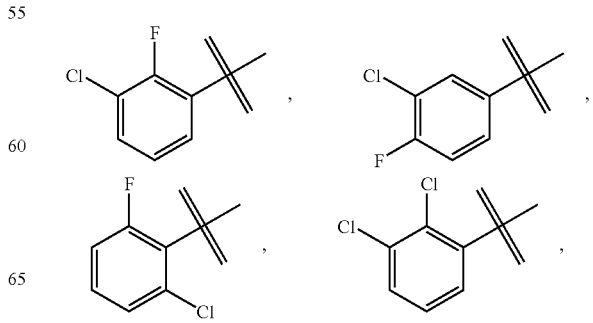

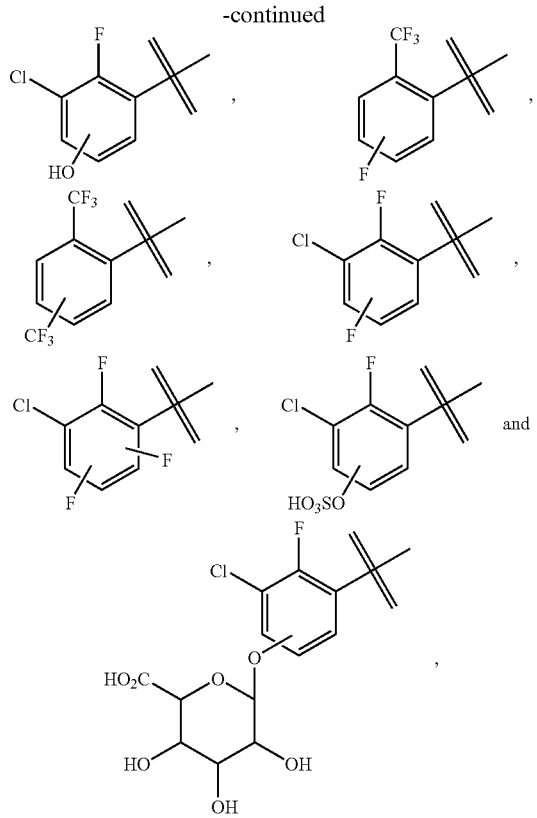

R is a hydrogen atom or

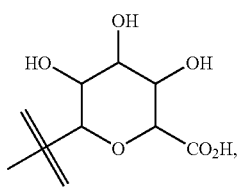

$R^1$

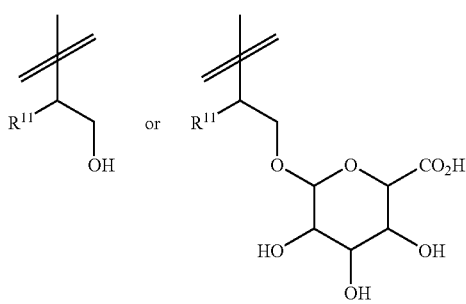

{wherein $R^{11}$ is —$(C_mH_{2m})$—$OR^{12}$, —$(C_mH_{2m})$—$SR^{12}$, —$(C_mH_{2m})$—$SO_2R^{12}$ (wherein $R^{12}$ is a $C_{1-4}$ alkyl group and m is an integer of 1 to 4), a saturated heterocyclic group, an isopropyl group or a tert-butyl group}, $R^{32}$ is a hydrogen atom, an ethyl group, a methoxy group, a hydroxyl group, a 2-hydroxyethoxy group, a 3-hydroxypropoxy group, a 4-hydroxybutyloxy group, a 2,2,2-trifluoroethyloxy group, —O—$(CH_2)_p$—$OR^{34}$, —O—$(CH_2)$—$NR^{35}R^{36}$, —O—$(CH_2)_p$—$CO_2R^{35}$, —O—$(CH_2)_p$—$CONR^{35}R^{37}$, —O—$(CH_2)_p$—$SO_2NR^{35}R^{37}$ (wherein $R^{34}$ is a $C_{1-4}$ alkyl group, $R^{35}$ and $R^{37}$ are the same or different and each is a hydrogen atom or a $C_{1-4}$ alkyl group, $R^{36}$ is a hydrogen atom, a $C_{1-4}$ alkyl group, an acetyl group or a mesyl group, and p is an integer of 1 to 4), a pyrrolidinyl group, a piperidinyl group, a piperazinyl group, a morpholinyl group, a thiomorpholinyl group (wherein each of the pyrrolidinyl group, piperidinyl group, piperazinyl group, morpholinyl group and thiomorpholinyl group is optionally substituted by 1 or 2 substituents selected from the group consisting of a hydroxyl group, a $C_{1-4}$ alkyl group, an oxo group, —$COR^{38}$, —$NR^{35}R^{37}$ and —$NR^{35}COR^{38}$, wherein $R^{35}$ and $R^{37}$ are as defined above and $R^{38}$ is a $C_{1-4}$ alkyl group), or

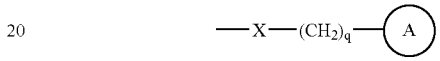

(wherein X is —O— or —NH—, ring A is a phenyl group or a heterocyclic group, wherein each of the phenyl group and the heterocyclic group is optionally substituted by at least one group independently selected from a cyano group, a mesyl group, a $C_{1-4}$ alkyl group, —$CO_2R^{35}$, —$CONR^{35}R^{37}$, —$SO_2NR^{35}R^{37}$ and —$COR^{38}$, wherein $R^{35}$, $R^{37}$ and $R^{38}$ are as defined above, and q is 0 or an integer of 1 to 4), $R^{33}$ is a hydrogen atom, a hydroxyl group, —O—$(CH_2)_n$—$OR^{39}$, —O—$(CH_2)_n$—$NR^{39}R^{31}$ or —O—$(CH_2)_n$—Ph (wherein $R^{39}$ and $R^{31}$ are the same or different and each is a hydrogen atom or a $C_{1-4}$ alkyl group and n is an integer of 1 to 4), $R^7$ is a hydrogen atom or a hydroxyl group, $R^{32}$ and $R^{33}$ may be linked to form an alkylenedioxy group, $R^1$ and $R^{33}$ may be linked to form

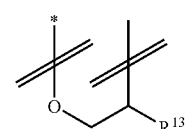

(wherein * shows the $R^{33}$ side and $R^{13}$ is a $C_{1-4}$ alkyl group optionally substituted by hydroxyl group(s)), provided that the compound represented by the formula [I] satisfies at least one condition of the following (1)-(7):

(1) the compound represented by the formula [I] is a compound represented by

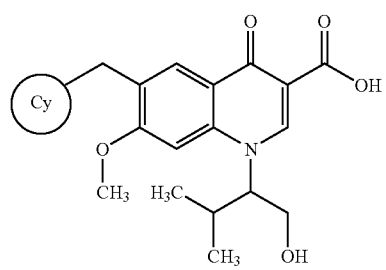

wherein ring Cy is a group selected from the group consisting of

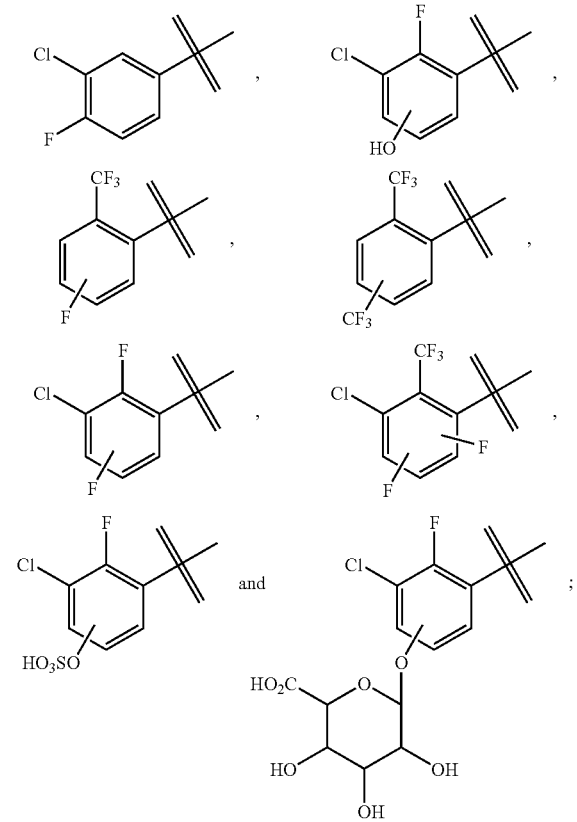

(2) the compound represented by the formula [I] is a compound represented by

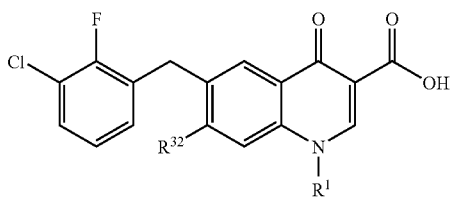

wherein $R^{32}$ is a hydrogen atom or a methoxy group, and $R^1$ is

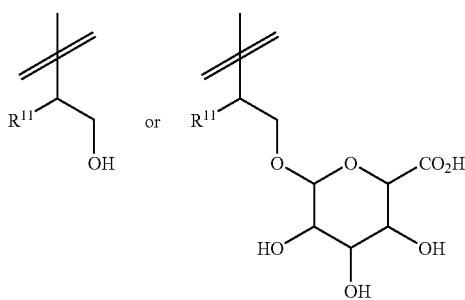

wherein $R^{11}$ is —$(C_mH_{2m})$—$OR^{12}$, —$(C_mH_{2m})$—$SR^{12}$, —$(C_mH_{2m})$—$SO_2R^{12}$ (wherein $R^{12}$ and m are as defined above), or a saturated heterocyclic group;

(3) the compound represented by the formula [I] is a compound represented by

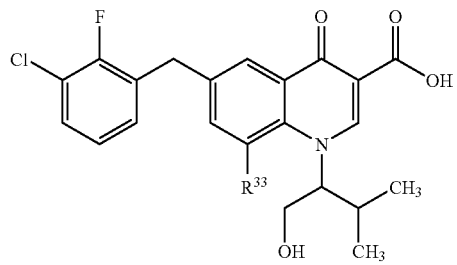

wherein $R^{33}$ is a hydroxyl group, —O—$(CH_2)_n$—$OR^{39}$, —O—$(CH_2)_n$—$NR^{39}R^{31}$, or —O—$(CH_2)_n$—Ph (wherein $R^{31}$, $R^{39}$ and n are as defined above);

(4) the compound represented by the formula [I] is a compound represented by

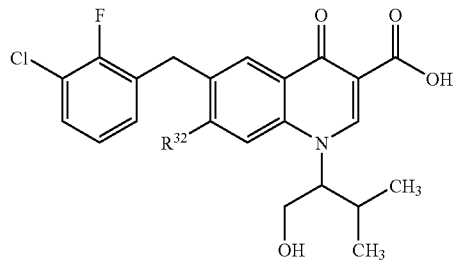

wherein $R^{32}$ is an ethyl group, a 4-hydroxybutyloxy group, a 2,2,2-trifluoroethyloxy group, —O—$(CH_2)_p$—$OR^{34}$, —O—$(CH_2)_p$—$NR^{35}R^{36}$, —O—$(CH_2)_p$—$CO_2R^{35}$, —O—$(CH_2)_p$—$CONR^{35}R^{37}$, —O—$(CH_2)_p$—$SO_2NR^{35}R^{37}$ (wherein $R^{34}$, $R^{35}$, $R^{36}$, $R^{37}$ and p are as defined above), a pyrrolidinyl group, a piperidinyl group, a piperazinyl group, a morpholinyl group, a thiomorpholinyl group (wherein each of the pyrrolidinyl group, piperidinyl group, piperazinyl group, morpholinyl group and thiomorpholinyl group is optionally substituted by 1 or 2 substituents selected from the group consisting of a hydroxyl group, a $C_{1-4}$ alkyl group, an oxo group, —$COR^{38}$, —$NR^{35}R^{37}$ and —$NR^{35}COR^{38}$, wherein $R^{35}$, $R^{37}$ and $R^{38}$ are as defined above), or

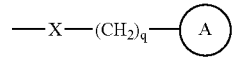

wherein X, ring A and q are as defined above;

(5) the compound represented by the formula [I] is a compound represented by

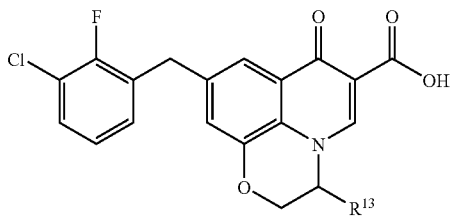

wherein $R^{13}$ is as defined above;

(6) the compound represented by the formula [I] is a compound represented by

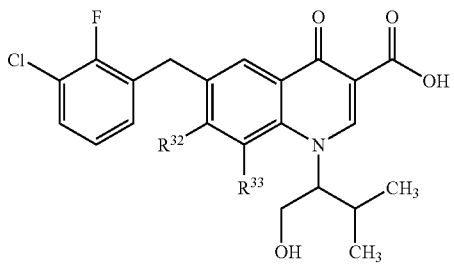

wherein $R^{32}$ and $R^{33}$ are linked to form an alkylenedioxy group; and (7) the compound represented by the formula [I] is 6-(2-chloro-6-fluorobenzyl)-1-(1-(hydroxymethyl)-2-methylpropyl)-7-methoxy-4-oxo-1,4-dihydroquinoline-3-carboxylic acid, 6-(2,3-dichlorobenzyl)-1-(1-(hydroxymethyl)-2-methylpropyl)-7-methoxy-4-oxo-1,4-dihydroquinoline-3-carboxylic acid, 6-(3-chloro-2-fluorobenzyl)-7-(2-hydroxyethoxy)-1-(1-(hydroxymethyl)-2-methylpropyl)-4-oxo-1,4-dihydroquinoline-3-carboxylic acid, 6-(3-chloro-2-fluorobenzyl)-1-(1-(hydroxymethyl)-2-methylpropyl)-7-(3-hydroxypropoxy)-4-oxo-1,4-dihydroquinoline-3-carboxylic acid, 6-(3-chloro-2-fluorobenzyl)-7-hydroxy-1-(1-(hydroxymethyl)-2-methylpropyl)-4-oxo-1,4-dihydroquinoline-3-carboxylic acid, 6-(3-chloro-2-fluorobenzyl)-1-(2,2-dimethyl-1-(hydroxymethyl)propyl)-7-(morpholin-4-yl)-4-oxo-1,4-dihydroquinoline-3-carboxylic acid, 6-((3-chloro-2-fluorophenyl)-hydroxy-methyl)-1-(1-hydroxymethyl-2-methylpropyl)-7-methoxy-4-oxo-1,4-dihydroquinoline-3-carboxylic acid, or 6-[6-(3-chloro-2-fluorobenzyl)-1-(1-hydroxymethyl-2-methylpropyl)-7-methoxy-4-oxo-1,4-dihydroquinoline-3-carbonyloxy]-3,4,5-trihydroxytetrahydropyran-2-carboxylic acid.

2. The 4-oxoquinoline compound of claim 1, wherein in the formula [I],

R is a hydrogen atom, ring Cy is a group selected from the group consisting of

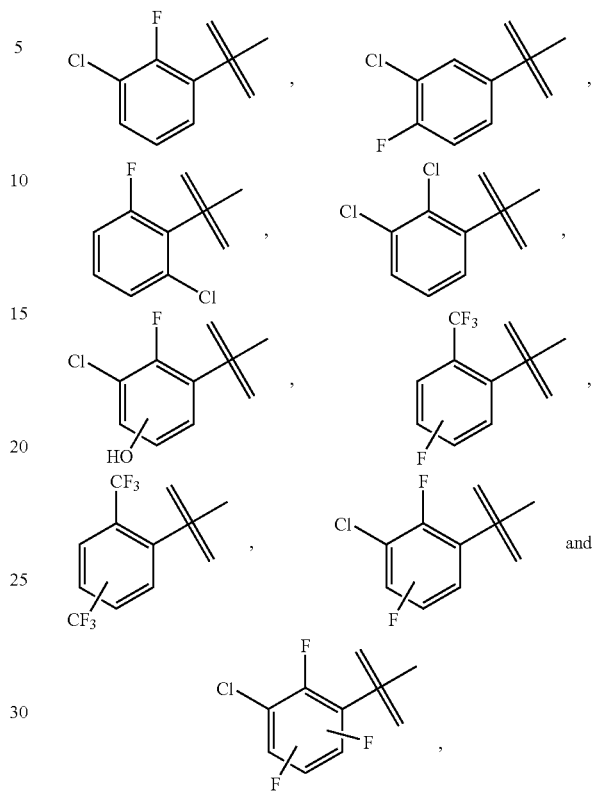

$R^1$ is

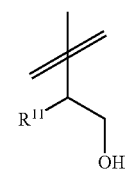

{wherein $R^{11}$ is —$(C_mH_{2m})$—$OR^{12}$, —$(C_mH_{2m})$—$SR^{12}$, —$(C_mH_{2m})$—$SO_2R^{12}$ (wherein $R^{12}$ is a $C_{1-4}$ alkyl group and m is an integer of 1 to 4), a saturated heterocyclic group, an isopropyl group or a tert-butyl group}, $R^{32}$ is a hydrogen atom, an ethyl group, a methoxy group, a hydroxyl group, a 2-hydroxyethoxy group, a 3-hydroxypropoxy group, a 4-hydroxybutyloxy group, a 2,2,2-trifluoroethyloxy group, —O—$(CH_2)_p$—$OR^{34}$, —O—$(CH_2)_p$—$NR^{35}R^{36}$, —O—$(CH_2)_p$—$CO_2R^{35}$, —O—$(CH_2)_p$—$CONR^{35}R^{37}$, —O—$(CH_2)_p$—$SO_2NR^{35}R^{37}$ (wherein $R^{34}$ is a $C_{1-4}$ alkyl group, $R^{35}$ and $R^{37}$ are the same or different and each is a hydrogen atom or a $C_{1-4}$ alkyl group, $R^{36}$ is a hydrogen atom, a $C_{1-4}$ alkyl group, an acetyl group or a mesyl group, and p is an integer of 1 to 4), a pyrrolidinyl group, a piperidinyl group, a piperazinyl group, a morpholinyl group, a thiomorpholinyl group (wherein each of the pyrrolidinyl group, piperidinyl group, piperazinyl group, morpholinyl group and thiomorpholinyl group is optionally substituted by 1 or 2 substituents selected from the group consisting of a hydroxyl group, a $C_{1-4}$ alkyl group, an oxo group, —$COR^{38}$, —$NR^{35}R^{37}$ and —$NR^{35}COR^{38}$, wherein $R^{35}$ and $R^{37}$ are as defined above and $R^{38}$ is a $C_{1-4}$ alkyl group), or

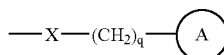

(wherein X is —O— or —NH—, ring A is a phenyl group or a heterocyclic group, wherein each of the phenyl group and the heterocyclic group is optionally substituted by at least one group independently selected from a cyano group, a mesyl group, a $C_{1-4}$ alkyl group, —$CO_2R^{35}$, —$CONR^{35}R^{37}$, —$SO_2NR^{35}R^{37}$ and —$COR^{38}$, wherein $R^{35}$, $R^{37}$ and $R^{38}$ are as defined above, and q is 0 or an integer of 1 to 4), $R^{33}$ is a hydrogen atom, a hydroxyl group, —O—$(CH_2)_n$—$OR^{39}$, —O—$(CH_2)_n$—$NR^{39}R^{31}$ or —O—$(CH_2)_n$—Ph (wherein $R^{39}$ and $R^{31}$ are the same or different and each is a hydrogen atom or a $C_{1-4}$ alkyl group and n is an integer of 1 to 4), $R^7$ is a hydrogen atom or a hydroxyl group, $R^{32}$ and $R^{33}$ may be linked to form an alkylenedioxy group, $R^1$ and $R^{33}$ may be linked to form

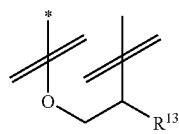

(wherein * shows the $R^{33}$ side and $R^{13}$ is a $C_{1-4}$ alkyl group optionally substituted by hydroxyl group(s)), provided that the compound represented by the formula [I] satisfies at least one condition of the following (1)-(7):

(1) the compound represented by the formula [I] is a compound represented by

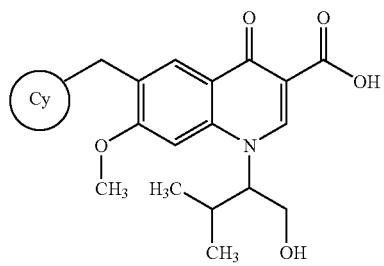

wherein ring Cy is a group selected from the group consisting of

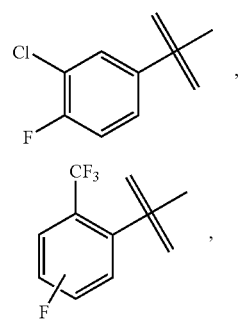

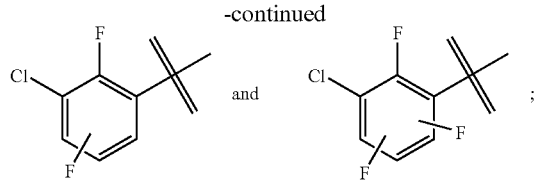

(2) the compound represented by the formula [I] is a compound represented by

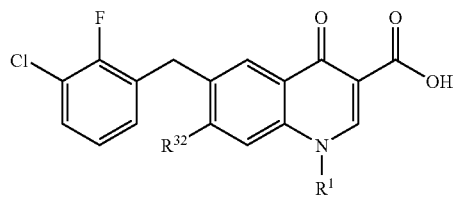

wherein $R^{32}$ is a hydrogen atom or a methoxy group, and $R^1$ is

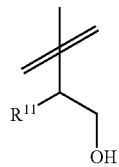

wherein $R^{11}$ is —$(C_mH_{2m})$—$OR^{12}$, —$(C_mH_{2m})$—$SR^{12}$, —$(C_mH_{2m})$—$SO_2R^{12}$ (wherein $R^{12}$ and m are as defined above), or a saturated heterocyclic group;

(3) the compound represented by the formula [I] is a compound represented by

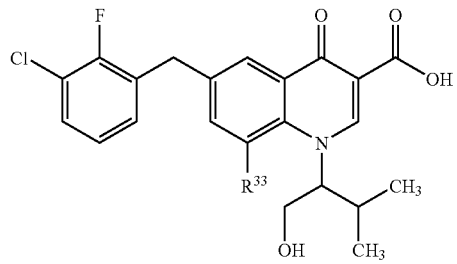

wherein $R^{33}$ is a hydroxyl group, —O—$(CH_2)_n$—$OR^{39}$, —O—$(CH_2)_n$—$NR^{39}R^{31}$ or —O—$(CH_2)_n$—Ph (wherein $R^{31}$, $R^{39}$ and n are as defined above);

(4) the compound represented by the formula [I] is a compound represented by

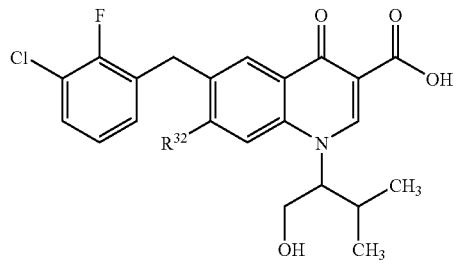

wherein $R^{32}$ is an ethyl group, a 4-hydroxybutyloxy group, a 2,2,2-trifluoroethyloxy group, —O—$(CH_2)_p$—$OR^{34}$, —O—$(CH_2)_p$—$NR^{35}R^{36}$, —O—$(CH_2)_p$—$CO_2R^{35}$, —O—$(CH_2)_p$—$CONR^{35}R^{37}$, —O—$(CH_2)_p$—$SO_2NR^{35}R^{37}$ (wherein $R^{34}$, $R^{35}$, $R^{36}$, $R^{37}$ and p are as defined above), a pyrrolidinyl group, a piperidinyl group, a piperazinyl group, a morpholinyl group, a thiomorpholinyl group (wherein each of the pyrrolidinyl group, piperidinyl group, piperazinyl group, morpholinyl group and thiomorpholinyl group is optionally substituted by 1 or 2 substituents selected from the group consisting of a hydroxyl group, a $C_{1-4}$ alkyl group, an oxo group, —$COR^{38}$, —$NR^{35}R^{37}$ and —$NR^{35}COR^{38}$, wherein $R^{35}$, $R^{37}$ and $R^{38}$ are as defined above), or

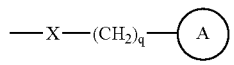

wherein X, ring A and q are as defined above;
(5) the compound represented by the formula [I] is a compound represented by

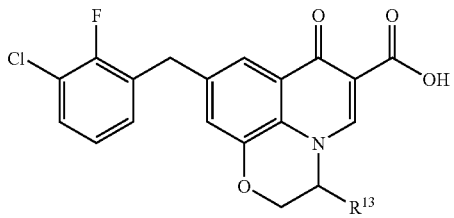

wherein $R^{13}$ is as defined above;
(6) the compound represented by the formula [I] is a compound represented by

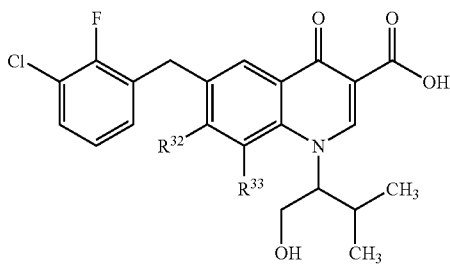

wherein $R^{32}$ and $R^{33}$ are linked to form an alkylenedioxy group; and
(7) the compound represented by the formula [I] is
  6-(2-chloro-6-fluorobenzyl)-1-(1-(hydroxymethyl)-2-methylpropyl)-7-methoxy-4-oxo-1,4-dihydroquinoline-3-carboxylic acid,
  6-(2,3-dichlorobenzyl)-1-(1-(hydroxymethyl)-2-methylpropyl)-7-methoxy-4-oxo-1,4-dihydroquinoline-3-carboxylic acid,
  6-(3-chloro-2-fluorobenzyl)-7-(2-hydroxyethoxy)-1-(1-(hydroxymethyl)-2-methylpropyl)-4-oxo-1,4-dihydroquinoline-3-carboxylic acid,
  6-(3-chloro-2-fluorobenzyl)-1-(1-(hydroxymethyl)-2-methylpropyl)-7-(3-hydroxypropoxy)-4-oxo-1,4-dihydroquinoline-3-carboxylic acid,
  6-(3-chloro-2-fluorobenzyl)-7-hydroxy-1-(1-(hydroxymethyl)-2-methylpropyl)-4-oxo-1,4-dihydroquinoline-3-carboxylic acid,
  6-(3-chloro-2-fluorobenzyl)-1-(2,2-dimethyl-1-(hydroxymethyl)propyl)-7-(morpholin-4-yl)-4-oxo-1,4-dihydroquinoline-3-carboxylic acid, or
  6-((3-chloro-2-fluorophenyl)-hydroxy-methyl)-1-(1-hydroxymethyl-2-methylpropyl)-7-methoxy-4-oxo-1,4-dihydroquinoline-3-carboxylic acid, or a pharmaceutically acceptable salt thereof.

3. The 4-oxoquinoline compound of claim 1, which is selected from the group consisting of
  6-(3-chloro-4-fluorobenzyl)-1-((1S)-1-(hydroxymethyl)-2-methylpropyl)-7-methoxy-4-oxo-1,4-dihydroquinoline-3-carboxylic acid,
  6-(3-chloro-2,6-difluorobenzyl)-1-((1S)-1-(hydroxymethyl)-2-methylpropyl)-7-methoxy-4-oxo-1,4-dihydroquinoline-3-carboxylic acid,
  6-(3-chloro-2-fluoro-6-hydroxybenzyl)-1-((1S)-1-(hydroxymethyl)-2-methylpropyl)-7-methoxy-4-oxo-1,4-dihydroquinoline-3-carboxylic acid,
  6-(3-chloro-2-fluoro-4-hydroxybenzyl)-1-((1S)-1-(hydroxymethyl)-2-methylpropyl)-7-methoxy-4-oxo-1,4-dihydroquinoline-3-carboxylic acid,
  6-(3-chloro-2,4-difluorobenzyl)-1-((1S)-1-(hydroxymethyl)-2-methylpropyl)-7-methoxy-4-oxo-1,4-dihydroquinoline-3-carboxylic acid,
  6-(3-chloro-2-fluoro-5-hydroxybenzyl)-1-((1S)-1-(hydroxymethyl)-2-methylpropyl)-7-methoxy-4-oxo-1,4-dihydroquinoline-3-carboxylic acid,
  6-(3-chloro-2,4,5-trifluorobenzyl)-1-((1S)-1-(hydroxymethyl)-2-methylpropyl)-7-methoxy-4-oxo-1,4-dihydroquinoline-3-carboxylic acid,
  6-(3-fluoro-2-(trifluoromethyl)benzyl)-1-((1S)-1-(hydroxymethyl)-2-methylpropyl)-7-methoxy-4-oxo-1,4-dihydroquinoline-3-carboxylic acid,
  6-(2,5-di(trifluoromethyl)benzyl)-1-((1S)-1-(hydroxymethyl)-2-methylpropyl)-7-methoxy-4-oxo-1,4-dihydroquinoline-3-carboxylic acid,
  6-(4-fluoro-2-(trifluoromethyl)benzyl)-1-((1S)-1-(hydroxymethyl)-2-methylpropyl)-7-methoxy-4-oxo-1,4-dihydroquinoline-3-carboxylic acid,
  6-(5-fluoro-2-(trifluoromethyl)benzyl)-1-((1S)-1-(hydroxymethyl)-2-methylpropyl)-7-methoxy-4-oxo-1,4-dihydroquinoline-3-carboxylic acid,
  6-(2-fluoro-6-(trifluoromethyl)benzyl)-1-((1S)-1-(hydroxymethyl)-2-methylpropyl)-7-methoxy-4-oxo-1,4-dihydroquinoline-3-carboxylic acid,
  6-(3-chloro-2-fluorobenzyl)-1-((1S)-2-hydroxy-1-(tetrahydropyran-4-yl)ethyl)-7-methoxy-4-oxo-1,4-dihydroquinoline-3-carboxylic acid,
  6-(3-chloro-2-fluorobenzyl)-1-(2-hydroxy-1-(piperidin-4-yl)ethyl)-7-methoxy-4-oxo-1,4-dihydroquinoline-3-carboxylic acid hydrochloride,
  6-(3-chloro-2-fluorobenzyl)-1-((1R)-1-(hydroxymethyl)-2-(methylthio)ethyl)-7-methoxy-4-oxo-1,4-dihydroquinoline-3-carboxylic acid,
  6-(3-chloro-2-fluorobenzyl)-1-((1R)-1-(hydroxymethyl)-2-mesylethyl)-7-methoxy-4-oxo-1,4-dihydroquinoline-3-carboxylic acid,
  6-(3-chloro-2-fluorobenzyl)-1-((1R)-1-(hydroxymethyl)-2-methyl-2-(methylthio)propyl)-7-methoxy-4-oxo-1,4-dihydroquinoline-3-carboxylic acid,
  6-(3-chloro-2-fluorobenzyl)-1-((1R)-1-(hydroxymethyl)-2-mesyl-2-methylpropyl)-7-methoxy-4-oxo-1,4-dihydroquinoline-3-carboxylic acid, 6-(3-chloro-2-fluorobenzyl)-1-((1R)-1-(hydroxymethyl)-2-(methylthio)ethyl)-4-oxo-1,4-dihydroquinoline-3-carboxylic acid, 6-(3-chloro-2-fluorobenzyl)-1-((1R)-1-(hydroxymethyl)-2-mesylethyl)-4-oxo-1,4-dihydroquinoline-3-carboxylic acid, 6-(3-chloro-2-fluorobenzyl)-1-((1R)-1-(hydroxymethyl)-2-methyl-2-(methylthio)propyl)-4-oxo-1,4-dihydroquinoline-3-carboxylic acid, 6-(3-chloro-2-fluorobenzyl)-1-((1R)-1-(hydroxymethyl)-2-mesyl-2-methylpropyl)-4-oxo-1,4-dihydroquinoline-3-carboxylic acid, 6-(3-chloro-2-fluorobenzyl)-1-((1R,2R)-1-(hydroxymethyl)-2-methoxypropyl)-7-methoxy-4-oxo-1,4-dihydroquinoline-3-carboxylic acid, 6-(3-chloro-2-fluorobenzyl)-1-((1S)-1-(hydroxymethyl)-3-(methylthio)propyl)-7-methoxy-4-oxo-1,4-dihydroquinoline-3-carboxylic acid, 6-(3-chloro-2-fluorobenzyl)-1-((1S)-1-(hydroxymethyl)-3-mesylpropyl)-7-methoxy-4-oxo-1,4-dihydroquinoline-3-carboxylic acid, 6-(3-chloro-2-fluorobenzyl)-1-((1R)-1-(hydroxymethyl)-2-methoxyethyl)-4-oxo-1,4-dihydroquinoline-3-carboxylic acid, 6-(3-chloro-2-fluorobenzyl)-1-((1R,2R)-1-(hydroxymethyl)-2-methoxypropyl)-4-oxo-1,4-dihydroquinoline-3-carboxylic acid, 6-(3-chloro-2-fluorobenzyl)-1-((1S)-1-(hydroxymethyl)-3-(methylthio)propyl)-4-oxo-1,4-dihydroquinoline-3-carboxylic acid, 6-(3-chloro-2-fluorobenzyl)-1-((1S)-1-(hydroxymethyl)-3-mesylpropyl)-4-oxo-1,4-dihydroquinoline-3-carboxylic acid, 6-(3-chloro-2-fluorobenzyl)-1-((1R)-1-(hydroxymethyl)-2-methoxyethyl)-7-methoxy-4-oxo-1,4-dihydroquinoline-3-carboxylic acid, 6-(3-chloro-2-fluorobenzyl)-8-(2-hydroxyethoxy)-1-((1S)-1-(hydroxymethyl)-2-methylpropyl)-4-oxo-1,4-dihydroquinoline-3-carboxylic acid, 6-(3-chloro-2-fluorobenzyl)-1-((1S)-1-(hydroxymethyl)-2-methylpropyl)-8-(3-hydroxypropoxy)-4-oxo-1,4-dihydroquinoline-3-carboxylic acid, 6-(3-chloro-2-fluorobenzyl)-8-(4-hydroxybutoxy)-1-((1S)-1-(hydroxymethyl)-2-methylpropyl)-4-oxo-1,4-dihydroquinoline-3-carboxylic acid, 6-(3-chloro-2-fluorobenzyl)-1-((1S)-1-(hydroxymethyl)-2-methylpropyl)-8-(2-methoxyethoxy)-4-oxo-1,4-dihydroquinoline-3-carboxylic acid, 6-(3-chloro-2-fluorobenzyl)-8-hydroxy-1-((1S)-1-(hydroxymethyl)-2-methylpropyl)-4-oxo-1,4-dihydroquinoline-3-carboxylic acid, 6-(3-chloro-2-fluorobenzyl)-8-(2-(dimethylamino)ethoxy)-1-((1S)-1-(hydroxymethyl)-2-methylpropyl)-4-oxo-1,4-dihydroquinoline-3-carboxylic acid, 6-(3-chloro-2-fluorobenzyl)-1-((1S)-1-(hydroxymethyl)-2-methylpropyl)-8-(3-methoxypropoxy)-4-oxo-1,4-dihydroquinoline-3-carboxylic acid, 6-(3-chloro-2-fluorobenzyl)-1-((1S)-1-(hydroxymethyl)-2-methylpropyl)-8-(4-methoxybutoxy)-4-oxo-1,4-dihydroquinoline-3-carboxylic acid, 8-benzyloxy-6-(3-chloro-2-fluorobenzyl)-1-((1S)-1-(hydroxymethyl)-2-methylpropyl)-4-oxo-1,4-dihydroquinoline-3-carboxylic acid, 6-(3-chloro-2-fluorobenzyl)-1-((1S)-1-(hydroxymethyl)-2-methylpropyl)-7-(2-methoxyethoxy)-4-oxo-1,4-dihydroquinoline-3-carboxylic acid, 6-(3-chloro-2-fluorobenzyl)-7-(2-(dimethylamino)ethoxy)-1-((1S)-1-(hydroxymethyl)-2-methylpropyl)-4-oxo-1,4-dihydroquinoline-3-carboxylic acid, 6-(3-chloro-2-fluorobenzyl)-1-((1S)-1-(hydroxymethyl)-2-methylpropyl)-7-((methylamino)sulfonylmethoxy)-4-oxo-1,4-dihydroquinoline-3-carboxylic acid, 6-(3-chloro-2-fluorobenzyl)-7-ethyl-1-((1S)-1-(hydroxymethyl)-2-methylpropyl)-4-oxo-1,4-dihydroquinoline-3-carboxylic acid, 6-(3-chloro-2-fluorobenzyl)-7-(4-hydroxybutoxy)-1-((1S)-1-(hydroxymethyl)-2-methylpropyl)-4-oxo-1,4-dihydroquinoline-3-carboxylic acid), 6-(3-chloro-2-fluorobenzyl)-7-(3-(dimethylamino)propoxy)-1-((1S)-1-(hydroxymethyl)-2-methylpropyl)-4-oxo-1,4-dihydroquinoline-3-carboxylic acid, 6-(3-chloro-2-fluorobenzyl)-7-(4-(dimethylamino)butoxy)-1-((1S)-1-(hydroxymethyl)-2-methylpropyl)-4-oxo-1,4-dihydroquinoline-3-carboxylic acid, 6-(3-chloro-2-fluorobenzyl)-1-((1S)-1-(hydroxymethyl)-2-methylpropyl)-7-(3-methoxypropoxy)-4-oxo-1,4-dihydroquinoline-3-carboxylic acid, 6-(3-chloro-2-fluorobenzyl)-1-((1S)-1-(hydroxymethyl)-2-methylpropyl)-7-(morpholin-4-yl)-4-oxo-1,4-dihydroquinoline-3-carboxylic acid, 6-(3-chloro-2-fluorobenzyl)-1-((1S)-1-(hydroxymethyl)-2-methylpropyl)-7-(4-methylpiperazin-1-yl)-4-oxo-1,4-dihydroquinoline-3-carboxylic acid, 7-(4-acetylpiperazin-1-yl)-6-(3-chloro-2-fluorobenzyl)-1-((1S)-1-(hydroxymethyl)-2-methylpropyl)-4-oxo-1,4-dihydroquinoline-3-carboxylic acid, 6-(3-chloro-2-fluorobenzyl)-1-((1S)-1-(hydroxymethyl)-2-methylpropyl)-4-oxo-7-(piperazin-1-yl)-1,4-dihydroquinoline-3-carboxylic acid, 6-(3-chloro-2-fluorobenzyl)-1-((1S)-1-(hydroxymethyl)-2-methylpropyl)-4-oxo-7-(2-(piperidin-1-yl)ethoxy)-1,4-dihydroquinoline-3-carboxylic acid, 6-(3-chloro-2-fluorobenzyl)-1-((1S)-1-(hydroxymethyl)-2-methylpropyl)-7-(1-methylpiperidin-4-yloxy)-4-oxo-1,4-dihydroquinoline-3-carboxylic acid, 6-(3-chloro-2-fluorobenzyl)-7-(4-ethylpiperazin-1-yl)-1-((1S)-1-(hydroxymethyl)-2-methylpropyl)-4-oxo-1,4-dihydroquinoline-3-carboxylic acid, 6-(3-chloro-2-fluorobenzyl)-1-((1S)-1-(hydroxymethyl)-2-methylpropyl)-7-(2-(morpholin-4-yl)ethoxy)-4-oxo-1,4-dihydroquinoline-3-carboxylic acid, 6-(3-chloro-2-fluorobenzyl)-1-((1S)-1-(hydroxymethyl)-2-methylpropyl)-4-oxo-7-(2-(pyrrolidin-1-yl)ethoxy)-1,4-dihydroquinoline-3-carboxylic acid, 7-(2-aminoethoxy)-6-(3-chloro-2-fluorobenzyl)-1-((1S)-1-(hydroxymethyl)-2-methylpropyl)-4-oxo-1,4-dihydroquinoline-3-carboxylic acid hydrochloride, 7-(3-aminopropoxy)-6-(3-chloro-2-fluorobenzyl)-1-((1S)-1-(hydroxymethyl)-2-methylpropyl)-4-oxo-1,4-dihydroquinoline-3-carboxylic acid hydrochloride, 6-(3-chloro-2-fluorobenzyl)-1-((1S)-1-(hydroxymethyl)-2-methylpropyl)-4-oxo-7-(pyridin-3-yloxy)-1,4-dihydroquinoline-3-carboxylic acid hydrochloride, 6-(3-chloro-2-fluorobenzyl)-1-((1S)-1-(hydroxymethyl)-2-methylpropyl)-7-(4-hydroxypiperidin-1-yl)-4-oxo-1,4-dihydroquinoline-3-carboxylic acid, 6-(3-chloro-2-fluorobenzyl)-7-(3,5-dimethylpiperazin-1-yl)-1-((1S)-1-(hydroxymethyl)-2-methylpropyl)-4-oxo-1,4-dihydroquinoline-3-carboxylic acid, 6-(3-chloro-2-fluorobenzyl)-1-((1S)-1-(hydroxymethyl)-2-methylpropyl)-7-((3R)-3-hydroxypyrrolidin-1-yl)-4-oxo-1,4-dihydroquinoline-3-carboxylic acid, 6-(3-chloro-2-fluorobenzyl)-1-((1S)-1-(hydroxymethyl)-2-methylpropyl)-7-((3S)-3-hydroxypyrrolidin-1-yl)-4-oxo-1,4-dihydroquinoline-3-carboxylic acid, 6-(3-chloro-2-fluorobenzyl)-1-((1S)-1-(hydroxymethyl)-2-methylpropyl)-4-oxo-7-(piperidin-4-yloxy)-1,4-dihydroquinoline-3-carboxylic acid), 7-((3S)-3-(acetylamino)pyrrolidin-1-yl)-6-(3-chloro-2-fluorobenzyl)-1-((1S)-1-(hydroxymethyl)-2-methylpropyl)-4-oxo-1,4-dihydroquinoline-3-carboxylic acid, 7-((3R)-3-(acetylamino)pyrrolidin-1-yl)-6-(3-chloro-2-fluorobenzyl)-1-((1S)-1-(hydroxymethyl)-2-methylpropyl)-4-oxo-1,4-dihydroquinoline-3-carboxylic acid, 6-(3-chloro-2-fluorobenzyl)-7-((dimethylamino)sulfonylmethoxy)-1-((1S)-1-(hydroxymethyl)-2-methylpropyl)-4-oxo-1,4-dihydroquinoline-3-carboxylic acid, 6-(3-chloro-2-fluorobenzyl)-1-((1S)-1-(hydroxymethyl)-2-methylpropyl)-7-((3R)-3-methylpiperazin-1-yl)-4-oxo-1,4-dihydroquinoline-3-carboxylic acid, 6-(3-chloro-2-fluorobenzyl)-1-((1S)-1-(hydroxymethyl)-2-methylpropyl)-7-((3S)-3-methylpiperazin-1-yl)-4-oxo-1,4-dihydroquinoline-3-carboxylic acid, 6-(3-chloro-2-fluorobenzyl)-7-(2,6-dimethylmorpholin-4-yl)-1-((1S)-1-(hydroxymethyl)-2-methylpropyl)-4-oxo-1,4-dihydroquinoline-3-carboxylic acid, 6-(3-chloro-2-fluorobenzyl)-1-((1S)-1-(hydroxymethyl)-2-methylpropyl)-4-oxo-7-(thiomorpholin-4-yl)-1,4-dihydroquinoline-3-carboxylic acid, 6-(3-chloro-2-fluorobenzyl)-1-((1S)-1-(hydroxymethyl)-2-methylpropyl)-4-oxo-7-(2-(piperazin-1-yl)ethoxy)-1,4-dihydroquinoline-3-carboxylic acid dihydrochloride, 7-(4-aminobutoxy)-6-(3-chloro-2-fluorobenzyl)-1-((1S)-1-(hydroxymethyl)-2-methylpropyl)-4-oxo-1,4-dihydroquinoline-3-carboxylic acid hydrochloride, 6-(3-chloro-2-fluorobenzyl)-1-((1S)-1-(hydroxymethyl)-2-methylpropyl)-4-oxo-7-(3-oxopiperazin-1-yl)-1,4-dihydroquinoline-3-carboxylic acid, 6-(3-chloro-2-fluorobenzyl)-1-((1S)-1-(hydroxymethyl)-2-methylpropyl)-4-oxo-7-(tetrahydropyran-4-yloxy)-1,4-dihydroquinoline-3-carboxylic acid, 6-(3-chloro-2-fluorobenzyl)-1-((1S)-1-(hydroxymethyl)-2-methylpropyl)-4-oxo-7-((3R)-pyrrolidin-3-yloxy)-1,4-dihydroquinoline-3-carboxylic acid hydrochloride, 7-((3S)-3-aminopyrrolidin-1-yl)-6-(3-chloro-2-fluorobenzyl)-1-((1S)-1-(hydroxymethyl)-2-methylpropyl)-4-oxo-1,4-dihydroquinoline-3-carboxylic acid, 7-((3R)-3-aminopyrrolidin-1-yl)-6-(3-chloro-2-fluorobenzyl)-1-((1S)-1-(hydroxymethyl)-2-methylpropyl)-4-oxo-1,4-dihydroquinoline-3-carboxylic acid, 6-(3-chloro-2-fluorobenzyl)-7-(1-(ethoxycarbonyl)piperidin-4-ylamino)-1-((1S)-1-(hydroxymethyl)-2-methylpropyl)-4-oxo-1,4-dihydroquinoline-3-carboxylic acid, 7-(2-(acetylamino)ethoxy)-6-(3-chloro-2-fluorobenzyl)-1-((1S)-1-(hydroxymethyl)-2-methylpropyl)-4-oxo-1,4-dihydroquinoline-3-carboxylic acid), 6-(3-chloro-2-fluorobenzyl)-1-((1S)-1-(hydroxymethyl)-2-methylpropyl)-4-oxo-7-(piperidin-4-ylamino)-1,4-dihydroquinoline-3-carboxylic acid, 7-benzyloxy-6-(3-chloro-2-fluorobenzyl)-1-((1S)-1-(hydroxymethyl)-2-methylpropyl)-4-oxo-1,4-dihydroquinoline-3-carboxylic acid, 6-(3-chloro-2-fluorobenzyl)-1-((1S)-1-(hydroxymethyl)-2-methylpropyl)-4-oxo-7-phenoxy-1,4-dihydroquinoline-3-carboxylic acid, 7-((1-acetylpiperidin-4-yl)oxy)-6-(3-chloro-2-fluorobenzyl)-1-((1S)-1-(hydroxymethyl)-2-methylpropyl)-4-oxo-1,4-dihydroquinoline-3-carboxylic acid, 6-(3-chloro-2-fluorobenzyl)-1-((1S)-1-(hydroxymethyl)-2-methylpropyl)-4-oxo-7-((3S)-pyrrolidin-3-yloxy)-1,4-dihydroquinoline-3-carboxylic acid hydrochloride, 6-(3-chloro-2-fluorobenzyl)-1-((1S)-1-(hydroxymethyl)-2-methylpropyl)-4-oxo-7-((3S)-tetrahydrofuran-3-yloxy)-1,4-dihydroquinoline-3-carboxylic acid, 6-(3-chloro-2-fluorobenzyl)-1-((1S)-1-(hydroxymethyl)-2-methylpropyl)-4-oxo-7-((3R)-tetrahydrofuran-3-yloxy)-1,4-dihydroquinoline-3-carboxylic acid, 6-(3-chloro-2-fluorobenzyl)-1-((1S)-1-(hydroxymethyl)-2-methylpropyl)-7-(2-(mesylamino)ethoxy)-4-oxo-1,4-dihydroquinoline-3-carboxylic acid, 7-(carboxymethoxy)-6-(3-chloro-2-fluorobenzyl)-1-((1S)-1-(hydroxymethyl)-2-methylpropyl)-4-oxo-1,4-dihydroquinoline-3-carboxylic acid), 6-(3-chloro-2-fluorobenzyl)-1-((1S)-1-(hydroxymethyl)-2-methylpropyl)-7-(2-(4-methylpiperazin-1-yl)ethoxy)-4-oxo-1,4-dihydroquinoline-3-carboxylic acid ditrifluoroacetate, 7-((aminosulfonyl)methoxy)-6-(3-chloro-2-fluorobenzyl)-1-((1S)-1-(hydroxymethyl)-2-methylpropyl)-4-oxo-1,4-dihydroquinoline-3-carboxylic acid, 6-(3-chloro-2-fluorobenzyl)-7-((dimethylaminocarbonyl)methoxy)-1-((1S)-1-(hydroxymethyl)-2-methylpropyl)-4-oxo-1,4-dihydroquinoline-3-carboxylic acid, 6-(3-chloro-2-fluorobenzyl)-1-((1S)-1-(hydroxymethyl)-2-methylpropyl)-7-((3S)-1-methylpyrrolidin-3-yloxy)-4-oxo-1,4-dihydroquinoline-3-carboxylic acid trifluoroacetate, 6-(3-chloro-2-fluorobenzyl)-1-((1S)-1-(hydroxymethyl)-2-methylpropyl)-7-((3R)-1-methylpyrrolidin-3-yloxy)-4-oxo-1,4-dihydroquinoline-3-carboxylic acid trifluoroacetate, 6-(3-chloro-2-fluorobenzyl)-7-(4-cyanobenzyloxy)-1-((1S)-1-(hydroxymethyl)-2-methylpropyl)-4-oxo-1,4-dihydroquinoline-3-carboxylic acid, 7-(4-carboxybenzyloxy)-6-(3-chloro-2-fluorobenzyl)-1-((1S)-1-(hydroxymethyl)-2-methylpropyl)-4-oxo-1,4-dihydroquinoline-3-carboxylic acid, 7-(4-(aminocarbonyl)benzyloxy)-6-(3-chloro-2-fluorobenzyl)-1-((1S)-1-(hydroxymethyl)-2-methylpropyl)-4-oxo-1,4-dihydroquinoline-3-carboxylic acid, 6-(3-chloro-2-fluorobenzyl)-1-((1S)-1-(hydroxymethyl)-2-methylpropyl)-4-oxo-7-(pyridin-2-ylmethoxy)-1,4-dihydroquinoline-3-carboxylic acid, 6-(3-chloro-2-fluorobenzyl)-1-((1S)-1-(hydroxymethyl)-2-methylpropyl)-4-oxo-7-(pyridin-4-ylmethoxy)-1,4-dihydroquinoline-3-carboxylic acid, 6-(3-chloro-2-fluorobenzyl)-1-((1S)-1-(hydroxymethyl)-2-methylpropyl)-4-oxo-7-(pyridin-3-ylmethoxy)-1,4-dihydroquinoline-3-carboxylic acid, 6-(3-chloro-2-fluorobenzyl)-1-((1S)-1-(hydroxymethyl)-2-methylpropyl)-4-oxo-7-(2,2,2-trifluoroethyloxy)-1,4-dihydroquinoline-3-carboxylic acid, 7-(4-(aminosulfonyl)benzyloxy)-6-(3-chloro-2-fluorobenzyl)-1-((1S)-1-(hydroxymethyl)-2-methylpropyl)-4-oxo-1,4-dihydroquinoline-3-carboxylic acid, 6-(3-chloro-2-fluorobenzyl)-1-((1S)-1-(hydroxymethyl)-2-methylpropyl)-7-(1-mesylpiperidin-4-yloxy)-4-oxo-1,4-dihydroquinoline-3-carboxylic acid, (3S)-8-(3-chloro-2-fluorobenzyl)-3-isopropyl-6-oxo-2,3-dihydro-6H-1-oxa-3a-aza-phenalene-5-carboxylic acid, 8-(3-chloro-2-fluorobenzyl)-3-hydroxymethyl-6-oxo-2,3-dihydro-6H-1-oxa-3a-aza-phenalene-5-carboxylic acid, 10-(3-chloro-2-fluorobenzyl)-5-((1S)-1-hydroxymethyl-2-methylpropyl)-8-oxo-2,3,5,8-tetrahydro-1,4-dioxa-5-aza-phenanthrene-7-carboxylic acid, 6-(2-chloro-6-fluorobenzyl)-1-((1S)-1-(hydroxymethyl)-2-methylpropyl)-7-methoxy-4-oxo-1,4-dihydroquinoline-3-carboxylic acid, 6-(2,3-dichlorobenzyl)-1-((1S)-1-(hydroxymethyl)-2-methylpropyl)-7-methoxy-4-oxo-1,4-dihydroquinoline-3-carboxylic acid, 6-(3-chloro-2-fluorobenzyl)-7-(2-hydroxyethoxy)-1-((1S)-1-(hydroxymethyl)-2-methylpropyl)-4-oxo-1,4-dihydroquinoline-3-carboxylic acid, 6-(3-chloro-2-fluorobenzyl)-1-((1S)-1-(hydroxymethyl)-2-methylpropyl)-7-(3-hydroxypropoxy)-4-oxo-1,4-dihydroquinoline-3-carboxylic acid, 6-(3-chloro-2-fluorobenzyl)-7-hydroxy-1-((1S)-1-(hydroxymethyl)-2-methylpropyl)-4-oxo-1,4-dihydroquinoline-3-carboxylic acid, 6-(3-chloro-2-fluorobenzyl)-1-((1S)-2,2-dimethyl-1-(hydroxymethyl)propyl)-7-(morpholin-4-yl)-4-oxo-1,4-dihydroquinoline-3-carboxylic acid, 6-((3-chloro-2-fluorophenyl)-hydroxy-methyl)-1-((1S)-1-hydroxymethyl-2-methylpropyl)-7-methoxy-4-oxo-1,4-dihydroquinoline-3-carboxylic acid, 1-[(1S)-1-((2R,3R,4S,5S,6S)-6-carboxy-3,4,5-trihydroxytetrahydropyran-2-yloxymethyl)-2-methylpropyl]-6-(3-chloro-2-fluorobenzyl)-7-methoxy-4-oxo-1,4-dihydroquinoline-3-carboxylic acid, (2S,3S,4S,5R,6S)-6-[6-(3-chloro-2-fluorobenzyl)-1-((1S)-1-hydroxymethyl-2-methylpropyl)-7-methoxy-4-oxo-1,4-dihydroquinoline-3-carbonyloxy]-3,4,5-trihydroxytetrahydropyran-2-carboxylic acid morphline salt, 6-[4-((2S,3R,4S,5S,6S)-6-carboxy-3,4,5-trihydroxytetrahydropyran-2-yloxy)-3-chloro-2-fluorobenzyl]-1-((1S)-1-hydroxymethyl-2-methylpropyl)-7-methoxy-4-oxo-1,4-dihydroquinoline-3-carboxylic acid, and 6-(3-chloro-2-fluoro-4-sodiumsulfonatobenzyl)-1-((1S)-1-hydroxymethyl-2-methylpropyl)-7-methoxy-4-oxo-1,4-dihydroquinoline-3-carboxylic acid, or a pharmaceutically acceptable salt thereof.

4. A pharmaceutical composition comprising a 4-oxoquinoline compound of claim 1, or a pharmaceutically acceptable salt thereof, and a pharmaceutically acceptable carrier.

5. A method for inhibiting integrase, comprising administering a pharmaceutically effective amount of a 4-oxoquinoline compound of claim 1, or a pharmaceutically acceptable salt thereof, to a mammal.

6. A method for the treatment of a viral infection, comprising administering a pharmaceutically effective amount of a 4-oxoquinoline compound of claim 1, or a pharmaceutically acceptable salt thereof, to a mammal.

7. A method for the prophylaxis or treatment of an HIV infection, comprising administering a pharmaceutically effective amount of a 4-oxoquinoline compound of claim 1 or a pharmaceutically acceptable salt thereof to a mammal.

8. The method for the treatment of an HIV infection according to claim 7, further comprising administering a pharmaceutically effective amount of at least one other anti-HIV active substances to a mammal.

9. A pharmaceutical composition for inhibiting integrase, comprising a 4-oxoquinoline compound of claim 1 or a pharmaceutically acceptable salt thereof, and a pharmaceutically acceptable carrier.

10. A commercial package comprising the composition of claim 9 and a written matter associated therewith, the written matter stating that the composition can or should be used for inhibiting integrase.

11. A commercial package comprising the composition of claim 4 and a written matter associated therewith, the written matter stating that the composition can or should be used for the treatment of a viral infection.

12. A commercial package comprising the composition of claim 4 and a written matter associated therewith, the written matter stating that the composition can or should be used for the treatment of an HIV infection.

13. A compound selected from the following structural formulae:

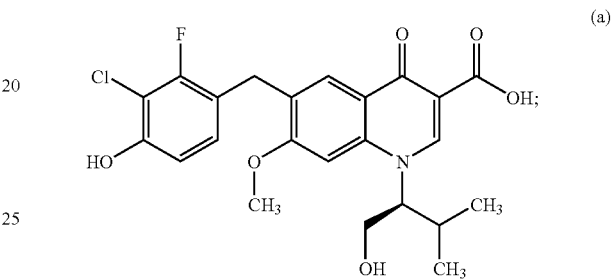

(a)

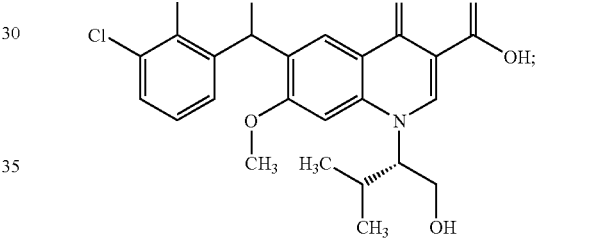

(b)

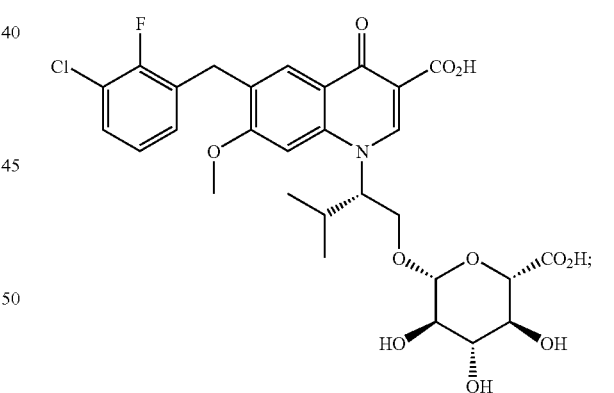

(c)

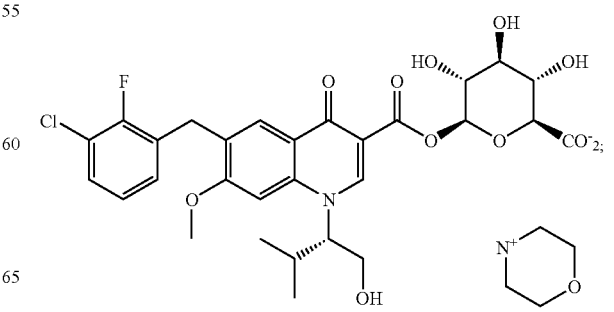

(d)

-continued
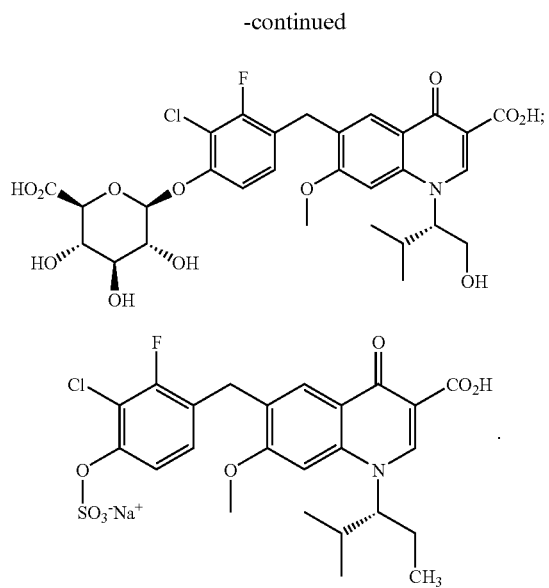
14. A compound selected from the following structural formulae:
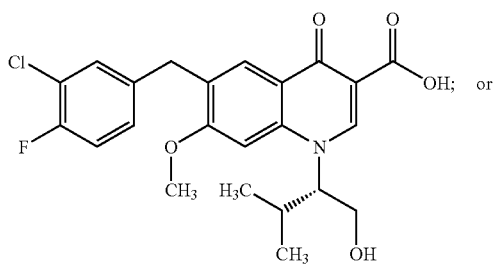
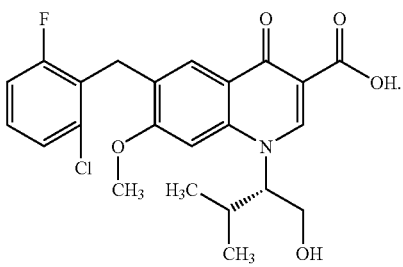
* * * * *

UNITED STATES PATENT AND TRADEMARK OFFICE
CERTIFICATE OF CORRECTION

PATENT NO. : 7,531,554 B2
APPLICATION NO. : 11/133470
DATED : May 12, 2009
INVENTOR(S) : Satoh et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 982 days.

Signed and Sealed this

Seventh Day of September, 2010

David J. Kappos
*Director of the United States Patent and Trademark Office*

UNITED STATES PATENT AND TRADEMARK OFFICE
CERTIFICATE OF CORRECTION

PATENT NO.       : 7,531,554 B2
APPLICATION NO.  : 11/133470
DATED            : May 12, 2009
INVENTOR(S)      : Motohide Satoh et al.

It is certified that error appears in the above-identified patent and that said Letters Patent is hereby corrected as shown below:

Col. 155 claim 13, Formula (f) reads:

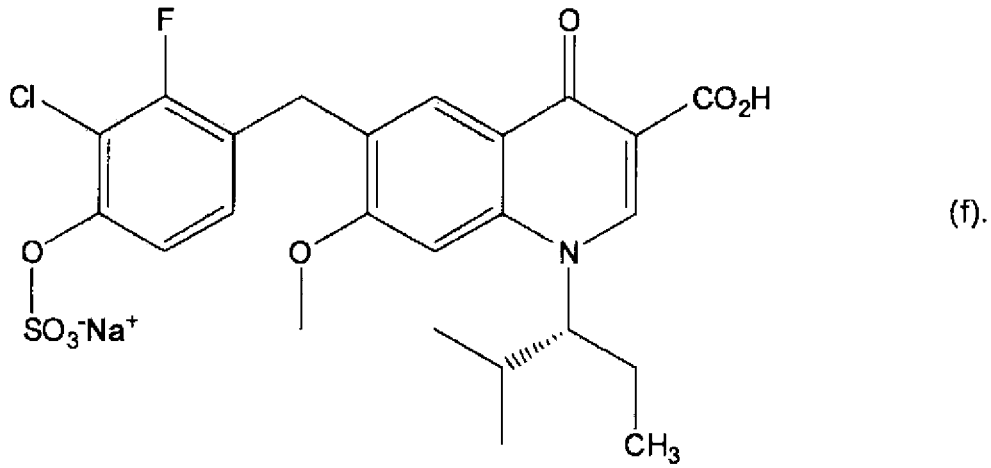

(f).

should read

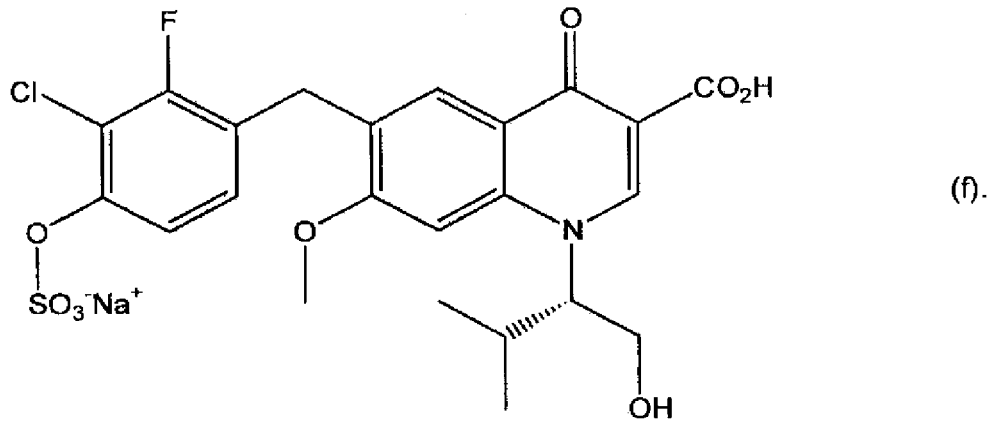

(f).

Signed and Sealed this
Twenty-fifth Day of January, 2011

David J. Kappos
*Director of the United States Patent and Trademark Office*

SEQUENCE LISTING

<160> NUMBER OF SEQ ID NOS: 4

<210> SEQ ID NO 1
<211> LENGTH: 32
<212> TYPE: DNA
<213> ORGANISM: Artificial Sequence
<220> FEATURE:
<223> OTHER INFORMATION: Donor plus strand for activity determination of HIV integrase.

<400> SEQUENCE: 1 accctttag tcagtgtgga aaatctctag ca                32

<210> SEQ ID NO 2
<211> LENGTH: 31
<212> TYPE: DNA
<213> ORGANISM: Artificial Sequence
<220> FEATURE:
<223> OTHER INFORMATION: Donor minus strand for activity determination of HIV integrase.

<400> SEQUENCE: 2
actgctagag attttccaca ctgactaaaa g                31

<210> SEQ ID NO 3
<211> LENGTH: 20
<212> TYPE: DNA
<213> ORGANISM: Artificial Sequence
<220> FEATURE:
<223> OTHER INFORMATION: Target plus strand for activity determination of HIV integrase.

<400> SEQUENCE: 3
tgaccaaggg ctaattcact                20

<210> SEQ ID NO 4
<211> LENGTH: 20
<212> TYPE: DNA
<213> ORGANISM: Artificial Sequence
<220> FEATURE:
<223> OTHER INFORMATION: Target minus strand for activity determination of HIV integrase.

<400> SEQUENCE: 4
agtgaattag cccttggtca                20